(12) United States Patent
Nara et al.

(10) Patent No.: US 10,174,044 B2
(45) Date of Patent: Jan. 8, 2019

(54) FUSED PYRIDINES AS KINASE INHIBITORS

(71) Applicant: BRISTOL-MYERS SQUIBB COMPANY, Princeton, NJ (US)

(72) Inventors: Susheel Jethanand Nara, Chembur (IN); Carolyn Diane Dzierba, Middletown, CT (US); John E. Macor, Washington Crossing, PA (US); Joanne J. Bronson, Durham, CT (US); Rajamani Ramkumar, Woodbridge, CT (US); Tarun Kumar Maishal, Bangalore (IN); Maheswaran Sivasamban Karatholuvhu, Bangalore (IN); Soodamani Thangavel, Krishnagiri (IN); Kamalraj Thiyagarajan, Gudiyattam (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/563,697

(22) PCT Filed: Apr. 4, 2016

(86) PCT No.: PCT/US2016/025837
§ 371 (c)(1),
(2) Date: Oct. 2, 2017

(87) PCT Pub. No.: WO2016/164295
PCT Pub. Date: Oct. 13, 2016

(65) Prior Publication Data
US 2018/0141956 A1    May 24, 2018

Related U.S. Application Data

(60) Provisional application No. 62/145,727, filed on Apr. 10, 2015.

(51) Int. Cl.
| | | |
|---|---|---|
| *A61K 31/436* | (2006.01) | |
| *C07D 491/052* | (2006.01) | |
| *C07D 471/04* | (2006.01) | |
| *C07D 491/04* | (2006.01) | |
| *A61P 25/28* | (2006.01) | |
| *A61P 25/02* | (2006.01) | |
| *A61P 25/04* | (2006.01) | |
| *A61P 25/18* | (2006.01) | |
| *A61P 25/16* | (2006.01) | |
| *C07B 59/00* | (2006.01) | |

(52) U.S. Cl.
CPC .......... *C07D 491/052* (2013.01); *A61P 25/02* (2018.01); *A61P 25/04* (2018.01); *A61P 25/16* (2018.01); *A61P 25/18* (2018.01); *A61P 25/28* (2018.01); *C07B 59/002* (2013.01); *C07D 471/04* (2013.01); *C07D 491/04* (2013.01); *C07B 2200/05* (2013.01)

(58) Field of Classification Search
CPC .............. A61K 31/436; A61K 31/4375; C07D 491/02; C07D 471/04
See application file for complete search history.

(56) References Cited

U.S. PATENT DOCUMENTS

| | | | | |
|---|---|---|---|---|
| 8,901,305 | B2 * | 12/2014 | Vrudhula | C07D 471/04 546/81 |
| 8,946,415 | B2 | 2/2015 | Bi et al. | |
| 8,969,565 | B2 | 3/2015 | Bi et al. | |
| 9,738,642 | B2 * | 8/2017 | Marcin | C07D 471/04 |
| 9,902,722 | B2 * | 2/2018 | Luo | C07D 471/04 |
| 9,932,320 | B2 * | 4/2018 | Hartz | C07D 401/04 |
| 2014/0080834 | A1 | 3/2014 | Lanthorn et al. | |

FOREIGN PATENT DOCUMENTS

| | | |
|---|---|---|
| CN | 1733708 A | 2/2006 |
| JP | 2007-217408 A | 8/2007 |
| WO | WO 94/12461 A1 | 6/1994 |
| WO | WO 96/21464 A1 | 7/1996 |
| WO | WO 03/086325 A2 | 10/2003 |
| WO | WO 2004/056745 A2 | 7/2004 |
| WO | WO 2004/072018 A1 | 8/2004 |
| WO | WO 2005/000309 A2 | 1/2005 |
| WO | WO 2006/012227 A2 | 2/2006 |
| WO | WO 2007/117715 A2 | 10/2007 |
| WO | WO 2008/022154 A2 | 2/2008 |
| WO | WO 2013/134036 A1 | 9/2013 |
| WO | WO 2014/022167 A1 | 2/2014 |
| WO | WO 2014/130258 A1 | 8/2014 |
| WO | WO 2015/002915 A1 | 1/2015 |
| WO | WO 2015/002926 A1 | 1/2015 |
| WO | WO 2015/038112 A1 | 3/2015 |
| WO | WO 2015/116060 A1 | 8/2015 |

OTHER PUBLICATIONS

Buonanno, A., "The neuregulin signaling pathway and schizophrenia: From genes to synapses and neural circuits", Brain Research Bulletin, vol. 83, pp. 122-131 (2010).
Conner, S.D. et al., "AAK1-Mediated 2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia from the Consortium on the Genetics of Schizophrenia", Am. J. Psychiatry, vol. 168, No. 9, pp. 930-946 (2011).

(Continued)

*Primary Examiner* — Alexander R Pagano
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

12 Claims, No Drawings
Specification includes a Sequence Listing.

(56) References Cited

OTHER PUBLICATIONS

Henderson, D.M. et al., "A Novel AAK1 Splice Variant Functions at Multiple Steps of the Endocytic Pathway", Molecular Biology of the Cell, vol. 18, pp. 2698-2706 (2007).

Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).

Jackson, A.P. et al., "Clathrin promotes incorporation of cargo into coated pits by activation of the AP2 adaptor µ2 kinase", The Journal of Cell Biology, vol. 163, No. 2, pp. 231-236 (2003).

Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).

Latourelle, J.C. et al., "Genomewide association study for onset age in Parkinson disease", BMC Medical Genetics, vol. 10 (2009), doi:10.1186/1471-2350-10-98.

Motley, A.M. et al., "Functional Analysis of AP-2 α and µ2 Subunits", Molecular Biology of the Cell, vol. 17, pp. 5298-5308 (2006).

Ricotta, D. et al., "Phosphorylation of the AP2µ subunit by AAK1 mediates high affinity binding to membrane protein sorting signals", The Journal of Cell Biology, vol. 156, No. 5, pp. 791-795 (2002).

Wen, L. et al., "Neuregulin 1 regulates pyramidal neuron activity via ErbB4 in parvalbumin-positive interneurons", Proc. Natl. Acad. Sci., vol. 107, No. 3, pp. 1211-1216 (2010).

Kostich, W. et al., "Inhibition of AAK1 Kinase as a Novel Therapeutic Approach to Treat Neuropathic Pain," J. Pharmacol. Exp. Ther., 358, pp. 371-386 (2016).

\* cited by examiner

FUSED PYRIDINES AS KINASE INHIBITORS

CROSS-REFERENCE TO RELATED APPLICATIONS

This application claims priority to Provisional patent application U.S. Ser. No. 62/145,727 filed Apr. 10, 2015, hereby incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In its first aspect the present disclosure provides a compound of formula (I)

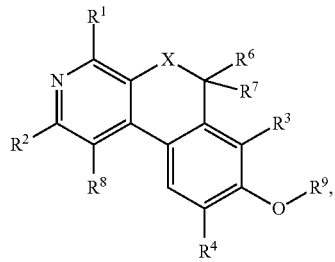

or a pharmaceutically acceptable salt thereof, wherein:

X is selected from O and $NR^5$;

$R^1$ and $R^2$ are independently selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, $C_1$-$C_3$alkylsulfonyl, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, halo$C_1$-$C_3$alkyl, $C_2$-$C_3$haloalkylamino, $C_2$-$C_3$haloalkylcarbonylamino, hydroxy, $C_1$-$C_3$alkylsulfonylamino, and $C_3$-$C_6$cycloalkylsulfonylamino;

$R^3$ and $R^4$ are independently selected from hydrogen, $C_1$-$C_3$alkoxy, $C_1$-$C_3$alkyl, cyano, —$CH_2OH$, —$CH_2OCH_3$, $CH(CH_3)OH$, $C(CH_3)_2OH$, $C_3$cycloalkyl, halo, and $C_1$-$C_3$haloalkyl;

$R^5$ is selected from hydrogen, —$CD_3$, $C_1$-$C_4$alkyl, $C_3$-$C_6$cycloalkyl, $C_1$-$C_4$hydroxyalkyl;

$R^6$ and $R^7$ are independently selected from hydrogen and $C_1$-$C_3$alkyl, or, $R^6$ and $R^7$, together with the carbon atom to which they are attached, from a carbonyl group;

$R^8$ is selected from hydrogen, $C_1$-$C_3$alkoxy, $C_1$-$C_3$alkyl, cyano, and halo;

$R^9$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxy$C_2$-$C_3$alkylamino, amino, aryl, deuterium, halo, $C_1$-$C_3$haloalkyl, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

$R^x$ and $R^y$, together with the nitrogen atom to which they are attached, form a three- to six-membered ring; and Y is selected from

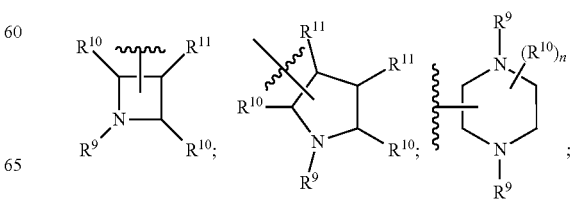

-continued

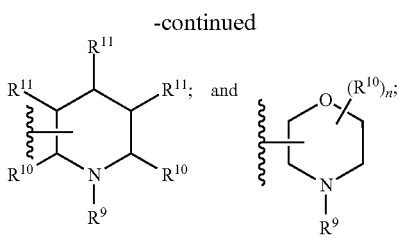

wherein $R^9$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^{10}$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and each $R^{11}$ is independently selected from hydrogen, $C_1$-$C_3$alkoxy and hydroxy.

In a first embodiment of the first aspect the present disclosure provides a compound of formula (I), or a pharmaceutically acceptable salt thereof, wherein $R^9$ is $C_5$-$C_7$alkyl optionally substituted with one, two or three groups independently selected from amino, deuterium, and halo. In a second embodiment of the first aspect X is $NR^5$ and $R^6$ and $R^7$, together with the carbon atom to which they are attached, from a carbonyl group. In a third embodiment of the first aspect $R^1$, $R^2$, $R^3$, and $R^4$ are each independently selected from hydrogen, cyano, halo, and $C_1$alkyl.

In a fourth embodiment of the first aspect the present disclosure provides a compound of formula (I), or a pharmaceutically acceptable salt thereof, wherein $R^9$ is $C_5$-$C_7$alkyl optionally substituted with one, two or three groups independently selected from amino, deuterium, and halo; X is O; and $R^6$ and $R^7$ are independently selected from hydrogen and $C_1$alkyl. in a fifth embodiment, $R^1$ is selected from hydrogen, $C_1$alkoxycarbonylamino, $C_1$alkyl, amino and halo; $R^2$ is selected from hydrogen, $C_1$-$C_3$alkoxycarbonylamino, $C_1$alkyl, $C_1$alkylcarbonylamino, $C_1$-$C_3$alkylsulfonyl, amino, halo, halo$C_1$alkyl, $C_2$haloalkylamino, $C_1$-alkylsulfonylamino, and $C_3$cycloalkylsulfonylamino; and $R^3$ and $R^4$ are selected from hydrogen, $C_1$alkyl, and halo.

In a third aspect the present disclosure provides composition comprising a pharmaceutically acceptable amount of a compound of formula (I), or a pharmaceutically acceptable salt thereof, and a pharmaceutically acceptable carrier.

In a fourth aspect the present disclosure provides a method of inhibiting adaptor associated kinase 1 (AAK1) activity, comprising contacting AAK1 with a compound of formula (I), or a pharmaceutically acceptable salt thereof.

In a fifth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fifth aspect the disease or disorder is selected from Alzheimer's disease, bipolar disorder, pain, Parkinson's disease, and schizophrenia. In a second embodiment of the fifth aspect the pain is neuropathic pain. In a third embodiment of the fifth aspect the neuropathic pain is fibromyalgia or peripheral neuropathy.

Other aspects of the present disclosure may include suitable combinations of embodiments disclosed herein.

Yet other aspects and embodiments may be found in the description provided herein.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^{10}$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylamino," as used herein, refers to —NHR wherein R is an alkoxyalkyl group.

The term "alkoxycarbonyl," as used herein, refers to an alkoxy group attached to the parent molecular moiety through a carbonyl group.

The term "alkoxycarbonylamino," as used herein, refers to an —NHR wherein R is an alkoxycarbonyl group.

The term "alkyl," as used herein, refers to a group derived from a straight or branched chain saturated hydrocarbon.

The term "alkylamino," as used herein refers to —NHR, wherein R is an alkyl group.

The term "alkylcarbonyl," as used herein, refers to an alkyl group attached to the parent molecular moiety through a carbonyl group.

The term "alkylcarbonylamino," as used herein, refers to —NHR wherein R is an alkylcarbonyl group.

The term "alkylsulfonyl," as used herein, refers to an alkyl group attached to the parent molecular moiety through a sulfonyl group.

The term "alkylsulfonylamino," as used herein, refers to an alkylsulfonyl group attached to the parent molecular moiety through an amino group.

The term "amino," as used herein, refers to —$NH_2$.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group.

Representative examples of aryl groups include, but are not limited to, indanyl, indenyl, naphthyl, phenyl, and tetrahydronaphthyl.

The term "arylalkyl," as used herein, refers to an alkyl group substituted with one, two, or three aryl groups.

The term "arylamino," as used herein, refers to —NHR wherein R is an aryl group.

The term "arylcarbonyl," as used herein, refers to an aryl group attached to the parent molecular moiety through a carbonyl group.

The term "arylcarbonylamino," as used herein refers to —NHR wherein R is an arylcarbonyl group.

The term "carbonyl," as used herein, refers to —C(O)—.

The term "cyano," as used herein, refers to —CN.

The term "cycloalkyl," as used herein, refers to a saturated monocyclic hydrocarbon ring system having zero heteroatoms. Representative examples of cycloalkyl groups include, but are not limited to, cyclopropyl, cyclopentyl, and cyclohexyl.

The term "cycloalkylamino," as used herein, refers to —NHR wherein R is a cycloalkyl group.

The term "cycloalkylcarbonyl," as used herein, refers to a cycloalkyl group attached to the parent molecular moiety through a carbonyl group.

The term "cycloalkylcarbonylamino," as used herein, refers to —NHR wherein R is a cycloalkylcarbonyl group.

The term "cycloalkyloxy," as used herein, refers to a cycloalkyl group attached to the parent molecular moiety through an oxygen atom.

The term "halo," as used herein, refers to Br, Cl, F, and/or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylamino," as used herein, refers to —NHR wherein R is a haloalkyl group.

The term "haloalkylcarbonyl," as used herein, refers to a haloalkyl group attached to the parent molecular moiety through a carbonyl group.

The term "haloalkylcarbonylamino," as used herein, refers to —NHR wherein R is a haloalkylcarbonyl group.

The term "hydroxy," as used herein, refers to —OH.

The term "hydroxyalkyl," as used herein, refers to an alkyl group substituted by one, two, or three hydroxy groups.

The term "sulfonyl," as used herein, refers to —SO$_2$.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthalenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lomoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

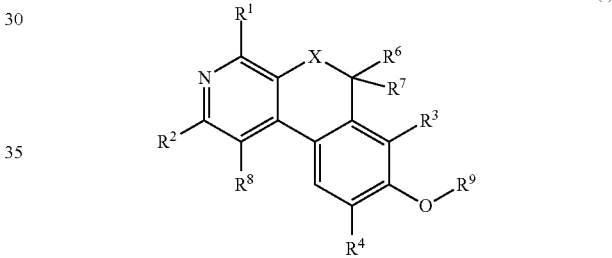

(I)

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: DMF for N,N-dimethylformamide; THF for tetrahydrofuran; DCM for dichloromethane; Me for methyl; dppf for 1,1'-bis(diphenylphosphanyl) ferrocene; MeOH for methanol; HATU for O-(7-azabenzotriazol-1-yl)-N,N,N',N'-tetramethyluronium hexafluorophosphate; EDC for 1-(3-dimethylaminopropyl)-3-ethylcarbodiimide hydrochloride; HOBT or HOBt for hydroxybenzotriazole; NMP for N-methylpyrrolidone; DMSO for dimethylsulfoxide; LAH for lithium aluminum hydride; Cbz for benzyloxycarbonyl; MeCN or ACN for acetonitrile; TFA for trifluoroacetic acid; LHMDS or LiHMDS for lithium bis(trimethylsilyl)amide; DIPEA for N,N-diisopropylethylamine; TEA or Et$_3$N for triethylamine; LDA for lithium diisopropylamide; BOC or Boc for tert-butoxycarbonyl; PMB for para-methoxybenzyl; Ac for acetyl; min for minutes; h for hours; RT or rt for room temperature or retention time (context will dictate); t$_R$ for retention time; DEA for diethylamine; DMAP for N,N-dimethylaminopyridine; EtOAc for ethyl acetate; dba for dibenzylideneacetone; SFC for super critical fluid chromatography; IPA for isopropyl alcohol, HPLC for high pressure liquid chromatography; LC/MS or LCMS for liquid chromatography mass spectrometry.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

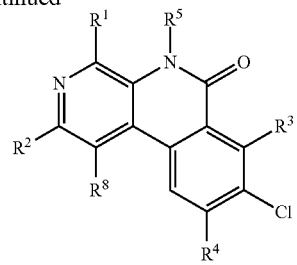

X = Cl, Br, I

Core intermediate of formula 4 is prepared by the methods outlined in Scheme 1. Pyridyl halides 1 and aryl boronic esters or acids 2 can be subjected to Suzuki cross coupling reaction under standard Suzuki conditions employing a base such as cesium or potassium carbonate and a catalyst such as Pd(PPh3)4 in a solvent such as DMF or THF and water, as described by Zhang, Lei et. al. (Journal of Medicinal Chemistry, 2011, 54, 1724-1739) to form the coupled amino ester which undergoes cyclization to form lactam 3 under the basic conditions. If R is hydrogen, the nitrogen can be alkylated with a base such as NaH and an alkylating agent such as an alkyl halide in a solvent such as DMF or DCM to afford core intermediate of the formula 4.

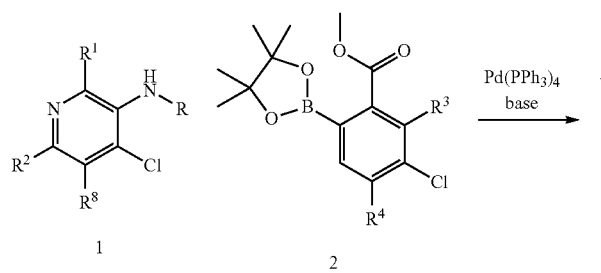

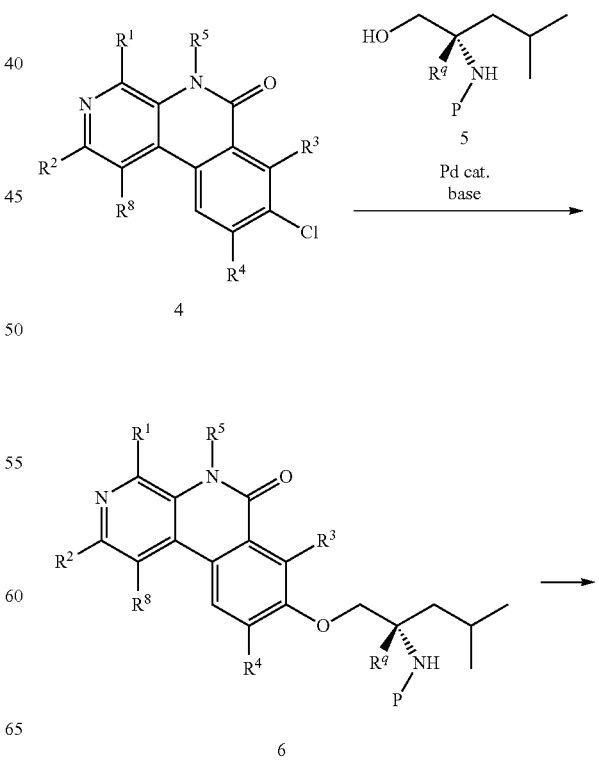

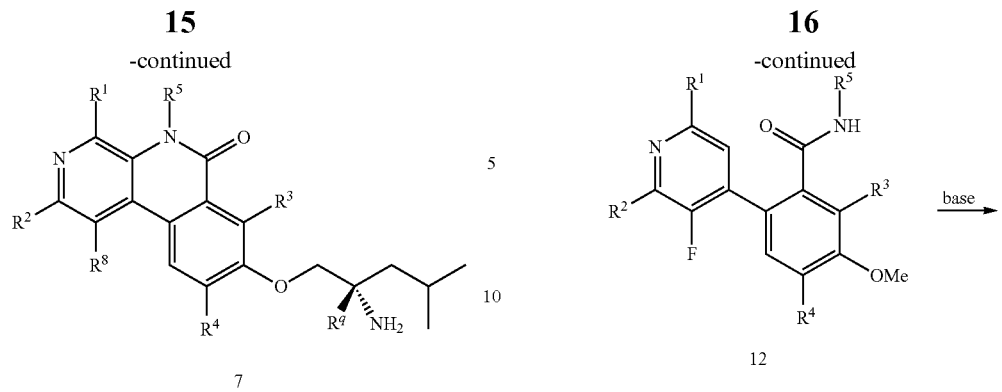

Compounds of formula 7 are prepared by the methods outlined in Scheme 2. Aryl halides 1 can be subjected to Buchwald coupling reaction with amino alcohol 5 under standard conditions employing a base such as cesium or potassium carbonate and a catalyst such as palladium II acetate or allylpalladium chloride dimer and a ligand such as di-tert-butyl(2',4',6'-triisopropyl-[1,1'-biphenyl]-2-yl)phosphine (t-butyl Xphos) in a solvent such as toluene or THF and water to afford ether 6. The constrained lactam ether analog represented by 6 can be subjected to deprotection of the side chain amino group using appropriate conditions as described in Protective Groups in Organic Synthesis (Greene, Wuts; 3rd ed., 1999, John Wiley & Sons, Inc.) to yield compounds represented by formula 7.

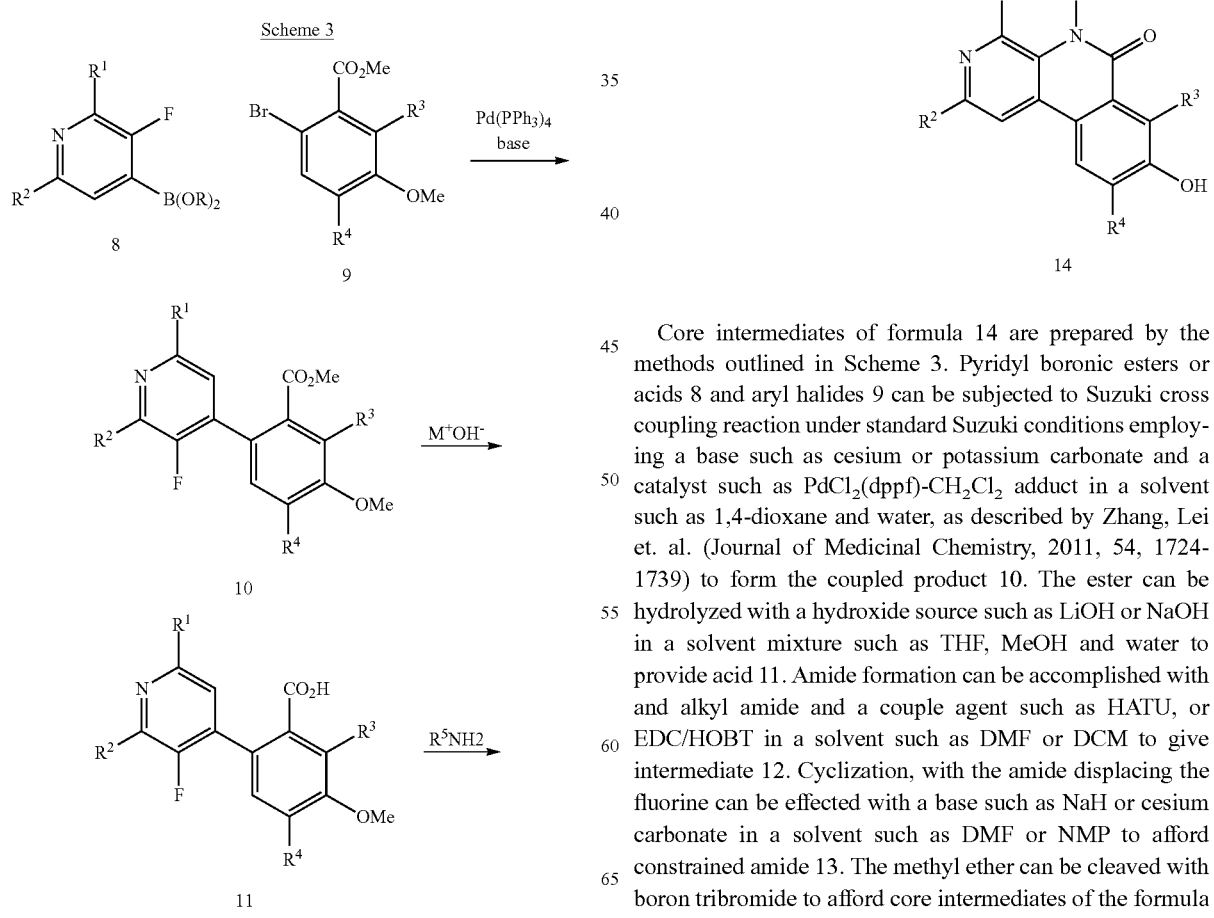

Core intermediates of formula 14 are prepared by the methods outlined in Scheme 3. Pyridyl boronic esters or acids 8 and aryl halides 9 can be subjected to Suzuki cross coupling reaction under standard Suzuki conditions employing a base such as cesium or potassium carbonate and a catalyst such as PdCl$_2$(dppf)-CH$_2$Cl$_2$ adduct in a solvent such as 1,4-dioxane and water, as described by Zhang, Lei et. al. (Journal of Medicinal Chemistry, 2011, 54, 1724-1739) to form the coupled product 10. The ester can be hydrolyzed with a hydroxide source such as LiOH or NaOH in a solvent mixture such as THF, MeOH and water to provide acid 11. Amide formation can be accomplished with and alkyl amide and a couple agent such as HATU, or EDC/HOBT in a solvent such as DMF or DCM to give intermediate 12. Cyclization, with the amide displacing the fluorine can be effected with a base such as NaH or cesium carbonate in a solvent such as DMF or NMP to afford constrained amide 13. The methyl ether can be cleaved with boron tribromide to afford core intermediates of the formula 14.

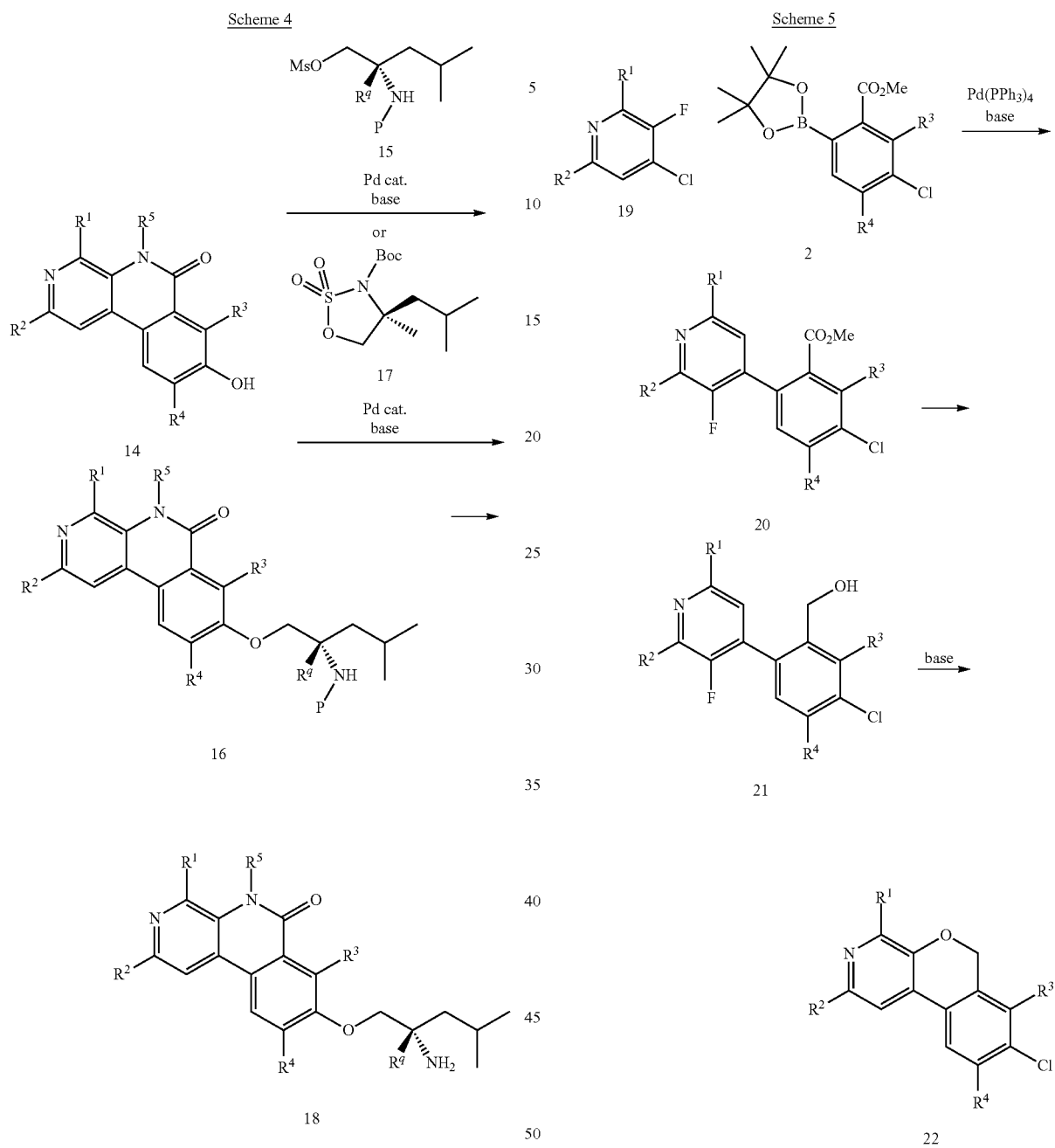

Compounds of formula 18 are prepared by the methods outlined in Scheme 4. Phenol 14 can be coupled to the mesylate of an amino alcohol (15) under basic conditions employing a base such as cesium or potassium carbonate in a solvent such as DMSO to afford ether 16. Alternatively, phenol 14 can be coupled to 1,2,3-oxathiazolidine 17 under basic conditions using a base such as NaH or potassium carbonate in a solvent such as DMF to provide ether 16. The constrained lactam ether analog represented by 16 can be subjected to deprotection of the side chain amino group using appropriate conditions as described in Protective Groups in Organic Synthesis (Greene, Wuts; 3rd ed., 1999, John Wiley & Sons, Inc.) to yield compounds represented by formula 18.

Core intermediates of formula 22 are prepared by the methods outlined in Scheme 5. Pyridyl halides 19 and aryl boronic esters or acids 2 can be subjected to Suzuki cross coupling reaction under standard Suzuki conditions employing a base such as cesium or potassium carbonate and a catalyst such as Pd(PPh$_3$)$_4$ in a solvent such as DMF or THF and water, as described by Zhang, Lei et. al. (Journal of Medicinal Chemistry, 2011, 54, 1724-1739) to provide biaryl intermediate 20. The ester can be reduced to the alcohol with a hydride source such as LAH in solvents such as THF or diethyl ether to provide intermediate 21. Cyclization with the alcohol displacing the fluorine can be effected with a base such as NaH or cesium carbonate in a solvent such as DMF or NMP to afford constrained pyran intermediates represented by formula 22.

Scheme 6

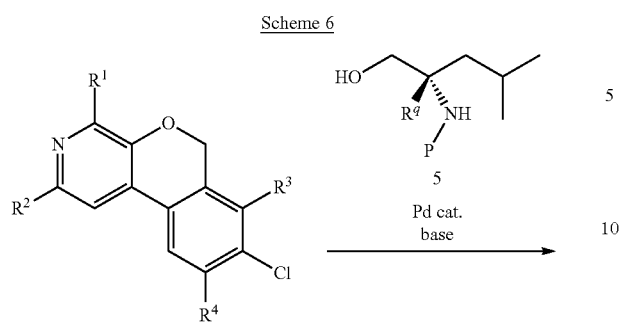

Compounds of formula 24 are prepared by the methods outlined in Scheme 6. Aryl halides 22 can be subjected to Buchwald coupling reaction with amino alcohol 5 under standard conditions employing a base such as cesium or potassium carbonate and a catalyst such as palladium II acetate or allylpalladium chloride dimer and a ligand such as di-tert-butyl(2',4',6'-triisopropyl-[1,1'-biphenyl]-2-yl)phosphine (t-butyl Xphos) in a solvent such as toluene or THF and water to afford ether 23. The constrained lactam ether analog represented by 23 can be subjected to deprotection of the side chain amino group using appropriate conditions as described in Protective Groups in Organic Synthesis (Greene, Wuts; 3rd ed., 1999, John Wiley & Sons, Inc.) to yield compounds represented by formula 24.

Scheme 7

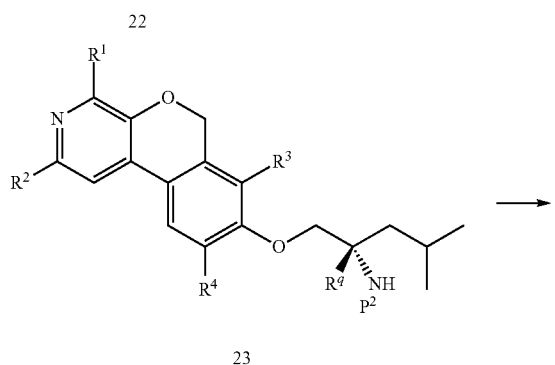

Core intermediates of formula 28 are prepared by the methods outlined in Scheme 7. Ester 20 can be reduced to the aldehyde with a reagent such as Dess-Martin Periodinane in a solvent such as DCM to provide intermediate 25. Treatment of the aldehyde with a Grignard reagent in solvents such as THF or diethyl ether provides alcohol 26. Alternatively, ester 20 can be treated directly with the Grignard reagent to afford tertiary alcohol 27. Cyclization with the alcohol (26 or 27) displacing the fluorine can be effected with a base such as NaH or cesium carbonate in a solvent such as DMF or NMP to afford constrained pyran intermediates represented by formula 28.

mediate alcohol 29. Cyclization with the alcohol displacing the fluorine can be effected with a base such as NaH or cesium carbonate in a solvent such as DMF or NMP to afford constrained pyran intermediate 30. The methyl ether can be cleaved with boron tribromide to afford core intermediates of the formula 31.

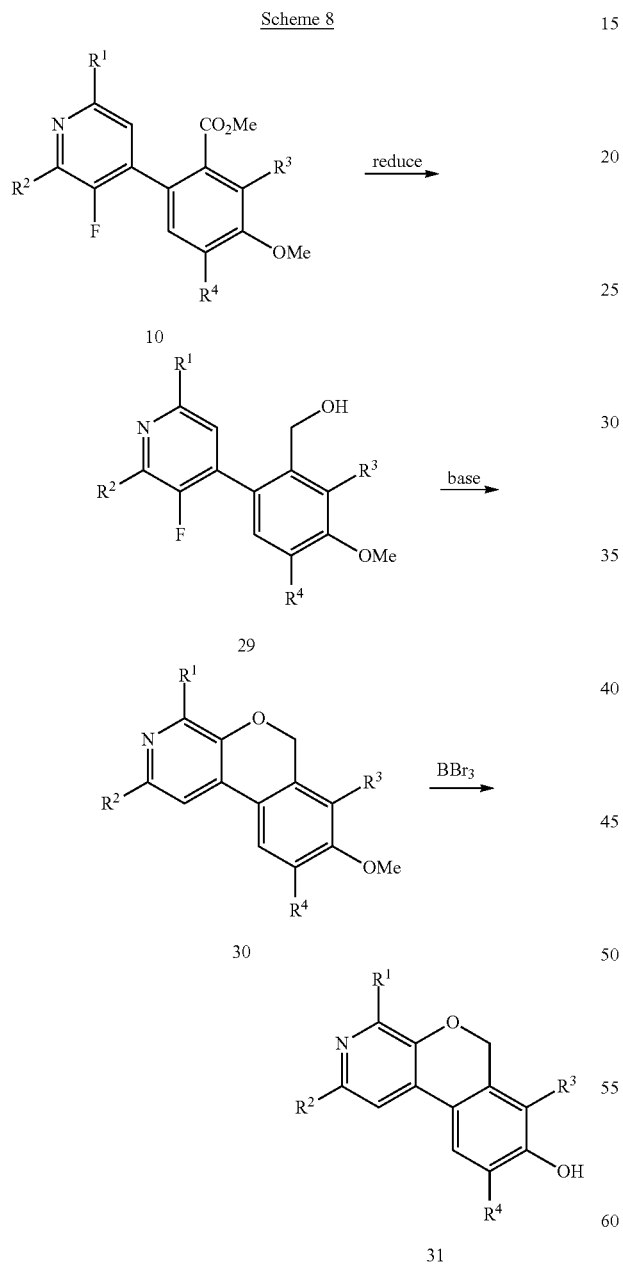

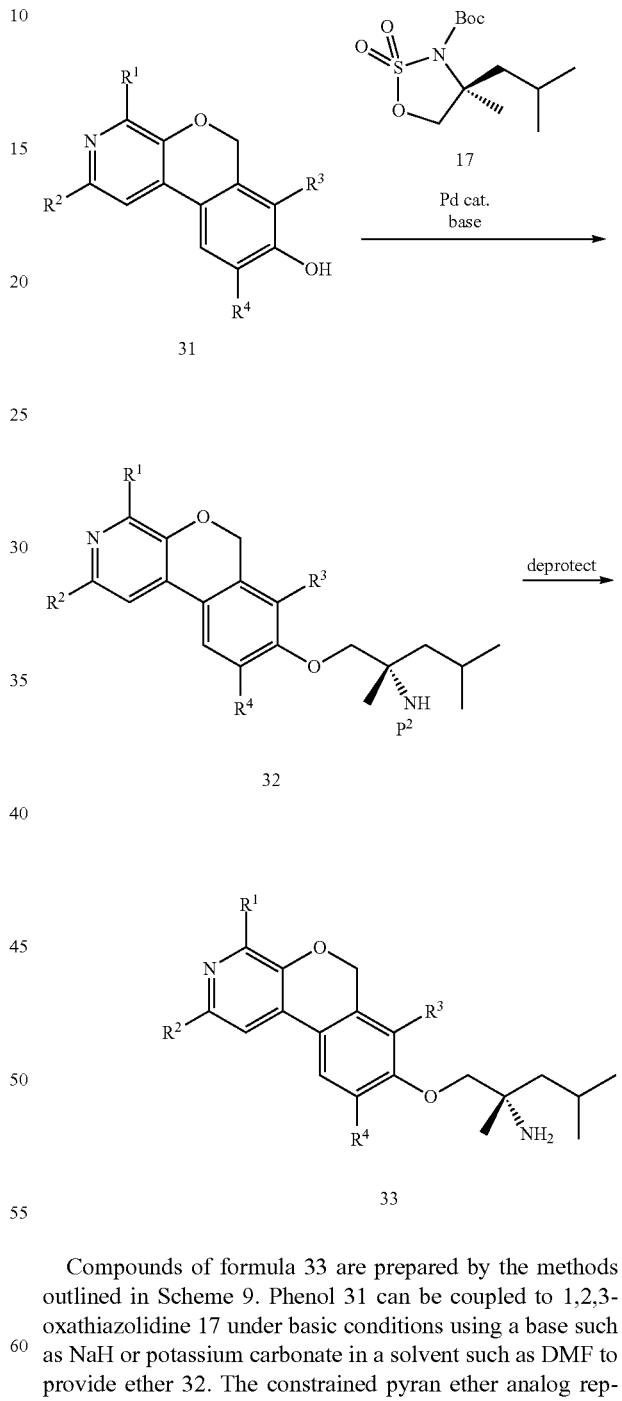

Core intermediates of formula 31 are prepared by the methods outlined in Scheme 8. The biaryl ester 10 can be reduced to the alcohol with a hydride source such as LAH in solvents such as THF or diethyl ether to provide inter- Compounds of formula 33 are prepared by the methods outlined in Scheme 9. Phenol 31 can be coupled to 1,2,3-oxathiazolidine 17 under basic conditions using a base such as NaH or potassium carbonate in a solvent such as DMF to provide ether 32. The constrained pyran ether analog represented by 32 can be subjected to deprotection of the side chain amino group using appropriate conditions as described in Protective Groups in Organic Synthesis (Greene, Wuts; 3rd ed., 1999, John Wiley & Sons, Inc.) to yield compounds represented by formula 33.

Scheme 10

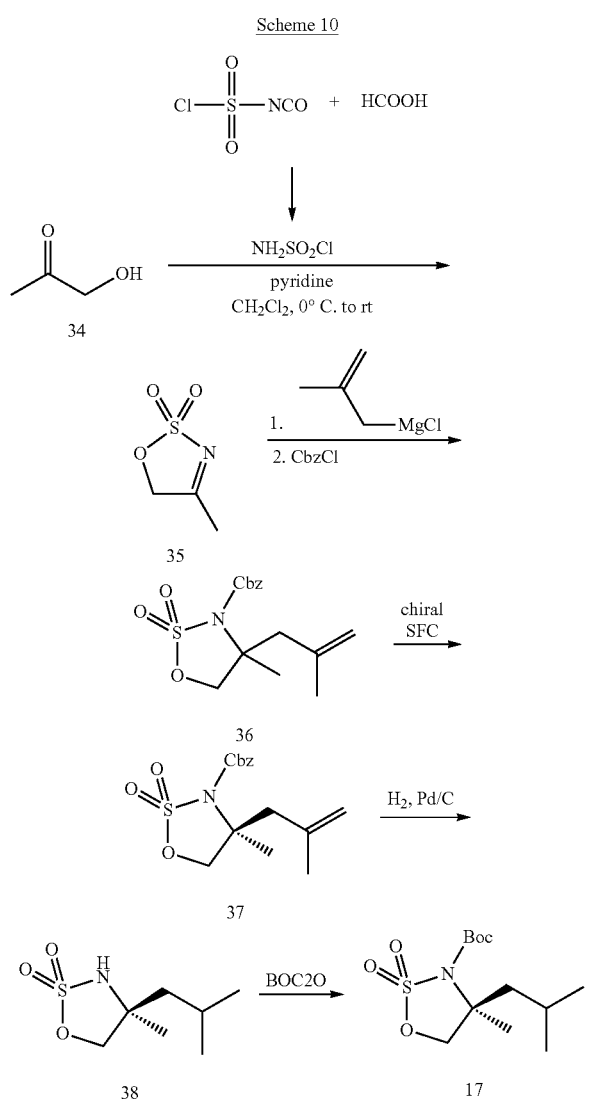

Intermediate 17 is prepared by the methods outlined in Scheme 10. Hydroxy acetone 34 was treated with sulfamoyl chloride (formed from the reaction of chlorosulfonyl isocyanate with formic acid) to give 4-methyl-5H-1,2,3-oxathiazole 2,2-dioxide 35. Alkylation of 35 with (2-methylallyl) magnesium chloride followed by Cbz protection gave intermediate 36. Racemic 36 was separated into the corresponding enantiomers via chiral SFC. The enantiomers were then carried forward separately. The (S)-enantiomer 37 was treated with $H_2$ and Pd/C to reduce the double bond and deprotect to give intermediate 38. Reprotection with $BOC_2O$ provided intermediate 17.

DESCRIPTION OF THE SPECIFIC EMBODIMENTS

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu or Waters Aquity LC coupled to a Waters Micromass ZQ using at least one of the following methods.

LC/MS Method A:
Column: Ascentis Express C18 (5×2.1 mm), 2.7 µm; Mobile Phase A: 2% MeCN—98% $H_2O$—10 mM $NH_4COOH$; Mobile Phase B: 98% ACN—2% $H_2O$—10 mM $NH_4COOH$; Temperature: 40° C. Detection: UV at 220 nm:
Gradient: 0% B, 0-100% B over 1.8 min, then a 0.8-min hold at 100% B; Flow: 1.2 mL/min.
A1: Gradient: 0% B, 0-100% B over 1.8 min, then a 0.8-min hold at 100% B; Flow: 1.2 mL/min.
A2: Gradient: 0% B, 0-100% B over 1.5 min, then a 1.7-min hold at 100% B; Flow: 1.0 mL/min.
A3: Gradient: 0% B, 0-100% B over 1.7 min, then a 1.3-min hold at 100% B; Flow: 1.0 mL/min.
LC/MS Method B:
Column: Waters Acquity UPLC BEH C18 (2.1×50 mm), 1.7 µm; Mobile Phase A: 5 mM $NH_4OAc$:ACN (95:5); Mobile Phase B: 5 mM $NH_4OAc$: ACN (5:95); Temperature: 50° C.; Gradient: 5-95% B over 1.7 min, then a 0.5-min hold at 95% B; Flow: 1.0 mL/min; Detection: UV at 220 nm.
LC/MS Method C:
Column: ZORBAX SB C18 (4.6×50 mm), 3.5 µm; Mobile Phase A: 10% MeOH-90% $H_2O$-0.1% TFA; Mobile Phase B: 90% MeOH-10% $H_2O$-0.1% TFA; Temperature: 35° C.; Detection: UV at 220 nm;
C1: Gradient: 10-100% B over 2.0 min, then a 1.0-min hold at 100% B; Flow: 5.0 mL/min.
C2: Gradient: 10-100% B over 1.8 min, then a 0.5-min hold at 100% B; Flow: 4.0 mL/min.
C3: Gradient: 10-100% B over 2.7 min, then a 1.3-min hold at 100% B; Flow: 1.0 mL/min.
LC/MS Method D:
Column—ACE Excel 2 C18 (50×3.0 mm) 2 µm; Mobile Phase A: 2% MeCN—98% $H_2O$—10 mM $NH_4COOH$; Mobile Phase B: 98% ACN—2% $H_2O$—10 mM $NH_4COOH$; Flow: 1.2 mL/min); Gradient: 5-100% B over 1.8 min, then a 0.8-min hold at 100% B; Temperature: 40° C.; Detection: UV at 220 nm.
LC/MS Method E:
Column: X-Bridge BEH C18 (50×2.1 mm), 2.5 µm; Mobile Phase A: ACN+$H_2O$ (2+98)+0.1% TFA; Mobile Phase B: ACN+$H_2O$ (98+2)+0.05% TFA; Flow: 1.0 mL/min.; λ=220 nm; Gradient: 2-98% B over 1.0 min, then a 1.6-min hold at 98% B.
LC/MS Method F:
Column: X-Bridge BEH C18 (50×2.1 mm), 2.5 µm; Mobile Phase A: 1% HCOOH in water; Mobile Phase B: ACN; Flow: 1.0 mL/min.; λ=220 nm; Gradient: 5-100% B over 2.5 min.
LC/MS Method G:
Column: ZORBAX SB AQ (4.6×50 mm), 3.5 micron; Mobile Phase A: 0.1% HCOOH in water; Mobile Phase B: ACN; Gradient: 0-100% B over 2.7 min, then hold at 100% B for 1.3 min.; Flow: 1.0 mL/min; Detection: UV at 220 nm.
LC/MS Method H:
Column: Phenomenex LUNA C18, 30×2, 3 µm; Solvent A=5% MeOH: 95% Water: 10 mM Ammonium Acetate; Solvent B=95% MeOH: 5% Water: 10 mM Ammonium Acetate; Flow rate: 0.8 mL/min; Starting B=0%; Final B=100%; Gradient time=4 min; Run time: 5 min.
LC/MS Method I:
Column: Waters BEH C18, 2.1×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 min, then a 0.5-min hold at 100% B; Flow: 0.5 mL/min; Detection: UV at 220 nm.

LC/MS Method J:
Column: Ascentis Express C18 (5×2.1 mm), 2.7 μm; Mobile Phase A: 95% Water: 5% Acetonitrile; 0.1% TFA; Mobile Phase B: 5% Water: 95% Acetonitrile; 0.1% TFA; Gradient: 0% B, 0-100% B over 3.0 min; Flow: 1.1 mL/min; Temperature: 50° C.; Detection: UV at 220 nm.
LC/MS Method K:
Column: Phenomenex LUNA C18, 30×2, 3 μm; Solvent A=5% MeOH: 95% Water: 10 mM Ammonium Acetate; Solvent B=95% MeOH: 5% Water: 10 mM Ammonium Acetate; Flow rate: 1 ml/min; Starting B=0%; Final B=100%; Gradient time=2 min; Run time: 3 min.
LC/MS Method L:
Column: Ascentis Express C18 (50×2.1 mm), 2.7 μm; Mobile Phase A: 90% 10 mM Ammonium Formate in Water: 10% ACN; Mobile Phase B: 10% 10 mM Ammonium Formate in Water: 90% ACN; Gradient: 0-100% B over 1.6 min, then hold at 100% B for 1.6 min; Flow: 1.0 mL/min.
LC/MS Method M:
Column: Ascentis Express C8 (50×2.1 mm), 2.7 μm; Mobile Phase A: 5:95 Acetonitrile:water with 10 mM NH$_4$OAc; Mobile Phase B: 95:5 Acetonitrile:water with 10 mM NH$_4$OAc; Temperature: 50° C.; Gradient: 0-100% B over 3 min; Flow: 1.1 mL/min.
LC/MS Method N:
Column: Waters Acquity SDS; Solvent A=100% H$_2$O w/ 0.05% TFA; Solvent B=100% ACN w/ 0.05% TFA; Flow rate: 0.8 mL/min; Starting B=2%; Final B=98%; Gradient time=1.6 min; Run time: 1.8 min.
HPLC Purity Methods:
HPLC Method A:
Column: SUNFIRE C18 4.6×150 mm, 3.5 micron SC/753; Solvent A=0.05% TFA IN WATER pH 2.5 adjusted using ammonia:Acetonitrile (95:5); Solvent B=Acetonitrile: 0.05% TFA IN WATER pH 2.5 adjusted using ammonia (95:5); Flow rate: 1.0 mL/min; Detection: UV at 220 and 254 nm.
A1: Gradient: 0-50% B over 15 min, then 50-100% B over 3, then hold at 100% B for 5 min; Flow: 1.0 mL/min.
A2: Gradient: 10-100% B over 12 min, then hold at 100% B over 3, then hold at 100% B for 5 min; Flow: 1.0 mL/min.
HPLC Method B:
Column: XBridge (150×4.6 mm) 3.5 micron SC/1072; Solvent A=0.05% TFA in Water pH2.5: Acetonitrile (95:5); Solvent B=Acetonitrile: 0.05% TFA in Water pH2.5 (95:5); Flow rate: 1.0 mL/min; Detection: UV at 220 and 254 nm.
B1: Gradient: 0-50% B over 15 min, then 50-100% B over 3, then hold at 100% B for 5 min; Flow: 1.0 mL/min;
B2: Gradient: 10-50% B over 15 min, then 50-100% B over 3 min; Flow: 1.0 mL/min;
B3: Gradient: 10-100% B over 12 min, then hold at 100% B for 3 min; Flow: 1.0 mL/min;
HPLC Method C:
Column: Ascentis Express C18 (50×2.1 mm), 2.7 μm; Mobile Phase A: 5:95 Acetonitrile:water with 10 mM NH$_4$OAc; Mobile Phase B: 95:5 Acetonitrile:water with 10 mM NH$_4$OAc; Temperature: 50° C.
C1: Gradient: 0-100% B over 3 min; Flow: 1.1 mL/min.
C2: Gradient: 0-100% B over 1.7 min, then hold at 100% B for 1.3 min; Flow: 1.0 mL/min.
HPLC Method D:
Column: Ascentis Express C18 (50×2.1 mm), 2.7 μm; Mobile Phase A: 5:95 Acetonitrile:water with 0.1% TFA; Mobile Phase B: 95:5 Acetonitrile:water with 0.1% TFA; Temperature: 50° C.; Gradient: 0-100% B over 3 min; Flow: 1.1 mL/min.

HPLC Method E:
Column: Eclipse XDB C18 (150×4.6 mm) 3.5 micron; Mobile Phase A: 20 mM NH$_4$OAc in water; Mobile Phase B: acetonitrile; Gradient: 10-100% B over 12 min, then hold at 100% B for 8 min; Flow: 1.0 mL/min.

Example 1

(S)-8-((2-amino-4-methylpentyl)oxy)benzo[c][1,7]naphthyridin-6(5H)-one

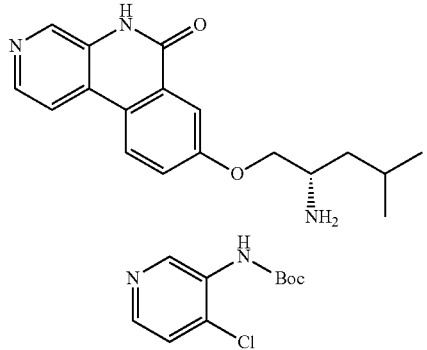

Part A: tert-butyl (4-chloropyridin-3-yl)carbamate

To a solution of 4-chloropyridin-3-amine (5.5 g, 42.8 mmol) in tetrahydrofuran (110 mL) at −10° C. was added LHMDS (86 mL, 86 mmol) dropwise. After complete addition the solution was stirred at −10° C. for 1 h. BOC$_2$O (9.93 mL, 42.8 mmol) was then added slowly. The reaction mixture was then warmed to room temperature and stirred for 1 h. The reaction was quenched by addition of saturated aqueous ammonium chloride solution (150 mL). The solution was extracted with ethyl acetate (3×150 mL) and washed with brine (150 mL). The combined organic extracts were dried over sodium sulfate and concentrated under reduced pressure. The residue was purified by silica gel chromatography (petroleum ether:ethyl acetate mobile phase) to yield tert-butyl (4-chloropyridin-3-yl)carbamate (4.5 g, 19.68 mmol, 46% yield). LC/MS (ESI) m/e 229.1 [(M+H)$^+$, calcd for C$_{10}$H$_4$ClN$_2$O$_2$, 229.1]; LC/MS retention time (Method B): t$_R$=1.09 min.

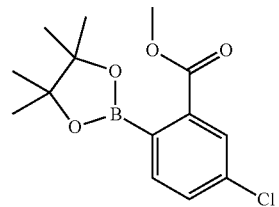 [SMILES: COC(=O)c1cc(Cl)ccc1B1OC(C)(C)C(C)(C)O1]

Part B. Methyl 5-chloro-2-(4,4,5,5-tetramethyl-1,3,2-dioxaborolan-2-yl)benzoate

To a stirred solution of methyl 2-bromo-5-chlorobenzoate (10 g, 40.1 mmol) in 1,4-dioxane (50 mL) cooled to −10° C. was added bis(pinacolato)diboron (12.21 g, 48.1 mmol) and PdCl$_2$(dppf) (1.466 g, 2.004 mmol) followed by potassium acetate (11.80 g, 120 mmol). The mixture was then heated to 90° C. overnight. The reaction mixture was cooled to room temperature, diluted with water (300 mL) and extracted with ethyl acetate (500 mL). The organic layer was separated and dried over sodium sulphate, filtered, and concentrated under reduced pressure. The residue was purified by silica gel chromatography (10% ethyl acetate in petroleum ether) to afford methyl 5-chloro-2-(4,4,5,5-tetramethyl-1,3,2-dioxaborolan-2-yl)benzoate (11.8 g, 39.8 mmol, 99% yield). LC/MS (ESI) m/e 297.2 [(M+H)$^+$, calcd for $C_{14}H_{19}BClO_4$, 297.1]; LC/MS retention time (Method A1): $t_R$=2.32 min; $^1$H NMR (400 MHz, CHLOROFORM-d) δ 7.92 (d, J=2.0 Hz, 1H), 7.49 (dd, J=8.0, 2.0 Hz, 1H), 7.45-7.41 (m, 1H), 3.92 (s, 3H), 1.41 (s, 12H).

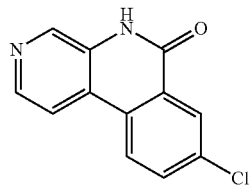 [SMILES: O=c1[nH]c2cnccc2c2ccc(Cl)cc12]

Part C: 8-chlorobenzo[c][1,7]naphthyridin-6(5H)-one

To a mixture of tert-butyl (4-chloropyridin-3-yl)carbamate (2.2 g, 6.69 mmol), methyl 5-chloro-2-(4,4,5,5-tetramethyl-1,3,2-dioxaborolan-2-yl)benzoate (2.58 g, 8.70 mmol) in DMF (40 mL) and water (10 mL) was added $K_2CO_3$ (1.387 g, 10.04 mmol) and tetrakis(triphenylphosphine)palladium(0) (0.387 g, 0.335 mmol). Nitrogen gas was bubbled through the stirred suspension for 10 min. The reaction mixture was stirred in microwave at 130° C. for 90 min. The reaction mixture was cooled to room temperature and diluted with ethyl acetate (150 mL). The organic layer was washed with water (2×50 mL) and brine (1×50 mL). The organic layer was dried over Na2SO4, filtered, and concentrated under reduced pressure to afford 8-chlorobenzo[c][1,7]naphthyridin-6(5H)-one (400 mg, 1.39 mmol, 21% yield) as a pale brown solid. LC/MS (ESI) m/e 231.0 [(M+H)$^+$, calcd for $C_{12}H_8ClN_2O$, 231.0]; LC/MS retention time (Method C1): $t_R$=1.23 min; $^1$H NMR (400 MHz, DMSO-d$_6$) δ 12.07 (s, 1H), 8.70 (s, 1H), 8.78 (d, J=8.8 Hz, 1H), 8.44 (d, J=5.2 Hz, 1H), 8.33 (d, J=5.2 Hz, 1H), 8.31 (d, J=2.4 Hz, 1H), 8.01 (dd, J=8.4, 2.4 Hz, 1H).

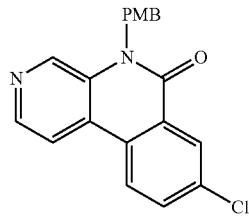

Part D: 8-chloro-5-(4-methoxybenzyl)benzo[c][1,7]naphthyridin-6(5H)-one

A solution of 8-chlorobenzo[c][1,7]naphthyridin-6(5H)-one (300 mg, 1.301 mmol) in DMF (12 mL) was cooled to 0° C. NaH (104 mg, 2.60 mmol) was added. The reaction mixture was stirred at 0° C. for 30 min. 4-Methoxybenzyl chloride (0.266 mL, 1.951 mmol) was added and the reaction mixture was stirred at 0° C. for 30 min then warmed to room temperature and allowed to stir overnight. Ice cold water (50 mL) was added to the reaction mixture. The solution was extracted with ethyl acetate (3×50 mL). The combined organic layers were washed with brine (1×50 mL), dried over Na$_2$SO$_4$, filtered and concentrated under reduced pressure. The residue was purified by silica gel chromatography (petroleum ether: ethyl acetate) to obtain 8-chloro-5-(4-methoxybenzyl)benzo[c][1,7]naphthyridin-6(5H)-one (20 mg, 0.055 mmol, 4% yield) as an off-white solid. LC/MS (ESI) m/e 351.0 [(M+H)$^+$, calcd for $C_{20}H_{16}ClN_2O_2$, 351.1]; LC/MS retention time (Method M): $t_R$=1.94 min; $^1$H NMR (400 MHz, DMSO-d$_6$) δ 8.82 (s, 1H), 8.73 (d, J=8.8 Hz, 1H), 8.49 (d, J=5.6 Hz, 1H), 8.44 (d, J=3.6 Hz, 1H), 8.43 (s, 1H), 8.05 (dd, J=8.4, 2.4 Hz, 1H), 7.25 (d, J=8.8 Hz, 2H), 6.88 (d, J=8.8 Hz, 2H), 5.65 (s, 2H), 3.71 (s, 3H).

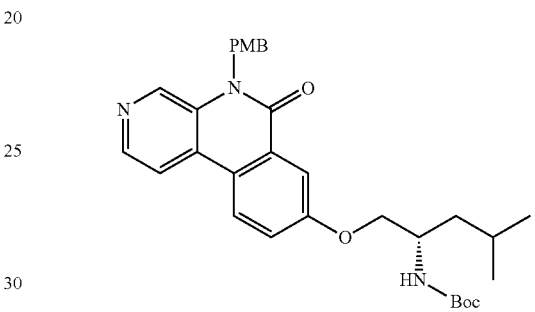

Part E: (S)-tert-butyl (4-methyl-1-((6-oxo-5,6-dihydrobenzo[c][1,7]naphthyridin-8-yl)oxy)pentan-2-yl)carbamate To a 15 mL pressure tube was added 8-chloro-5-(4-methoxybenzyl)benzo[c][1,7]naphthyridin-6(5H)-one (70 mg, 0.200 mmol) and (S)-tert-butyl (1-hydroxy-4-methylpentan-2-yl)carbamate (130 mg, 0.599 mmol) in toluene (2 mL) to give a brown solution. Di-tert-butyl(2',4',6'-triisopropyl-[1,1'-biphenyl]-2-yl)phosphine (50.8 mg, 0.120 mmol) and Cs$_2$CO$_3$ (98 mg, 0.299 mmol) were added. The reaction solution was purged with nitrogen for 10 min, then palladium(II) acetate (13.44 mg, 0.060 mmol) was added. The reaction solution was again purged with nitrogen for 10 min then heated at 85° C. overnight. The reaction mixture was cooled to room temperature and filtered through diatomaceous earth (Celite®). The filtrate was diluted with ethyl acetate (25 mL) and washed with water (15 mL) and brine (10 mL). The organic extract layer was dried over sodium sulfate, filtered, and concentrated under reduced pressure. The residue was purified by silica gel chromatography (petroleum ether: ethyl acetate) to afford (S)-tert-butyl (4-methyl-1-((6-oxo-5,6-dihydrobenzo[c][1,7]naphthyridin-8-yl)oxy)pentan-2-yl)carbamate (50 mg, 0.054 mmol, 27% yield) as a pale brown solid. LC/MS (ESI) m/e 532.5 [(M+H)$^+$, calcd for $C_{31}H_{38}N_3O_5$, 532.3]; LC/MS retention time (Method B): $t_R$=1.21 min; $^1$H NMR (400 MHz, MeOD) δ 8.73 (d, J=8.8 Hz, 1H), 8.53 (d, J=5.6 Hz, 1H), 8.38 (d, J=3.6 Hz, 1H), 8.30 (d, J=8.8 Hz, 1H), 8.04 (d, J=3.6 Hz, 1H), 7.58 (dd, J=8.8, 3.6 Hz, 1H), 7.23 (d, J=8.8 Hz, 2H), 6.88 (d, J=8.8 Hz, 2H), 5.72 (s, 2H), 4.03-4018 (m, 2H), 3.82-3.70 (m, 1H), 3.76 (s, 3H), 1.71-1.79 (m, 1H), 1.50-1.64 (m, 1H), 1.46 (s, 9H), 1.22-1.15 (m, 1H), 1.00 (t, J=7.6 Hz, 6H), one exchangeable proton not observed.

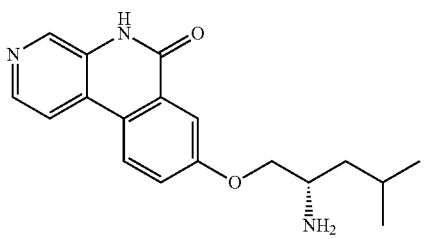 [SMILES: CC(C)C[C@H](N)COc1ccc2c(c1)c(=O)[nH]c1cnccc12]

Part F: (S)-8-((2-amino-4-methylpentyl)oxy)benzo[c][1,7]naphthyridin-6(5H)-one

To (S)-tert-butyl (1-((5-(4-methoxybenzyl)-6-oxo-5,6-dihydrobenzo[c][1,7]naphthyridin-8-yl)oxy)-4-methylpentan-2-yl)carbamate (430 mg, 0.202 mmol) was added TFA (8 mL, 104 mmol) and methanesulfonic acid (0.013 mL, 0.202 mmol) dropwise. The reaction mixture was heated to 75° C. for 16 h. The reaction mixture was then cooled to room temperature and the solvents were removed under reduced pressure. The residue was dissolved in water (10 mL) and acidified with 0.75N HCl. The aqueous layer was washed with ethyl acetate (3×10 mL) then basified with solid $Na_2CO_3$ and the solution saturated with solid sodium chloride. The aqueous layer was extracted with 5% methanol in DCM (5×15 mL). The combined organic layers were dried over sodium sulphate, filtered, and concentrated under reduced pressure. The residue was purified by prep HPLC (TFA in water and acetonitrile). Obtained (S)-8-((2-amino-4-methylpentyl)oxy)benzo[c][1,7]naphthyridin-6(5H)-one, TFA salt (45 mg, 0.137 mmol, 68% yield) as a pale yellow solid. LC/MS (ESI) m/e 312.2 [(M+H)$^+$, calcd for $C_{18}H_{22}N_3O_2$, 312.2]; LC/MS retention time (Method A): $t_R$=0.99 min; $^1$H NMR (400 MHz, CD$_3$OD) δ 8.70 (s, 1H), 8.70 (s, 1H), 8.63 (d, J=9.0 Hz, 1H), 8.43-8.51 (m, 2H), 8.05 (d, J=2.8 Hz, 1H), 7.70 (dd, J=8.9, 2.9 Hz, 1H), 4.49 (dd, J=10.5, 3.3 Hz, 1H), 4.31 (dd, J=10.5, 6.3 Hz, 1H), 3.80 (dd, J=6.5, 3.0 Hz, 1H), 1.67-1.88 (m, 3H), 1.07 (dd, J=6.5, 4.8 Hz, 6H), two exchangeable protons not observed; HPLC purity (Method A1): 99% $t_R$=7.15 min; HPLC purity (Method B1): 99% $t_R$=7.35 min.

Example 2

(S)-8-((2-amino-4-methylpentyl)oxy)-5-methylbenzo[c][1,7]naphthyridin-6(5H)-one

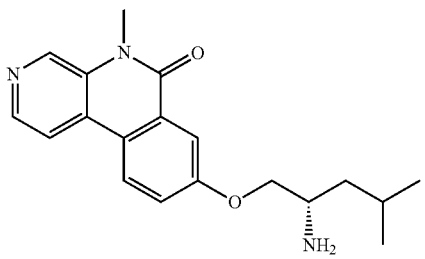

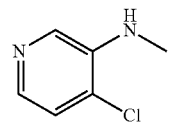

Part A: 4-chloro-N-methylpyridin-3-amine

To DMF (25 mL) cooled to 0° C. was carefully added NaH (0.933 g, 23.34 mmol). To this was added a solution of 4-chloropyridin-3-amine (2.5 g, 19.45 mmol) in DMF (25 mL) dropwise over a period of 5 min. The reaction mixture was stirred at 0° C. for 30 min. Methyl iodide (1.22 mL, 19.45 mmol) was added and the reaction mixture was stirred at 0° C. for 30 min then at room temperature overnight. The reaction mixture was quenched with ice cold water (100 mL). The aqueous layer was extracted with ethyl acetate (3×75 mL). The combined the organic layers were washed with water (1×100 mL) then brine (1×100 mL). The organic layer was dried over $Na_2SO_4$, filtered, and concentrated under reduced pressure. The residue was purified by silica gel chromatography (petroleum ether:ethyl acetate mobile phase) to yield 4-chloro-N-methylpyridin-3-amine (1.1 g, 7.71 mmol, 40% yield). $^1$H NMR (400 MHz, CHLOROFORM-d) δ 8.02 (s, 1H), 7.89 (d, J=4.8 Hz, 1H), 7.17 (d, J=5.2 Hz, 1H), 4.25 (s, 1H), 2.97 (d, J=5.2 Hz, 3H).

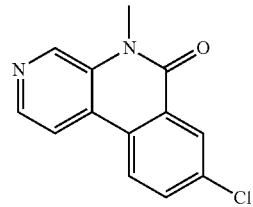 [SMILES: Cn1c(=O)c2cc(Cl)ccc2c2ccncc21]

Part B: 8-chloro-5-methylbenzo[c][1,7]naphthyridin-6(5H)-one

To a mixture of 4-chloro-N-methylpyridin-3-amine (0.50 g, 3.51 mmol), methyl 5-chloro-2-(4,4,5,5-tetramethyl-1,3,2-dioxaborolan-2-yl)benzoate (1.35 g, 4.56 mmol) (Example 1, Part B) in tetrahydrofuran (10 mL) and water (2.5 mL), was added $Cs_2CO_3$ (2.29 g, 7.01 mmol) and tetrakis(triphenylphosphine)palladium(0) (0.203 g, 0.175 mmol) were added. Nitrogen gas was bubbled through the stirred suspension for 10 min. The reaction mixture was heated at 80° C. overnight in a sealed pressure tube. The reaction mixture was cooled to room temperature and diluted with water (50 mL). The aqueous layer was extracted with ethyl acetate (3×25 mL). The combined the organic layers were washed with brine (1×50 mL), dried over Na2SO4, filtered, and concentrated under reduced pressure. The residue was purified by silica gel chromatography (petroleum ether:ethyl acetate) to yield 8-chloro-5-methylbenzo[c][1,7]naphthyridin-6(5H)-one (150 mg, 0.460 mmol, 13% yield) as a pale brown solid. LC/MS (ESI) m/e 245.0 [(M+H)$^+$, calcd for $C_{13}H_{10}ClN_2O$, 245.1]; LC/MS retention time (Method M): $t_R$=1.94 min; $^1$H NMR (400 MHz, DMSO-d$_6$) δ 8.97 (s, 1H), 8.70 (d, J=8.4 Hz, 1H), 8.55 (d, J=5.2 Hz, 1H), 8.41 (d, J=5.2 Hz, 1H), 8.34 (d, J=2.4 Hz, 1H), 8.00 (dd, J=8.4, 2.4 Hz, 1H), 3.80 (s, 3H).

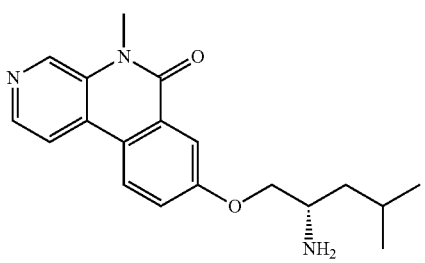 [SMILES: CC(C)C[C@H](N)COc1ccc2c(c1)c(=O)n(C)c1cnccc21]

Part C: (S)-8-((2-amino-4-methylpentyl)oxy)-5-methylbenzo[c][1,7]naphthyridin-6(5H)-one Prepared as described in Example 1, Parts G and F. Obtained (S)-8-((2-amino-4-methylpentyl)oxy)-5-methylbenzo[c][1,7]naphthyridin-6(5H)-one (45 mg, 0.137 mmol, 38% yield over two steps) as a pale yellow solid. LC/MS (ESI) m/e 326.2 [(M+H)$^+$, calcd for $C_{19}H_{24}N_3O_2$, 326.2]; LC/MS retention time (Method C2): $t_R$=1.02 min; $^1$H NMR (400 MHz, METHANOL-d$_4$) δ 9.04 (br. s., 1H), 8.67 (d, J=9.0 Hz, 1H), 8.66-8.57 (m, 2H), 8.10 (d, J=3.0 Hz, 1H), 7.70 (dd, J=9.0, 3.0 Hz, 1H), 4.51 (dd, J=10.5, 3.5 Hz, 1H), 4.33 (dd, J=10.5, 6.5 Hz, 1H), 3.93 (s, 3H), 3.80 (qd, J=6.9, 3.3 Hz, 1H), 1.92-1.62 (m, 3H), 1.08 (d, J=6.4 Hz, 3H), 1.07 (d, J=6.4 Hz, 3H), two exchangeable protons not observed; HPLC purity (Method A1): 98% $t_R$=5.37 min; HPLC purity (Method B2): 98% $t_R$=7.08 min.

Example 3

(S)-8-((2-amino-4-methylpentyl)oxy)-5,9-dimethylbenzo[c][1,7]naphthyridin-6(5H)-one

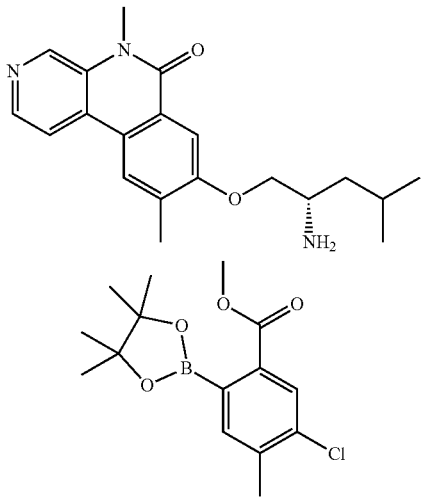

Part A. Methyl 5-chloro-4-methyl-2-(4,4,5,5-tetramethyl-1,3,2-dioxaborolan-2-yl)benzoate To a pressure tube was added methyl 2-bromo-5-chloro-4-methylbenzoate (3.1 g, 11.76 mmol) in 1,4-dioxane (62 mL). To this was added bis(pinacolato)diboron (3.29 g, 12.94 mmol) and potassium acetate (3.58 g, 36.5 mmol). Nitrogen gas was bubbled through the solution for 10 min. PdCl$_2$(dppf) (0.344 g, 0.471 mmol) was added and N$_2$ gas was bubbled through the solution for 10 min. Closed the pressure tube tightly and heated to 80° C. for 12 h. The reaction mixture was cooled to room temperature and filtered through a bed of diatomaceous earth (Celite®), washing the bed with ethyl acetate. Water was added to the filtrate and the solution extracted ethyl acetate (2×100 mL). The combined organic layers were washed with brine (50 mL), dried over sodium sulphate, filtered, and concentrated under reduced pressure. The residue was purified by silica gel chromatography (hexanes and ethyl acetate) to afford methyl 5-chloro-4-methyl-2-(4,4,5,5-tetramethyl-1,3,2-dioxaborolan-2-yl)benzoate (1.6 g, 5.15 mmol, 44% yield) as a white solid. LC/MS (ESI) m/e 311.2 [(M+H)$^+$, calcd for $C_{15}H_{21}BClO_4$, 311.1]; LC/MS retention time (Method B): $t_R$=1.06 min; $^1$H NMR (400 MHz, CHLOROFORM-d) δ 7.92 (s, 1H), 7.34 (s, 1H), 3.90 (s, 3H), 2.41 (s, 3H), 1.41 (s, 12H).

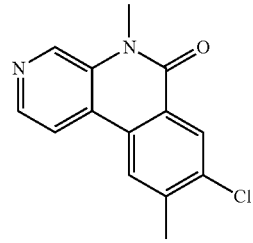 [SMILES: Cc1cc2c(cc1Cl)c(=O)n(C)c1cnccc21]

Part B: 8-chloro-5,9-dimethylbenzo[c][1,7]naphthyridin-6(5H)-one

To a microwave vial was added 4-chloro-N-methylpyridin-3-amine (300 mg, 2.10 mmol) (Example 2, Part A) in tetrahydrofuran (6 mL) and water (3 mL) followed by methyl 5-chloro-4-methyl-2-(4,4,5,5-tetramethyl-1,3,2-dioxaborolan-2-yl)benzoate (719 mg, 2.31 mmol) and cesium carbonate (2057 mg, 6.31 mmol). N2 gas was bubbled through the solution for 5 min. Tetrakis(triphenylphosphine)palladium(0) (243 mg, 0.210 mmol) was added and N2 was bubbled through the solution for 10 min. The reaction mixture was heated to 100° C. for 1 h. The reaction mixture was then cooled to room temperature and diluted with water (50 mL). The aqueous layer was extracted with ethyl acetate (3×25 mL). The combined the organic layers were washed with brine (1×50 mL), dried over Na$_2$SO$_4$, filtered, and concentrated under reduced pressure. The residue was purified by silica gel chromatography (petroleum ether:ethyl acetate mobile phase) to yield 8-chloro-5,9-dimethylbenzo[c][1,7]naphthyridin-6(5H)-one (30 mg, 0.116 mmol, 6% yield) as an off-white solid. LC/MS (ESI) m/e 259.1 [(M+H)$^+$, calcd for $C_{14}H_{12}ClN_2O$, 259.1]; LC/MS retention time (Method B): $t_R$=0.88 min.

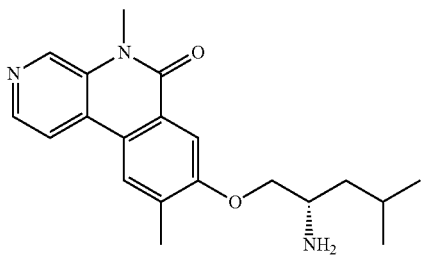

Part C: (S)-8-((2-amino-4-methylpentyl)oxy)-5,9-dimethylbenzo[c][1,7]naphthyridin-6(5H)-one Prepared as described in Example 1, Parts G and F. Obtained (S)-8-((2-amino-4-methylpentyl)oxy)-5,9-dimethylbenzo[c][1,7]naphthyridin-6(5H)-one (5 mg, 0.015 mmol, 7% yield over two steps) as an off-white solid. LC/MS (ESI) m/e 340.2 [(M+H)$^+$, calcd for $C_{20}H_{26}N_3O_2$, 340.2]; LC/MS retention time (Method D): $t_R$=1.67 min; $^1$H NMR (400 MHz, CD$_3$OD) δ 9.07 (s, 1H), 8.79 (d, J=6.0 Hz, 1H), 8.62 (d, J=6.4 Hz, 1H), 8.58 (s, 1H), 8.04 (s, 1H), 4.53 (dd, J=10.8, 3.2 Hz, 1H), 4.39 (dd, J=10.8, 6.0 Hz, 1H), 3.93 (s, 3H), 3.90-3.82 (m, 1H), 2.61 (s, 3H), 1.88-1.71 (m, 3H), 1.08 (d, J=6.4 Hz, 3H), 1.07 (d, J=6.4 Hz, 3H), two exchangeable protons not observed; HPLC purity (Method A1): 99% $t_R$=8.77 min; HPLC purity (Method B1): 99% $t_R$=9.29 min.

Example 4

(S)-8-((2-amino-4-methylpentyl)oxy)-4,5,9-trimethylbenzo[c][1,7]naphthyridin-6(5H)-one

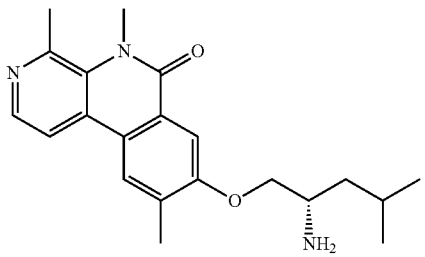 [SMILES: Cc1cc2c(cc1OC[C@@H](N)CC(C)C)c(=O)n(C)c1c(C)nccc21]

Prepared as described in Example 3. Obtained (S)-8-((2-amino-4-methylpentyl)oxy)-4,5,9-trimethylbenzo[c][1,7]naphthyridin-6(5H)-one (1.63 mg, 4.01 μmol, 3% yield over the last three steps) as pale pink solid. LC/MS (ESI) m/e 354.2 [(M+H)$^+$, calcd for $C_{21}H_{28}N_3O_2$, 354.2]; LC/MS retention time (Method M): $t_R$=1.64 min; $^1$H NMR (400 MHz, METHANOL-d$_4$) δ 8.36 (s, 1H), 8.34 (d, J=5.0 Hz, 1H), 8.14 (d, J=5.0 Hz, 1H), 7.90 (s, 1H), 4.46 (dd, J=10.5, 3.5 Hz, 1H), 4.32 (dd, J=10.5, 6.0 Hz, 1H), 3.88 (s, 3H), 3.86-3.78 (m, 1H), 2.93 (s, 3H), 2.55 (s, 3H), 1.91-1.66 (m, 3H), 1.08 (d, J=4.5 Hz, 3H), 1.07 (d, J=4.5 Hz, 3H), two exchangeable protons not observed; HPLC purity (Method A1): 88% $t_R$=7.85 min; HPLC purity (Method B1): 94% $t_R$=8.99 min.

Example 5

(S)-8-((2-amino-4-methylpentyl)oxy)-9-chloro-4,5-dimethylbenzo[c][1,7]naphthyridin-6(5H)-one

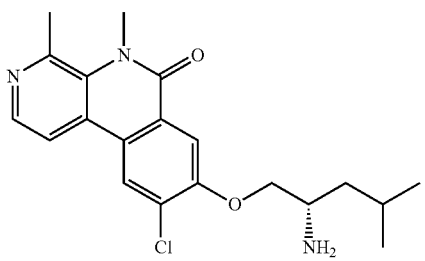

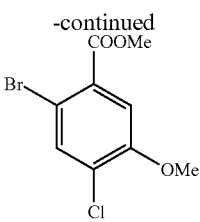

Part A: Methyl 2-bromo-4-chloro-5-methoxybenzoate

To a solution of methyl 4-chloro-3-methoxybenzoate (6.7 g, 33.4 mmol) in acetic acid (18 mL) and water (18 mL) was added Br$_2$ (2.58 mL, 50.1 mmol) dropwise. The reaction mixture was then heated to 60° C. for 12 h. The mixture was cooled to room temperature and diluted with water (25 mL). The solution was extracted with ethyl acetate (2×25 mL). The combined organic layers were washed with brine, dried over sodium sulphate and concentrated under reduced pressure to afford methyl 2-bromo-4-chloro-5-methoxybenzoate (8.5 g, 30.4 mmol, 91% yield) as an orange solid. LC/MS (ESI) m/e 278.9 [(M+H)$^+$, calcd for $C_9H_9BrClO_3$, 279.0]; LC/MS retention time (Method E): $t_R$=0.69 min; $^1$H NMR (400 MHz, CHLOROFORM-d) δ 7.67 (s, 1H), 7.38 (s, 1H), 3.94 (s, 3H), 3.93 (s, 3H).

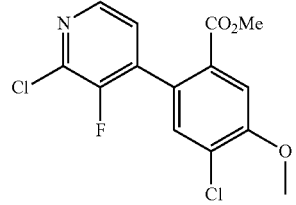 [SMILES: COC(=O)c1cc(OC)c(Cl)cc1-c1ccnc(Cl)c1F]

Part B: Methyl 4-chloro-2-(2-chloro-3-fluoropyridin-4-yl)-5-methoxybenzoate

A solution of (2-chloro-3-fluoropyridin-4-yl)boronic acid (3.45 g, 19.68 mmol), methyl 2-bromo-4-chloro-5-methoxybenzoate (5 g, 17.89 mmol), and K$_2$CO$_3$ (7.42 g, 53.7 mmol) in dioxane (40 mL) and water (15 mL) was purged with nitrogen gas 10 min. PdCl$_2$(dppf)-CH$_2$Cl$_2$ adduct (1.46 g, 1.79 mmol) was added to the reaction mixture and again nitrogen gas was bubbled through the solution for another 10 min. The reaction mixture was heated to reflux overnight. The reaction mixture was then allowed to cool to room temperature and concentrated under reduced pressure. The residue was diluted with ethyl acetate (100 mL) and filtered through diatomaceous earth (Celite®). The filtrate was concentrated under reduced pressure. The residue was purified by silica-gel chromatography (petroleum ether/EtOAc) to afford methyl 4-chloro-2-(2-chloro-3-fluoropyridin-4-yl)-5-methoxybenzoate (1.8 g, 5.45 mmol, 31% yield) as an off-white solid. LC/MS (ESI) m/e 329.8 [(M+H)$^+$, calcd for $C_{14}H_{11}Cl_2NO_3$, 330.0]; LC/MS retention time (Method A2): $t_R$=2.30 min; $^1$H NMR (400 MHz, DMSO-d$_6$) δ 8.33 (d, J=5.0 Hz, 1H), 7.67 (m, 2H), 7.53 (t, J=5.3 Hz, 1H), 4.01 (s, 3H), 3.71 (s, 3H).

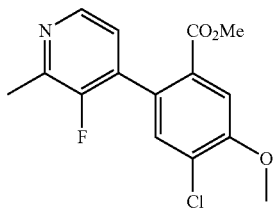

Part C: Methyl 4-chloro-2-(3-fluoro-2-methylpyridin-4-yl)-5-methoxybenzoate

To a solution of methyl 4-chloro-2-(2-chloro-3-fluoropyridin-4-yl)-5-methoxybenzoate (0.44 g, 1.33 mmol) and $K_2CO_3$ (0.460 g, 3.33 mmol) in dioxane (15 mL) and water (3 mL) was added methylboronic acid (0.088 g, 1.47 mmol). Nitrogen gas was bubbled through the solution for 15 min. $PdCl_2(dppf)\text{-}CH_2Cl_2$ adduct (0.109 g, 0.133 mmol) was added to the reaction mixture and again nitrogen gas was bubbled through the solution for 10 min. The reaction mixture was heated at 110° C. overnight. The reaction mixture was then allowed to cool to room temperature and concentrated under reduced pressure. The residue was diluted with ethyl acetate (50 mL) and water (50 mL) and filtered through diatomaceous earth (Celite®). The filtrate was extracted with ethyl acetate (2×30 mL). The combined organic layers were washed with brine, dried over sodium sulphate, filtered, and concentrated under reduced pressure. The residue was purified by silica gel chromatography (0-40% petroleum ether/EtOAc) to afford methyl 4-chloro-2-(3-fluoro-2-methylpyridin-4-yl)-5-methoxybenzoate (0.32 g, 1.03 mmol, 78% yield) as a brown color semi-solid. LC/MS (ESI) m/e 310.3 [(M+H)$^+$, calcd for $C_{15}H_{14}ClFNO_3$, 310.1]; LC/MS retention time (Method B): $t_R$=1.03 min; $^1$H NMR (400 MHz, CHLOROFORM-d) δ 8.33 (d, J=4.8 Hz, 1H), 7.58 (s, 1H), 7.34 (s, 1H), 7.10-7.01 (m, 1H), 4.01 (s, 3H), 3.72 (s, 3H), 1.56 (s, 3H).

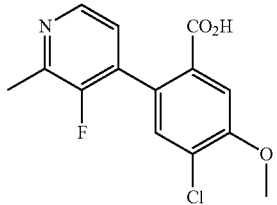

Part D: 4-chloro-2-(3-fluoro-2-methylpyridin-4-yl)-5-methoxybenzoic acid

To a solution of methyl 4-chloro-2-(3-fluoro-2-methylpyridin-4-yl)-5-methoxybenzoate (0.1 g, 0.323 mmol) in MeOH (2 mL) and water (2 mL) was added LiOH (0.031 g, 1.29 mmol) and the mixture stirred at 25° C. for 4 h. The reaction mixture was concentrated under reduced pressure and the residue acidified with saturated aqueous citric acid. The aqueous mixture was extracted with EtOAc (2×20 mL). The organic layer was separated, dried over sodium sulphate, filtered, and concentrated under reduced pressure to afford 4-chloro-2-(3-fluoro-2-methylpyridin-4-yl)-5-methoxybenzoic acid (68 mg, 0.230 mmol, 71% yield) as a brown solid. LC/MS (ESI) m/e 296.3 [(M+H)$^+$, calcd for $C_{14}H_{12}ClFNO_3$, 296.1]; LC/MS retention time (Method B): $t_R$=1.03 min; $^1$H NMR (400 MHz, CHLOROFORM-d) δ 8.33 (d, J=5.3 Hz, 1H), 7.70 (s, 1H), 7.35 (s, 1H), 7.16 (t, J=5.4 Hz, 1H), 4.03 (s, 3H), 2.45 (d, J=3.0 Hz, 3H).

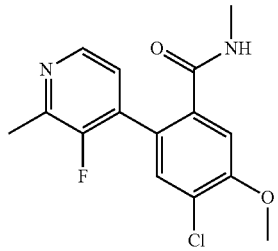

Part E: 4-Chloro-2-(3-fluoro-2-methylpyridin-4-yl)-5-methoxy-N-methylbenzamide

To a 100 mL round bottom flask was added 4-chloro-2-(3-fluoro-2-methylpyridin-4-yl)-5-methoxybenzoic acid (0.25 g, 0.634 mmol), HATU (0.241 g, 0.634 mmol), and DIPEA (0.554 mL, 3.17 mmol) in DMF (5 mL). To this solution was added methylamine hydrochloride (0.214 g, 3.17 mmol) and the mixture stirred at 25° C. for 4 h. The mixture was concentrated under reduced pressure. The residue was purified by silica gel chromatography to afford 4-chloro-2-(3-fluoro-2-methylpyridin-4-yl)-5-methoxy-N-methylbenzamide (0.178 g, 0.577 mmol, 91% yield) as a brown solid. LC/MS (ESI) m/e 309.0 [(M+H)$^+$, calcd for $C_{14}H_{12}ClFNO_3$, 309.1]; LC/MS retention time (Method A3): $t_R$=1.90 min; $^1$H NMR (400 MHz, DMSO-$d_6$) δ 8.33 (t, J=2.5 Hz, 1H), 8.27 (d, J=5.0 Hz, 1H), 7.50 (s, 1H), 7.34 (s, 1H), 7.19 (t, J=5.3 Hz, 1H), 3.98 (s, 3H), 2.65 (d, J=4.5 Hz, 3H), 2.45 (d, J=3.5 Hz, 3H).

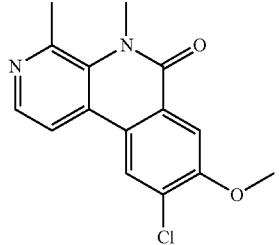 [SMILES: COc1cc2c(=O)n(C)c3c(C)nccc3c2cc1Cl]

Part F: 9-Chloro-8-methoxy-4,5-dimethylbenzo[c][1,7]naphthyridin-6(5H)-one

To a stirred solution of 4-chloro-2-(3-fluoro-2-methylpyridin-4-yl)-5-methoxy-N-methylbenzamide (0.145 g, 0.470 mmol) in NMP (5 mL) was added $Cs_2CO_3$ (0.459 g, 1.409 mmol) in one portion at room temperature and the reaction was stirred at 100° C. for 12 h. The reaction mixture was diluted with ice water (10 mL) and stirred for 30 min. A white precipitate formed. The solid was collected by vacuum filtration and air dried to afford 9-chloro-8-methoxy-4,5-dimethylbenzo[c][1,7]naphthyridin-6(5H)-one (0.11 g, 0.373 mmol, 79% yield) as a off-white solid which was taken into the next step without further purification. LC/MS (ESI) m/e 289.0 [(M+H)$^+$, calcd for $C_{15}H_{14}ClN_2O_2$, 289.1]; LC/MS retention time (Method A): $t_R$=2.27 min; $^1$H NMR (400 MHz, DMSO-$d_6$) δ 8.45 (d, J=4.5 Hz, 1H), 8.28 (d, J=5.0 Hz, 1H), 7.60 (s, 1H), 7.42 (t, J=5.3 Hz, 1H), 7.40 (s, 1H), 3.99 (s, 3H), 2.67 (d, J=4.5 Hz, 3H), 2.51 (under DMSO peak) (s, 3H).

1.76-1.61 (m, 2H), 1.45 (s, 9H), 1.41-1.32 (m, 1H), 0.95 (d, J=3.8 Hz, 3H), 0.93 (d, J=3.8 Hz, 3H).

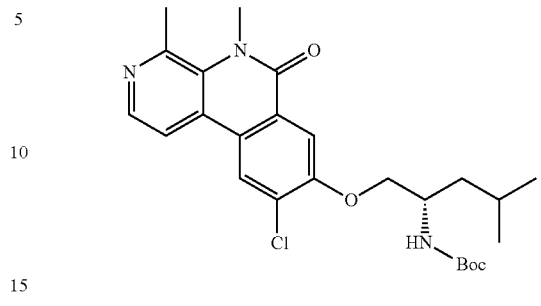

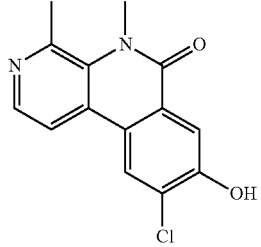 [SMILES: Cc1nccc2c3cc(Cl)c(O)cc3c(=O)n(C)c12]

Part G: 9-chloro-8-hydroxy-4,5-dimethylbenzo[c][1,7]naphthyridin-6(5H)-one

To a solution of 9-chloro-8-methoxy-4,5-dimethylbenzo[c][1,7]naphthyridin-6(5H)-one (0.05 g, 0.173 mmol) in dichloromethane (5 mL) at −10° C. was added BBr$_3$ (1M solution in DCM) (0.5 mL, 5.29 mmol) and the reaction mixture was warmed to room temperature and stirred for 12 h. The reaction mixture was cooled to 0° C. and methanol (5 mL) was added to quench any remaining BBr$_3$. The solvent was evaporated under reduced pressure. The residue was purified via silica gel chromatography (0-10% CHCl$_3$/MeOH) to afford 9-chloro-8-hydroxy-4,5-dimethylbenzo[c][1,7]naphthyridin-6(5H)-one (0.03 g, 0.109 mmol, 63% yield) as an off-white solid. LC/MS (ESI) m/e 275.3 [(M+H)$^+$, calcd for C$_{14}$H$_{12}$ClN$_2$O$_2$, 275.1]; LC/MS retention time (Method B): $t_R$=0.62 min; $^1$H NMR (400 MHz, DMSO-$d_6$) δ 8.88 (s, 1H), 8.68 (br. s., 1H), 8.57 (d, J=6.0 Hz, 1H), 7.93 (s, 1H), 3.79 (s, 3H), 3.00 (s, 3H), one exchangeable proton not seen.

Part I: (S)-tert-butyl (1-((9-chloro-4,5-dimethyl-6-oxo-5,6-dihydrobenzo[c][1,7]naphthyridin-8-yl)oxy)-4-methylpentan-2-yl)carbamate To a solution of 9-chloro-8-hydroxy-4,5-dimethylbenzo[c][1,7]naphthyridin-6(5H)-one (1.0 mL, 0.364 mmol) in DMSO (4 mL) at room temperature was added K$_2$CO$_3$ (0.151 g, 1.092 mmol) and Cs$_2$CO$_3$ (0.356 g, 1.09 mmol) followed by slow addition of (S)-2-((tert-butoxycarbonyl)amino)-4-methylpentyl methanesulfonate (0.323 g, 1.09 mmol) and the reaction mixture stirred at 100° C. for 12 h. The reaction mixture was allowed to cool to room temperature and water (10 mL) and EtOAc (20 mL) were added. The organic layer was separated and washed with water (3×10 mL), brine (1×10 mL), dried over sodium sulphate, filtered, and concentrated under reduced pressure. The residue was purified by silica gel chromatography (10-60% petroleum ether/EtOAc) to afford (S)-tert-butyl (1-((9-chloro-4,5-dimethyl-6-oxo-5,6-dihydrobenzo[c][1,7]naphthyridin-8-yl)oxy)-4-methylpentan-2-yl)carbamate (58 mg, 0.122 mmol, 34% yield) as a brown semi-solid. This was taken into the next step without further purification. LC/MS (ESI) m/e 474.3 [(M+H)$^+$, calcd for C$_{25}$H$_{33}$ClN$_3$O$_4$, 474.2]; LC/MS retention time (Method B): $t_R$=1.17 min.

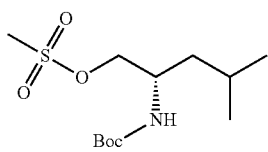 [SMILES: CC(C)C[C@@H](COS(C)(=O)=O)NC(=O)OC(C)(C)C]

Part H: (S)-2-((tert-butoxycarbonyl)amino)-4-methylpentyl methanesulfonate

To a stirred solution of (S)-tert-butyl (1-hydroxy-4-methylpentan-2-yl)carbamate (1.6 g, 7.36 mmol) in CH$_2$Cl$_2$ (15 mL) at 0° C. was added TEA (2.05 mL, 14.73 mmol). The solution was stirred for 5 min. Methanesulfonyl chloride (0.57 mL, 7.36 mmol) was added dropwise at 0° C. and the reaction mixture was warmed to room temperature and stirred for 1 h. The reaction mixture was quenched with water (15 mL) and the solution extracted with DCM (2×15 mL). The combined organic layers were washed with brine (10 mL), dried over sodium sulphate, filtered, and concentrated under reduced pressure to yield (S)-2-((tert-butoxycarbonyl)amino)-4-methylpentyl methanesulfonate (1.7 g, 5.75 mmol, 78% yield) which was taken to the next step without purification. $^1$H NMR (400 MHz, CHLOROFORM-d) δ 4.53 (d, J=8.0 Hz, 1H), 4.36-4.21 (m, 1H), 4.15 (dd, J=10.0, 4.3 Hz, 1H), 3.96-3.85 (m, 1H), 3.03 (s, 3H),

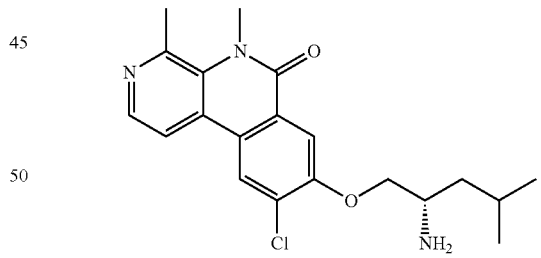

Part J: (S)-8-((2-amino-4-methylpentyl)oxy)benzo[c][1,7]naphthyridin-6(5H)-one

To a solution of (S)-tert-butyl (1-((9-chloro-4,5-dimethyl-6-oxo-5,6-dihydrobenzo[c][1,7]naphthyridin-8-yl)oxy)-4-methylpentan-2-yl)carbamate (58 mg, 0.061 mmol) in DCM (2 ml) at 0° C. was added 4M HCl in 1,4-dioxane (1 mL, 10.58 mmol). The solution was warmed to room temperature and stirred for 4 h. The reaction mixture was concentrated under reduced pressure. The residue was taken up in EtOAc (10 mL) and saturated aqueous sodium bicarbonate (10 mL) was added. The mixture was extracted with EtOAc (3×10 mL). The combined organics were washed with water (3×10 mL), brine (1×10 mL), dried over sodium sulphate, filtered, and concentrated under reduced pressure. The residue was purified by prep LC/MS (acetonitrile:water with 10 mM NH₄OAc) to afford (S)-8-((2-amino-4-methylpentyl)oxy)benzo[c][1,7]naphthyridin-6(5H)-one (1.04 mg, 2.78 μmol, 5% yield over two steps) as a pale yellow solid. LC/MS (ESI) m/e 374.0 [(M+H)$^+$, calcd for $C_{20}H_{25}ClN_3O_2$, 374.2]; LC/MS retention time (Method J): $t_R$=1.60 min; $^1$H NMR (400 MHz, METHANOL-$d_4$) δ 8.44 (s, 1H), 8.27 (d, J=5.5 Hz, 1H), 8.00 (d, J=5.5 Hz, 1H), 7.73 (s, 1H), 3.96-3.78 (m, 4H), 3.69 (d, J=5.0 Hz, 2H), 2.90 (s, 3H), 1.81 (tt, J=13.4, 6.9 Hz, 1H), 1.62 (ddd, J=7.4, 6.4, 1.8 Hz, 2H), 1.05 (d, J=6.5 Hz, 3H), 0.97 (d, J=6.5 Hz, 3H), two exchangeable protons not observed; HPLC purity (Method C1): 99% $t_R$=1.60 min; HPLC purity (Method D): 100% $t_R$=1.11 min.

Example 6

8-((2-amino-5,5,5-trifluoropentyl)oxy)-5,9-dimethyl-benzo[c][1,7]naphthyridin-6(5H)-one

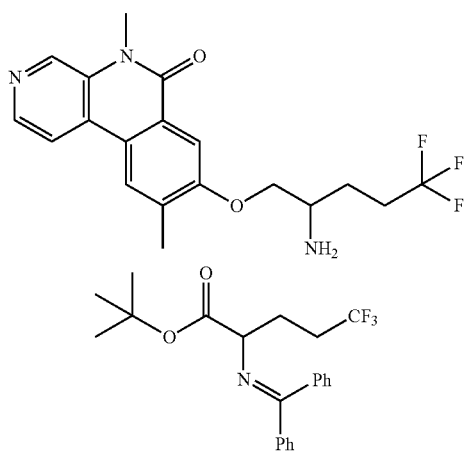

Part A. Tert-butyl 2-(diphenylmethyleneamino)-5,5,5-trifluoropentanoate

To a stirred solution of tert-butyl 2-((diphenylmethylene)amino)acetate (1 g, 3.39 mmol) in THF (20 mL) cooled to −78° C. under a nitrogen atmosphere was added a 2M solution of LDA in THF (2.54 mL, 5.08 mmol) dropwise over 30 min. To this mixture was then added 3,3,3-trifluoropropyl trifluoromethanesulfonate (1.083 g, 4.40 mmol). The reaction was gradually warmed to room temperature and stirred for 4 h. The reaction mixture was quenched by addition of saturated aqueous ammonium chloride at 0° C. The reaction mixture was then extracted with ethyl acetate (3×10 mL). The combined organic extracts were washed with water (1×10 mL) and brine (1×10 mL), dried over sodium sulfate, filtered, and then concentrated under reduced pressure. The crude oil was purified by silica gel chromatography (2% ethyl acetate in hexane) to afford tert-butyl 2-((diphenylmethylene)amino)-5,5,5-trifluoropentanoate (800 mg, 2.02 mmol, 60% yield) as a yellow oil. LC/MS (ESI) m/e 391.9 [(M+H)$^+$, calcd for $C_{22}H_{25}F_3NO_2$, 392.2]; LC/MS retention time (Method A): $t_R$=2.49 min.

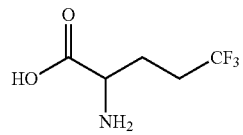

Part B. 2-amino-5,5,5-trifluoropentanoic acid (Hydrochloride Salt)

A stirred solution of tert-butyl 2-((diphenylmethylene)amino)-5,5,5-trifluoropentanoate (800 mg, 2.02 mmol) in 50% aqueous HCl (0.123 mL, 2.02 mmol) was refluxed at 100° C. for 8 h. The reaction mixture was cooled to room temperature and concentrated under reduced pressure to afford 2-amino-5,5,5-trifluoropentanoic acid hydrochloride (400 mg, 1.82 mmol, 90% yield, 78% purity by LC/MS) as a white solid. LC/MS (ESI) m/e 171.7 [(M+H)$^+$, calcd for $C_5H_7F_3O_2$, 172.1]; LC/MS retention time (Method A): $t_R$=0.28 min.

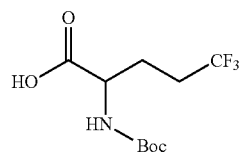 [SMILES: CC(C)(C)OC(=O)NC(CCC(F)(F)F)C(=O)O]

Part C. 2-(tert-butoxycarbonylamino)-5,5,5-trifluoropentanoic Acid

To a stirred solution of 2-amino-5,5,5-trifluoropentanoic acid hydrochloride (400 mg, 1.50 mmol, 78% by LC/MS) in THF (8 mL) and water (8 mL) at room temperature was added K₂CO₃ (831 mg, 6.01 mmol) and the solution stirred for 10 min. To this mixture was added Boc₂O (656 mg, 3.01 mmol). The reaction mixture was stirred for 8 h at room temperature then concentrated under reduced pressure. The aqueous layer was washed with ethyl acetate (3×5 mL). The aqueous layer was acidified with saturated citric acid solution (5 mL) and extracted with ethyl acetate (3×8 mL). The combined organic layers were washed with water (3×5 mL) followed by brine (1×10 mL), dried over sodium sulfate and concentrated under reduced pressure to afford 2-((tert-butoxycarbonyl)amino)-5,5,5-trifluoropentanoic acid (500 mg, 1.84 mmol, 100% yield) as a colorless oil. The material was taken into the next step without further purification. $^1$H NMR (400 MHz, CDCl₃) δ 5.04 (s, 1H), 4.38 (s, 1H), 2.15-2.28 (m, 2H), 1.91-1.95 (m, 2H), 1.46 (s, 9H).

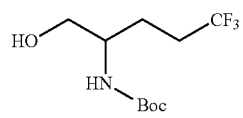 [SMILES: CC(C)(C)OC(=O)NC(CO)CCC(F)(F)F]

Part D. Tert-butyl 5,5,5-trifluoro-1-hydroxypentan-2-ylcarbamate

To a stirred solution of 2-((tert-butoxycarbonyl)amino)-5,5,5-trifluoropentanoic acid (500 mg, 1.84 mmol) in THF (15 mL) cooled to −10° C. under nitrogen atmosphere was added N-methylmorphine (0.223 mL, 2.03 mmol) followed by isobutyl chloroformate (0.266 mL, 2.03 mmol) dropwise. The solution was then stirred for 30 min then filtered. The filtrate was added to sodium borohydride (147 mg, 3.87 mmol) in water (10 mL), stirred for 5 min and diluted with ethyl acetate (10 mL). The organic layer was separated and washed with brine (2×10 mL), dried (Na$_2$SO$_4$) and evaporated under reduced pressure to afford tert-butyl (5,5,5-trifluoro-1-hydroxypentan-2-yl)carbamate (400 mg, 1.56 mmol, 84% yield) as a white solid which was taken to the next step without further purification. $^1$H NMR (400 MHz, MeOD) δ 3.44-3.56 (m, 3H), 2.16-2.26 (m, 2H), 1.83-1.92 (m, 1H), 1.57-1.67 (m, 1H), 1.47 (s, 9H).

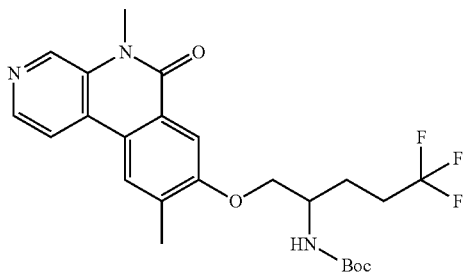 [SMILES: Cc1cc2c(cc1OCC(CCC(F)(F)F)NC(=O)OC(C)(C)C)c(=O)n(C)c1cnccc21]

Part E: Tert-butyl (1-((5,9-dimethyl-6-oxo-5,6-dihydrobenzo[c][1,7]naphthyridin-8-yl)oxy)-5,5,5-trifluoropentan-2-yl)carbamate In a pressure tube was added 8-chloro-5,9-dimethylbenzo[c][1,7]naphthyridin-6(5H)-one (100 mg, 0.387 mmol) (prepared in Example 3, Part B), cesium carbonate (189 mg, 0.580 mmol) and di-tert-butyl(2',4',6'-triisopropyl-[1,1'-biphenyl]-2-yl)phosphine (9.85 mg, 0.023 mmol) in toluene (2 mL). Nitrogen gas was bubbled through the solution for 5 min. To this mixture was added palladium(II) acetate (2.60 mg, 0.012 mmol) and nitrogen gas was bubbled through the solution for 10 min. The pressure tube was sealed and heated to 80° C. for 12 h. The reaction mixture was cooled to room temperature then filtered through diatomaceous earth (Celite®), washing with ethyl acetate. The filtrate was concentrated under reduced pressure and the residue was purified via silica gel chromatography (hexane/ethyl acetate) to afford tert-butyl (1-((5,9-dimethyl-6-oxo-5,6-dihydrobenzo[c][1,7]naphthyridin-8-yl)oxy)-5,5,5-trifluoropentan-2-yl)carbamate (150 mg, 0.228 mmol, 59% yield) as a pale brown solid. LC/MS (ESI) m/e 480.6 [(M+H)$^+$, calcd for C$_{24}$H$_{29}$F$_3$N$_3$O$_4$, 480.2]; LC/MS retention time (Method E): t$_R$=0.86 min.

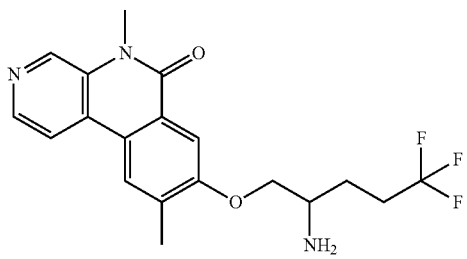 [SMILES: Cc1cc2c(cc1OCC(N)CCC(F)(F)F)c(=O)n(C)c1cnccc21]

Part F: 8-((2-amino-5,5,5-trifluoropentyl)oxy)-5,9-dimethylbenzo[c][1,7]naphthyridin-6(5H)-one To a solution of tert-butyl (1-((5,9-dimethyl-6-oxo-5,6-dihydrobenzo[c][1,7]naphthyridin-8-yl)oxy)-5,5,5-trifluoropentan-2-yl)carbamate (150 mg, 0.228 mmol) in MeOH (3 mL) at 0° C. was added TFA (0.141 mL, 1.83 mmol) dropwise. The solution was stirred at 0° C. for 5 min, then at room temperature for 3 h. The reaction mixture was concentrated under reduced pressure. The residue was purified via prep HPLC (0.1% TFA in ACN:Water) to afford 8-((2-amino-5,5,5-trifluoropentyl)oxy)-5,9-dimethylbenzo[c][1,7]naphthyridin-6(5H)-one, 2 TFA (14.8 mg, 0.024 mmol, 10% yield) as pale brown solid. LC/MS (ESI) m/e 380.2 [(M+H)$^+$, calcd for C19H$_{21}$F$_3$N$_3$O$_2$, 380.2]; LC/MS retention time (Method F): t$_R$=1.50 min; $^1$H NMR (400 MHz, METHANOL-d$_4$) δ 7.46 (br. s., 1H), 7.04 (br. s., 2H), 6.95 (s, 1H), 6.45 (s, 1H), 2.99 (dd, J=10.5, 3.5 Hz, 1H), 2.88 (dd, J=10.5, 5.5 Hz, 1H), 2.37 (s, 3H), 2.35-2.27 (m, 1H), 1.03 (s, 3H), 1.01-0.88 (m, 2H), 0.79-0.53 (m, 2H), two exchangeable protons not observed; HPLC purity (Method A1): 99% t$_R$=8.41 min; HPLC purity (Method B1): 99% t$_R$=9.16 min.

Example 7

8-((2-amino-2,4-dimethylpentyl)oxy)-5-methylbenzo[c][1,7]naphthyridin-6(5H)-one

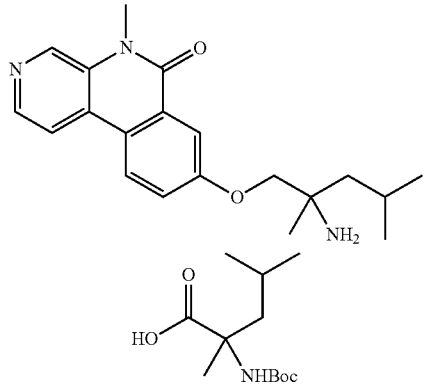

Part A.
2-(tert-butoxycarbonylamino)-2,4-dimethylpentanoic acid

To a stirred solution of 2-amino-2,4-dimethylpentanoic acid (1 g, 6.89 mmol) in tetrahydrofuran (15 mL) and water (15 mL) was added K$_2$CO$_3$ (3.81 g, 27.5 mmol) and the reaction mixture was stirred at room temperature for 10 min. To the resultant mixture BOC$_2$O (3.20 mL, 13.77 mmol) was added dropwise and the reaction mixture was allowed to stir at room temperature for 14 h. The reaction mixture was then concentrated under reduced pressure. The aqueous layer was washed with ethyl acetate (3×15 mL) and acidified with a saturated aqueous solution of citric acid (25 mL) then extracted with ethyl acetate (3×50 mL). The combined organic extracts were washed with water (2×15 mL), brine (1×20 mL), dried over sodium sulfate and concentrated under reduced pressure to afford 2-((tert-butoxycarbonyl)amino)-2,4-dimethylpentanoic acid (1.6 g, 6.89 mmol, quantitative yield) as a white solid. ¹H NMR (400 MHz, CDCl₃) δ 5.36 (bs, 1H), 2.10 (m, 1H), 1.77 (m, 2H), 1.74-1.65 (m, 3H), 1.59 (s, 9H), 0.89 (m, 3H), 0.94 (m, 3H).

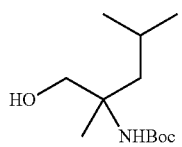

Part B. tert-butyl 1-hydroxy-2,4-dimethylpentan-2-ylcarbamate

To a stirred solution of 2-((tert-butoxycarbonyl)amino)-2,4-dimethylpentanoic acid (1.6 g, 6.52 mmol) in tetrahydrofuran (40 mL) cooled to −10° C. under nitrogen atmosphere was added N-methylmorpholine (0.860 mL, 7.83 mmol) followed by isobutyl chloroformate (1.028 mL, 7.83 mmol) dropwise and the reaction mixture was stirred for 30 min. The reaction mixture was then filtered and the filtrate was added dropwise to a suspension of NaBH₄ (0.494 g, 13.04 mmol) in water (20 mL). The reaction mixture was stirred for 10 min then diluted with ethyl acetate (30 mL). The organic layer was separated and washed with brine (2×20 mL), dried over Na₂SO₄ and evaporated under reduced pressure. The residue was purified by silica gel chromatography (30% ethyl acetate and pet ether) to afford tert-butyl (1-hydroxy-2,4-dimethylpentan-2-yl)carbamate (1.1 g, 4.76 mmol, 73% yield) as a colorless oil. ¹H NMR (400 MHz, DMSO-d₆) δ 6.09 (s, 1H), 4.61 (t, J=7.6 Hz, 1H), 3.35 (m, 2H), 1.8-1.6 (m, 2H), 1.44-1.35 (m, 10H), 1.09 (s, 3H), 0.86 (m, 6H).

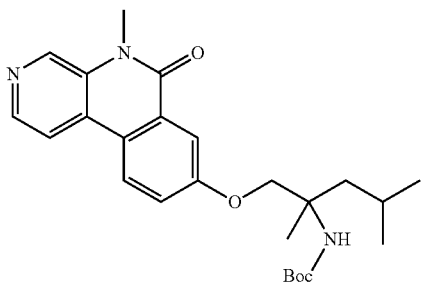 [SMILES: CC(C)CC(C)(COc1ccc2c(c1)c(=O)n(C)c1cnccc21)NC(=O)OC(C)(C)C]

Part C: Tert-butyl (2,4-dimethyl-1-((5-methyl-6-oxo-5,6-dihydrobenzo[c][1,7]naphthyridin-8-yl)oxy) pentan-2-yl)carbamate To a solution of 8-chloro-5-methylbenzo[c][1,7]naphthyridin-6(5H)-one (30 mg, 0.123 mmol) (prepared in Example 2, Part B) in toluene (0.3 mL) was added di-tert-butyl(2',4',6'-triisopropyl-3-methoxy-6-methyl-[1,1'-biphenyl]-2-yl) phosphine (2.30 mg, 4.90 μmol) and tert-butyl (1-hydroxy-2,4-dimethylpentan-2-yl)carbamate (70.9 mg, 0.307 mmol). Argon gas was bubbled through the solution for 5 min. To this was added cesium carbonate (59.9 mg, 0.184 mmol) and argon gas was bubbled through the solution for 5 min. Allylpalladium chloride dimer (0.90 mg, 2.45 μmol) was added and argon gas was again bubbled through the solution for 5 min. The tube was sealed and heated to 90° C. for 23 h. The reaction mixture was cooled to room temperature then filtered through diatomaceous earth (Celite®), washing with ethyl acetate and methanol. The filtrate was concentrated under reduced pressure to afford tert-butyl (2,4-dimethyl-1-((5-methyl-6-oxo-5,6-dihydrobenzo[c][1,7] naphthyridin-8-yl)oxy)pentan-2-yl)carbamate (50 mg, 0.114 mmol, 93% yield) as a colorless solid. LC/MS (ESI) m/e 440.2 [(M+H)⁺, calcd for C₂₅H₃₄N₃O₄, 440.3]; LC/MS retention time (Method E): t_R=1.56 min.

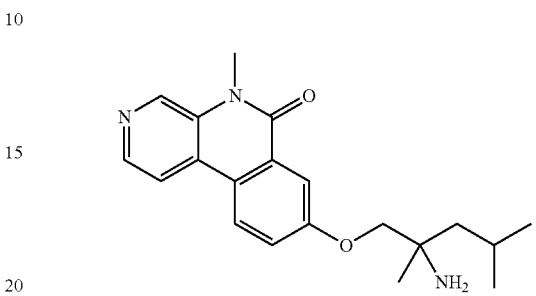

Part D: 8-((2-Amino-2,4-dimethylpentyl)oxy)-5-methylbenzo[c][1,7]naphthyridin-6(5H)-one To a solution of tert-butyl (2,4-dimethyl-1-((5-methyl-6-oxo-5,6-dihydrobenzo[c][1,7]naphthyridin-8-yl)oxy)pentan-2-yl)carbamate (50 mg, 0.114 mmol) in DCM (1 mL) cooled to 0° C. was added TFA (1 mL, 12.98 mmol). The mixture was stirred at 0° C. for 30 min, then at room temperature for 3 h. The solvent was removed under reduced pressure and the residue purified via prep HPLC (0.1% TFA in ACN) to afford 8-((2-amino-2,4-dimethylpentyl)oxy)-5-methylbenzo[c][1,7]naphthyridin-6(5H)-one, 2 TFA (17.3 mg, 0.030 mmol, 27% yield) as a pale yellow solid. LC/MS (ESI) m/e 340.2 [(M+H)⁺, calcd for C₂₀H₂₆N₃O₂, 340.2]; LC/MS retention time (Method E): t_R=0.50 min; ¹H NMR (400 MHz, METHANOL-d₄) δ 8.98 (br. s., 1H), 8.63 (d, J=9.0 Hz, 1H), 8.56 (br. s., 1H), 8.47 (d, J=5.5 Hz, 1H), 8.09 (d, J=3.0 Hz, 1H), 7.69 (dd, J=8.8, 2.8 Hz, 1H), 4.41-4.32 (m, 1H), 4.30-4.21 (m, 1H), 3.93 (s, 3H), 2.00-1.84 (m, 2H), 1.81-1.70 (m, 1H), 1.56 (s, 3H), 1.10 (d, J=6.5 Hz, 3H), 1.06 (d, J=6.5 Hz, 3H), two exchangeable protons not observed; HPLC purity (Method A1): 99% t_R=8.36 min; HPLC purity (Method B1): 99% t_R=9.25 min.

Example 8

8-((2-amino-2,4-dimethylpentyl)oxy)benzo[c][1,7]naphthyridin-6(5H)-one

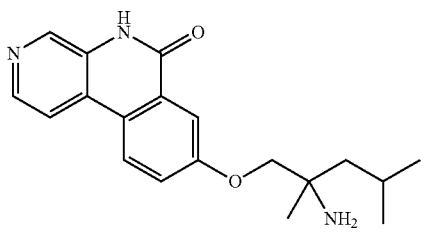

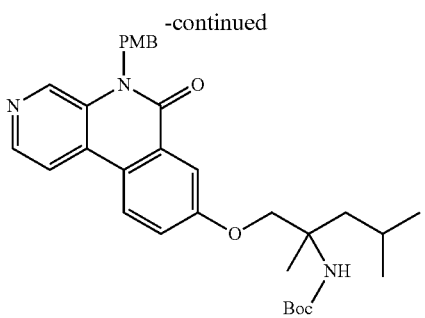

Part A: Tert-butyl (1-((5-(4-methoxybenzyl)-6-oxo-5,6-dihydrobenzo[c][1,7]naphthyridin-8-yl)oxy)-2,4-dimethylpentan-2-yl)carbamate To a solution of 8-chloro-5-(4-methoxybenzyl)benzo[c][1,7]naphthyridin-6(5H)-one (100 mg, 0.285 mmol) (prepared in Example 1, Part D) in toluene (1 mL) was added di-tert-butyl(2',4',6'-triisopropyl-3-methoxy-6-methyl-[1,1'-biphenyl]-2-yl)phosphine (5.34 mg, 0.011 mmol) and tert-butyl (1-hydroxy-2,4-dimethylpentan-2-yl)carbamate (99 mg, 0.428 mmol) (prepared in Example 7, Part B). Argon gas was bubbled through the solution for 5 min. To this was added cesium carbonate (139 mg, 0.428 mmol) and argon gas was bubbled through the solution for 5 min. Allylpalladium chloride dimer (2.086 mg, 5.70 µmol) was added and argon gas was again bubbled through the solution for 5 mins. The tube was sealed and heated to 90° C. for 23 h. The reaction mixture was filtered through diatomaceous earth (Celite®), washing with ethyl acetate and methanol. The filtrate was concentrated under reduced pressure to afford tert-butyl (1-((5-(4-methoxybenzyl)-6-oxo-5,6-dihydrobenzo[c][1,7]naphthyridin-8-yl)oxy)-2,4-dimethylpentan-2-yl)carbamate (140 mg, 0.257 mmol, 90% yield) as a colorless solid. LC/MS (ESI) m/e 546.2 [(M+H)$^+$, calcd for $C_{32}H_{40}N_3O_5$, 546.3]; LC/MS retention time (Method E): $t_R$=1.02 min.

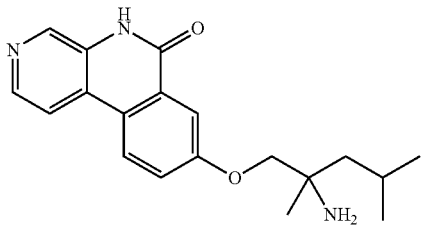 [SMILES: CC(C)CC(C)(N)COc1ccc2c(c1)c(=O)[nH]c1cnccc12]

Part B: 8-((2-amino-2,4-dimethylpentyl)oxy)benzo[c][1,7]naphthyridin-6(5H)-one To tert-butyl (1-((5-(4-methoxybenzyl)-6-oxo-5,6-dihydrobenzo[c][1,7]naphthyridin-8-yl)oxy)-2,4-dimethylpentan-2-yl)carbamate (140 mg, 0.257 mmol) was added TFA (2 mL, 26.0 mmol) and methanesulfonic acid (8.33 µL, 0.128 mmol) and the mixture was heated to 80° C. for 5 h. The reaction mixture was cooled to room temperature and concentrated under reduced pressure. The residue was purified via prep HPLC (0.1% TFA in ACN) to afford 8-((2-amino-2,4-dimethylpentyl)oxy)benzo[c][1,7]naphthyridin-6(5H)-one, 2 TFA (40 mg, 0.070 mmol, 27% yield) as a pale yellow solid. LC/MS (ESI) m/e 326.2 [(M+H)$^+$, calcd for $C_{19}H_{24}N_3O_2$, 326.2]; LC/MS retention time (Method A3): $t_R$=1.76 min; $^1$H NMR (400 MHz, METHANOL-$d_4$) δ 8.70 (br. s., 1H), 8.63 (d, J=8.8 Hz, 1H), 8.48 (d, J=5.6 Hz, 1H), 8.44 (d, J=5.6 Hz, 1H), 8.06 (d, J=2.8 Hz, 1H), 7.71 (dd, J=8.8, 2.8 Hz, 1H), 4.36 (d, J=10.0 Hz, 1H), 4.26 (d, J=10.0 Hz, 1H), 1.94-1.87 (m, 2H), 1.78-1.74 (m, 1H), 1.56 (s, 3H), 1.09 (d, J=6.5 Hz, 3H), 1.05 (d, J=6.5 Hz, 3H), two exchangeable protons not observed; HPLC purity (Method A1): 98% $t_R$=7.70 min; HPLC purity (Method B1): 98% $t_R$=8.42 min.

Example 9

8-((2-amino-2,4-dimethylpentyl)oxy)-4,5-dimethylbenzo[c][1,7]naphthyridin-6(5H)-one

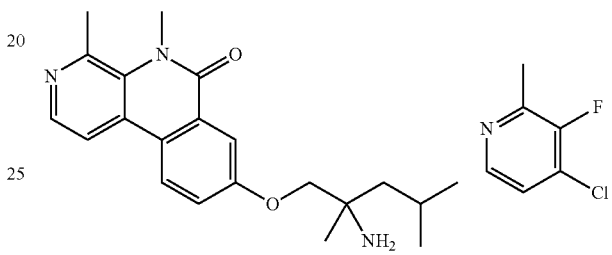

Part A: 4-Chloro-3-fluoro-2-methylpyridine

To a solution of 2,2,6,6-tetramethylpiperidine (6.47 mL, 38.0 mmol) in tetrahydrofuran (130 mL) cooled to 0° C. was added N-butyllithium (15.21 mL, 38.0 mmol) dropwise. The solution was cooled to −78° C. and 4-chloro-3-fluoropyridine (5 g, 38.0 mmol) was added dropwise and the solution stirred for 25 min. Iodomethane (2.38 mL, 38.0 mmol) was added and the solution stirred at −78° C. for 30 min, then at room temperature for 12 h. The reaction mixture was quenched with saturated aqueous sodium bicarbonate and extracted with ethyl acetate (2×25 mL). The combined organic layers were washed with brine (15 mL), dried over sodium sulphate, filtered, and concentrated under reduced pressure. The residue was purified by silica gel chromatography (hexane and ethyl acetate) to afford 4-chloro-3-fluoro-2-methylpyridine (2 g, 13.74 mmol, 36% yield) as colorless oil. $^1$H NMR (400 MHz, CHLOROFORM-d) δ 8.34 (s, 1H), 8.28 (s, 1H), 2.40 (s, 3H).

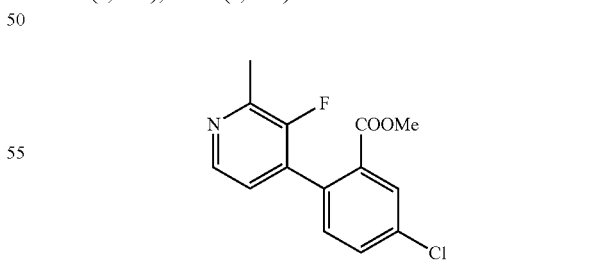

Part B: Methyl 5-chloro-2-(3-fluoro-2-methylpyridin-4-yl)benzoate

To a microwave vial was added 4-chloro-3-fluoro-2-methylpyridine (2.5 g, 17.17 mmol) 1,4-dioxane (10 mL) and water (5 mL). To this was added methyl 5-chloro-2-(4, 4,5,5-tetramethyl-1,3,2-dioxaborolan-2-yl)benzoate (5.60 g, 18.89 mmol) (prepared in Example 1, Part B) and cesium carbonate (11.19 g, 34.3 mmol). N₂ was bubbled through the mixture for 5 min. To this was added tetrakis(triphenylphosphine)palladium(0) (0.992 g, 0.859 mmol) and N₂ was bubbled through the mixture for 5 min. The reaction mixture was heated in the microwave at 100° C. for 2 h. The reaction mixture was cooled to room temperature and extracted with DCM (3×5 mL). The organic layer was washed with water (2×50 mL) and brine (1×50 mL). The organic layer was dried over Na₂SO₄, filtered and concentrated under reduced pressure. The residue was purified via silica gel chromatography (hexane and ethyl acetate) to afford methyl 5-chloro-2-(3-fluoro-2-methylpyridin-4-yl)benzoate (1.1 g, 3.93 mmol, 23% yield) as brown oil. LC/MS (ESI) m/e 280.0 [(M+H)⁺, calcd for C₁₄H₁₂ClNO₂, 280.1]; LC/MS retention time (Method B): $t_R$=1.01 min.

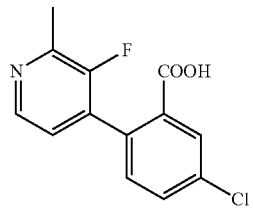 [SMILES: Cc1nccc(-c2ccc(Cl)cc2C(=O)O)c1F]

Part C:
5-Chloro-2-(3-fluoro-2-methylpyridin-4-yl)benzoic acid

To methyl 5-chloro-2-(3-fluoro-2-methylpyridin-4-yl)benzoate (2.2 g, 7.87 mmol) in tetrahydrofuran (10 mL), MeOH (10 mL), and water (10 mL) was added lithium hydroxide (1.130 g, 47.2 mmol). The solution was stirred at room temperature for 12 h. The solution was concentrated under reduced pressure. The residue was diluted with water and adjusted the pH to 3 using 1.5N HCl and extracted with DCM (2×5 mL). The combined organic layers were dried over sodium sulphate, filtered, and concentrated under reduced pressure to afford 5-chloro-2-(3-fluoro-2-methylpyridin-4-yl)benzoic acid (1.5 g, 5.65 mmol, 72% yield) as pale yellow oil. LC/MS (ESI) m/e 266.8 [(M+H)⁺, calcd for C₁₃H₁₀ClFNO₂, 266.0]; LC/MS retention time (Method E): $t_R$=0.77 min.

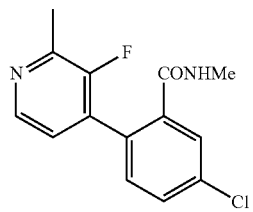

Part D: 5-Chloro-2-(3-fluoro-2-methylpyridin-4-yl)-N-methylbenzamide

To 5-chloro-2-(3-fluoro-2-methylpyridin-4-yl)benzoic acid (1.5 g, 5.65 mmol) in DMF (3 mL) cooled to 0° C. was added HOBT (1.73 g, 11.29 mmol) and EDC (1.62 g, 8.47 mmol). The mixture was stirred for 5 min. To this was added methylamine hydrochloride (1.53 g, 22.58 mmol) and the mixture stirred for 5 min. DIPEA (2.96 mL, 16.94 mmol) was added and the mixture stirred for 12 h. The reaction mixture was diluted with ice water and extracted with DCM (2×10 mL). The combined organic layers were washed with brine, dried over sodium sulphate, filtered, and concentrated under reduced pressure to afford 5-chloro-2-(3-fluoro-2-methylpyridin-4-yl)-N-methylbenzamide (1.1 g, 3.95 mmol, 70% yield) light pink solid. LC/MS (ESI) m/e 279.0 [(M+H)⁺, calcd for C₁₄H₁₃ClN₂O, 279.1]; LC/MS retention time (Method E): $t_R$=0.51 min.

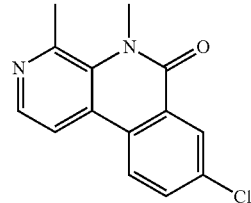 [SMILES: Cc1nccc2c3ccc(Cl)cc3c(=O)n(C)c12]

Part E: 8-chloro-4,5-dimethylbenzo[c][1,7]naphthyridin-6(5H)-one

To a solution of 5-chloro-2-(3-fluoro-2-methylpyridin-4-yl)-N-methylbenzamide (1.1 g, 3.95 mmol) in tetrahydrofuran (6 mL) cooled to 0° C. was added NaH (0.316 g, 7.89 mmol) in portions. The mixture was stirred at 0° C. for 30 min, then at room temperature for 12 h. The reaction mixture was quenched with ice water. The solid that was formed was collected by vacuum filtration. The solid was purified by prep HPLC (10 mmol ammonium acetate in ACN:water pH adjusted to 4 using acetic acid) to afford 8-chloro-4,5-dimethylbenzo[c][1,7]naphthyridin-6(5H)-one (105 mg, 0.406 mmol, 10% yield) as a white solid. LC/MS (ESI) m/e 258.8 [(M+H)⁺, calcd for C₁₄H₁₂ClN₂O, 259.1]; LC/MS retention time (Method A3): $t_R$=1.91 min; ¹H NMR (300 MHz, CHLOROFORM-d) δ 8.54 (d, J=2.3 Hz, 1H), 8.45 (d, J=5.3 Hz, 1H), 8.22 (d, J=8.7 Hz, 1H), 7.85 (d, J=5.3 Hz, 1H), 7.77 (dd, J=8.7, 2.3 Hz, 1H), 3.87 (s, 3H), 2.93 (s, 3H).

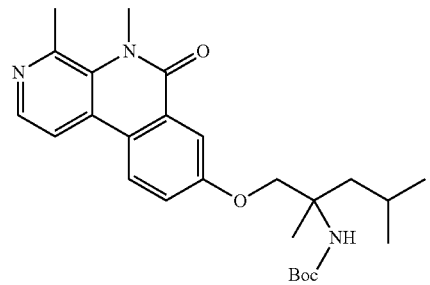 [SMILES: Cc1nccc2c3ccc(OCC(C)(CC(C)C)NC(=O)OC(C)(C)C)cc3c(=O)n(C)c12]

Part F: Tert-butyl (1-((4,5-dimethyl-6-oxo-5,6-dihydrobenzo[c][1,7]naphthyridin-8-yl)oxy)-2,4-dimethylpentan-2-yl)carbamate To a solution of 8-chloro-4,5-dimethylbenzo[c][1,7]naphthyridin-6(5H)-one (0.100 g, 0.387 mmol) in toluene (1 mL) was added tert-butyl (1-hydroxy-2,4-dimethylpentan-2-yl)carbamate (0.179 g, 0.773 mmol) (prepared in Example 7, Part B) and Cs₂CO₃ (0.252 g, 0.773 mmol). Argon gas was bubbled through the solution for 5 min. To this was added allylpalladium chloride dimer (4.24 mg, 0.012 mmol) and di-tert-butyl(2',4',6'-triisopropyl-3-methoxy-6-methyl-[1,1'-biphenyl]-2-yl)phosphine (10.87 mg, 0.023 mmol) and argon gas was again bubbled through the solution for 5 mins. The tube was sealed and heated to 90° C. for 21 h. The reaction mixture was filtered through diatomaceous earth (Celite®), washing with ethyl acetate. The filtrate was concentrated under reduced pressure to afford tert-butyl (1-((4,5-dimethyl-6-oxo-5,6-dihydrobenzo[c][1,7]naphthyridin-8-yl)oxy)-2,4-dimethylpentan-2-yl)carbamate (0.250 g, 0.283 mmol, 73% yield) as a colorless solid. LC/MS (ESI) m/e 454.2 [(M+H)$^+$, calcd for $C_{26}H_{36}N_3O_4$, 454.3]; LC/MS retention time (Method A3): $t_R$=2.34 min.

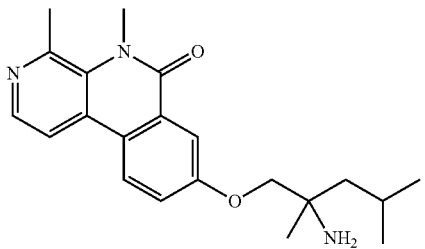 [SMILES: Cc1nccc2c3ccc(OCC(C)(N)CC(C)C)cc3c(=O)n(C)c12]

Part G: 8-((2-amino-2,4-dimethylpentyl)oxy)-4,5-dimethylbenzo[c][1,7]naphthyridin-6(5H)-one, 2 TFA To tert-butyl (1-((4,5-dimethyl-6-oxo-5,6-dihydrobenzo[c][1,7]naphthyridin-8-yl)oxy)-2,4-dimethylpentan-2-yl)carbamate (0.250 g, 0.281 mmol) was added 4N HCl in dioxane (1 mL, 32.9 mmol) and the mixture was stirred at room temperature for 2 h. The reaction mixture was concentrated under reduced pressure. The residue was purified via prep HPLC (0.1% TFA in ACN) to afford 8-((2-amino-2,4-dimethylpentyl)oxy)-4,5-dimethylbenzo[c][1,7]naphthyridin-6(5H)-one, 2 TFA (82.5 mg, 0.141 mmol, 50% yield) as a pale yellow solid. LC/MS (ESI) m/3 354.0 [(M+H)$^+$, calcd for $C_{19}H_{24}N_3O_2$, 354.2]; LC/MS retention time (Method J): $t_R$=0.75 min; $^1$H NMR (400 MHz, METHANOL-$d_4$) δ ppm 1.02-1.12 (m, 6H) 1.55 (s, 3H) 1.74 (d, J=8.97 Hz, 1H) 1.84-1.97 (m, 2H) 3.10 (s, 3H) 3.35-3.39 (m, 2H) 3.93 (s, 3H) 4.00 (s, 1H) 4.25-4.32 (m, 1H) 4.34-4.40 (m, 1H) 7.71 (dd, J=8.94, 2.79 Hz, 1H) 8.08 (d, J=2.76 Hz, 1H) 8.47 (d, J=6.09 Hz, 1H) 8.58-8.69 (m, 2H), two exchangeable protons not observed; HPLC purity (Method C1): 95% $t_R$=1.09 min; HPLC purity (Method D): 95% $t_R$=0.75 min.

Example 10

(S)-8-((2-amino-2,4-dimethylpentyl)oxy)-4,5-dimethylbenzo[c][1,7]naphthyridin-6(5H)-one

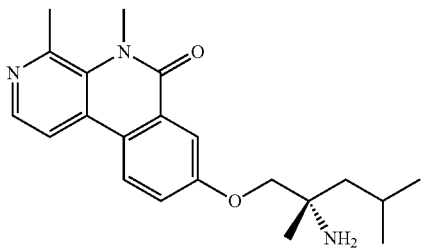 [SMILES: Cc1nccc2c3ccc(OC[C@@](C)(N)CC(C)C)cc3c(=O)n(C)c12]

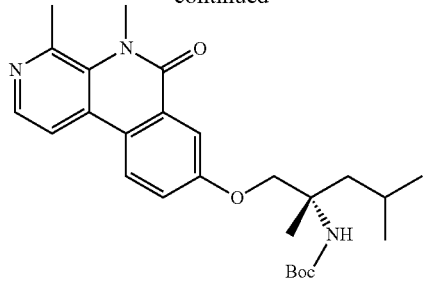

Part A: (S)-tert-butyl (1-((4,5-dimethyl-6-oxo-5,6-dihydrobenzo[c][1,7]naphthyridin-8-yl)oxy)-2,4-dimethylpentan-2-yl)carbamate Racemic tert-butyl (1-((4,5-dimethyl-6-oxo-5,6-dihydrobenzo[c][1,7]naphthyridin-8-yl)oxy)-2,4-dimethylpentan-2-yl)carbamate (60 mg, 0.132 mmol) (Example 9, Part F) was subjected to chiral resolution via HPLC. (CHIRAL CEL ADH column 50% (0.2% DEA in n-hexane):50% ethanol). Enantiomer 1: (S)-tert-butyl (1-((4,5-dimethyl-6-oxo-5,6-dihydrobenzo[c][1,7]naphthyridin-8-yl)oxy)-2,4-dimethylpentan-2-yl)carbamate (20 mg, 0.042 mmol, 32% yield); Chiral HPLC purity (Column: CHIRAL CEL ADH (250×4.6 mm) 5 micron; Mobile phase A: 0.2% DEA in n-Hexane (50) B: Ethanol (50); Flow 1.0 mL/min): 100% $t_R$=6.51 min (racemate shows peaks at $t_R$=6.51 and 9.24 min). Absolute stereochemistry assumed based on the potency of the final compound relative to its enantiomer, with the (S)-enantiomer showing better potency then the (R)-enantiomer.

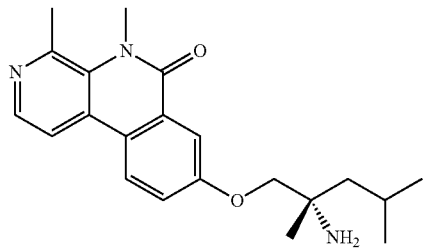

Part B: (S)-8-((2-amino-2,4-dimethylpentyl)oxy)-4,5-dimethylbenzo[c][1,7]naphthyridin-6(5H)-one To a solution of (S)-tert-butyl (1-((4,5-dimethyl-6-oxo-5,6-dihydrobenzo[c][1,7]naphthyridin-8-yl)oxy)-2,4-dimethylpentan-2-yl)carbamate (0.017 g, 0.037 mmol) in DCM (0.5 mL) cooled to 0° C. was added 4 N HCl in 1,4-dioxane) (0.5 mL, 16.46 mmol). The mixture was warmed to room temperature and stirred for 1 h. The reaction mixture was concentrated under reduced pressure. Obtained (S)-8-((2-amino-2,4-dimethylpentyl)oxy)-4,5-dimethylbenzo[c][1,7]naphthyridin-6(5H)-one, 2 HCl (15.73 mg, 0.037 mmol, 98% yield). LC/MS (ESI) m/3 354.2 [(M+H)$^+$, calcd for $C_{19}H_{24}N_3O_2$, 354.2]; LC/MS retention time (Method A3): $t_R$=1.82 min; $^1$H NMR (400 MHz, METHANOL-$d_4$) δ 8.63-8.65 (m, 3H), 8.46 (d, J=6.00 Hz, 1H), 8.07 (d, J=2.80 Hz, 1H), 7.71 (dd, J=2.40, 9.00 Hz, 1H), 4.37 (d, J=10.40 Hz, 1H), 4.27 (d, J=10.00 Hz, 1H), 3.92 (s, 3H), 3.10 (s, 3H), 1.85-1.86 (m, 2H), 1.70-1.71 (m, 1H), 1.54 (s, 3H), 1.05 (dd, J=6.40, 20.00 Hz, 6H), two exchangeable protons not observed; HPLC purity (Method A1): 95% $t_R$=8.15 min; HPLC purity (Method B1): 99% $t_R$=9.17 min.

Example 11

(R)-8-((2-amino-2,4-dimethylpentyl)oxy)-4,5-dimethylbenzo[c][1,7]naphthyridin-6(5H)-one

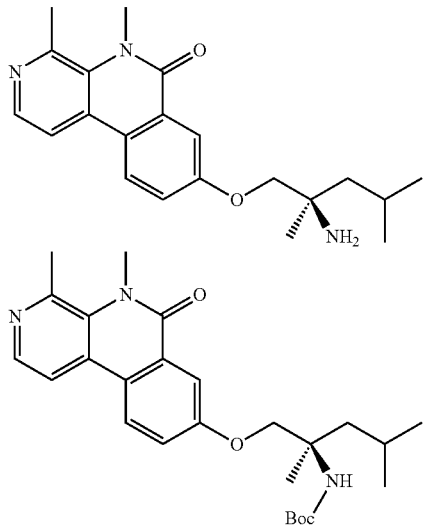

Part A: (R)-tert-butyl (1-((4,5-dimethyl-6-oxo-5,6-dihydrobenzo[c][1,7]naphthyridin-8-yl)oxy)-2,4-dimethylpentan-2-yl)carbamate Racemic tert-butyl (1-((4,5-dimethyl-6-oxo-5,6-dihydrobenzo[c][1,7]naphthyridin-8-yl)oxy)-2,4-dimethylpentan-2-yl)carbamate (60 mg, 0.132 mmol) (Example 9, Part F) was subjected to chiral resolution via HPLC. (CHIRAL CEL ADH column 50% (0.2% DEA in n-hexane):50% ethanol).

Enantiomer 2: (R)-tert-butyl (1-((4,5-dimethyl-6-oxo-5,6-dihydrobenzo[c][1,7]naphthyridin-8-yl)oxy)-2,4-dimethylpentan-2-yl)carbamate (23 mg, 0.048 mmol, 36% yield); Chiral HPLC purity (Column: CHIRAL CEL ADH (250×4.6 mm) 5 micron; Mobile phase A: 0.2% DEA in n-Hexane (50) B: Ethanol (50); Flow 1.0 mL/min): 100% $t_R$=9.24 min (racemate shows peaks at $t_R$=6.51 and 9.24 min). Absolute stereochemistry assumed based on the potency of the final compound relative to its enantiomer, with the (S)-enantiomer showing better potency then the (R)-enantiomer.

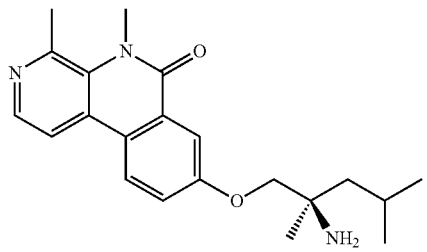 [SMILES: Cc1nccc2c3ccc(OC[C@](C)(N)CC(C)C)cc3c(=O)n(C)c12]

Part B: (R)-8-((2-amino-2,4-dimethylpentyl)oxy)-4,5-dimethylbenzo[c][1,7]naphthyridin-6(5H)-one To a solution of (R)-tert-butyl (1-((4,5-dimethyl-6-oxo-5,6-dihydrobenzo[c][1,7]naphthyridin-8-yl)oxy)-2,4-dimethylpentan-2-yl)carbamate (0.0198 g, 0.044 mmol) in DCM (0.5 mL) cooled to 0° C. was added 4 N HCl in 1,4-dioxane (0.5 mL, 16.46 mmol). The mixture was warmed to room temperature and stirred for 1 h. The reaction mixture was concentrated under reduced pressure. Obtained (R)-8-((2-amino-2,4-dimethylpentyl)oxy)-4,5-dimethylbenzo[c][1,7]naphthyridin-6(5H)-one, 2 HCl (15.73 mg, 0.037 mmol, 98% yield). LC/MS (ESI) m/3 354.2 [(M+H)$^+$, calcd for $C_{19}H_{24}N_3O_2$, 354.2]; LC/MS retention time (Method A3): $t_R$=1.82 min; $^1$H NMR (400 MHz, METHANOL-$d_4$) δ 8.61-8.63 (m, 2H), 8.46 (d, J=6.40 Hz, 1H), 8.07 (d, J=2.80 Hz, 1H), 7.71 (dd, J=2.80, 8.80 Hz, 1H), 4.37 (d, J=10.40 Hz, 1H), 4.27 (d, J=10.40 Hz, 1H), 3.92 (s, 3H), 3.09 (s, 3H), 1.85-1.86 (m, 2H), 1.72-1.74 (m, 1H), 1.54 (s, 3H), 1.05 (dd, J=6.40, 20.00 Hz, 6H), two exchangeable protons not observed; HPLC purity (Method A1): 95% $t_R$=8.13 min; HPLC purity (Method B1): 99% $t_R$=9.16 min.

Example 12

8-((2-amino-1,1-dideutero-2,4-dimethylpentyl)oxy)-9-chloro-5-ethyl-4-methylbenzo[c][1,7]naphthyridin-6(5H)-one

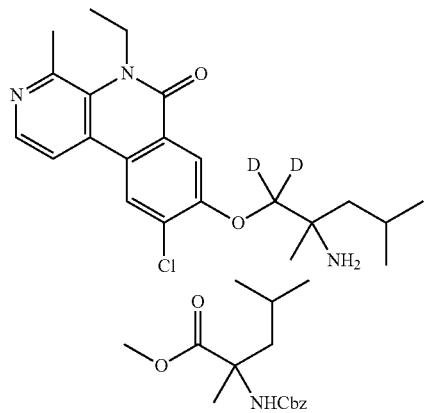

Part A. Methyl 2-(((benzyloxy)carbonyl)amino)-2,4-dimethylpentanoate

To a stirred solution of methyl 2-amino-2,4-dimethylpentanoate (28 g, 176 mmol), DIPEA (154 mL, 879 mmol) in THF (300 mL) at 0° C. was added benzyl chloroformate (30.1 mL, 211 mmol). The reaction mixture was warmed to room temperature and stirred overnight. Ethyl acetate (500 mL) and water (250 mL) were added to the reaction mixture. The organic layer was separated, dried over Na$_2$SO$_4$, filtered and concentrated under reduced pressure. The residue was purified by silica gel chromatography to afford methyl 2-(((benzyloxy)carbonyl)amino)-2,4-dimethylpentanoate (40 g, 136 mmol, 78% yield) as a brown oil. $^1$H NMR (400 MHz, CHLOROFORM-d) δ 7.41-7.29 (m, 5H), 5.81 (br. s., 1H), 5.10 (s, 2H), 3.76 (s, 3H), 2.24 (d, J=14.8 Hz, 1H), 1.74-1.66 (m, 1H), 1.64-1.54 (m, 4H), 0.89 (d, J=6.5 Hz, 3H), 0.80 (d, J=6.5 Hz, 3H); LCMS (ESI) m/e 294.1 [(M+H)+, calcd C$_{16}$H$_{24}$NO$_4$, 294.2]; LC/MS retention time (Method N): t$_R$=1.07 min.

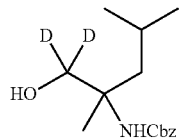

Part B. Benzyl (1,1-dideutero-1-hydroxy-2,4-dimethylpentan-2-yl)carbamate

To a solution of methyl 2-(((benzyloxy)carbonyl)amino)-2,4-dimethylpentanoate (2 g, 6.82 mmol) in THF (10 mL) at 0° C. was slowly added lithium aluminum deuteride (0.286 g, 6.82 mmol). The reaction mixture was allowed to warm to room temperature and stirred for 12 h. The reaction mixture was cooled to 0° C. and quenched with saturated aqueous NaOH (0.5 mL) and water (1 mL). The reaction mixture was then filtered through diatomaceous earth (Celite®), eluting with additional THF (10 mL). The filtrate was then concentrated under reduced pressure. The crude material was purified by silica gel chromatography (0-30% EtOAc in petroleum ether) to afford benzyl (1,1-dideutero-1-hydroxy-2,4-dimethylpentan-2-yl)carbamate (1.6 g, 5.98 mmol, 88% yield) as a colorless oil. $^1$H NMR (400 MHz, DMSO-d$_6$) δ 7.45-7.27 (m, 5H), 4.98 (d, J=4.5 Hz, 2H), 1.76-1.58 (m, 2H), 1.43-1.34 (m, 1H), 1.14 (s, 3H), 0.87 (d, J=3.5 Hz, 3H), 0.86 (d, J=3.5 Hz, 3H), two exchangeable protons not observed.

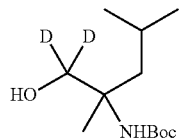

Part C. tert-butyl (1,1-dideutero-1-hydroxy-2,4-dimethylpentan-2-yl)carbamate To a stirred solution of benzyl (1,1-dideutero-1-hydroxy-2,4-dimethylpentan-2-yl)carbamate (1.5 g, 5.61 mmol) in MeOH (15 mL) was added BOC$_2$O (2.61 mL, 11.22 mmol), TEA (1.56 mL, 11.22 mmol) followed by portionwise addition of Pd/C (1.19 g, 1.12 mmol) under a nitrogen atmosphere. The reaction mixture was purged with H$_2$ gas and stirred under 1 atm hydrogen pressure at room temperature for 12 h. The reaction mixture was diluted with methanol (50 mL), filtered through diatomaceous earth (Celite®). The bed was washed with methanol (50 mL). The volatiles were evaporated to dryness under reduced pressure and the residue obtained was purified by silica gel column chromatography (0-20% EtOAc in petroleum ether) to afford tert-butyl (1,1-dideutero-1-hydroxy-2,4-dimethylpentan-2-yl)carbamate (1.08 g, 4.17 mmol, 74% yield) as a off-white semi solid. $^1$H NMR: 400 MHz, DMSO-d6: δ 6.06 (s, 1H), 4.57 (s, 1H), 1.69-1.62 (m, 2H), 1.43-1.38 (m, 1H), 1.28 (s, 9H), 1.10 (s, 3H), 0.86 (q, J=-20.00 Hz, 6H).

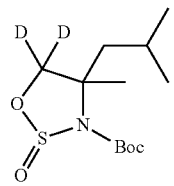 [SMILES: [2H]C1([2H])OS(=O)N(C(=O)OC(C)(C)C)C1(C)CC(C)C]

Part D. tert-butyl 5,5-dideutero-4-isobutyl-4-methyl-1,2,3-oxathiazolidine-3-carboxylate 2-oxide To a stirred solution of SOCl$_2$ (0.375 mL, 5.14 mmol) in DCM (10 mL) cooled to 0° C. was added imidazole (1.02 g, 15.00 mmol) followed by TEA (1.31 mL, 9.43 mmol) dropwise under a nitrogen atmosphere. The reaction mixture was stirred at 0° C. for 20 min. A solution of tert-butyl (1,1-dideutero-1-hydroxy-2,4-dimethylpentan-2-yl)carbamate (1.0 g, 4.29 mmol) in DCM (5 mL) was added dropwise to the reaction mixture at 0° C. and the reaction mixture was allowed to warm to room temperature and stirring continued for 12 h. The reaction mixture was quenched with water (20 mL) and extracted with DCM (2×20 mL). The combined organic extracts were washed with brine (20 mL), dried over sodium sulphate, filtered and volatiles were evaporated to dryness under reduced pressure to afford crude tert-butyl 5,5-dideutero-4-isobutyl-4-methyl-1,2,3-oxathiazolidine-3-carboxylate 2-oxide (1.16 g, 4.15 mmol, 97% yield) as a colorless oil. The product was carried forward without purification. $^1$H NMR (400 MHz, DMSO-d$_6$) δ 1.83-1.58 (m, 3H), 1.48 (s, 3H), 1.46 (s, 9H), 0.94 (d, J=6.5 Hz, 3H), 0.85 (d, J=6.5 Hz, 3H).

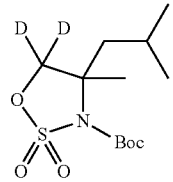 [SMILES: [2H]C1([2H])OS(=O)(=O)N(C(=O)OC(C)(C)C)C1(C)CC(C)C]

Part E. Tert-butyl 5,5-dideuterio-4-isobutyl-4-methyl-1,2,3-oxathiazolidine-3-carboxylate 2,2-dioxide To a stirred solution of tert-butyl 5,5-dideutero-4-isobutyl-4-methyl-1,2,3-oxathiazolidine-3-carboxylate 2-oxide (0.8 g, 2.86 mmol) in acetonitrile (7 mL) and water (5 mL) cooled to 0° C. was added ruthenium(III) chloride hydrate (1.61 g, 7.16 mmol) and the mixture stirred for 30 min. Sodium periodate (0.122 g, 0.573 mmol) was added portionwise to the reaction mixture at 0° C. and the reaction mixture was allowed to warm to room temperature and stirred for 4 h. The reaction mixture was diluted with water (50 mL) and extracted with ethyl acetate (2×25 mL). The combined organic extracts were washed with water (25 mL), brine (25 mL), dried over sodium sulphate, filtered, and concentrated under reduced pressure. The residue was purified by silica gel chromatography (0-30% EtOAc in petroleum ether) to afford tert-butyl 5,5-dideuterio-4-isobutyl-4-methyl-1,2,3-oxathiazolidine-3-carboxylate 2,2-dioxide (0.48 g, 1.544 mmol, 54% yield) as an off-white semi-solid in good purity based on $^1$H NMR. $^1$H NMR (400 MHz, DMSO-d$_6$) δ 1.93-1.81 (m, 1H), 1.79-1.61 (m, 2H), 1.48 (s, 9H), 1.48 (s, 3H), 0.93 (d, J=6.5 Hz, 3H), 0.91 (d, J=6.5 Hz, 3H).

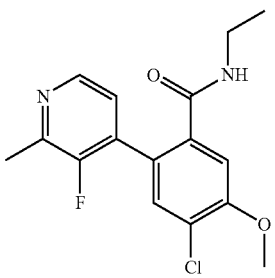 [SMILES: CCNC(=O)c1cc(OC)c(Cl)cc1-c1ccnc(C)c1F]

Part F: 4-chloro-N-ethyl-2-(3-fluoro-2-methylpyridin-4-yl)-5-methoxybenzamide

To a 100 mL round bottom flask was added 4-chloro-2-(3-fluoro-2-methylpyridin-4-yl)-5-methoxybenzoic acid (0.15 g, 0.507 mmol) (prepared in Example 5, Part D), HATU (0.193 g, 0.507 mmol), and DIPEA (0.089 mL, 0.507 mmol) in DMF (5 mL). To this solution was added ethanamine hydrochloride (0.041 g, 0.507 mmol) and the mixture stirred at room temperature for 12 h. The mixture was concentrated under reduced pressure. The residue was purified by silica gel chromatography to afford 4-chloro-N-ethyl-2-(3-fluoro-2-methylpyridin-4-yl)-5-methoxybenzamide (0.13 g, 0.403 mmol, 79% yield) as a brown solid. LC/MS (ESI) m/e 323.1 [(M+H)$^+$, calcd for C$_{16}$H$_{17}$ClFN$_2$O$_2$, 323.1]; LC/MS retention time (Method B): t$_R$=0.94 min; $^1$H NMR (400 MHz, DMSO-d$_6$) δ 8.32 (s, 1H), 8.27 (d, J=5.0 Hz, 1H), 7.51 (s, 1H), 7.30 (s, 1H), 7.21 (t, J=5.3 Hz, 1H), 3.97 (s, 3H), 3.17-3.07 (m, 2H), 2.44 (d, J=3.5 Hz, 3H), 0.98 (t, J=7.3 Hz, 3H).

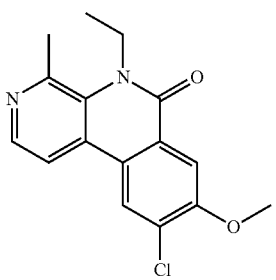 [SMILES: CCn1c(=O)c2cc(OC)c(Cl)cc2c2ccnc(C)c21]

Part G: 9-Chloro-5-ethyl-8-methoxy-4-methylbenzo[c][1,7]naphthyridin-6(5H)-one

To a stirred solution of 4-chloro-N-ethyl-2-(3-fluoro-2-methylpyridin-4-yl)-5-methoxybenzamide (0.13 g, 0.403 mmol) in NMP (5 mL) was added Cs$_2$CO$_3$ (0.394 g, 1.21 mmol) in one portion at room temperature under nitrogen atmosphere and the reaction was stirred at 100° C. for 12 h. The reaction mixture was diluted with ice water (10 mL) and extracted with EtOAc (2×20 mL). The combined organic extracts were washed with water (1×10 mL), dried over sodium sulphate, filtered, and concentrated under reduced pressure to afford 9-chloro-5-ethyl-8-methoxy-4-methylbenzo[c][1,7]naphthyridin-6(5H)-one (94 mg, 0.258 mmol, 64% yield, 85% purity) as a an off-white solid which was taken into the next step without further purification. LC/MS (ESI) m/e 303.0 [(M+H)$^+$, calcd for C$_{16}$H$_{16}$ClN$_2$O$_2$, 303.1]; LC/MS retention time (Method J): t$_R$=0.93 min; $^1$H NMR (400 MHz, DMSO-d$_6$) δ 8.74 (s, 1H), 8.34 (d, J=5.20 Hz, 1H), 8.23 (d, J=5.20 Hz, 1H), 7.91 (s, 1H), 4.41 (q, J=20.80 Hz, 2H), 4.04 (s, 3H), 2.88 (s, 3H), 1.32 (t, J=14.00 Hz, 3H).

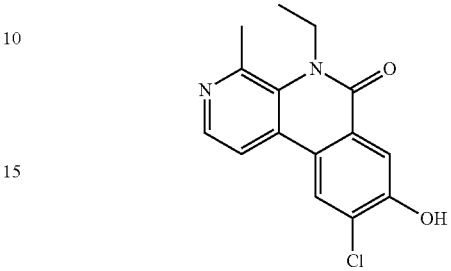

Part H: 9-Chloro-5-ethyl-8-hydroxy-4-methylbenzo[c][1,7]naphthyridin-6(5H)-one

To a solution of 9-chloro-5-ethyl-8-methoxy-4-methylbenzo[c][1,7]naphthyridin-6(5H)-one (0.074 g, 0.244 mmol) in dichloromethane (5 mL) at 0° C. was added BBr$_3$ (0.231 mL, 2.44 mmol) and the reaction mixture was stirred at 0° C. for 5 min then warmed to room temperature and stirred for 5 h. The reaction mixture was cooled to 0° C. and methanol (5 mL) was added. The solvent was evaporated under reduced pressure. The residue was purified via prep LC/MS (acetonitrile:water with 10 mM NH$_4$OAc) to afford 9-chloro-5-ethyl-8-hydroxy-4-methylbenzo[c][1,7]naphthyridin-6(5H)-one (4.4 mg, 0.014 mmol, 6% yield) as a pale yellow solid. LC/MS (ESI) m/e 289.3 [(M+H)$^+$, calcd for C$_{15}$H$_{14}$ClN$_2$O$_2$, 289.1]; LC/MS retention time (Method J): t$_R$=1.05 min; $^1$H NMR (400 MHz, METHANOL-d$_4$) δ 8.50 (s, 1H), 8.31 (d, J=5.0 Hz, 1H), 8.08 (d, J=5.5 Hz, 1H), 7.89 (s, 1H), 4.50 (q, J=7.0 Hz, 2H), 2.94 (s, 3H), 1.41 (t, J=7.0 Hz, 3H), one exchangeable proton not seen.

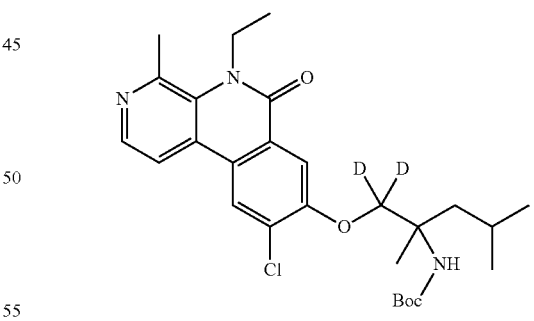

Part I: Tert-butyl (1-((9-chloro-5-ethyl-4-methyl-6-oxo-5,6-dihydrobenzo[c][1,7]naphthyridin-8-yl)oxy)-1,1-dideutero-2,4-dimethylpentan-2-yl)carbamate To a stirred solution of ethyl 9-chloro-5-ethyl-8-hydroxy-4-methylbenzo[c][1,7]naphthyridin-6(5H)-one (40 mg, 0.139 mmol) in DMF (4 mL), cooled to 0° C. was added K$_2$CO$_3$ (19.15 mg, 0.139 mmol) in portions followed by slow addition of tert-butyl 5,5-dideutero-4-isobutyl-4- methyl-1,2,3-oxathiazolidine-3-carboxylate 2-oxide (49.1 mg, 0.166 mmol). The reaction mixture was allowed to slowly warm to room temperature then stirred at 60° C. for 24 h. The reaction mixture was cooled to 0° C. and quenched with aqueous ammonium chloride (10 mL) dropwise. The aqueous layer was extracted with ethyl acetate (2×20 mL). The combined the organic extracts were washed with water (2×20 mL), brine (10 mL), dried over sodium sulphate, filtered, and concentrated under reduced pressure to afford tert-butyl (1-((9-chloro-5-ethyl-4-methyl-6-oxo-5,6-dihydrobenzo[c][1,7]naphthyridin-8-yl)oxy)-1,1-dideutero-2,4-dimethylpentan-2-yl)carbamate (50 mg, 0.099 mmol, 72% crude yield) as a brown semi-solid which was carried forward without further purification. LC/MS (ESI) m/e 504.3 [(M+H)$^+$, calcd for $C_{27}H_{35}D_2ClN_3O_4$, 504.3]; LC/MS retention time (Method B): $t_R$=1.40 min.

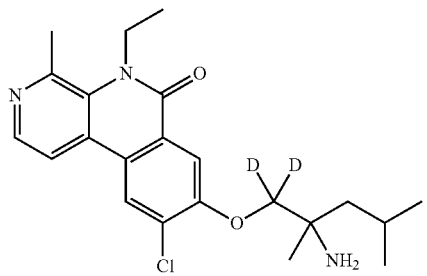 [SMILES: [2H]C([2H])(Oc1cc2c(=O)n(CC)c3c(C)nccc3c2cc1Cl)C(C)(N)CC(C)C]

Part J: 8-((2-amino-1,1-dideutero-2,4-dimethylpentyl)oxy)-9-chloro-5-ethyl-4-methylbenzo[c][1,7]naphthyridin-6(5H)-one To a solution of tert-butyl (1-((9-chloro-5-ethyl-4-methyl-6-oxo-5,6-dihydrobenzo[c][1,7]naphthyridin-8-yl)oxy)-1,1-dideutero-2,4-dimethylpentan-2-yl)carbamate (0.048 g, 0.044 mmol) in DCM (2 mL) cooled to 0° C. was added TFA (3.37 μL, 0.044 mmol). The mixture was warmed to room temperature and stirred for 4 h. The reaction mixture was concentrated under reduced pressure. The residue was purified by prep LC/MS (methanol:water with 10 mM NH$_4$OAc) to afford 8-((2-amino-1,1-dideutero-2,4-dimethylpentyl)oxy)-9-chloro-5-ethyl-4-methylbenzo[c][1,7]naphthyridin-6(5H)-one (2.9 mg, 6.89 μmol, 16% yield) as a pale yellow solid. LC/MS (ESI) m/3 404.2 [(M+H)$^+$, calcd for $C_{22}H_{27}D_2ClN_3O_2$, 404.2]; LC/MS retention time (Method A2): $t_R$=2.11 min; $^1$H NMR (400 MHz, METHANOL-d$_4$) δ 8.64 (s, 1H), 8.35 (d, J=5.5 Hz, 1H), 8.14 (d, J=5.0 Hz, 1H), 8.03 (s, 1H), 4.54 (q, J=7.0 Hz, 2H), 2.96 (s, 3H), 1.92-1.79 (m, 2H), 1.73-1.64 (m, 1H), 1.47 (s, 3H), 1.42 (t, J=7.0 Hz, 3H), 1.06 (d, J=6.5 Hz, 3H), 1.03 (d, J=6.5 Hz, 3H), two exchangeable protons not observed; HPLC purity (Method C1): 97% $t_R$=1.53 min; HPLC purity (Method D): 99% $t_R$=0.87 min.

Example 13

8-((2-amino-1,1-dideutero-2,4-dimethylpentyl)oxy)-4,5-dimethylbenzo[c][1,7]naphthyridin-6(5H)-one

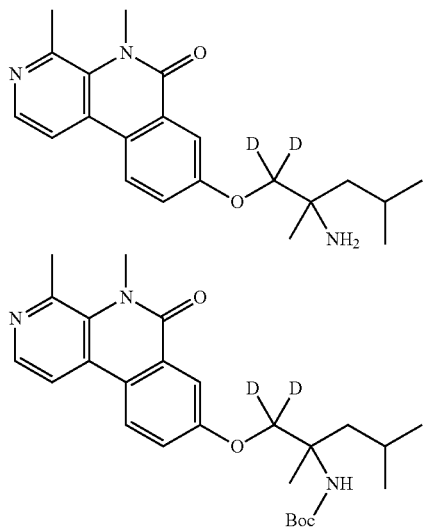

Part A: Tert-butyl (1-((4,5-dimethyl-6-oxo-5,6-dihydrobenzo[c][1,7]naphthyridin-8-yl)oxy)-1,1-difluoro-2,4-dimethylpentan-2-yl)carbamate To a stirred solution of ethyl 8-hydroxy-4,5-dimethylbenzo[c][1,7]naphthyridin-6(5H)-one (40 mg, 0.102 mmol) in DMF (4 mL), cooled to 0° C. was added NaH (2.44 mg, 0.102 mmol) portionwise followed by slow addition of tert-butyl 5,5-dideutero-4-isobutyl-4-methyl-1,2,3-oxathiazolidine-3-carboxylate 2-oxide (30.0 mg, 0.102 mmol). The reaction mixture was allowed to slowly warm to room temperature then stirred at 60° C. for 12 h. The reaction mixture was cooled to 0° C. then quenched with aqueous ammonium chloride (10 mL) dropwise and extracted with ethyl acetate (2×20 mL). The combined the organic extracts were washed with water (2×20 mL), brine (10 mL), dried over sodium sulphate, filtered, and concentrated under reduced pressure to afford tert-butyl (1-((4,5-dimethyl-6-oxo-5,6-dihydrobenzo[c][1,7]naphthyridin-8-yl)oxy)-1,1-difluoro-2,4-dimethylpentan-2-yl)carbamate (60 mg, 0.025 mmol, 25% crude yield) as a brown semi-solid which was carried without further purification. LC/MS (ESI) m/e 456.2 [(M+H)$^+$, calcd for $C_{26}H_{34}D_2N_3O_4$, 456.3]; LC/MS retention time (Method G): $t_R$=2.21 min.

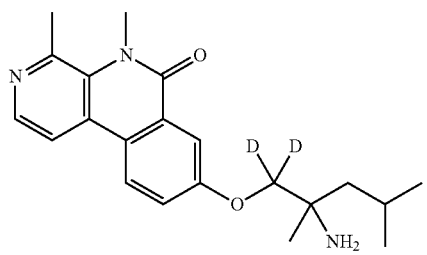 [SMILES: [2H]C([2H])(Oc1ccc2c(c1)c(=O)n(C)c1c(C)nccc21)C(C)(N)CC(C)C]

Part B: 8-((2-amino-1,1-dideutero-2,4-dimethylpentyl)oxy)-4,5-dimethylbenzo[c][1,7]naphthyridin-6(5H)-one To a solution of tert-butyl (1-((4,5-dimethyl-6-oxo-5,6-dihydrobenzo[c][1,7]naphthyridin-8-yl)oxy)-1,1-difluoro-2,4-dimethylpentan-2-yl)carbamate (60 mg, 0.021 mmol) in DCM (2 mL) cooled to 0° C. was added TFA (2 mL, 26.0 mmol). The mixture was warmed to room temperature and stirred for 4 h. The reaction mixture was cooled to 0° C. and carefully quenched with saturated aqueous sodium bicarbonate and stirred at room temperature for 30 min. The reaction mixture was transferred to a separatory funnel and the organic layer separated. The aqueous layer was extracted with DCM (2×20 mL). The combined organic layers were washed with water (10 mL), dried over sodium sulphate, filtered, and concentrated under reduced pressure. The residue was purified by prep LC/MS (methanol:water with 10 mM $NH_4OAc$) to afford 8-((2-amino-1,1-dideutero-2,4-dimethylpentyl)oxy)-4,5-dimethylbenzo[c][1,7]naphthyridin-6(5H)-one (5.4 mg, 0.012 mmol, 58% yield for two steps) as a pale yellow solid. LC/MS (ESI) m/3 356.2 [(M+H)$^+$, calcd for $C_{21}H_{26}D_2N_3O_2$, 356.2]; LC/MS retention time (Method J): $t_R$=1.10 min; $^1$H NMR (400 MHz, METHANOL-$d_4$) δ ppm 8.52 (d, J=9.04 Hz, 1H), 8.35 (d, J=5.33 Hz, 1H), 8.14 (d, J=5.40 Hz, 1H), 8.00 (d, J=2.82 Hz, 1H), 7.62 (dd, J=8.91, 2.82 Hz, 1H), 3.88-3.90 (m, 3H), 2.92-2.95 (m, 3H), 1.82-1.93 (m, 2H), 1.68-1.75 (m, 1H), 1.52 (s, 3H), 1.06 (dd, J=17.76, 6.46 Hz, 6H), two exchangeable protons not observed; HPLC purity (Method C1): 96% $t_R$=1.10 min; HPLC purity (Method D): 97% $t_R$=0.69 min.

Example 14

(S)-8-((2-amino-2,4-dimethylpentyl)oxy)-2,5-dimethylbenzo[c][1,7]naphthyridin-6(5H)-one

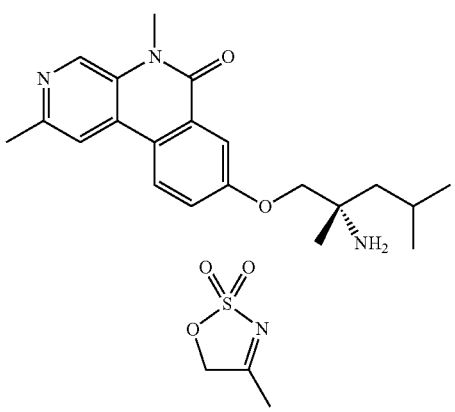

Part A. 4-methyl-5H-1,2,3-oxathiazole 2,2-dioxide

Step 1 Sulfamoyl chloride formation: In a 1000 mL, 4 neck round-bottomed flask equipped with a mechanical stirrer and an addition funnel, was charged DCM (400 mL) and chlorosulfonyl isocyanate (124 mL, 1430 mmol). Under N2, this solution was cooled to 0° C. Then formic acid (53.9 mL, 1430 mmol) was added to DCM (100 mL) and this solution was transferred to the addition funnel and the solution was added slowly to the vigorously stirring reaction mixture. Gradually a thick slurry formed. A slow exotherm was observed so additional dry ice was added to acetone bath. Once the temperature was stabilized, addition of the formic acid was continued (the addition was done in ~25 min). The mixture was allowed to gradually warm to room temperature and was stirred overnight.

Step 2: A separate 5 L, 4 neck reaction flask was charged with hydroxyacetone (72.5 mL, 953 mmol), pyridine (116 mL, 1430 mmol), and DCM (2000 mL). This solution was cooled to −5° C. under $N_2$. The sulfamoyl chloride solution was added slowly via Teflon tube over 10 min. After complete addition, the reaction was stirred for 15 min then the ice bath was removed and the reaction mixture allowed to warm to room temperature. As the reaction progressed, a gummy material formed. The material was purified via silica gel chromatography (300 g silica gel eluting with DCM). Obtained 4-methyl-5H-1,2,3-oxathiazole 2,2-dioxide (72.4 g, 536 mmol, 56% yield) as a colorless solid. $^1$H NMR (400 MHz, CHLOROFORM-d) δ 5.09 (s, 2H), 2.44 (s, 3H); LCMS (ESI) m/e 136.0 [(M+H)$^+$, calcd for $C_3H_6NO_3S$ 136.0]; LC/MS retention time (Method H): $t_R$=0.66 min.

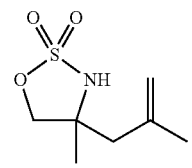

Part B. 2-(tert-butoxycarbonylamino)-2,4-dimethylpentanoic acid 4-methyl-4-(2-methylallyl)-1,2,3-oxathiazolidine 2,2-dioxide A suspension of 4-methyl-5H-1,2,3-oxathiazole 2,2-dioxide (0.541 g, 4 mmol) in methyl tert-butyl ether (30 mL) was cooled below 0° C. with an ice/IPA bath. To the cooled solution was added a solution of (2-methylallyl)magnesium chloride, 0.5 M in THF (9.60 mL, 4.80 mmol). The reaction mixture was allowed to warm to room temperature overnight. It was then quenched with a saturated solution of $NH_4Cl$ (50 mL) and EtOAc (20 mL) was added. The organic phase was separated, washed with brine (50 mL), dried over Na2SO4, filtered, and concentrated under reduced pressure to give 2-(tert-butoxycarbonylamino)-2,4-dimethylpentanoic acid 4-methyl-4-(2-methylallyl)-1,2,3-oxathiazolidine 2,2-dioxide (0.567 g, 2.96 mmol, 74% yield). $^1$H NMR (400 MHz, CHLOROFORM-d) δ 5.06 (quin, J=1.5 Hz, 1H), 4.87 (dd, J=1.7, 0.8 Hz, 1H), 4.50 (br. s., 1H), 4.40 (d, J=8.6 Hz, 1H), 4.29 (d, J=8.7 Hz, 1H), 2.56 (d, J=13.8 Hz, 1H), 2.40-2.30 (m, 1H), 1.86 (br. s, 3H), 1.49 (s, 3H); LCMS (ESI) m/e 192.1 [(M+H)$^+$, calcd for $C_7H_{14}NO_3S$ 192.1]; LC/MS retention time (Method H): $t_R$=0.50 min.

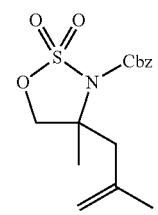 [SMILES: C=C(C)CC1(C)COS(=O)(=O)N1C(=O)OCc1ccccc1]

Part C. benzyl 4-methyl-4-(2-methylallyl)-1,2,3-oxathiazolidine-3-carboxylate 2,2-dioxide To a N₂ flushed, 100 mL round-bottomed flask was added a solution of 4-methyl-4-(2-methylallyl)-1,2,3-oxathiazolidine 2,2-dioxide (0.55 g, 2.88 mmol) in THF (10 mL). A solution of potassium tert-butoxide (4.31 mL, 4.31 mmol) in THF was added. The temperature rose to 27° C. and the solution became a suspension. The mixture was stirred at room temperature for 1 h. Benzyl carbonochloridate (1.03 mL, 7.19 mmol) was added slowly. The reaction mixture was stirred at room temperature for 2 h. The reaction mixture was then quenched with water (50 mL) and extracted with EtOAc (2×70 mL). The organic extracts were washed with brine (50 mL), dried over Na₂SO₄, filtered, and concentrated under reduced pressure. The residue was purified by silica gel chromatography (ethyl acetate/hexanes) to give benzyl 4-methyl-4-(2-methylallyl)-1,2,3-oxathiazolidine-3-carboxylate 2,2-dioxide (0.66 g, 2.028 mmol, 71% yield). $^1$H NMR (400 MHz, CHLOROFORM-d) δ 7.58-7.32 (m, 5H), 5.43-5.25 (m, 2H), 5.01 (t, J=1.5 Hz, 1H), 4.81 (d, J=0.9 Hz, 1H), 4.63 (d, J=9.5 Hz, 1H), 4.21 (d, J=9.5 Hz, 1H), 2.87 (d, J=14.1 Hz, 1H), 2.56 (d, J=14.1 Hz, 1H), 1.78 (br. s, 3H), 1.64 (s, 3H); LCMS (ESI) m/e 326.1 [(M+H)⁺, calcd for C₁₅H₂₀NO₅S 326.1]; LC/MS retention time (Method I): $t_R$=1.07 min.

The racemic compounds was separated by chiral super critical fluid chromatography (Column: OJ-H (3×25 cm, 5 μm); Mobile Phase: CO2/MeOH (90/10)) to give the two enantiomers.

Analytical super critical fluid chromatography conditions: Column: OJ-H (0.46×25 cm, 5 μm); BPR pressure: 100 bars; Temperature: 35° C.; Flow rate: 3.0 mL/min; Mobile Phase: CO₂/MeOH (90/10); Detector Wavelength: UV 200-400 nm
Enantiomer 1: (S)-benzyl 4-methyl-4-(2-methylallyl)-1,2,3-oxathiazolidine-3-carboxylate 2,2-dioxide HPLC retention time=2.53 min.
Enantiomer 2: (R)-benzyl 4-methyl-4-(2-methylallyl)-1,2,3-oxathiazolidine-3-carboxylate 2,2-dioxide HPLC retention time=2.97 min.

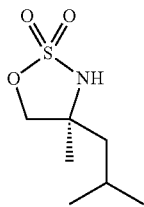

Part D. (S)-4-isobutyl-4-methyl-1,2,3-oxathiazolidine 2,2-dioxide

To a stirred solution of (S)-benzyl 4-methyl-4-(2-methylallyl)-1,2,3-oxathiazolidine-3-carboxylate 2,2-dioxide (800 mg, 2.46 mmol) in MeOH (20 mL) was added Pd/C (262 mg, 0.246 mmol) under a nitrogen atmosphere and the reaction mixture was stirred under 1 atm hydrogen pressure for 16 h. The reaction mixture was passed through diatomaceous earth (Celite®) and the pad was washed with EtOAc (15 mL). The organic layer was evaporated under reduced pressure to afford (S)-4-isobutyl-4-methyl-1,2,3-oxathiazolidine 2,2-dioxide (462 mg, 2.39 mmol, 97% yield, 95% purity) as colorless oil. The material was carried forward without further purification. $^1$H NMR (400 MHz, DMSO-d₆) δ ppm 7.69 (br, 1H) 4.33 (d, J=8.03 Hz, 1H) 4.17-4.26 (m, 1H) 1.68-1.81 (m, 1H) 1.53-1.63 (m, 1H) 1.43-1.51 (m, 1H) 1.34 (s, 3H) 0.81-1.00 (m, 6H).

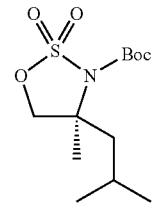 [SMILES: CC(C)C[C@@]1(C)COS(=O)(=O)N1C(=O)OC(C)(C)C]

Part E. (S)-tert-butyl 4-isobutyl-4-methyl-1,2,3-oxathiazolidine-3-carboxylate 2,2-dioxide To a stirred solution of (S)-4-isobutyl-4-methyl-1,2,3-oxathiazolidine 2,2-dioxide (7 g, 15.21 mmol) in DCM (70 mL) cooled to 0° C. was added DMAP (1.86 g, 15.21 mmol) and BOC₂O (5.30 mL, 22.82 mmol) The reaction mixture was stirred at room temperature for 12 h. The reaction mixture was transferred to a separatory funnel containing water (20 mL) and was extracted with DCM (2×60 mL). The combined organic layers were washed with brine (50 mL), dried over (Na2SO4), filtered, and concentrated under reduced pressure. The residue was purified via silica gel chromatography (30% ethyl acetate in petroleum ether) to afford (S)-tert-butyl 4-isobutyl-4-methyl-1,2,3-oxathiazolidine-3-carboxylate 2,2-dioxide (4.4 g, 14.70 mmol, 97% yield) as a colorless oil. $^1$H NMR (400 MHz, CHLOROFORM-d) δ 4.45 (d, J=9.0 Hz, 1H), 4.20 (d, J=9.0 Hz, 1H), 2.07-1.98 (m, J=8.0 Hz, 1H), 1.83-1.69 (m, 2H), 1.59 (s, 3H), 1.56 (s, 9H), 0.99 (dd, J=8.0, 6.5 Hz, 6H).

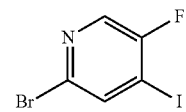

Part F: 2-Bromo-5-fluoro-4-iodopyridine

To a stirred solution of 2-bromo-5-fluoropyridine (10 g, 56.8 mmol) in tetrahydrofuran (120 mL) cooled to −78° C. was added LDA, 2M in THF (34.1 mL, 68.2 mmol). The solution was stirred at −78° C. for 40 min then 12 (14.42 g, 56.8 mmol) in THF (50 mL) was added and the solution stirred at −78° C. for 30 min. The reaction mixture was quenched with water (500 mL) and allowed to warm to room temperature. The reaction mixture was extracted with ethyl acetate (2×500 mL). The combined organic layers were washed with saturated sodium thiosulphate (500 mL), dried over sodium sulphate, filtered, and concentrated under reduced pressure. The residue was purified by silica gel chromatography (3% ethyl acetate in petroleum ether) to afford 2-bromo-5-fluoro-4-iodopyridine (12 g, 39.8 mmol, 70% yield). LC/MS (ESI) m/e 301.0 [(M+H)⁺, calcd for C₅H₃BrFN, 301.9]; LC/MS retention time (Method E): $t_R$=0.93 min; $^1$H NMR (400 MHz, CHLOROFORM-d) δ 8.13 (s, 1H), 7.91 (d, J=4.4 Hz, 1H).

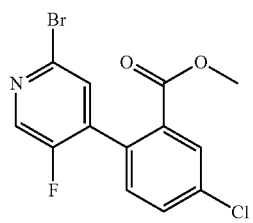 [SMILES: COC(=O)c1cc(Cl)ccc1-c1cc(Br)ncc1F]

Part G: Methyl 2-(2-bromo-5-fluoropyridin-4-yl)-5-chlorobenzoate

To a stirred solution of methyl 5-chloro-2-(4,4,5,5-tetramethyl-1,3,2-dioxaborolan-2-yl)benzoate (11.79 g, 39.8 mmol) (prepared in Example 1, Part B) in 1,4-dioxane (150 mL) and water (16 mL) was added 2-bromo-5-fluoro-4-iodopyridine (10 g, 33.1 mmol) followed by Pd(Ph$_3$P)$_4$ (1.91 g, 1.66 mmol) and Cs$_2$CO$_3$ (21.59 g, 66.3 mmol). N$_2$ gas was bubbled through the solution for 30 min then the reaction mixture was heated to 90° C. overnight. The reaction mixture was cooled to room temperature, diluted with water (150 mL), and extracted with ethyl acetate (180 mL). The organic layer was washed with brine, dried over Na2SO4, filtered, and concentrated under reduced pressure. The residue was purified via silica gel chromatography (8% ethyl acetate in petroleum ether) to afford methyl 2-(2-bromo-5-fluoropyridin-4-yl)-5-chlorobenzoate (5.5 g, 15.96 mmol, 48% yield) as a yellow solid. LC/MS (ESI) m/e 344.0 [(M+H)$^+$, calcd for C$_{14}$H$_{12}$ClNO$_2$, 344.0]; LC/MS retention time (Method A2): t$_R$=2.34 min. $^1$H NMR (400 MHz, CHLOROFORM-d) δ 8.24 (d, J=1.5 Hz, 1H), 8.07 (d, J=2.5 Hz, 1H), 7.64-7.58 (dd, J=8.5, 2.5 Hz, 1H), 7.40 (d, J=5.5 Hz, 1H), 7.29-7.23 (d, J=8.0 Hz, 1H), 3.78 (s, 3H).

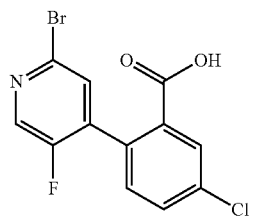 [SMILES: O=C(O)c1cc(Cl)ccc1-c1cc(Br)ncc1F]

Part H: 2-(2-Bromo-5-fluoropyridin-4-yl)-5-chlorobenzoic acid

To methyl 2-(2-bromo-5-fluoropyridin-4-yl)-5-chlorobenzoate (5.0 g, 13.79 mmol) in tetrahydrofuran (50 mL), MeOH (50 mL), and water (50 mL) was added LiOH (3.30 g, 138 mmol). The solution was stirred at room temperature for 12 h. The solution was concentrated under reduced pressure. The residue was diluted with water and adjusted the pH to 3 using 1.5N HCl and extracted with EtOAc (2×5 mL). The combined organic layers were dried over sodium sulphate, filtered, and concentrated under reduced pressure to afford 2-(2-bromo-5-fluoropyridin-4-yl)-5-chlorobenzoic acid (4.0 g, 11.77 mmol, 85% yield) as a brown solid. LC/MS (ESI) m/e 327.8 [(M–H)$^-$, calcd for C$_{12}$H$_{15}$BrClFNO$_2$, 327.9]; LC/MS retention time (Method A3): t$_R$=1.66 min; $^1$H NMR (400 MHz, DMSO-d$_6$) δ 8.46 (d, J=1.5 Hz, 1H), 7.98 (d, J=2.0 Hz, 1H), 7.81 (dd, J=8.3, 2.3 Hz, 1H), 7.77 (d, J=5.5 Hz, 1H), 7.53 (d, J=8.0 Hz, 1H), one exchangeable proton not observed.

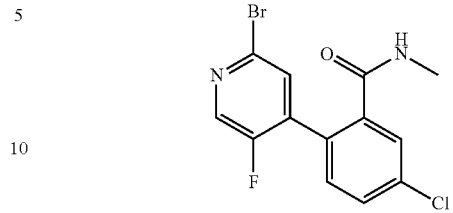

Part I: 2-(2-Bromo-5-fluoropyridin-4-yl)-5-chloro-N-methylbenzamide

To a solution of 2-(2-bromo-5-fluoropyridin-4-yl)-5-chlorobenzoic acid (4.0 g, 12.10 mmol) in DCM (60 mL) cooled to 0° C. was added oxalyl chloride (6.36 mL, 72.6 mmol) followed by a catalytic amount of DMF (0.469 mL, 6.05 mmol). The reaction mixture was heated to 40° C. for 60 min. The acid chloride formation was confirmed by the addition of methanol to an aliquot of the reaction mixture and formation of methyl ester was confirmed by LC/MS: LC/MS (ESI) m/e 344.2 [(M–H)$^-$, calcd for C$_{13}$H$_9$BrClFNO$_2$, 344.0]; LC/MS retention time (Method B): t$_R$=1.11 min. The reaction mixture was concentrated under reduced pressure to afford 2-(2-bromo-5-fluoropyridin-4-yl)-5-chlorobenzoyl chloride (4.0 g, 11.46 mmol, 95% crude yield) as a brown solid.

To a solution of 2-(2-bromo-5-fluoropyridin-4-yl)-5-chlorobenzoyl chloride (2.0 g, 5.73 mmol) dissolved in dichloromethane (150 mL) cooled to 0° C. was added methylamine hydrochloride (3.87 g, 57.3 mmol) and triethylamine (11.98 mL, 86 mmol). The mixture was stirred at 0° C. for 2 h. The reaction mixture was quenched with water (250 mL) and extracted with dichloromethane (380 mL) The combined organic layers were washed with brine, dried over sodium sulphate, filtered, and concentrated under reduced pressure to afford 2-(2-bromo-5-fluoropyridin-4-yl)-5-chloro-N-methylbenzamide (2.0 g, 4.48 mmol, 78% yield) as a brown solid. LC/MS (ESI) m/e 343.0 [(M+H)$^+$, calcd for C$_{13}$H$_{10}$BrClFN$_2$O, 343.0]; LC/MS retention time (Method A3): t$_R$=1.99 min; $^1$H NMR (400 MHz, DMSO-d$_6$) δ 8.55-8.47 (m, 1H), 8.44 (d, J=1.5 Hz, 1H), 7.73-7.68 (m, 2H), 7.67 (d, J=5.5 Hz, 1H), 7.52 (d, J=8.0 Hz, 1H), 3.32 (s, 3H).

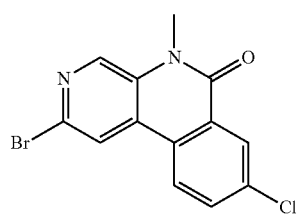 [SMILES: Cn1c(=O)c2cc(Cl)ccc2c2cc(Br)ncc21]

Part J: 2-Bromo-8-chloro-5-methylbenzo[c][1,7]naphthyridin-6(5H)-one

To a solution of 2-(2-bromo-5-fluoropyridin-4-yl)-5-chloro-N-methylbenzamide (2.0 g, 5.82 mmol) in tetrahydrofuran (10 mL) cooled to 0° C. was added NaH (0.466 g, 11.64 mmol) in portions. The mixture was warmed to room temperature and stirred for 3 h. The reaction mixture was quenched with water (20 mL) and concentrated under reduced pressure. The residue was diluted with water (200 mL). The solid that formed was collected by vacuum filtration and washed with water (100 mL). Obtained 2-bromo-8-chloro-5-methylbenzo[c][1,7]naphthyridin-6(5H)-one (1.8 g, 5.50 mmol, 95% yield) as a pale brown solid. The material was carried forward without further purification. LC/MS (ESI) m/e 323.0 [(M+H)$^+$, calcd for $C_{13}H_9BrClN_2O$, 323.0]; LC/MS retention time (Method A3): $t_R$=2.19 min; $^1$H NMR (400 MHz, DMSO-d$_6$) δ 8.78 (d, J=8.5 Hz, 1H), 8.76 (s, 1H), 8.71 (s, 1H), 8.34 (d, J=2.5 Hz, 1H), 8.00 (dd, J=8.8, 2.3 Hz, 1H), 3.76 (s, 3H).

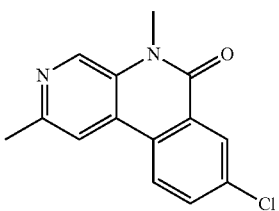 [SMILES: Cc1cc2c3ccc(Cl)cc3c(=O)n(C)c2cn1]

Part K: 8-chloro-2,5-dimethylbenzo[c][1,7]naphthyridin-6(5H)-one

To a solution of methyl 2-bromo-8-chloro-5-methylbenzo[c][1,7]naphthyridin-6(5H)-one (0.5 g, 1.55 mmol) and K$_2$CO$_3$ (0.641 g, 4.64 mmol) in dioxane (10 mL) and water (1 mL) was added methylboronic acid (0.231 g, 3.86 mmol). Nitrogen gas was bubbled through the solution for 15 min. PdCl$_2$(dppf)-CH$_2$Cl$_2$ adduct (0.126 g, 0.155 mmol) was added to the reaction mixture and again nitrogen gas was bubbled through the solution for 20 min. The reaction mixture was then heated at 100° C. for 16 h. The reaction mixture was allowed to cool to room temperature and concentrated under reduced pressure. The residue was diluted with ethyl acetate (10 mL) and water (10 mL) and filtered through diatomaceous earth (Celite®). The filtrate was extracted with ethyl acetate (2×10 mL). The combined organic layers were washed with brine, dried over sodium sulphate, filtered, and concentrated under reduced pressure to afford crude 8-chloro-2,5-dimethylbenzo[c][1,7]naphthyridin-6(5H)-one (0.2 g, 0.765 mmol, 50% yield) as a brown solid. This material was carried forward without further purification. LC/MS (ESI) m/e 259.0 [(M+H)$^+$, calcd for $C_{14}H_{12}ClN_2O$, 259.1]; LC/MS retention time (Method A3): $t_R$=1.72 min; $^1$H NMR (400 MHz, DMSO-d$_6$) δ 8.82 (s, 1H), 8.67 (d, J=9.0 Hz, 1H), 8.36-8.31 (m, 1H), 8.29 (s, 1H), 7.98 (dd, J=8.8, 2.3 Hz, 1H), 3.77 (s, 3H), 2.61 (s, 3H).

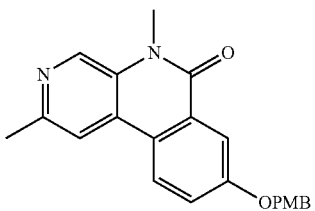

Part L: 8-((4-Methoxybenzyl)oxy)-2,5-dimethylbenzo[c][1,7]naphthyridin-6(5H)-one To a stirred solution of 8-chloro-2,5-dimethylbenzo[c][1,7]naphthyridin-6(5H)-one (0.2 g, 0.773 mmol) in 1,4-dioxane (8 mL) was added allylpalladium chloride dimer (0.012 g, 0.032 mmol) followed by (4-methoxyphenyl)methanol (0.534 g, 3.87 mmol), Rockphos (0.030 g, 0.063 mmol), and Cs$_2$CO$_3$ (0.504 g, 1.546 mmol). The reaction mixture was then heated to 90° C. overnight. The reaction mixture diluted with THF (50 mL) and filtered through diatomaceous earth (Celite®) washing with THF (50 mL). The mother liquor was concentrated under reduced pressure. To the residue was added diethyl ether (50 mL) and the mixture stirred for 30 min. The solid formed was collected by vacuum filtration and air dried. Obtained 8-((4-methoxybenzyl)oxy)-2,5-dimethylbenzo[c][1,7]naphthyridin-6(5H)-one (0.16 g, 0.444 mmol, 57% yield) as a pale yellow solid which was carried forward without further purification. LC/MS (ESI) m/e 361.2 [(M+H)$^+$, calcd for $C_{22}H_{21}N_2O_3$, 361.2]; LC/MS retention time (Method A3): $t_R$=2.10 min; $^1$H NMR (400 MHz, DMSO-d$_6$) δ 8.75 (s, 1H), 8.54 (d, J=9.0 Hz, 1H), 8.18 (s, 1H), 7.89 (d, J=3.0 Hz, 1H), 7.55 (dd, J=8.8, 2.8 Hz, 1H), 7.47-7.39 (m, 2H), 6.98 (d, J=8.5 Hz, 2H), 5.22 (s, 2H), 3.77 (s, 3H), 3.77 (s, 3H), 2.58 (s, 3H).

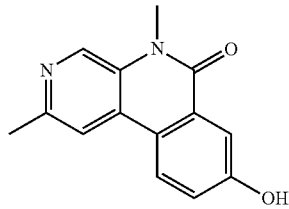 [SMILES: Cc1cc2c3ccc(O)cc3c(=O)n(C)c2cn1]

Part M: 8-Hydroxy-2,5-dimethylbenzo[c][1,7]naphthyridin-6(5H)-one

To a stirred solution of 8-((4-methoxybenzyl)oxy)-2,5-dimethylbenzo[c][1,7]naphthyridin-6(5H)-one (0.16 g, 0.444 mmol) in DCM (20 mL) cooled to 0° C. was added TFA (1.37 mL, 17.76 mmol). The reaction mixture was stirred for 30 min at 0° C., then at ambient temperature for 2 h. The reaction mixture was quenched with saturated sodium bicarbonate and extracted with DCM (30 mL). The combined organic layers were washed with brine, dried over sodium sulphate, filtered, and concentrated under reduced pressure to afford 8-hydroxy-2,5-dimethylbenzo[c][1,7]naphthyridin-6(5H)-one (0.06 g, 0.242 mmol, 55% yield) as an off-white solid which was carried forward without further purification. LC/MS (ESI) m/e 241.2 [(M+H)$^+$, calcd for $C_{14}H_{13}N_2O_2$, 241.1]; LC/MS retention time (Method A3): $t_R$=1.69 min; $^1$H NMR (400 MHz, DMSO-d$_6$) δ 10.43 (s, 1H), 8.72 (s, 1H), 8.46 (d, J=9.0 Hz, 1H), 8.13 (s, 1H), 7.73 (d, J=2.5 Hz, 1H), 7.32 (dd, J=8.8, 2.8 Hz, 1H), 3.75 (s, 3H), 2.58 (s, 3H).

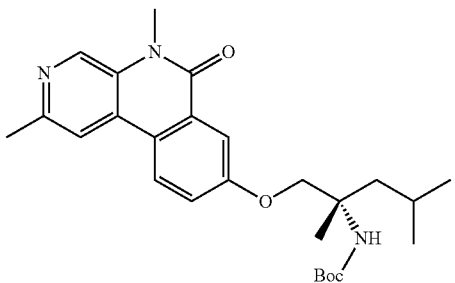 [SMILES: Cc1cc2c3ccc(OC[C@](C)(CC(C)C)NC(=O)OC(C)(C)C)cc3c(=O)n(C)c2cn1]

Part N: (S)-tert-butyl (1-((2,5-dimethyl-6-oxo-5,6-dihydrobenzo[c][1,7]naphthyridin-8-yl)oxy)-2,4-dimethylpentan-2-yl)carbamate To a solution of 8-hydroxy-2,5-dimethylbenzo[c][1,7]naphthyridin-6(5H)-one (0.03 g, 0.125 mmol) was added K₂CO₃ (0.035 g, 0.250 mmol) and (S)-tert-butyl 4-isobutyl-4-methyl-1,2,3-oxathiazolidine-3-carboxylate 2,2-dioxide (0.044 g, 0.150 mmol) in DMF (5 mL) at room temperature to give a brown color solution under stirring. The reaction mixture was heated to 80° C. overnight. The reaction mixture was filtered through diatomaceous earth (Celite®) washing with ethyl acetate (20 mL). The filtrate was concentrated under reduced pressure. The residue was purified by silica gel chromatography (50% ethyl acetate in petroleum ether) to afford (S)-tert-butyl (1-((2,5-dimethyl-6-oxo-5,6-dihydrobenzo[c][1,7]naphthyridin-8-yl)oxy)-2,4-dimethylpentan-2-yl)carbamate (0.05 g, 0.101 mmol, 81% yield) as a brown solid. LC/MS (ESI) m/e 454.4 [(M+H)⁺, calcd for $C_{26}H_{36}N_3O_4$, 454.3]; LC/MS retention time (Method A3): $t_R$=2.37 min; ¹H NMR (400 MHz, DMSO-d₆) δ 8.76 (s, 1H), 8.55 (d, J=9.0 Hz, 1H), 8.20 (s, 1H), 7.80 (d, J=3.0 Hz, 1H), 7.50 (dd, J=8.8, 2.8 Hz, 1H), 4.28 (d, J=9.0 Hz, 1H), 4.07 (d, J=9.0 Hz, 1H), 3.78 (s, 3H), 2.31 (s, 3H), 1.93-1.83 (m, 1H), 1.79-1.59 (m, 2H), 1.48 (s, 9H), 1.34 (s, 3H), 0.92 (d, J=6.8 Hz 3H), 0.88 (d, J=6.8 Hz 3H), one exchangeable proton not observed.

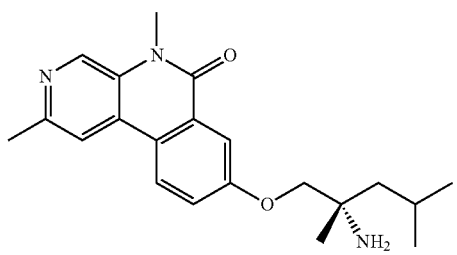 [SMILES: Cc1cc2c3ccc(OC[C@@](C)(N)CC(C)C)cc3c(=O)n(C)c2cn1]

Part O: (S)-8-((2-amino-2,4-dimethylpentyl)oxy)-2,5-dimethylbenzo[c][1,7]naphthyridin-6(5H)-one To (S)-tert-butyl (1-((2,5-dimethyl-6-oxo-5,6-dihydrobenzo[c][1,7]naphthyridin-8-yl)oxy)-2,4-dimethylpentan-2-yl)carbamate (0.05 g, 0.110 mmol) cooled to 0° C. was added 4M HCl in 1,4-dioxane (0.551 mL, 2.21 mmol). The mixture was warmed to room temperature and stirred for 2 h. The reaction mixture was diluted with saturated aqueous sodium bicarbonate (20 mL) and extracted with ethyl acetate (30 mL). The organic layer was separated, dried over anhydrous sodium sulphate, filtered, and concentrated under reduced pressure. The residue was purified via prep HPLC (methanol:water with 10 mM NH₄OAc) to afford (S)-8-((2-amino-2,4-dimethylpentyl)oxy)-2,5-dimethylbenzo[c][1,7]naphthyridin-6(5H)-one (0.018 g, 0.050 mmol, 45% yield) as a pale yellow solid. LC/MS (ESI) m/3 354.2 [(M+H)⁺, calcd for $C_{21}H_{28}N_3O_2$, 354.2]; LC/MS retention time (Method A): $t_R$=1.21 min; ¹H NMR (400 MHz, METHANOL-d₄) δ 8.74 (s, 1H), 8.54 (d, J=9.0 Hz, 1H), 8.18 (s, 1H), 8.00 (d, J=2.5 Hz, 1H), 7.60 (dd, J=8.8, 2.8 Hz, 1H), 4.23-4.09 (m, 2H), 3.88 (s, 3H), 2.68 (s, 3H), 1.91-1.83 (m, 1H), 1.81-1.61 (m, 2H), 1.44 (s, 3H), 1.07 (d, J=7.0 Hz, 3H), 1.03 (d, J=7.0 Hz, 3H), two exchangeable protons not observed; HPLC purity (Method C1): 98% $t_R$=1.21 min; HPLC purity (Method D): 98% $t_R$=0.75 min.

Example 15

(S)-8-((2-amino-2,4-dimethylpentyl)oxy)-7-chloro-4,5-dimethylbenzo[c][1,7]naphthyridin-6(5H)-one

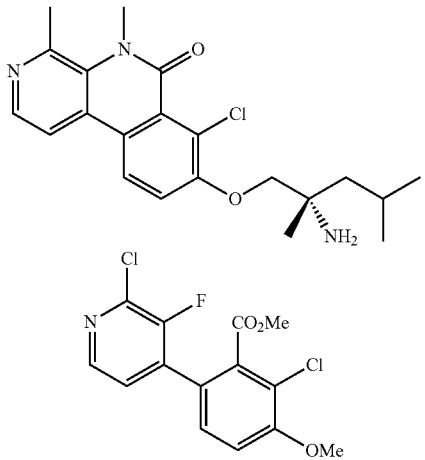

Part A: Methyl 2-chloro-6-(2-chloro-3-fluoropyridin-4-yl)-3-methoxybenzoate

To a stirred solution of methyl 6-bromo-2-chloro-3-methoxybenzoate (5 g, 16.99 mmol), (2-chloro-3-fluoropyridin-4-yl)boronic acid (3.58 g, 20.39 mmol) and K₂CO₃ (3.71 g, 26.8 mmol) in 1,4-dioxane (65 mL) and water (5 mL) was added PdCl₂(dppf)-CH₂Cl₂ adduct (0.876 g, 1.07 mmol). Argon was bubbled through the solution for 10 min. The reaction mixture was heated to 95° C. for 16 h. The reaction mixture was cooled to room temperature and filtered through diatomaceous earth (Celite®) washing with EtOAc. The filtrate was concentrated under reduced pressure. The residue was diluted with water (20 mL), and extracted with ethyl acetate (40 mL). The organic layer was washed with brine, dried over Na2SO4, filtered, and concentrated under reduced pressure. The residue was purified via silica gel chromatography (30% EtOAc in hexane) to afford methyl 2-chloro-6-(2-chloro-3-fluoropyridin-4-yl)-3-methoxybenzoate (2 g, 5.93 mmol, 35% yield) as an off-white solid. LC/MS (ESI) m/e 330.0 [(M+H)⁺, calcd for $C_{14}H_{11}Cl_2FNO_3$, 330.0]; LC/MS retention time (Method A3): $t_R$=2.24 min; ¹H NMR (400 MHz, CHLOROFORM-d) δ 8.20 (d, J=5.0 Hz, 1H), 7.29 (dd, J=8.5, 1.5 Hz, 1H), 7.19 (t, J=5.0 Hz, 1H), 7.08 (d, J=8.5 Hz, 1H), 3.99 (s, 3H), 3.73 (s, 3H).

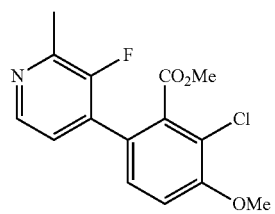 [SMILES: COC(=O)c1c(-c2ccnc(C)c2F)ccc(OC)c1Cl]

Part B: Methyl 2-chloro-6-(3-fluoro-2-methylpyridin-4-yl)-3-methoxybenzoate

To a solution of methyl 2-chloro-6-(2-chloro-3-fluoropyridin-4-yl)-3-methoxybenzoate (1.8 g, 5.45 mmol) and $K_2CO_3$ (1.51 g, 10.90 mmol), in dioxane (34 mL) and water (5 mL) was added methylboronic acid (0.653 g, 10.90 mmol). Argon gas was bubbled through the solution for 15 min. $PdCl_2(dppf)-CH_2Cl_2$ adduct (0.445 g, 0.545 mmol) was added to the reaction mixture and again argon gas was bubbled through the solution for 10 min. The reaction mixture was heated at 100° C. for 2 h. The reaction mixture was allowed to cool to room temperature and filtered through diatomaceous earth (Celite®) washing with EtOAc (2×10 mL). The filtrate was concentrated under reduced pressure. The residue was diluted with water (20 mL) and extracted with ethyl acetate (20 mL). The separated organic layer was washed with brine, dried over sodium sulphate, filtered, and concentrated under reduced pressure. The residue was purified via silica gel chromatography (40% EtOAc in hexanes) to afford methyl 2-chloro-6-(3-fluoro-2-methylpyridin-4-yl)-3-methoxybenzoate (1 g, 3.13 mmol, 57% yield) as an off-white solid. LC/MS (ESI) m/e 310.2 [(M+H)$^+$, calcd for $C_{15}H_{14}ClFNO_3$, 310.1]; LC/MS retention time (Method E): $t_R$=0.76 min; $^1$H NMR (400 MHz, CHLOROFORM-d) δ 8.29 (d, J=4.8 Hz, 1H), 7.29 (dd, J=8.5, 1.5 Hz, 1H), 7.10-7.03 (m, 2H), 3.98 (s, 3H), 3.71 (s, 3H), 2.57 (d, J=3.3 Hz, 3H).

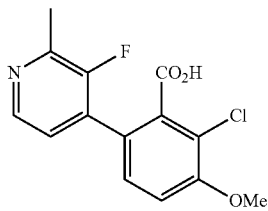 [SMILES: COc1ccc(-c2ccnc(C)c2F)c(C(=O)O)c1Cl]

Part C: 2-Chloro-6-(3-fluoro-2-methylpyridin-4-yl)-3-methoxybenzoic acid

To methyl 2-chloro-6-(3-fluoro-2-methylpyridin-4-yl)-3-methoxybenzoate (1 g, 3.13 mmol) in tetrahydrofuran (3.3 mL), MeOH (3.3 mL), and water (3.3 mL) was added LiOH (0.749 g, 31.3 mmol). The solution was stirred at 50° C. for 16 h. The solution was cooled to room temperature and concentrated under reduced pressure. The residue was cooled to 0° C. and diluted with water and adjusted the pH to 2 using conc. HCl (1.4 mL). EtOAc (15 mL) was added and the mixture stirred for 30 min at room temperature. The layers were separated. The organic layer was washed with brine (10 mL), dried over sodium sulphate, filtered, and concentrated under reduced pressure to afford 2-chloro-6-(3-fluoro-2-methylpyridin-4-yl)-3-methoxybenzoic acid (0.7 g, 2.37 mmol, 76% yield) as an off-white solid. LC/MS (ESI) m/e 296.2 [(M+H)$^+$, calcd for $C_{14}H_{12}ClFNO_3$, 296.1]; LC/MS retention time (Method E): $t_R$=0.63 min; $^1$H NMR (400 MHz, DMSO-$d_6$) δ 13.64 (br. s., 1H), 8.33 (d, J=5.0 Hz, 1H), 7.48-7.39 (m, 1H), 7.38-7.31 (m, 1H), 7.21 (t, J=5.5 Hz, 1H), 3.96 (s, 3H), 2.50 (d, J=3.0 Hz, 3H).

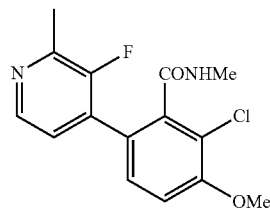

Part D: 2-Chloro-6-(3-fluoro-2-methylpyridin-4-yl)-3-methoxy-N-methylbenzamide To a stirred solution of 2-chloro-6-(3-fluoro-2-methylpyridin-4-yl)-3-methoxybenzoic acid (0.715 g, 2.42 mmol), EDC HCl (1.39 g, 7.25 mmol), HOBT (0.555 g, 3.63 mmol) and methylamine hydrochloride (0.816 g, 12.09 mmol) in DMF (7 mL) at 0° C. was added DIPEA (2.112 mL, 12.09 mmol) and the mixture was stirred for 10 min. The reaction mixture was allowed to warm to room temperature and stirred for 16 h. The reaction mixture was quenched with ice water and diluted with EtOAc (40 mL). The separated organic layer was washed with brine, dried over $Na_2SO_4$, filtered, and concentrated under reduced pressure. The solid residue was washed with hexane (10 mL) and diethyl ether (10 mL) and air dried. Obtained 2-chloro-6-(3-fluoro-2-methylpyridin-4-yl)-3-methoxy-N-methylbenzamide (0.5 g, 1.318 mmol, 55% yield) as a pale yellow solid. LC/MS (ESI) m/e 309.2 [(M+H)$^+$, calcd for $C_{15}H_{15}ClFN_2O_2$, 309.1]; LC/MS retention time (Method A3): $t_R$=1.84 min; $^1$H NMR (400 MHz, CHLOROFORM-d) δ 8.28 (d, J=5.0 Hz, 1H), 7.28-7.24 (m, 1H), 7.22-7.16 (m, 1H), 7.03 (d, J=8.5 Hz, 1H), 3.97 (s, 3H), 2.79 (d, J=5.0 Hz, 3H), 2.56 (d, J=3.3 Hz, 3H), one exchangeable proton not observed.

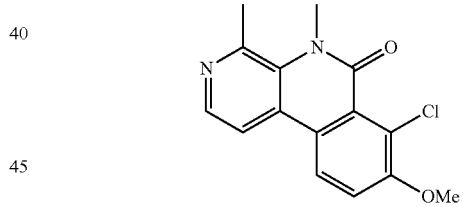

Part E: 7-Chloro-8-methoxy-4,5-dimethylbenzo[c][1,7]naphthyridin-6(5H)-one

To a solution of 2-chloro-6-(3-fluoro-2-methylpyridin-4-yl)-3-methoxy-N-methylbenzamide (0.4 g, 1.05 mmol) in NMP (8 mL) was added $Cs_2CO_3$ (1.03 g, 3.16 mmol). The mixture was heated to 110° C. for 16 h under N2. The reaction mixture was allowed to cool to room temperature and diluted with EtOAc (20 mL) and water (7 mL). Stirred for 10 min. Separated the layers and washed the organic layer with brine, dried over $Na_2SO_4$, filtered, and concentrated under reduced pressure. The solid residue was washed with diethyl ether (2×5 mL) to afford 7-chloro-8-methoxy-4,5-dimethylbenzo[c][1,7]naphthyridin-6(5H)-one (0.2 g, 0.644 mmol, 61% yield) as an off white solid. LC/MS (ESI) m/e 289.2 [(M+H)$^+$, calcd for $C_{15}H_{14}ClN_2O_2$, 289.1]; LC/MS retention time (Method A3): $t_R$=1.85 min; $^1$H NMR (400 MHz, METHANOL-$d_4$) δ 8.48 (d, J=12.4 Hz, 1H), 8.31 (d, J=7.2 Hz, 1H), 8.07 (d, J=6.8 Hz, 1H), 7.66 (d, J=12.4 Hz, 1H), 4.06 (s, 3H), 3.77 (s, 3H), 2.86 (s, 3H).

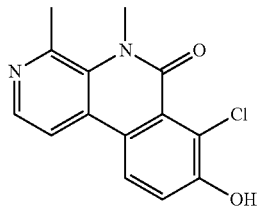 [SMILES: Cc1nccc2c3ccc(O)c(Cl)c3c(=O)n(C)c12]

Part F: 7-Chloro-8-hydroxy-4,5-dimethylbenzo[c][1,7]naphthyridin-6(5H)-one

To a stirred solution of 7-chloro-8-methoxy-4,5-dimethylbenzo[c][1,7]naphthyridin-6(5H)-one (0.2 g, 0.644 mmol) in DCM (20 mL) at 0° C. was added BBr$_3$ in DCM (15 mL, 15.00 mmol) and the mixture stirred for 10 min at 0° C. The reaction mixture was allowed to warm to room temperature and stirred for 16 h. The reaction mixture was cooled to 0° C. and quenched with 10% aqueous NaHCO$_3$ (18 mL) and extracted with DCM (2×20 mL). The combined organic extracts were washed with brine, dried over Na$_2$SO$_4$, filtered, and concentrated under reduced pressure. The residue was purified by silica gel column chromatography (50% EtOAc in hexane) to afford 7-chloro-8-hydroxy-4,5-dimethylbenzo[c][1,7]naphthyridin-6(5H)-one (0.080 g, 0.239 mmol, 37% yield) as an off white solid. LC/MS (ESI) m/e 275.2 [(M+H)$^+$, calcd for C$_{14}$H$_{12}$ClN$_2$O$_2$, 275.1]; LC/MS retention time (Method A3): t$_R$=1.64 min; $^1$H NMR (400 MHz, DMSO-d$_6$) δ 10.95 (s, 1H), 8.40 (d, J=9.0 Hz, 1H), 8.33-8.24 (m, 1H), 8.03 (d, J=5.0 Hz, 1H), 7.47 (d, J=8.5 Hz, 1H), 3.66 (s, 3H), 2.79 (s, 3H).

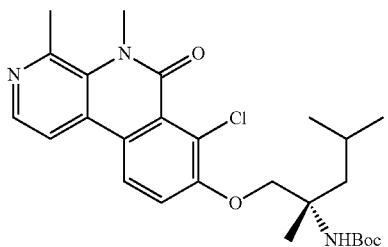 [SMILES: Cc1nccc2c3ccc(OC[C@](C)(CC(C)C)NC(=O)OC(C)(C)C)c(Cl)c3c(=O)n(C)c12]

Part G: (S)-tert-butyl (1-((7-chloro-4,5-dimethyl-6-oxo-5,6-dihydrobenzo[c][1,7]naphthyridin-8-yl)oxy)-2,4-dimethylpentan-2-yl)carbamate To a solution of 7-chloro-8-hydroxy-4,5-dimethylbenzo[c][1,7]naphthyridin-6(5H)-one (0.080 g, 0.239 mmol) in DMF (2 mL) was added K$_2$CO$_3$ (0.066 g, 0.477 mmol) and (S)-tert-butyl 4-isobutyl-4-methyl-1,2,3-oxathiazolidine-3-carboxylate 2,2-dioxide (0.084 g, 0.286 mmol) (prepared in Example 14, Part D). The reaction mixture was heated to 80° C. for 16 h. The reaction mixture was cooled to room temperature and diluted with water (4 mL). The solution was extracted with EtOAc (2×5 mL). The combined organic extracts were washed with brine, dried over Na2SO4, filtered, and concentrated under reduced pressure to afford (S)-tert-butyl (1-((7-chloro-4,5-dimethyl-6-oxo-5,6-dihydrobenzo[c][1,7]naphthyridin-8-yl)oxy)-2,4-dimethylpentan-2-yl)carbamate (0.120 g, 0.234 mmol, 98% yield) was carried forward without further purification. LC/MS (ESI) m/e 488.5 [(M+H)$^+$, calcd for C$_{26}$H$_{35}$ClN$_3$O$_4$, 488.2]; LC/MS retention time (Method B): t$_R$=1.25 min.

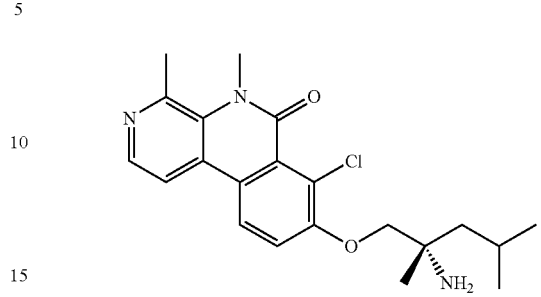

Part H: (S)-8-((2-amino-2,4-dimethylpentyl)oxy)-7-chloro-4,5-dimethylbenzo[c][1,7]naphthyridin-6(5H)-one To (S)-tert-butyl (1-((7-chloro-4,5-dimethyl-6-oxo-5,6-dihydrobenzo[c][1,7]naphthyridin-8-yl)oxy)-2,4-dimethylpentan-2-yl)carbamate (0.120 g, 0.234 mmol) cooled to 0° C. was added 4M HCl in 1,4-dioxane (2 mL, 8.00 mmol). The mixture was warmed to room temperature and stirred for 1 h. The reaction mixture was concentrated under reduced pressure. The residue was purified via prep HPLC (methanol:water with 10 mM NH$_4$OAc) to afford (S)-8-((2-amino-2,4-dimethylpentyl)oxy)-7-chloro-4,5-dimethylbenzo[c][1,7]naphthyridin-6(5H)-one (0.033 g, 0.083 mmol, 35% yield) as a pale yellow solid. LC/MS (ESI) m/3 388.4 [(M+H)$^+$, calcd for C$_{21}$H$_{27}$ClN$_3$O$_2$, 388.2]; LC/MS retention time (Method B): t$_R$=0.79 min; $^1$H NMR (400 MHz, METHANOL-d$_4$) δ 8.50 (d, J=9.5 Hz, 1H), 8.33 (d, J=5.5 Hz, 1H), 8.09 (d, J=5.5 Hz, 1H), 7.70 (d, J=9.0 Hz, 1H), 4.20 (q, J=9.9 Hz, 2H), 3.79 (s, 3H), 2.88 (s, 3H), 1.93-1.81 (m, 2H), 1.73-1.63 (m, 1H), 1.48 (s, 3H), 1.07 (d, J=6.5 Hz, 3H), 1.04 (d, J=6.0 Hz, 3H), two exchangeable protons not observed; HPLC purity (Method C1): 96% t$_R$=1.18 min; HPLC purity (Method D): 98% t$_R$=0.76 min.

Example 16

(S)-8-((2-amino-2,4-dimethylpentyl)oxy)-9-chloro-5-ethyl-4-methylbenzo[c][1,7]naphthyridin-6(5H)-one

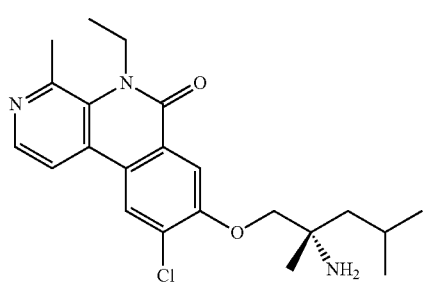 [SMILES: CCn1c(=O)c2cc(OC[C@@](C)(N)CC(C)C)c(Cl)cc2c2ccnc(C)c21]

Prepared as described in Example 12, Parts G and H, using (S)-tert-butyl 4-isobutyl-4-methyl-1,2,3-oxathiazolidine-3-carboxylate 2,2-dioxide (52.4 mg, 0.179 mmol) as the coupling partner. Obtained (S)-8-((2-amino-2,4-dimethylpentyl)oxy)-9-chloro-5-ethyl-4-methylbenzo[c][1,7]naphthyridin-6(5H)-one (4.4 mg, 10.61 μmol, 13% yield for two steps) as a pale yellow solid. LC/MS (ESI) m/3 402.2 [(M+H)+, calcd for C$_{22}$H$_{29}$ClN$_3$O$_2$, 402.2]; LC/MS retention time (Method A3): t$_R$=2.04 min; $^1$H NMR (400 MHz, METHANOL-d$_4$) δ 8.57-8.75 (m, 1H), 8.36 (d, J=5.52 Hz, 1H), 8.14 (d, J=5.52 Hz, 1H), 8.04 (s, 1H), 4.51-4.58 (m, 2H), 4.21-4.28 (m, 2H), 2.96 (s, 3H), 1.82-1.92 (m, 2H), 1.67-1.73 (m, 1H), 1.48 (s, 3H), 1.42 (t, J=7.03 Hz, 3H), 1.02-1.09 (m, 6H), two exchangeable protons not observed; HPLC purity (Method C1): 96% t$_R$=1.53 min; HPLC purity (Method D): 96% t$_R$=0.86 min.

Example 17

(S)-8-((2-amino-2,4-dimethylpentyl)oxy)-9-chloro-2,5-dimethylbenzo[c][1,7]naphthyridin-6(5H)-one

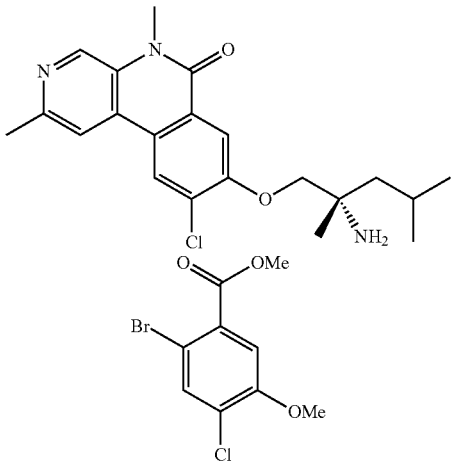

Part A: methyl 2-bromo-4-chloro-5-methoxybenzoate

To a solution of methyl 4-chloro-3-methoxybenzoate (5 g, 24.92 mmol) in acetic acid (15 mL) and water (15 mL) at 0° C. was added Br$_2$ (1.28 mL, 24.92 mmol). The reaction mixture was warmed to 60° C. and stirred for 12 h. The reaction mixture was cooled to room temperature and concentrated under reduced pressure. The residue was purified by silica gel chromatography (0-30% EtOAc in petroleum ether) to afford methyl 2-bromo-4-chloro-5-methoxybenzoate (5.6 g, 20.03 mmol, 80% yield) as an off-white solid. LC/MS (ESI) m/e 279.1 [(M+H)+, calcd for C$_9$H$_9$BrClO$_3$, 279.0]; LC/MS retention time (Method B): t$_R$=0.76 min.

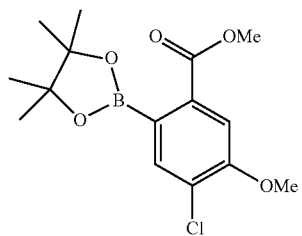 [SMILES: COC(=O)c1cc(OC)c(Cl)cc1B1OC(C)(C)C(C)(C)O1]

Part B: Methyl 4-chloro-5-methoxy-2-(4,4,5,5-tetramethyl-1,3,2-dioxaborolan-2-yl)benzoate To a stirred solution of methyl 2-bromo-4-chloro-5-methoxybenzoate (2.0 g, 7.16 mmol) in 1,4-dioxane (25 mL) was added bis(pinacolato)diboron (2.0 g, 7.87 mmol), potassium acetate (2.1 g, 21.47 mmol), and PdCl$_2$(dppf)-CH$_2$Cl$_2$ adduct (0.292 g, 0.358 mmol). N$_2$ was bubbled through the solution for 10 min then the mixture was heated to 90° C. overnight. The reaction mixture was cooled to room temperature then filtered through diatomaceous earth (Celite®) washing with EtOAc (100 mL). The filtrate was concentrated under reduced pressure. The residue was purified by silica gel chromatography (12% ethyl acetate in pet ether) to afford methyl 4-chloro-5-methoxy-2-(4,4,5,5-tetramethyl-1,3,2-dioxaborolan-2-yl)benzoate (1.4 g, 4.29 mmol, 60% yield) as a brown solid. $^1$H NMR (300 MHz, CHLOROFORM-d) δ 7.50 (d, J=2.6 Hz, 1H), 7.28 (s, 1H), 3.96 (s, 3H), 3.93 (s, 3H), 1.42 (s, 6H), 1.28 (s, 6H).

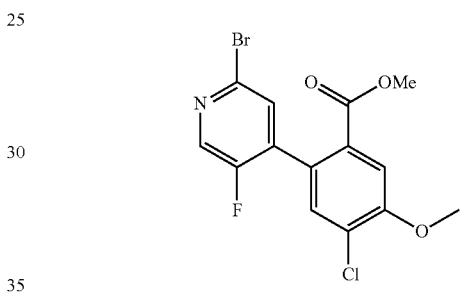

Part C: Methyl 2-(2-bromo-5-fluoropyridin-4-yl)-4-chloro-5-methoxybenzoate

To a solution of 2-bromo-5-fluoro-4-iodopyridine (1.2 g, 3.98 mmol) in DMF (15 mL) and water (2.5 mL) was added methyl 4-chloro-5-methoxy-2-(4,4,5,5-tetramethyl-1,3,2-dioxaborolan-2-yl)benzoate (1.43 g, 4.37 mmol) followed by PdCl$_2$(dppf)-CH$_2$Cl$_2$ adduct (0.325 g, 0.398 mmol) and Cs$_2$CO$_3$ (1.30 g, 3.98 mmol). N$_2$ gas was bubbled through the solution for 20 min. The reaction mixture was heated at 90° C. for 16 h. The reaction mixture was allowed to cool to room temperature and concentrated under reduced pressure. The residue was diluted water (50 mL) and extracted with ethyl acetate (80 mL). The separated organic layer was washed with brine, dried over sodium sulphate, filtered, and concentrated under reduced pressure. The residue was purified via silica gel chromatography (15% EtOAc in hexanes) to afford methyl 2-(2-bromo-5-fluoropyridin-4-yl)-4-chloro-5-methoxybenzoate (0.7 g, 1.15 mmol, 29% yield) as a yellow oil. LC/MS (ESI) m/e 374.0 [(M+H)+, calcd for C$_{14}$H$_{11}$BrClFNO$_3$, 374.0]; LC/MS retention time (Method A3): t$_R$=2.26 min; $^1$H NMR (400 MHz, CHLOROFORM-d) δ 8.23 (d, J=1.5 Hz, 1H), 7.62 (s, 1H), 7.41 (d, J=5.5 Hz, 1H), 7.33 (s, 1H), 4.02 (s, 3H), 3.76 (s, 3H).

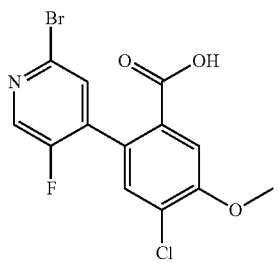 [SMILES: COc1cc(C(=O)O)c(-c2cc(Br)ncc2F)cc1Cl]

Part D: 2-(2-Bromo-5-fluoropyridin-4-yl)-4-chloro-5-methoxybenzoic acid

To methyl 2-(2-bromo-5-fluoropyridin-4-yl)-4-chloro-5-methoxybenzoate (0.7 g, 1.87 mmol) in MeOH (10 mL) and water (10 mL) was added NaOH (2.99 g, 74.7 mmol). The solution was stirred at 60° C. for 16 h. The solution was cooled to room temperature and concentrated under reduced pressure. The residue was diluted with water (50 mL) and adjusted the pH to 3 using 1.5N HCl. The solution was extracted with EtOAc (100 mL). The organic layer was dried over sodium sulphate, filtered, and concentrated under reduced pressure to afford 2-(2-bromo-5-fluoropyridin-4-yl)-4-chloro-5-methoxybenzoic acid (0.6 g, 1.21 mmol, 65% yield) as a white solid. LC/MS (ESI) m/e 360.0 [(M+H)$^+$, calcd for $C_{13}H_9BrClFNO_3$, 360.0]; LC/MS retention time (Method A3): $t_R$=1.92 min.

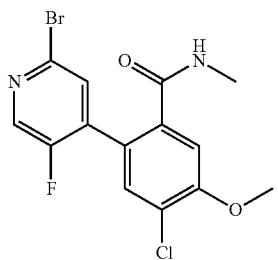 [SMILES: CNC(=O)c1cc(OC)c(Cl)cc1-c1cc(Br)ncc1F]

Part E: 2-(2-Bromo-5-fluoropyridin-4-yl)-4-chloro-5-methoxy-N-methylbenzamide

A solution of 2-(2-bromo-5-fluoropyridin-4-yl)-4-chloro-5-methoxybenzoic acid (0.6 g, 1.664 mmol), EDC (0.638 g, 3.33 mmol), HOBT (0.382 g, 2.50 mmol), methylamine hydrochloride (0.562 g, 8.32 mmol), and DIPEA (1.45 mL, 8.32 mmol) in DMF (12 mL) was stirred at room temperature for 16 h. The reaction mixture was concentrated under reduced pressure. The residue was diluted with water (70 mL). The precipitate that formed was collected by vacuum filtration and air dried to afford 2-(2-bromo-5-fluoropyridin-4-yl)-4-chloro-5-methoxy-N-methylbenzamide (0.5 g, 0.910 mmol, 55% yield) as a brown solid. LC/MS (ESI) m/e 373.0 [(M+H)$^+$, calcd for $C_{14}H_{12}BrClFN_2O_2$, 373.0]; LC/MS retention time (Method A3): $t_R$=1.95 min; $^1$H NMR (300 MHz, DMSO-$d_6$) δ 8.44 (d, J=4.5 Hz, 1H), 8.39 (d, J=1.5 Hz, 1H), 7.67 (d, J=5.7 Hz, 1H), 7.60 (s, 1H), 7.38 (s, 1H), 3.98 (s, 3H), 2.67 (d, J=4.5 Hz, 3H).

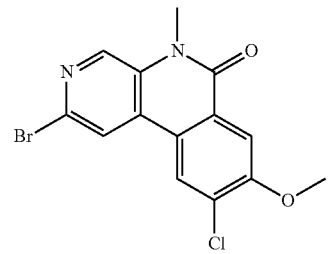 [SMILES: COc1cc2c(=O)n(C)c3cnc(Br)cc3c2cc1Cl]

Part F: 2-Bromo-9-chloro-8-methoxy-5-methyl-benzo[c][1,7]naphthyridin-6(5H)-one

To a solution of 2-(2-bromo-5-fluoropyridin-4-yl)-4-chloro-5-methoxy-N-methylbenzamide (0.5 g, 0.910 mmol) in tetrahydrofuran (20 mL) cooled to 0° C. was added NaH (0.073 g, 1.82 mmol) in portions. The mixture was stirred at room temperature for 1.5 h. The reaction mixture was quenched with water (50 mL) then concentrated under reduced pressure. The residue was diluted with water (100 mL) which afforded a brown solid. The solid was collected by vacuum filtration and washed with water (100 mL) and air dried to afford 2-bromo-9-chloro-8-methoxy-5-methyl-benzo[c][1,7]naphthyridin-6(5H)-one (0.27 g, 0.725 mmol, 80% yield) as a brown solid. LC/MS (ESI) m/e 353.0 [(M+H)$^+$, calcd for $C_{14}H_{11}BrClN_2O_2$, 353.0]; LC/MS retention time (Method A3): $t_R$=2.11 min; $^1$H NMR (400 MHz, DMSO-$d_6$) δ 8.90 (s, 1H), 8.69 (d, J=5.0 Hz, 2H), 7.90 (s, 1H), 4.06 (s, 3H), 3.75 (s, 3H).

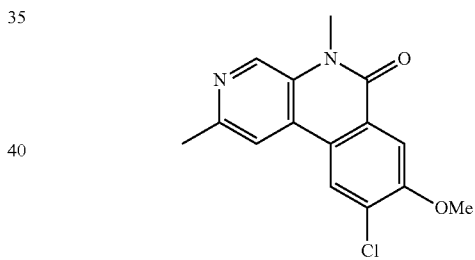

Part G: 9-Chloro-8-methoxy-2,5-dimethylbenzo[c][1,7]naphthyridin-6(5H)-one

To a solution of 2-bromo-9-chloro-8-methoxy-5-methyl-benzo[c][1,7]naphthyridin-6(5H)-one (0.26 g, 0.735 mmol) and $Cs_2CO_3$ (0.719 g, 2.21 mmol), in 1,4-dioxane (10 mL) and water (1 mL) was added trimethylboroxine (0.092 g, 0.735 mmol) followed by $PdCl_2(dppf)$-$CH_2Cl_2$ adduct (0.030 g, 0.037 mmol). N2 gas was bubbled through the solution for 20 min. The reaction mixture was heated at 80° C. for 2 h. The reaction mixture was allowed to cool to room temperature and filtered through diatomaceous earth (Celite®) washing with DCM (50 mL). The DCM layer was washed with water (50 mL), dried over sodium sulphate, filtered, and concentrated under reduced pressure. The residue was purified via silica gel chromatography (60% EtOAc in petroleum ether) to afford 9-chloro-8-methoxy-2,5-dimethylbenzo[c][1,7]naphthyridin-6(5H)-one (0.13 g, 0.325 mmol, 44% yield) as a brown solid. LC/MS (ESI) m/e 289.0 [(M+H)$^+$, calcd for $C_{15}H_{14}ClN_2O_2$, 289.1]; LC/MS retention time (Method A3): $t_R$=1.71 min.

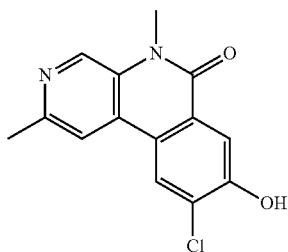 [SMILES: Cc1cc2c3cc(Cl)c(O)cc3c(=O)n(C)c2cn1]

Part H: 9-chloro-8-hydroxy-2,5-dimethylbenzo[c][1,7]naphthyridin-6(5H)-one

To a stirred solution of 9-chloro-8-methoxy-2,5-dimethylbenzo[c][1,7]naphthyridin-6(5H)-one (0.11 g, 0.274 mmol) in DCM (10 mL) at −20° C. was added BBr$_3$ (0.39 mL, 4.11 mmol) and the mixture stirred for 10 min at −20° C., then at room temperature for 3 h. The reaction mixture quenched with saturated aqueous NaHCO$_3$ (30 mL) and extracted with DCM (2×50 mL). The combined organic extracts were washed with brine, dried over Na$_2$SO$_4$, filtered, and concentrated under reduced pressure to afford 9-chloro-8-hydroxy-2,5-dimethylbenzo[c][1,7]naphthyridin-6(5H)-one (0.07 g, 0.134 mmol, 49% crude yield, 53% purity by LC) as a brown solid which was carried forward without further purification. LC/MS (ESI) m/e 275.0 [(M+H)$^+$, calcd for C$_{14}$H$_{12}$ClN$_2$O$_2$, 275.1]; LC/MS retention time (Method A3): t$_R$=1.52 min.

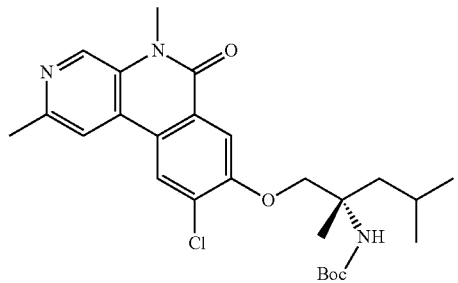 [SMILES: Cc1cc2c3cc(Cl)c(OC[C@](C)(CC(C)C)NC(=O)OC(C)(C)C)cc3c(=O)n(C)c2cn1]

Part I: (S)-tert-butyl (1-((9-chloro-2,5-dimethyl-6-oxo-5,6-dihydrobenzo[c][1,7]naphthyridin-8-yl)oxy)-2,4-dimethylpentan-2-yl)carbamate To a solution of 9-chloro-8-hydroxy-2,5-dimethylbenzo[c][1,7]naphthyridin-6(5H)-one (0.07 g, 0.134 mmol) in DMF (5 mL) was added K$_2$CO$_3$ (0.037 g, 0.267 mmol) and (S)-tert-butyl 4-isobutyl-4-methyl-1,2,3-oxathiazolidine-3-carboxylate 2,2-dioxide (0.047 g, 0.160 mmol) (prepared in Example 14, Part D). The reaction mixture was heated to 80° C. for 16 h. The reaction mixture was cooled to room temperature and filtered through diatomaceous earth (Celite®) washing with EtOAc (20 mL). The filtrate was concentrated under reduced pressure. The residue was purified by silica gel chromatography (50% EtOAc in petroleum ether) to afford (S)-tert-butyl (1-((9-chloro-2,5-dimethyl-6-oxo-5,6-dihydrobenzo[c][1,7]naphthyridin-8-yl)oxy)-2,4-dimethylpentan-2-yl)carbamate (0.036 g, 0.059 mmol, 44% yield) was carried forward without further purification. LC/MS (ESI) m/e 488.2 [(M+H)$^+$, calcd for C$_{26}$H$_{35}$ClN$_3$O$_4$, 488.2]; LC/MS retention time (Method A3): t$_R$=2.43 min.

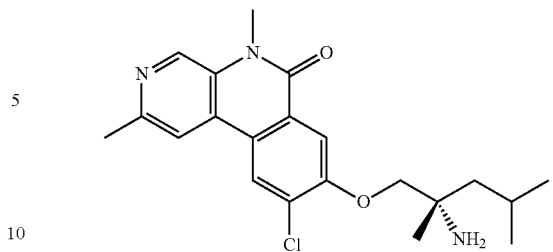

Part J: (S)-8-((2-amino-2,4-dimethylpentyl)oxy)-9-chloro-2,5-dimethylbenzo[c][1,7]naphthyridin-6(5H)-one To (S)-tert-butyl (1-((9-chloro-2,5-dimethyl-6-oxo-5,6-dihydrobenzo[c][1,7]naphthyridin-8-yl)oxy)-2,4-dimethylpentan-2-yl)carbamate (0.036 g, 0.059 mmol) in DCM (3 mL) cooled to 0° C. was added 4M HCl in 1,4-dioxane (0.30 mL, 1.18 mmol). The mixture was warmed to room temperature and stirred for 1 h. The reaction mixture was diluted with saturated aqueous sodium bicarbonate (20 mL) and extracted with ethyl acetate (30 mL). The organic layer was separated, dried over anhydrous sodium sulphate, filtered, and concentrated under reduced pressure. The residue was purified via prep HPLC (methanol:water with 10 mM NH$_4$OAc) to afford (S)-8-((2-amino-2,4-dimethylpentyl)oxy)-9-chloro-2,5-dimethylbenzo[c][1,7]naphthyridin-6(5H)-one (0.01 g, 0.025 mmol, 43% yield) as a brown solid. LC/MS (ESI) m/3 388.2 [(M+H)$^+$, calcd for C$_{21}$H$_{27}$ClN$_3$O$_2$, 388.2]; LC/MS retention time (Method A3): t$_R$=1.55 min; $^1$H NMR (400 MHz, METHANOL-d$_4$) δ 8.70 (s, 1H), 8.57 (s, 1H), 8.09 (s, 1H), 7.97 (s, 1H), 4.19-4.03 (m, 2H), 3.84 (s, 3H), 2.67 (s, 3H), 1.97-1.82 (m, 1H), 1.77-1.56 (m, 2H), 1.38 (s, 3H), 1.04 (t, J=7.0 Hz, 6H), two exchangeable protons not observed; HPLC purity (Method A1): 98% t$_R$=9.39 min; HPLC purity (Method B1): 98% t$_R$=10.60 min.

Example 18

(S)-8-((2-amino-2,4-dimethylpentyl)oxy)-7-chloro-2,5-dimethylbenzo[c][1,7]naphthyridin-6(5H)-one

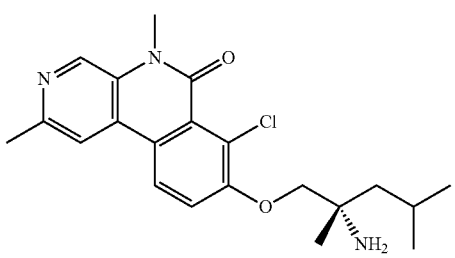 [SMILES: Cc1cc2c3ccc(OC[C@@](C)(N)CC(C)C)c(Cl)c3c(=O)n(C)c2cn1]

Prepared as described in Example 17. Obtained (S)-8-((2-amino-2,4-dimethylpentyl)oxy)-7-chloro-2,5-dimethylbenzo[c][1,7]naphthyridin-6(5H)-one (0.01 g, 0.025 mmol, 38% yield) as a brown solid. LC/MS (ESI) m/3 388.2 [(M+H)$^+$, calcd for C$_{21}$H$_{27}$ClN$_3$O$_2$, 388.2]; LC/MS retention time (Method A3): t$_R$=1.53 min; $^1$H NMR (400 MHz, METHANOL-d$_4$) δ 8.66 (s, 1H), 8.54 (d, J=9.0 Hz, 1H), 8.14 (s, 1H), 7.71 (d, J=8.5 Hz, 1H), 4.37-4.19 (m, 2H), 3.80 (s, 3H), 2.67 (s, 3H), 1.96-1.85 (m, 2H), 1.80-1.66 (m, 1H), 1.53 (s, 3H), 1.08 (d, J=6.5 Hz, 3H), 1.05 (d, J=6.0 Hz, 3H), two exchangeable protons not observed; HPLC purity (Method A1): 95% t$_R$=8.74 min; HPLC purity (Method B1): 96% t$_R$=10.02 min.

Example 19

(S)-8-((2-amino-2,4-dimethylpentyl)oxy)-5-ethyl-4-methylbenzo[c][1,7]naphthyridin-6(5H)-one

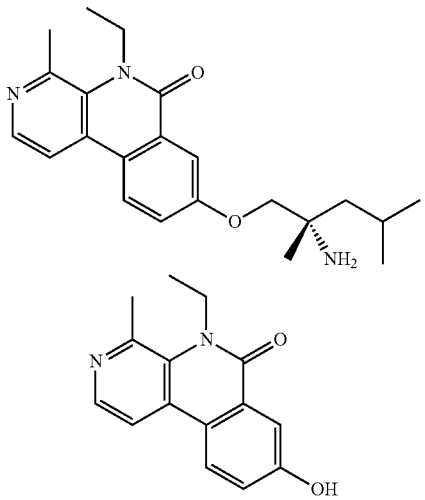

Part A: (S)-8-((2-amino-2,4-dimethylpentyl)oxy)-5-ethyl-4-methylbenzo[c][1,7]naphthyridin-6(5H)-one Prepared as described in Example 5, Parts A-G to afford 5-ethyl-8-hydroxy-4-methylbenzo[c][1,7]naphthyridin-6(5H)-one (0.35 g, 1.38 mmol, 82% yield for the final step) as an off-white solid. LC/MS (ESI) m/e 255.2 [(M+H)$^+$, calcd for C$_{15}$H$_{15}$N$_2$O$_2$, 255.1]; LC/MS retention time (Method A): t$_R$=1.93 min.

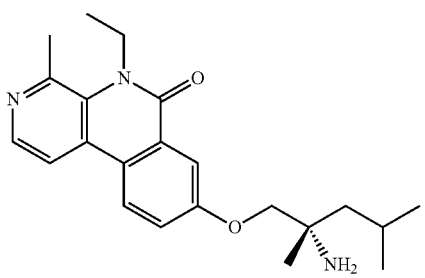 [SMILES: CCn1c(=O)c2cc(OC[C@@](C)(N)CC(C)C)ccc2c2ccnc(C)c21]

Part B: 5-Ethyl-8-hydroxy-4-methylbenzo[c][1,7]naphthyridin-6(5H)-one

Prepared as described in Example 14, Parts N and O to afford (S)-8-((2-amino-2,4-dimethylpentyl)oxy)-5-ethyl-4-methylbenzo[c][1,7]naphthyridin-6(5H)-one (37.3 mg, 0.100 mmol, 25% yield for two steps) as a pale yellow solid. LC/MS (ESI) m/e 368.2 [(M+H)$^+$, calcd for C$_{22}$H$_{30}$N$_3$O$_2$, 368.2]; LC/MS retention time (Method A3): t$_R$=1.50 min; $^1$H NMR (400 MHz, METHANOL-d$_4$) δ 8.60 (d, J=9.0 Hz, 1H), 8.50-8.45 (m, 1H), 8.44-8.37 (m, 1H), 8.04 (d, J=3.0 Hz, 1H), 7.72-7.64 (m, 1H), 4.54 (q, J=7.0 Hz, 2H), 4.36 (d, J=10.0 Hz, 1H), 4.30-4.21 (m, 1H), 3.06 (s, 3H), 1.99-1.84 (m, 2H), 1.80-1.69 (m, 1H), 1.55 (s, 3H), 1.48 (t, J=7.0 Hz, 3H), 1.10 (d, J=6.5 Hz, 3H), 1.05 (d, J=6.0 Hz, 3H), two exchangeable protons not observed; HPLC purity (Method C1): 99% t$_R$=1.50 min; HPLC purity (Method D): 96% t$_R$=0.79 min.

Example 20

(S)-8-((2-amino-2,4-dimethylpentyl)oxy)-2,5,7-trimethylbenzo[c][1,7]naphthyridin-6(5H)-one

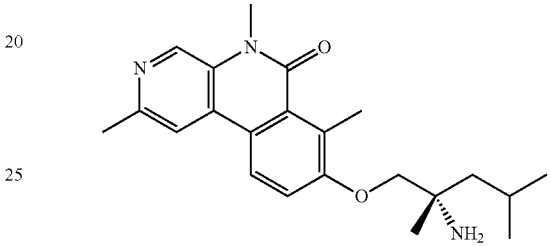

Prepared as described in Example 17. Obtained (S)-8-((2-amino-2,4-dimethylpentyl)oxy)-2,5,7-trimethylbenzo[c][1,7]naphthyridin-6(5H)-one (0.005 g, 0.014 mmol, 32% yield) as a colorless solid. LC/MS (ESI) m/3 368.2 [(M+H)$^+$, calcd for C$_{22}$H$_{30}$N$_3$O$_2$, 368.2]; LC/MS retention time (Method J): t$_R$=1.29 min; $^1$H NMR (400 MHz, METHANOL-d$_4$) δ 8.63 (s, 1H), 8.44 (d, J=9.0 Hz, 1H), 8.13 (s, 1H), 7.58 (d, J=9.0 Hz, 1H), 4.21-4.07 (m, 2H), 3.78 (s, 3H), 2.92 (s, 3H), 2.65 (s, 3H), 1.98-1.77 (m, 2H), 1.74-1.63 (m, 1H), 1.47 (s, 3H), 1.07 (d, J=6.5 Hz, 3H), 1.03 (d, J=6.0 Hz, 3H), two exchangeable protons not observed; HPLC purity (Method C1): 99% t$_R$=1.29 min; HPLC purity (Method D): 99% t$_R$=0.82 min.

Example 21

(S)-8-((2-amino-2,4-dimethylpentyl)oxy)-5-(2-hydroxyethyl)-4-methylbenzo[c][1,7]naphthyridin-6(5H)-one

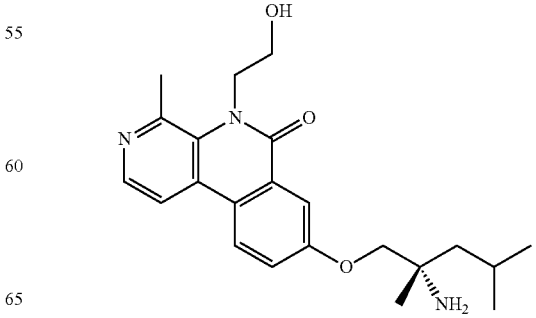

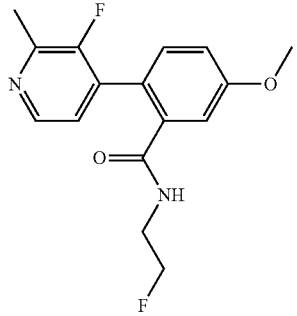

Part A: 2-(3-Fluoro-2-methylpyridin-4-yl)-N-(2-fluoroethyl)-5-methoxybenzamide Prepared as described in Example 5, Parts A-E to afford 2-(3-fluoro-2-methylpyridin-4-yl)-N-(2-fluoroethyl)-5-methoxybenzamide (0.16 g, 0.522 mmol, 68% yield for the final step) as a brown solid. LC/MS (ESI) m/e 307.2 [(M+H)$^+$, calcd for $C_{16}H_{17}FN_2O_2$, 307.1]; LC/MS retention time (Method A3): $t_R$=2.00 min.

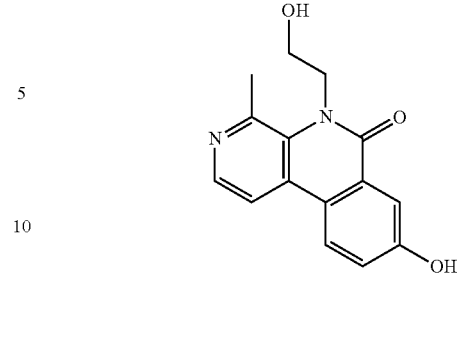

Part C: 8-hydroxy-5-(2-hydroxyethyl)-4-methyl-benzo[c][1,7]naphthyridin-6(5H)-one To a stirred solution of 5-(2-hydroxyethyl)-8-methoxy-4-methylbenzo[c][1,7]naphthyridin-6(5H)-one (0.08 g, 0.281 mmol) in DCM (5 mL) at 0° C. was added BBr$_3$ (0.027 mL, 0.281 mmol) and the mixture was allowed to warm to room temperature and stirred for 3 h. The reaction mixture was cooled to 0° C. and slowly quenched with methanol then concentrated under reduced pressure. The residue was rinsed with ethyl acetate (10 mL) and air dried to afford 8-hydroxy-5-(2-hydroxyethyl)-4-methylbenzo[c][1,7]naphthyridin-6(5H)-one (0.06 g, 0.133 mmol, 47% yield) as an off-white solid which was taken forward without further purification. LC/MS (ESI) m/e 271.2 [(M+H)$^+$, calcd for $C_{15}H_{15}N_2O_3$, 271.1]; LC/MS retention time (Method A3): $t_R$=1.74 min.

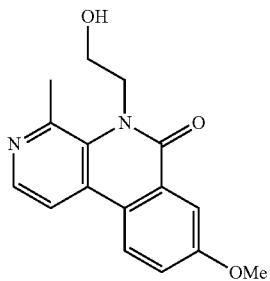 [SMILES: COc1ccc2c(c1)c(=O)n(CCO)c1c(C)nccc21]

Part B: 5-(2-Fluoroethyl)-8-methoxy-4-methylbenzo[c][1,7]naphthyridin-6(5H)-one To a stirred solution of 2-(3-fluoro-2-methylpyridin-4-yl)-N-(2-fluoroethyl)-5-methoxybenzamide (0.14 g, 0.457 mmol) in NMP (2 mL) was added Cs$_2$CO$_3$ (0.447 g, 1.37 mmol) in one portion at room temperature under nitrogen atmosphere and the reaction was stirred at 100° C. for 12 h. The reaction mixture was diluted with water (10 mL) and extracted with ethyl acetate (2×20 mL). The combined organic extracts were washed with water (3×10 mL), dried over sodium sulphate, filtered, and concentrated under reduced pressure to afford 5-(2-fluoroethyl)-8-methoxy-4-methylbenzo[c][1,7]naphthyridin-6(5H)-one (0.106 g, 0.370 mmol, 81% yield) as an off-white solid which was carried forward without further purification. The fluorine hydrolyzed to the hydroxyl during the reaction. LC/MS (ESI) m/e 285.2 [(M+H)$^+$, calcd for $C_{16}H_{17}N_2O_3$, 285.1]; LC/MS retention time (Method A3): $t_R$=2.18 min.

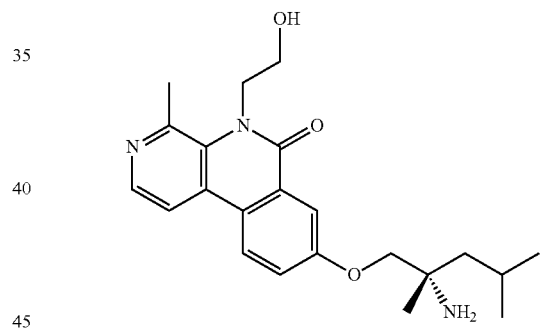

Part C: (S)-8-((2-Amino-2,4-dimethylpentyl)oxy)-5-(2-hydroxyethyl)-4-methylbenzo[c][1,7]-naphthyridin-6(5H)-one Prepared as described in Example 14, Parts N and O to afford (S)-8-((2-amino-2,4-dimethylpentyl)oxy)-5-(2-hydroxyethyl)-4-methylbenzo[c][1,7]naphthyridin-6(5H)-one (35.4 mg, 0.090 mmol, 41% yield for two steps) as a pale yellow solid. LC/MS (ESI) m/e 384.2 [(M+H)$^+$, calcd for $C_{22}H_{30}N_3O_2$, 384.2]; LC/MS retention time (Method J): $t_R$=0.94 min; $^1$H NMR (400 MHz, METHANOL-d$_4$) δ 8.51 (d, J=9.0 Hz, 1H), 8.35 (d, J=5.5 Hz, 1H), 8.15 (d, J=5.5 Hz, 1H), 8.00 (d, J=2.5 Hz, 1H), 7.61 (dd, J=8.8, 2.8 Hz, 1H), 4.70 (t, J=5.8 Hz, 2H), 4.33-4.25 (m, 1H), 4.24-4.12 (m, 1H), 3.84 (t, J=5.8 Hz, 2H), 2.91 (s, 3H), 1.93-1.79 (m, 2H), 1.73-1.64 (m, 1H), 1.51 (s, 3H), 1.09 (d, J=6.5 Hz, 3H), 1.05 (d, J=6.5 Hz, 3H), three exchangeable protons not observed; HPLC purity (Method C1): 98% $t_R$=0.94 min; HPLC purity (Method D): 96% $t_R$=0.64 min.

Example 22

(S)-8-((2-amino-2,4-dimethylpentyl)oxy)-9-chloro-4-methyl-5-(trideuteromethyl)benzo[c][1,7]naphthyridin-6(5H)-one

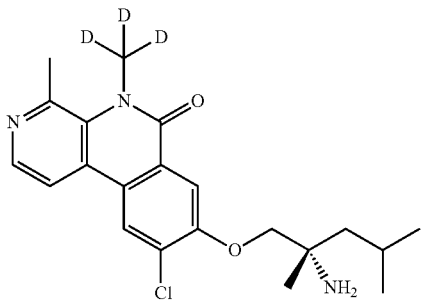 [SMILES: [2H]C([2H])([2H])n1c(=O)c2cc(OC[C@@](C)(N)CC(C)C)c(Cl)cc2c2ccnc(C)c21]

Prepared as described in Example 15, Parts G and H, using deuterated methyl amine, HCl as the coupling partner in Part D. Obtained (S)-8-((2-amino-2,4-dimethylpentyl)oxy)-9-chloro-4-methyl-5-(trideuteromethyl)benzo[c][1,7]naphthyridin-6(5H)-one (7.8 mg, 0.020 mmol, 22% yield for the last two steps) as a pale yellow solid. LC/MS (ESI) m/3 391.0 [(M+H)$^+$, calcd for $C_{21}H_{24}D_3ClN_3O_2$, 391.2]; LC/MS retention time (Method J): $t_R$=0.75 min; $^1$H NMR (400 MHz, METHANOL-$d_4$) δ 8.65 (s, 1H), 8.36 (d, J=5.0 Hz, 1H), 8.13 (d, J=5.0 Hz, 1H), 8.05 (s, 1H), 4.35-4.22 (m, 2H), 2.94 (s, 3H), 1.94-1.82 (m, 2H), 1.78-1.67 (m, 1H), 1.51 (s, 3H), 1.08 (d, J=6.5 Hz, 3H), 1.05 (d, J=6.0 Hz, 3H), two exchangeable protons not observed; HPLC purity (Method C1): 99% $t_R$=1.30 min; HPLC purity (Method D): 98% $t_R$=0.75 min.

Example 23

(S)-8-((2-amino-2,4-dimethylpentyl)oxy)-4-methyl-5-(trideuteromethyl)benzo[c][1,7]naphthyridin-6(5H)-one

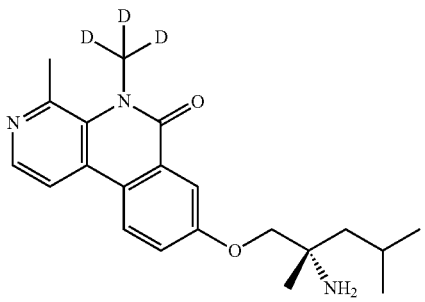

Prepared as described in Example 15, Parts G and H, using deuterated methyl amine, HCl as the coupling partner in Part D. Obtained (S)-8-((2-amino-2,4-dimethylpentyl)oxy)-4-methyl-5-(trideuteromethyl)benzo[c][1,7]naphthyridin-6(5H)-one (9.9 mg, 0.026 mmol, 19% yield for the last two steps) as an off-white solid. LC/MS (ESI) m/3 357.2 [(M+H)$^+$, calcd for $C_{21}H_{25}D_3N_3O_2$, 357.2]; LC/MS retention time (Method A2): $t_R$=1.81 min; $^1$H NMR (400 MHz, METHANOL-$d_4$) δ 8.48 (d, J=9.0 Hz, 1H), 8.34 (d, J=5.5 Hz, 1H), 8.13 (d, J=5.5 Hz, 1H), 7.96 (d, J=3.0 Hz, 1H), 7.57 (dd, J=9.0, 3.0 Hz, 1H), 4.13-3.99 (m, 2H), 2.93 (s, 3H), 1.91-1.81 (m, 1H), 1.75-1.55 (m, 2H), 1.36 (s, 3H), 1.05 (d, J=7.0 Hz, 3H), 1.02 (d, J=6.5 Hz, 3H), two exchangeable protons not observed; HPLC purity (Method A1): 92% $t_R$=7.94 min; HPLC purity (Method C2): 97% $t_R$=1.97 min.

Example 24

(S)-8-((2-amino-2,4-dimethylpentyl)oxy)-5-cyclopropyl-4-methyl-6-oxo-5,6-dihydrobenzo[c][1,7]naphthyridine-9-carbonitrile

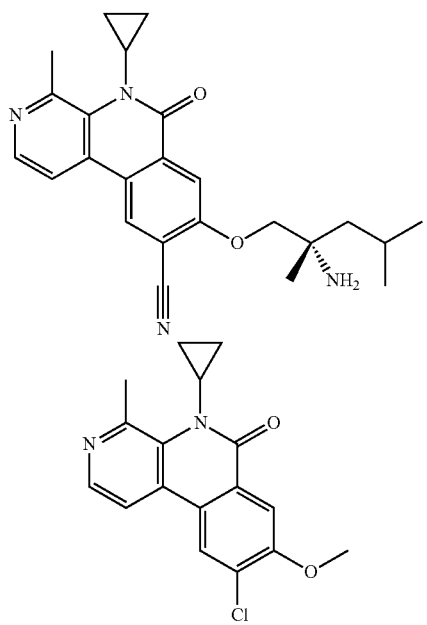

Part A: 9-Chloro-5-cyclopropyl-8-methoxy-4-methylbenzo[c][1,7]naphthyridin-6(5H)-one Prepared as described in Example 5, Parts A-F to afford 9-chloro-5-cyclopropyl-8-methoxy-4-methylbenzo[c][1,7]naphthyridin-6(5H)-one (0.06 g, 0.191 mmol, 80% yield for the final step) as an off-white semi-solid. LC/MS (ESI) m/e 315.0 [(M+H)$^+$, calcd for $C_{17}H_{16}ClN_2O_2$, 315.1]; LC/MS retention time (Method A3): $t_R$=2.25 min.

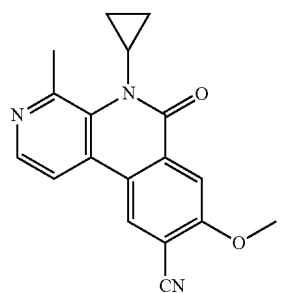 [SMILES: COc1cc2c(=O)n(C3CC3)c3c(C)nccc3c2cc1C#N]

Part B: 5-Cyclopropyl-8-methoxy-4-methyl-6-oxo-5,6-dihydrobenzo[c][1,7]naphthyridine-9-carbonitrile To a stirred solution of 9-chloro-5-cyclopropyl-8-methoxy-4-methylbenzo[c][1,7]naphthyridin-6(5H)-one (0.06 g, 0.191 mmol) in DMA (5 mL) was added zinc cyanide (0.060 g, 0.572 mmol) and zinc powder (0.012 g, 0.191 mmol). Nitrogen gas was bubbled through the solution for 10 min. PdCl$_2$(dppf)-CH$_2$Cl$_2$ Adduct (0.016 g, 0.019 mmol) was added and the reaction mixture stirred at 110° C. for 48 h. The reaction mixture was allowed to cool to room temperature. Water (10 mL) and ethyl acetate (10 mL) were added and the mixture stirred for 10 min. The organic layer was separated and the aqueous layer was extracted with ethyl acetate (2×10 mL). The combined the organic layers were washed with water (3×15 mL), brine (1×10 mL), dried over sodium sulphate, filtered, and concentrated under reduced pressure to afford 5-cyclopropyl-8-methoxy-4-methyl-6-oxo-5,6-dihydrobenzo[c][1,7]naphthyridine-9-carbonitrile (50 mg, 0.082 mmol, 43% yield) as a brown solid which was carried forward without further purification. LC/MS (ESI) m/e 306.0 [(M+H)$^+$, calcd for C$_{18}$H$_{16}$N$_3$O$_2$, 306.2]; LC/MS retention time (Method A3): t$_R$=1.85 min.

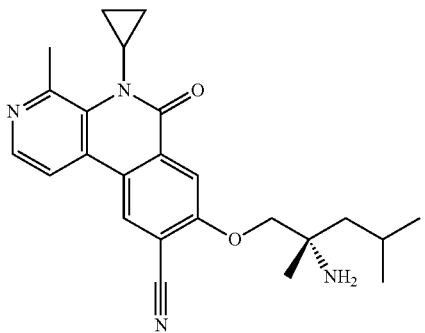 [SMILES: Cc1nccc2c3cc(C#N)c(OC[C@@](C)(N)CC(C)C)cc3c(=O)n(C3CC3)c12]

Part C: (S)-8-((2-amino-2,4-dimethylpentyl)oxy)-5-cyclopropyl-4-methyl-6-oxo-5,6-dihydrobenzo[c][1,7]naphthyridine-9-carbonitrile Prepared as described in Example 14, Parts M-O to afford (S)-8-((2-amino-2,4-dimethylpentyl)oxy)-5-cyclopropyl-4-methyl-6-oxo-5,6-dihydrobenzo[c][1,7]naphthyridine-9-carbonitrile (1.2 mg, 2.73 μmol, 3% yield for two steps) as a pale yellow solid. LC/MS (ESI) m/e 405.2 [(M+H)$^+$, calcd for C$_{24}$H$_{29}$N$_4$O$_2$, 405.2]; LC/MS retention time (Method J): t$_R$=0.76 min; $^1$H NMR (400 MHz, METHANOL-d$_4$) δ 9.06 (s, 1H), 8.50-8.46 (m, 1H), 8.45-8.40 (m, 1H), 8.16 (s, 1H), 4.53-4.42 (m, 2H), 3.74-3.71 (m, 1H), 3.12 (s, 3H), 2.07-1.72 (m, 5H), 1.60 (s, 3H), 1.37-1.27 (m, 2H), 1.11 (d, J=6.5 Hz, 3H), 1.08 (d, J=6.5 Hz, 3H), two exchangeable protons not observed; HPLC purity (Method C1): 91% t$_R$=1.25 min; HPLC purity (Method D): 91% t$_R$=0.76 min.

Example 25

(S)-8-((2-amino-2,4-dimethylpentyl)oxy)-9-chloro-5-isopropyl-4-methylbenzo[c][1,7]naphthyridin-6(5H)-one

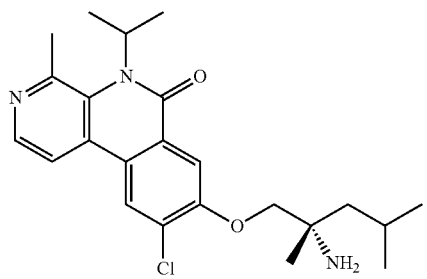 [SMILES: Cc1nccc2c3cc(Cl)c(OC[C@@](C)(N)CC(C)C)cc3c(=O)n(C(C)C)c12]

Prepared as described in Example 15 using 9-chloro-8-hydroxy-5-isopropyl-4-methylbenzo[c][1,7]naphthyridin-6(5H)-one (0.08 g, 0.264 mmol) (prepared in Example 5, Part G) and (S)-tert-butyl 4-isobutyl-4-methyl-1,2,3-oxathiazolidine-3-carboxylate 2,2-dioxide (0.093 g, 0.317 mmol) (prepared in Example 14, Part E) as the coupling partners in Part G. Obtained (S)-8-((2-amino-2,4-dimethylpentyl)oxy)-9-chloro-5-isopropyl-4-methylbenzo[c][1,7]naphthyridin-6(5H)-one (0.5 mg, 1.67 μmol, 1% yield for the last five steps) as a pale brown film. LC/MS (ESI) m/e 416.2 [(M+H)$^+$, calcd for C$_{23}$H$_{31}$ClN$_3$O$_2$, 416.2]; LC/MS retention time (Method J): t$_R$=1.39 min; $^1$H NMR (400 MHz, METHANOL-d$_4$) δ 8.28 (d, J=5.0 Hz, 1H), 7.35-7.28 (m, 2H), 7.20 (s, 1H), 4.32-4.14 (m, 2H), 4.01 (dd, J=13.1, 6.0 Hz, 1H), 2.54 (d, J=3.0 Hz, 3H), 2.01-1.83 (m, 2H), 1.72 (dd, J=13.8, 4.8 Hz, 1H), 1.55 (s, 3H), 1.14-1.01 (m, 12H), two exchangeable protons not observed; HPLC purity (Method C1): 98% t$_R$=1.33 min; HPLC purity (Method D): 96% t$_R$=0.90 min.

Example 26

(S)-8-((2-amino-2,4-dimethylpentyl)oxy)-4,5,9-trimethylbenzo[c][1,7]naphthyridin-6(5H)-one

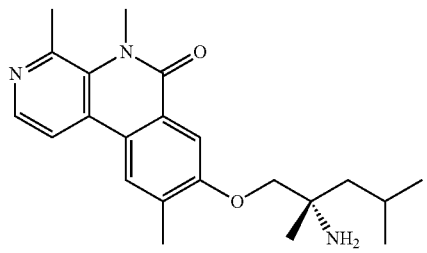 [SMILES: Cc1cc2c(cc1OC[C@@](C)(N)CC(C)C)c(=O)n(C)c1c(C)nccc21]

Prepared as described in Example 15 using 8-hydroxy-4,5,9-trimethylbenzo[c][1,7]naphthyridin-6(5H)-one (50 mg, 0.197 mmol) (prepared as described in Example 3) and (S)-tert-butyl 4-isobutyl-4-methyl-1,2,3-oxathiazolidine-3-carboxylate 2,2-dioxide (57.7 mg, 0.197 mmol) (prepared in Example 14, Part E) as the coupling partners in Part G. Obtained (S)-8-((2-amino-2,4-dimethylpentyl)oxy)-4,5,9-trimethylbenzo[c][1,7]naphthyridin-6(5H)-one (21.7 mg, 0.059 mmol, 3% yield for two steps) as a pale yellow solid.

LC/MS (ESI) m/e 368.0 [(M+H)+, calcd for $C_{22}H_{30}N_3O_2$, 368.2]; LC/MS retention time (Method J): $t_R$=0.79 min; $^1$H NMR (400 MHz, METHANOL-$d_4$) δ 8.36 (s, 1H), 8.34 (d, J=5.0 Hz, 1H), 8.14 (d, J=5.5 Hz, 1H), 7.89 (s, 1H), 4.33-4.17 (m, 2H), 3.88 (s, 3H), 2.93 (s, 3H), 2.57 (s, 3H), 1.94-1.82 (m, 2H), 1.79-1.64 (m, 1H), 1.54 (s, 3H), 1.09 (d, J=6.5 Hz, 3H), 1.05 (d, J=6.0 Hz, 3H), two exchangeable protons not observed; HPLC purity (Method C1): 94% $t_R$=1.32 min; HPLC purity (Method D): 97% $t_R$=0.79 min.

Example 27

(S)-8-((2-amino-2,4-dimethylpentyl)oxy)-9-chloro-4,5-dimethylbenzo[c][1,7]naphthyridin-6(5H)-one

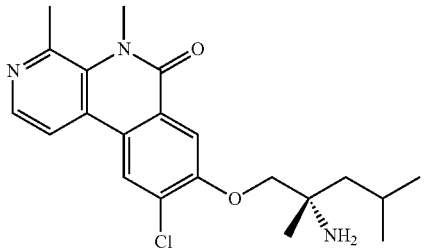 [SMILES: Cc1nccc2c3cc(Cl)c(OC[C@@](C)(N)CC(C)C)cc3c(=O)n(C)c12]

Prepared as described in Example 15 using 9-chloro-8-hydroxy-4,5-dimethylbenzo[c][1,7]naphthyridin-6(5H)-one (110 mg, 0.400 mmol) (prepared in Example 5, Part G) and (S)-tert-butyl 4-isobutyl-4-methyl-1,2,3-oxathiazolidine-3-carboxylate 2,2-dioxide (117 mg, 0.400 mmol) (prepared in Example 14, Part E) as the coupling partners in Part G. Obtained (S)-8-((2-amino-2,4-dimethylpentyl)oxy)-9-chloro-4,5-dimethylbenzo[c][1,7]naphthyridin-6(5H)-one (16.7 mg, 0.043 mmol, 19% yield for two steps) as a pale yellow solid. LC/MS (ESI) m/e 388.0 [(M+H)+, calcd for $C_{21}H_{27}ClN_3O_2$, 388.2]; LC/MS retention time (Method J): $t_R$=0.80 min; $^1$H NMR (400 MHz, METHANOL-$d_4$) δ 8.61 (s, 1H), 8.34 (d, J=5.5 Hz, 1H), 8.10 (d, J=5.5 Hz, 1H), 8.00 (s, 1H), 4.20-4.09 (m, 2H), 3.87 (s, 3H), 2.93 (s, 3H), 1.91-1.81 (m, 1H), 1.78-1.58 (m, 2H), 1.39 (s, 3H), 1.04 (d, J=6.5 Hz, 3H), 1.02 (d, J=6.5 Hz, 3H), two exchangeable protons not observed; HPLC purity (Method C1): 97% $t_R$=1.43 min; HPLC purity (Method D): 97% $t_R$=0.80 min.

Example 28

(S)-8-((2-amino-2,4-dimethylpentyl)oxy)-9-chloro-4-methylbenzo[c][1,7]naphthyridin-6(5H)-one

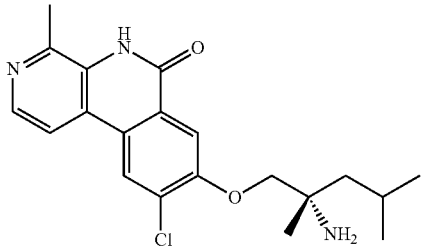 [SMILES: Cc1nccc2c1[nH]c(=O)c1cc(OC[C@@](C)(N)CC(C)C)c(Cl)cc12]

Prepared as described in Example 15 using 9-chloro-8-hydroxy-4-methylbenzo[c][1,7]-naphthyridin-6(5H)-one (0.4 g, 1.53 mmol) and (S)-tert-butyl 4-isobutyl-4-methyl-1,2,3-oxathiazolidine-3-carboxylate 2,2-dioxide (0.54 g, 1.84 mmol) as the coupling partners in Part G. Obtained (S)-8-((2-amino-2,4-dimethylpentyl)oxy)-9-chloro-4-methylbenzo[c][1,7]naphthyridin-6(5H)-one (0.5 mg, 1.27 μmol, 1% yield for the last five steps) as a pale yellow film. LC/MS (ESI) m/e 374.0 [(M+H)+, calcd for $C_{20}H_{25}ClN_3O_2$, 374.2]; LC/MS retention time (Method L): $t_R$=1.21 min; $^1$H NMR (400 MHz, METHANOL-$d_4$) δ 8.98 (s, 1H), 8.75-8.73 (m, 1H), 8.51 (d, J=6.4 Hz, 1H), 8.16 (d, J=5.6 Hz, 1H), 3.14 (s, 3H), 2.07-1.90 (m, 2H), 1.87-1.84 (m, 1H), 1.65 (s, 3H), 1.13 (d, J=6.4 Hz, 3H), 1.09 (d, J=6.4 Hz, 3H), two exchangeable protons not observed, water suppressed in NMR, also suppressed OCH2 protons; HPLC purity (Method C1): 95% $t_R$=1.21 min.

Example 29

(S)-1-((6H-isochromeno[3,4-c]pyridin-8-yl)oxy)-4-methylpentan-2-amine

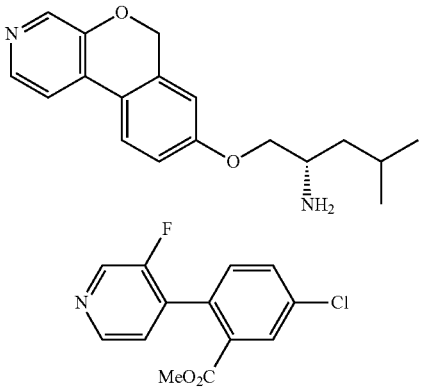

Part A: Methyl 5-chloro-2-(3-fluoropyridin-4-yl)benzoate

To a mixture of 4-chloro-3-fluoropyridine (3 g, 22.81 mmol), methyl 5-chloro-2-(4,4,5,5-tetramethyl-1,3,2-dioxaborolan-2-yl)benzoate (8.12 g, 27.4 mmol) (prepared in Example 1, Part B) in THF (60 mL) and water (30 mL), was added cesium carbonate (14.9 g, 45.6 mmol). Nitrogen gas was bubbled through the stirred suspension for 5 min. Tetrakis(triphenylphosphine)palladium(0) (1.32 g, 1.14 mmol) was added and nitrogen gas was bubbled through the stirred suspension for 5 min. The reaction mixture was stirred in microwave at 80° C. for 12 h. The reaction mixture was cooled to room temperature and diluted with water and extracted with ethyl acetate (2×15 mL). The combined organic layers were washed with brine (10 mL), dried over sodium sulphate, filtered, and concentrated under reduced pressure. The residue was purified via silica gel chromatography (hexane and ethyl acetate gradient) to afford methyl 5-chloro-2-(3-fluoropyridin-4-yl)benzoate (700 mg, 2.37 mmol, 10% yield) as a yellow solid. LC/MS (ESI) m/e 266.1 [(M+H)+, calcd for $C_{13}H_{10}ClFNO_2$, 266.0]; LC/MS retention time (Method B): $t_R$=0.96 min; $^1$H NMR (400 MHz, CHLOROFORM-d) δ 8.49 (s, 1H), 8.48 (d, J=2.4 Hz, 1H), 8.04 (d, J=2.4 Hz, 1H), 7.60 (dd, J=8.4, 2.0 Hz, 1H), 7.28 (m, 1H), 7.21 (d, J=5.2 Hz, 1H), 3.74 (s, 3H).

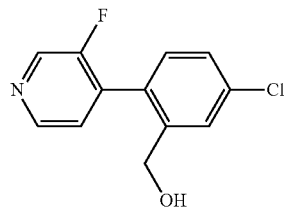 [SMILES: OCc1cc(Cl)ccc1-c1ccncc1F]

Part B: (5-Chloro-2-(3-fluoropyridin-4-yl)phenyl)methanol

To a solution of methyl 5-chloro-2-(3-fluoropyridin-4-yl) benzoate (650 mg, 2.45 mmol) tetrahydrofuran (12 mL) cooled to 0° C. was added LAH (7.34 mL, 7.34 mmol) dropwise over a period of 5 min. The reaction mixture was stirred for 15 min at 0° C., then at room temperature for 1 h. The reaction mixture was quenched with saturated aqueous ammonium chloride (5 mL) and extracted with ethyl acetate (3×5 mL). The combined organic layers were washed with brine, dried over sodium sulphate, filtered, and concentrated under reduced pressure to afford (5-chloro-2-(3-fluoropyridin-4-yl)phenyl)methanol (550 mg, 1.20 mmol, 49% yield) as a light yellow solid. LC/MS (ESI) m/e 238.0 [(M+H)$^+$, calcd for $C_{12}H_{10}ClFNO$, 238.0]; LC/MS retention time (Method B): $t_R$=0.77 min; $^1$H NMR (400 MHz, CHLOROFORM-d) δ 8.55 (d, J=1.2 Hz, 1H), 8.48 (dd, J=4.8, 1.2 Hz, 1H), 7.67 (d, J=2.0 Hz, 1H), 7.38 (dd, J=8.0, 2.0 Hz, 1H), 7.26-7.18 (m, 2H), 4.53 (s, 3H).

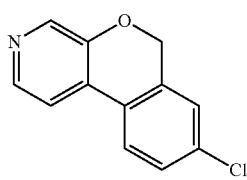 [SMILES: Clc1ccc2c(c1)COc1cnccc1-2]

Part C: 8-chloro-6H-isochromeno[3,4-c]pyridine

To a solution of (5-chloro-2-(3-fluoropyridin-4-yl)phenyl)methanol (550 mg, 2.31 mmol) in tetrahydrofuran (11 mL) cooled to 0° C. was added NaH (111 mg, 4.63 mmol) in two portions over a period of 5 min. The reaction mixture was stirred at 0° C. for 15 min, then at room temperature for 2 h. The reaction mixture was quenched with ice water and extracted with ethyl acetate (2×5 mL). The combined organic layers were washed with brine (5 mL), dried, filtered, and concentrated under reduced pressure to afford 8-chloro-6H-isochromeno[3,4-c]pyridine (180 mg, 0.604 mmol, 26% yield) as a pale pink solid. LC/MS (ESI) m/e 218.0 [(M+H)$^+$, calcd for $C_{12}H_9ClNO$, 218.0]; LC/MS retention time (Method B): $t_R$=0.91 min; $^1$H NMR (400 MHz, CHLOROFORM-d) δ 8.36 (s, 1H), 8.30 (d, J=5.2 Hz, 1H), 7.67 (d, J=8.4 Hz, 1H), 7.51 (d, J=4.8 Hz, 1H), 7.41 (d, J=2.0 Hz, 1H), 7.20 (d, J=2.0 Hz, 1H), 5.16 (s, 2H).

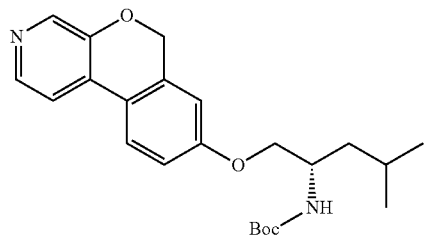 [SMILES: CC(C)C[C@@H](COc1ccc2c(c1)COc1cnccc1-2)NC(=O)OC(C)(C)C]

Part D: (S)-tert-butyl (1-((6H-isochromeno[3,4-c]pyridin-8-yl)oxy)-4-methylpentan-2-yl)carbamate In a pressure tube was added 8-chloro-6H-isochromeno [3,4-c]pyridine (50 mg, 0.230 mmol), cesium carbonate (112 mg, 0.345 mmol) and di-tert-butyl(2',4',6'-triisopropyl-[1,1'-biphenyl]-2-yl)phosphine (58.5 mg, 0.138 mmol) in toluene (1 mL). N$_2$ was bubbled through the solution for 5 min. To this was added N-Boc L-Leucinol (148 mg, 0.689 mmol) and N$_2$ was bubbled through the solution for 5 min. Palladium(II) acetate (15.47 mg, 0.069 mmol) was added and N$_2$ was bubbled through the solution for 10 min. The pressure tube was sealed and heated to 80° C. for 12 h. The reaction mixture was cooled to room temperature and filtered through diatomaceous earth (Celite®) washing with EtOAc. The filtrate was concentrated under reduced pressure. The residue was purified by preparative TLC (hexane and ethyl acetate) to afford (S)-tert-butyl (1-((6H-isochromeno[3,4-c] pyridin-8-yl)oxy)-4-methylpentan-2-yl)carbamate (30 mg, 0.056 mmol, 25% yield) as a brown solid. LC/MS (ESI) m/e 399.4 [(M+H)$^+$, calcd for $C_{23}H_{31}N_2O_4$, 399.2]; LC/MS retention time (Method B): $t_R$=1.24 min.

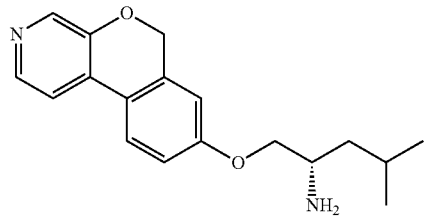 [SMILES: CC(C)C[C@H](N)COc1ccc2c(c1)COc1cnccc1-2]

Part E: (S)-1-((6H-isochromeno[3,4-c]pyridin-8-yl)oxy)-4-methylpentan-2-amine To (S)-tert-butyl (1-((6H-isochromeno[3,4-c]pyridin-8-yl)oxy)-4-methylpentan-2-yl)carbamate (30 mg, 0.075 mmol) in diethyl ether (2 mL) cooled to 0° C. was added 2N HCl in diethyl ether (0.023 mL, 0.753 mmol). The reaction mixture was warmed to room temperature and stirred for 2 h. The reaction mixture was concentrated under reduced pressure. The residue was purified by prep HPLC (0.1% TFA water and ACN) to afford (S)-1-((6H-isochromeno[3,4-c]pyridin-8-yl)oxy)-4-methylpentan-2-amine (7.35 mg, 0.024 mmol, 32% yield) as an off-white solid. LC/MS (ESI) m/e 299.2 [(M+H)$^+$, calcd for $C_{18}H_{23}N_2O_2$, 299.2]; LC/MS retention time (Method M): $t_R$=1.78 min; $^1$H NMR (400 MHz, CD$_3$OD) δ 8.40 (s, 1H), 8.34 (d, J=6.0 Hz, 1H), 8.18 (d, J=5.6 Hz, 1H), 8.05 (d, J=8.8 Hz, 1H), 7.22 (dd, J=8.8, 2.4 Hz, 1H), 7.05 (d, J=2.4 Hz, 1H), 5.41 (s, 2H), 4.37 (dd, J=10.4, 3.2 Hz, 1H), 4.19 (dd, J=10.8, 6.4 Hz, 1H), 3.76-3.71 (m, 1H), 1.85-1.62 (m, 3H), 1.05 (d, J=6.8 Hz, 3H), 1.04 (d, J=6.8 Hz, 3H), two exchangeable protons not observed; HPLC purity (Method A1): 91% $t_R$=7.78 min; HPLC purity (Method B2): 92% $t_R$=8.46 min.

Example 30

(2S)-4-methyl-1-(((6-methyl-6H-isochromeno[3,4-c]pyridin-8-yl)oxy)pentan-2-amine

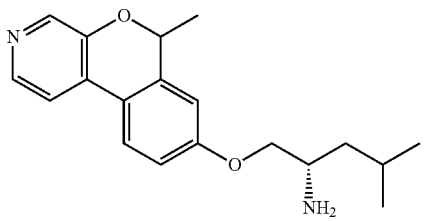

Part A:
5-Chloro-2-(3-fluoropyridin-4-yl)benzaldehyde

To a solution of (5-chloro-2-(3-fluoropyridin-4-yl)phenyl)methanol (1 g, 4.21 mmol) (prepared in Example 29, Part B) in DCM (10 mL) cooled to 0° C. was added Dess-Martin Periodinane (2.68 g, 6.31 mmol) in five portions. The reaction mixture was then stirred at 0° C. for 1 h, then at room temperature for 2 h. The reaction mixture was quenched with saturated aqueous bicarbonate and extracted with DCM (3×50 mL). The combined organic layers were washed with brine, dried over sodium sulphate, filtered, and concentrated under reduced pressure. The residue was purified via silica gel chromatography (EtOAc in hexanes) to afford 5-chloro-2-(3-fluoropyridin-4-yl)benzaldehyde (450 mg, 1.74 mmol, 41% yield) as an orange solid. LC/MS (ESI) m/e 236.0 [(M+H)$^+$, calcd for $C_{12}H_8ClFNO$, 236.0]; LC/MS retention time (Method B): $t_R$=0.89 min; $^1$H NMR (400 MHz, CHLOROFORM-d) δ 9.86 (d, J=2.8 Hz, 1H), 8.60 (d, J=2.0 Hz, 1H), 8.56 (dd, J=4.4, 0.8 Hz, 1H), 8.03 (d, J=2.4 Hz, 1H), 7.69 (dd, J=8.0, 2.4 Hz, 1H), 7.36 (d, J=8.4 Hz, 1H), 7.29 (d, J=5.2 Hz, 1H), 7.27 (d, J=4.8 Hz, 1H).

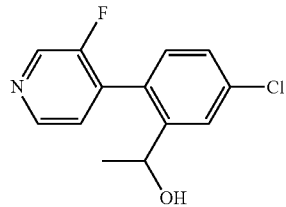 [SMILES: CC(O)c1cc(Cl)ccc1-c1ccncc1F]

Part B: 1-(5-Chloro-2-(3-fluoropyridin-4-yl)phenyl)ethanol

To a solution of 5-chloro-2-(3-fluoropyridin-4-yl)benzaldehyde (400 mg, 1.70 mmol) in tetrahydrofuran (8 mL) cooled to −40° C. was added methylmagnesium bromide (0.70 mL, 2.04 mmol) dropwise. The reaction mixture was stirred at −40° C. for 2 h, then warmed to room temperature. The reaction mixture was quenched with saturated aqueous ammonium chloride and extracted with ethyl acetate (2×15 mL). The combined organic layers were washed with brine, dried, filtered, and concentrated under reduced pressure to afford 1-(5-chloro-2-(3-fluoropyridin-4-yl)phenyl)ethanol (470 mg, 1.27 mmol, 75% yield) as brown oil LC/MS (ESI) m/e 252.1 [(M+H)$^+$, calcd for $C_{13}H_{12}ClFNO$, 252.1]; LC/MS retention time (Method B): $t_R$=0.82 min; $^1$H NMR (400 MHz, CHLOROFORM-d) δ 8.55 (d, J=1.2 Hz, 1H), 8.49 (dd, J=4.8, 0.8 Hz, 1H), 7.72 (d, J=2.0 Hz, 1H), 7.35 (dd, J=8.0, 2.0 Hz, 1H), 7.23-7.19 (m, 1H), 7.11 (d, J=8.4 Hz, 1H), 4.74 (q, J=6.4 Hz, 1H), 1.35 (d, J=6.4 Hz, 3H), one exchangeable proton not observed.

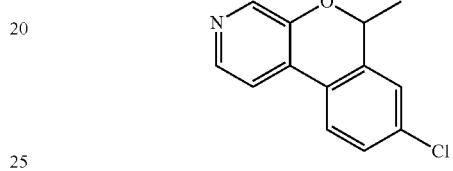

Part C: 8-Chloro-6-methyl-6H-isochromeno[3,4-c]pyridine

To a solution of 1-(5-chloro-2-(3-fluoropyridin-4-yl)phenyl)ethanol (470 mg, 1.27 mmol) in tetrahydrofuran (10 mL) cooled to 0° C. was added NaH (102 mg, 2.54 mmol) in portions over a period of 5 min. The reaction mixture was stirred at 0° C. for 1 h, then at room temperature for 1 h. The reaction mixture was quenched with ice and extracted with ethyl acetate (2×15 mL). The combined organic layers were washed with brine (15 mL), dried, filtered, and concentrated under reduced pressure to afford 8-chloro-6-methyl-6H-isochromeno[3,4-c]pyridine (300 mg, 1.14 mmol, 90% yield) as a brown solid. LC/MS (ESI) m/e 232.0 [(M+H)$^+$, calcd for $C_{13}H_{11}ClNO$, 232.1]; LC/MS retention time (Method B): $t_R$=0.99 min; $^1$H NMR (400 MHz, CHLOROFORM-d) δ 8.35 (s, 1H), 8.29 (d, J=5.2 Hz, 1H), 7.68 (d, J=8.0 Hz, 1H), 7.52 (d, J=5.2 Hz, 1H), 7.39 (dd, J=8.4, 2.0 Hz, 1H), 7.19 (d, J=2.0 Hz, 1H), 5.31 (q, J=6.4 Hz, 1H), 1.59 (d, J=6.4 Hz, 3H).

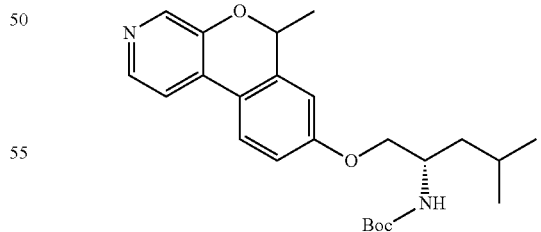

Part D: Tert-butyl ((2S)-4-methyl-1-((6-methyl-6H-isochromeno[3,4-c]pyridin-8-yl)oxy)pentan-2-yl)carbamate In a pressure tube was added 8-chloro-6-methyl-6H-isochromeno[3,4-c]pyridine (50 mg, 0.216 mmol), cesium carbonate (105 mg, 0.324 mmol), and di-tert-butyl(2',4',6'- triisopropyl-[1,1'-biphenyl]-2-yl)phosphine (55.0 mg, 0.129 mmol) in toluene (2 mL). N₂ was bubbled through the solution for 5 min. To this was added N-Boc L-Leucinol (139 mg, 0.647 mmol) and N2 was bubbled through the solution for 5 min. Palladium(II) acetate (14.54 mg, 0.065 mmol) was added and N₂ was bubbled through the solution for 10 min. The pressure tube was sealed and heated to 80° C. for 12 h. The reaction mixture was cooled to room temperature and filtered through diatomaceous earth (Celite®) washing with EtOAc. The filtrate was concentrated under reduced pressure. The residue was purified by silica gel chromatography (hexane and ethyl acetate) to afford tert-butyl ((2S)-4-methyl-1-((6-methyl-6H-isochromeno[3,4-c]pyridin-8-yl)oxy)pentan-2-yl)carbamate (50 mg, 0.115 mmol, 53% yield) as an off-white solid. LC/MS (ESI) m/e 413.3 [(M+H)⁺, calcd for $C_{24}H_{33}N_2O_4$, 413.2]; LC/MS retention time (Method B): $t_R$=1.20 min; ¹H NMR (400 MHz, CHLOROFORM-d) δ 8.30 (s, 1H), 8.24 (d, J=5.2 Hz, 1H), 7.67 (d, J=8.8 Hz, 1H), 7.48 (d, J=5.2 Hz, 1H), 6.93 (dd, J=8.8, 2.4 Hz, 1H), 6.72 (s, 1H), 5.30 (q, J=6.4 Hz, 1H), 4.71-4.45 (m, 1H), 4.10-3.92 (m, 2H), 3.74-3.60 (m, 1H), 1.65-1.60 (m, 1H), 1.60 (d, J=6.4 Hz, 3H), 1.54 (m, 9H), 1.45-1.28 (m, 2H), 0.98 (d, J=6.4 Hz, 3H), 0.95 (d, J=6.4 Hz, 3H).

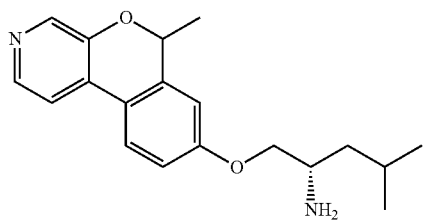 [SMILES: CC(C)C[C@H](N)COc1ccc2c(c1)C(C)Oc1cnccc1-2]

Part E: (2S)-4-methyl-1-((6-methyl-6H-isochromeno[3,4-c]pyridin-8-yl)oxy)pentan-2-amine To tert-butyl ((2S)-4-methyl-1-((6-methyl-6H-isochromeno[3,4-c]pyridin-8-yl)oxy)pentan-2-yl)carbamate (35 mg, 0.085 mmol) in DCM (2 mL) cooled to 0° C. was added TFA (0.065 mL, 0.848 mmol) dropwise over a period of 5 min. The reaction mixture was stirred at 0° C. for 15 min then warmed to room temperature and stirred for 3 h. The reaction mixture was concentrated under reduced pressure. The residue was taken up in water and washed with ethyl acetate (10 mL). The organic layer was discarded. Adjusted the pH of the aqueous layer to pH=10 using sodium carbonate and extracted with DCM (3×5 mL). The combined organic layers were washed with brine, dried over sodium sulphate, filtered, and concentrated under reduced pressure to afford (2S)-4-methyl-1-((6-methyl-6H-isochromeno[3,4-c]pyridin-8-yl)oxy)pentan-2-amine (13.8 mg, 0.040 mmol, 47% yield) as a brown oil. LC/MS (ESI) m/e 313.2 [(M+H)⁺, calcd for $C_{19}H_{25}N_2O_2$, 313.2]; LC/MS retention time (Method M): $t_R$=1.82 min; ¹H NMR (400 MHz, CD₃OD) δ 8.16 (s, 1H), 8.15 (s, 1H), 7.86 (d, J=8.8 Hz, 1H), 7.74 (d, J=5.2 Hz, 1H), 7.08 (dd, J=8.4, 2.4 Hz, 1H), 7.06 (d, J=2.4 Hz, 1H), 6.91 (d, J=2.4 Hz, 1H), 5.42 (q, J=6.4 Hz, 1H), 4.07 (dd, J=9.2, 4.0 Hz, 1H), 3.91-3.85 (m, 1H), 1.85-1.80 (m, 1H), 1.58 (d, J=6.4 Hz, 3H), 1.47-1.40 (m, 2H), 1.01 (d, J=6.4 Hz, 3H), 0.99 (d, J=6.4 Hz, 3H), two exchangeable protons not observed; HPLC purity (Method A1): 91% $t_R$=7.93 min; HPLC purity (Method B1): 92% $t_R$=9.01 min.

Example 31

(S)-1-((6,6-dimethyl-6H-isochromeno[3,4-c]pyridin-8-yl)oxy)-4-methylpentan-2-amine

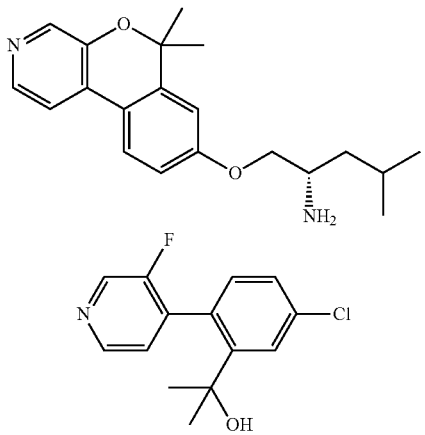

Part A: 2-(5-Chloro-2-(3-fluoropyridin-4-yl)phenyl)propan-2-ol

To a solution of methyl 5-chloro-2-(3-fluoropyridin-4-yl)benzoate (600 mg, 2.26 mmol) (prepared in Example 29, Part A) in tetrahydrofuran (20 mL) cooled to −50° C. was added methylmagnesium bromide (3.76 mL, 11.29 mmol) dropwise over 15 min. The reaction mixture was stirred at −50° C. for 3 h, then warmed to room temperature and stirred for 12 h. The reaction mixture was quenched with saturated aqueous ammonium chloride and extracted with ethyl acetate (2×25 mL). The combined organic layers were washed with brine, dried, filtered, and concentrated under reduced pressure to afford 2-(5-chloro-2-(3-fluoropyridin-4-yl)phenyl)propan-2-ol (90 mg, 0.335 mmol, 15% yield) as brown oil. LC/MS (ESI) m/e 266.0 [(M+H)⁺, calcd for $C_{14}H_{14}ClFNO$, 266.1]; LC/MS retention time (Method B): $t_R$=0.90 min; ¹H NMR (400 MHz, CHLOROFORM-d) δ 8.49-8.47 (m, 2H), 8.05-8.03 (m, 1H), 7.61-7.59 (m, 1H), 7.29-7.21 (m, 2H), 3.74 (s, 6H), 1.73 (s, 1H).

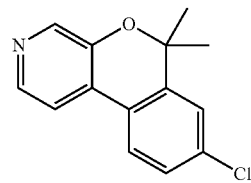 [SMILES: CC1(C)Oc2cnccc2-c2ccc(Cl)cc21]

Part B: 8-Chloro-6,6-dimethyl-6H-isochromeno[3,4-c]pyridine

To a solution of 2-(5-chloro-2-(3-fluoropyridin-4-yl)phenyl)propan-2-ol (90 mg, 0.339 mmol) in tetrahydrofuran (3 mL) cooled to 0° C. was added NaH (27.1 mg, 0.677 mmol) in portions over a period of 5 min. The reaction mixture was stirred at 0° C. for 1 h, then at room temperature for 3 h. The reaction mixture was quenched with ice and extracted with ethyl acetate (3×5 mL). The combined organic layers were washed with brine (5 mL), dried, filtered, and concentrated under reduced pressure. The residue was purified via silica gel chromatography (EtOAc in hexanes) to afford 8-chloro-6,6-dimethyl-6H-isochromeno[3,4-c]pyridine (70 mg, 0.259 mmol, 77% yield) as an off-white solid. LC/MS (ESI) m/e 246.1 [(M+H)$^+$, calcd for $C_{14}H_{13}ClNO$, 246.1]; LC/MS retention time (Method M): $t_R$=1.99 min; $^1$H NMR (400 MHz, $CD_3OD$) δ 8.22-8.21 (m, 2H), 7.93 (dd, J=7.6, 1.2 Hz, 1H), 7.83 (d, J=5.2 Hz, 1H), 7.49-7.47 (m, 2H), 1.68 (s, 6H).

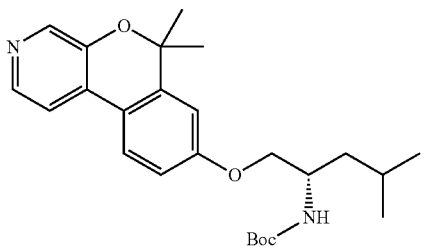 [SMILES: CC(C)C[C@@H](COc1ccc2c(c1)C(C)(C)Oc1cnccc1-2)NC(=O)OC(C)(C)C]

Part C: (S)-tert-butyl (1-((6,6-dimethyl-6H-isochromeno[3,4-c]pyridin-8-yl)oxy)-4-methylpentan-2-yl)carbamate In a pressure tube was added 8-chloro-6,6-dimethyl-6H-isochromeno[3,4-c]pyridine (70 mg, 0.285 mmol), cesium carbonate (139 mg, 0.427 mmol), and di-tert-butyl(2',4',6'-triisopropyl-[1,1'-biphenyl]-2-yl)phosphine (72.6 mg, 0.171 mmol) in toluene (2 mL). $N_2$ was bubbled through the solution for 5 min. To this was added N-Boc L-Leucinol (184 mg, 0.855 mmol) and N2 was bubbled through the solution for 5 min. Palladium(II) acetate (19.19 mg, 0.085 mmol) was added and N2 was bubbled through the solution for 10 min. The pressure tube was sealed and heated to 80° C. for 12 h. The reaction mixture was cooled to room temperature and filtered through diatomaceous earth (Celite®) washing with EtOAc. The filtrate was concentrated under reduced pressure. The residue was purified by silica gel chromatography (hexane and ethyl acetate) to afford (S)-tert-butyl (1-((6,6-dimethyl-6H-isochromeno[3,4-c]pyridin-8-yl)oxy)-4-methylpentan-2-yl)carbamate (50 mg, 0.117 mmol, 41% yield) as an off white solid. LC/MS (ESI) m/e 427.4 [(M+H)$^+$, calcd for $C_{25}H_{35}N_2O_4$, 427.3]; LC/MS retention time (Method M): $t_R$=2.23 min.

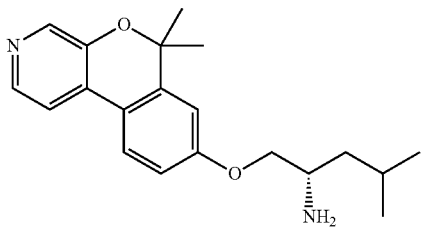 [SMILES: CC(C)C[C@H](N)COc1ccc2c(c1)C(C)(C)Oc1cnccc1-2]

Part D: (S)-1-((6,6-dimethyl-6H-isochromeno[3,4-c]pyridin-8-yl)oxy)-4-methylpentan-2-amine To (S)-tert-butyl (1-((6,6-dimethyl-6H-isochromeno[3,4-c]pyridin-8-yl)oxy)-4-methylpentan-2-yl)carbamate (50 mg, 0.105 mmol) in diethyl ether (2 mL) cooled to 0° C. was added 2N hydrogen chloride in diethyl ether (38.5 mg, 1.06 mmol). The reaction mixture was stirred at 0° C. for 15 min then warmed to room temperature and stirred for 3 h. The reaction mixture was concentrated under reduced pressure. The residue was purified by prep HPLC (0.1% TFA in ACN:water) to afford (S)-1-((6,6-dimethyl-6H-isochromeno [3,4-c]pyridin-8-yl)oxy)-4-methylpentan-2-amine (25 mg, 0.076 mmol, 72% yield) as a colorless solid. LC/MS (ESI) m/e 327.2 [(M+H)$^+$, calcd for $C_{20}H_{27}N_2O_2$, 327.2]; LC/MS retention time (Method M): $t_R$=1.96 min; $^1$H NMR (400 MHz, $CD_3OD$) δ 8.42 (s, 1H), 8.39 (d, J=8.8 Hz, 1H), 8.31 (d, J=6.0 Hz, 1H), 8.14 (d, J=8.8 Hz, 1H), 7.15 (d, J=2.4 Hz, 1H), 7.14 (s, 1H), 4.42-4.37 (m, 1H), 4.26-4.18 (m, 1H), 3.80-3.66 (m, 1H), 1.88-1.77 (m, 1H), 1.76 (s, 6H), 1.75-1.61 (m, 2H), 1.06 (d, J=6.4 Hz, 3H), 1.05 (d, J=6.4 Hz, 3H), two exchangeable protons not observed; HPLC purity (Method A1): 99% $t_R$=8.34 min; HPLC purity (Method B1): 99% $t_R$=9.38 min.

Example 32

(S)-4-methyl-1-((9-methyl-6H-isochromeno[3,4-c]pyridin-8-yl)oxy)pentan-2-amine

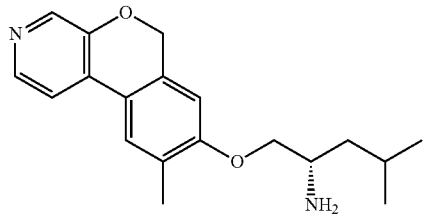 [SMILES: Cc1cc2c(cc1OC[C@@H](N)CC(C)C)COc1cnccc1-2]

Prepared as described in Example 29. Obtained (S)-4-methyl-1-((9-methyl-6H-isochromeno[3,4-c]pyridin-8-yl)oxy)pentan-2-amine (117.6 mg, 0.365 mmol, 72% yield for the last step) as a yellow solid. LC/MS (ESI) m/e 313.2 [(M+H)$^+$, calcd for $C_{19}H_{25}N_2O_2$, 313.2]; LC/MS retention time (Method B): $t_R$=0.90 min; $^1$H NMR (400 MHz, $CD_3OD$) δ 8.44 (s, 1H), 8.38 (d, J=6.4 Hz, 1H), 8.31 (d, J=6.0 Hz, 1H), 7.97 (s, 1H), 7.02 (s, 1H), 5.46 (s, 2H), 4.38 (dd, J=10.8, 3.2 Hz, 1H), 4.24 (dd, J=10.4, 5.6 Hz, 1H), 3.80-3.77 (m, 1H), 2.42 (s, 3H), 1.85-1.68 (m, 3H), 1.07 (d, J=6.4 Hz, 3H), 1.05 (d, J=6.4 Hz, 3H), two exchangeable protons not observed; HPLC purity (Method A2): 98% $t_R$=8.24 min; HPLC purity (Method B1): 97% $t_R$=8.93 min.

Example 33

(S)—N-(8-((2-amino-4-methylpentyl)oxy)-6H-isochromeno[3,4-c]pyridin-2-yl)acetamide

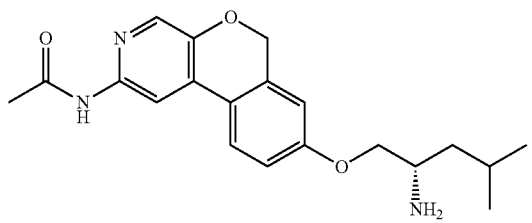

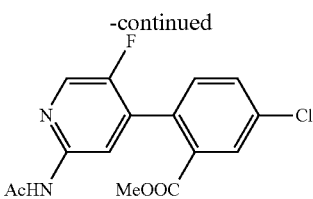

Part A: Methyl 2-(2-acetamido-5-fluoropyridin-4-yl)-5-chlorobenzoate

In a pressure tube was added methyl 2-(2-bromo-5-fluoropyridin-4-yl)-5-chlorobenzoate (900 mg, 2.61 mmol) (prepared in Example 14, Part G) in 1,4-dioxane (6 mL) followed by cesium carbonate (1872 mg, 5.75 mmol) and XANTPHOS (136 mg, 0.235 mmol). Nitrogen gas was bubbled through the stirred suspension for 5 min. Acetamide (309 mg, 5.22 mmol) and $Pd_2(dba)_3$ (191 mg, 0.209 mmol) were added and nitrogen gas was bubbled through the stirred suspension for 5 min. The tube was sealed and heated to 100° C. for 12 h. The reaction mixture was cooled to room temperature and filtered through diatomaceous earth (Celite®), washing with ethyl acetate. The filtrate was concentrated under reduced pressure. The residue was purified via silica gel chromatography (hexane and ethyl acetate) to afford methyl 2-(2-acetamido-5-fluoropyridin-4-yl)-5-chlorobenzoate (300 mg, 0.930 mmol, 36% yield) as a white solid. LC/MS (ESI) m/e 323.1 [(M+H)$^+$, calcd for $C_{15}H_{13}ClFN_2O_3$, 323.1]; LC/MS retention time (Method B): $t_R$=0.91 min; $^1$H NMR (400 MHz, CHLOROFORM-d) δ 8.21 (d, J=5.8 Hz, 1H), 8.10 (d, J=1.3 Hz, 1H), 8.03 (d, J=2.3 Hz, 1H), 7.89 (br. s., 1H), 7.59 (dd, J=8.3, 2.3 Hz, 1H), 7.33 (d, J=8.3 Hz, 1H), 3.76 (s, 3H), 2.21 (s, 3H).

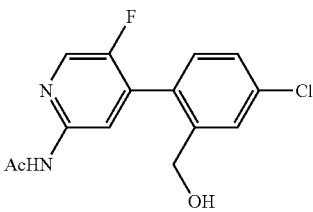 [SMILES: CC(=O)Nc1cc(-c2ccc(Cl)cc2CO)c(F)cn1]

Part B: N-(4-(4-chloro-2-(hydroxymethyl)phenyl)-5-fluoropyridin-2-yl)acetamide To a solution of methyl 2-(2-acetamido-5-fluoropyridin-4-yl)-5-chlorobenzoate (300 mg, 0.930 mmol) tetrahydrofuran (2.5 mL) cooled to 0° C. was added LAH (0.930 mL, 0.930 mmol) dropwise over a period of 5 min. The reaction mixture was stirred for 1 h at 0° C. then at room temperature for 1 h. The reaction mixture was carefully quenched with saturated aqueous ammonium chloride and extracted with ethyl acetate (2×15 mL). The combined organic layers were washed with brine, dried over sodium sulphate, filtered, and concentrated under reduced pressure to afford N-(4-(4-chloro-2-(hydroxymethyl)phenyl)-5-fluoropyridin-2-yl)acetamide (100 mg, 0.339 mmol, 37% yield) as an orange oil. The material was carried forward without further purification. LC/MS (ESI) m/e 295.1 [(M+H)$^+$, calcd for $C_{14}H_{13}ClFN_2O_2$, 295.1]; LC/MS retention time (Method B): $t_R$=0.80 min; $^1$H NMR (400 MHz, CHLOROFORM-d) δ 8.18 (s, 1H), 8.16 (d, J=5.6 Hz, 1H), 7.88 (s, 1H), 7.65 (d, J=2.0 Hz, 1H), 7.36 (dd, J=8.0, 2.0 Hz, 1H), 7.22 (d, J=8.0 Hz, 1H), 4.55 (d, J=4.4 Hz, 2H), 2.21 (s, 3H).

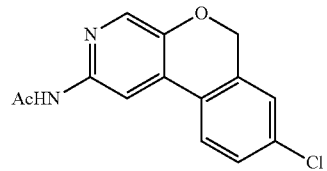 [SMILES: CC(=O)Nc1cc2c(cn1)OCc1cc(Cl)ccc1-2]

Part C: N-(8-chloro-6H-isochromeno[3,4-c]pyridin-2-yl)acetamide

To a solution of N-(4-(4-chloro-2-(hydroxymethyl)phenyl)-5-fluoropyridin-2-yl)acetamide (90 mg, 0.305 mmol) in DMF (1 mL) was added $K_2CO_3$ (169 mg, 1.22 mmol). The reaction mixture was stirred at 90° C. for 12 h. The reaction mixture was quenched with water and extracted with DCM (3×5 mL). The combined organic layers were washed with brine (5 mL), dried, filtered and concentrated under reduced pressure. The residue was purified via silica gel chromatography (EtOAc in hexanes) to afford N-(8-chloro-6H-isochromeno[3,4-c]pyridin-2-yl)acetamide (30 mg, 0.109 mmol, 36% yield) as an off-white solid. LC/MS (ESI) m/e 275.1 [(M+H)$^+$, calcd for $C_{14}H_{12}ClN_2O_2$, 275.1]; LC/MS retention time (Method B): $t_R$=0.88 min; $^1$H NMR (400 MHz, CHLOROFORM-d) δ 9.52 (s, 1H), 8.00 (s, 1H), 7.85 (br s, 1H), 7.78 (d, J=8.4 Hz, 1H), 7.41 (d, J=2.4 Hz, 1H), 7.18 (d, J=1.2 Hz, 1H), 5.12 (s, 2H), 2.22 (s, 3H).

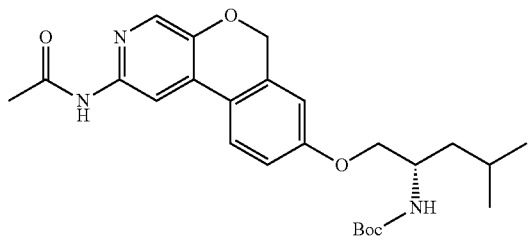 [SMILES: CC(=O)Nc1cc2c(cn1)OCc1cc(OC[C@H](CC(C)C)NC(=O)OC(C)(C)C)ccc1-2]

Part D: (S)-tert-butyl (1-((2-acetamido-6H-isochromeno[3,4-c]pyridin-8-yl)oxy)-4-methylpentan-2-yl)carbamate In a pressure tube was added N-(8-chloro-6H-isochromeno[3,4-c]pyridin-2-yl)acetamide (400 mg, 1.03 mmol), cesium carbonate (674 mg, 2.07 mmol), di-tert-butyl(2',4',6'-triisopropyl-3-methoxy-6-methyl-[1,1'-biphenyl]-2-yl)phosphine (29.1 mg, 0.062 mmol), allylpalladium chloride dimer (11.4 mg, 0.031 mmol), and (S)-tert-butyl (1-hydroxy-4-methylpentan-2-yl)carbamate (449 mg, 2.07 mmol) in toluene (8 mL). $N_2$ was bubbled through the solution for 10 min. The pressure tube was sealed and heated to 90° C. for 12 h. The reaction mixture was cooled to room temperature and filtered through diatomaceous earth (Celite®) washing with EtOAc. The filtrate was washed with water, dried over sodium sulphate, filtered, and concentrated under reduced pressure. The residue was purified by silica gel chromatography (petroleum ether and ethyl acetate) to afford (S)-tert-butyl (1-((2-acetamido-6H-isochromeno[3,4-c]pyridin-8-yl)oxy)-4-methylpentan-2-yl)carbamate (150 mg, 0.329 mmol, 32% yield) as an off-white solid. LC/MS (ESI) m/e 456.4 [(M+H)⁺, calcd for $C_{25}H_{34}N_3O_5$, 456.3]; LC/MS retention time (Method B): $t_R$=1.09 min.

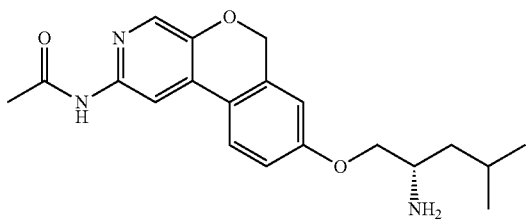 [SMILES: CC(=O)Nc1cc2c(cn1)OCc1cc(OC[C@@H](N)CC(C)C)ccc1-2]

Part E: (S)—N-(8-((2-amino-4-methylpentyl)oxy)-6H-isochromeno[3,4-c]pyridin-2-yl)acetamide To (S)-tert-butyl (1-((2-acetamido-6H-isochromeno[3,4-c]pyridin-8-yl)oxy)-4-methylpentan-2-yl)carbamate (21 mg, 0.046 mmol) in DCM (1 mL) cooled to 0° C. was added 2N HCl in dioxane (1 mL, 4.00 mmol). The reaction mixture was stirred at 0° C. for 15 min then warmed to room temperature and stirred for 2 h. The reaction mixture was concentrated under reduced pressure. The residue was taken up in water and the pH of the aqueous layer adjusted to pH=14 using sodium carbonate and the solution extracted with DCM (2×10 mL). The combined organic layers were washed with brine, dried over sodium sulphate, filtered, and concentrated under reduced pressure. The residue was purified via prep HPLC (10 mmol ammonium acetate pH 4.5 adjusted with AcOH:ACN) to afford (S)—N-(8-((2-amino-4-methylpentyl)oxy)-6H-isochromeno[3,4-c]pyridin-2-yl) acetamide (6.33 mg, 0.017 mmol, 38% yield) as an off-white solid. LC/MS (ESI) m/e 356.0 [(M+H)⁺, calcd for $C_{20}H_{26}N_3O_3$, 356.2]; LC/MS retention time (Method J): $t_R$=1.86 min; ¹H NMR (400 MHz, METHANOL-d₄) δ 8.37 (s, 1H), 7.95 (s, 1H), 7.79 (d, J=9.0 Hz, 1H), 7.07 (dd, J=8.5, 2.5 Hz, 1H), 6.90 (d, J=2.5 Hz, 1H), 5.15 (s, 2H), 4.05 (dd, J=9.5, 4.0 Hz, 1H), 3.87 (dd, J=9.3, 7.3 Hz, 1H), 3.27 (dq, J=9.6, 3.8 Hz, 1H), 2.20 (s, 3H), 1.89-1.72 (m, 1H), 1.55-1.35 (m, 2H), 1.01 (d, J=6.5 Hz, 3H), 0.98 (d, J=6.5 Hz, 3H), two exchangeable protons not observed; HPLC purity (Method A1): 97% $t_R$=9.54 min; HPLC purity (Method B1): 97% $t_R$=10.04 min.

Example 34

(S)-methyl (8-((2-amino-4-methylpentyl)oxy)-6H-isochromeno[3,4-c]pyridin-2-yl)carbamate

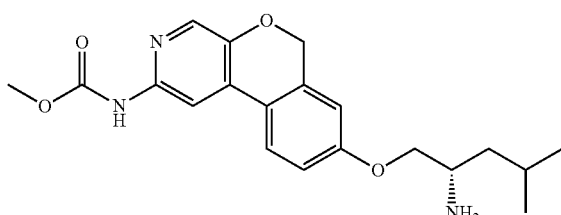

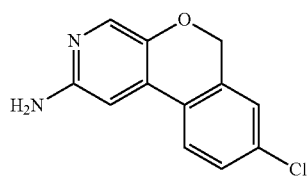

Part A: 8-Chloro-6H-isochromeno[3,4-c]pyridin-2-amine

A solution of flask N-(8-chloro-6H-isochromeno[3,4-c]pyridin-2-yl)acetamide (220 mg, 0.641 mmol) (prepared in Example 33, Part C) HCl, 50% in water (3 ml, 49.4 mmol) was heated to 100° C. for 3 h. The reaction mixture was quenched with 10% NaOH (4 mL) and extracted with ethyl acetate (2×10 mL). The combined organic layers were washed with brine (5 mL), dried, filtered, and concentrated under reduced pressure to afford 8-chloro-6H-isochromeno[3,4-c]pyridin-2-amine (170 mg, 0.548 mmol, 86% yield) as a brown solid which was carried forward without further purification. LC/MS (ESI) m/e 233.0 [(M+H)⁺, calcd for $C_{12}H_{10}ClN_2O$, 233.1]; LC/MS retention time (Method B): $t_R$=0.83 min; ¹H NMR (400 MHz, DMSO-d₆) δ 7.75 (d, J=8.4 Hz, 1H), 7.20 (s, 1H), 7.50 (dd, J=8.4, 2.0 Hz, 1H), 7.45 (d, J=2.0 Hz, 1H), 6.85 (s, 1H), 5.60 (br s, 2H), 5.03 (s, 2H).

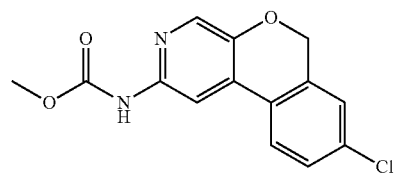 [SMILES: COC(=O)Nc1cc2c(cn1)OCc1cc(Cl)ccc1-2]

Part B: Methyl (8-chloro-6H-isochromeno[3,4-c]pyridin-2-yl)carbamate

To a solution of 8-chloro-6H-isochromeno[3,4-c]pyridin-2-amine (100 mg, 0.322 mmol) in CHCl₃ (5 mL) cooled to 0° C. was added pyridine (0.16 mL, 1.93 mmol) and methyl carbonochloridate (60.9 mg, 0.645 mmol) dropwise followed by DMAP (3.94 mg, 0.032 mmol). The reaction mixture was stirred at room temperature for 5 h. The reaction mixture was quenched with water and extracted with DCM (3×5 mL). The combined organic layers were washed with brine (5 mL), dried, filtered, and concentrated under reduced pressure to afford methyl (8-chloro-6H-isochromeno[3,4-c]pyridin-2-yl)carbamate (120 mg, 0.268 mmol, 83% yield) as an off-white solid. LC/MS (ESI) m/e 291.1 [(M+H)⁺, calcd for $C_{14}H_{12}ClN_2O_3$, 291.1]; LC/MS retention time (Method B): $t_R$=0.93 min.

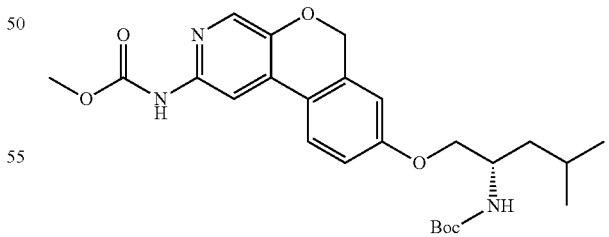

Part D: (S)-methyl (8-((2-(Boc-amino)-4-methylpentyl)oxy)-6H-isochromeno[3,4-c]pyridin-2-yl)carbamate In a pressure tube was added methyl (8-chloro-6H-isochromeno[3,4-c]pyridin-2-yl)carbamate (80 mg, 0.275 mmol), cesium carbonate (179 mg, 0.550 mmol), di-tertbutyl(2',4',6'-triisopropyl-3-methoxy-6-methyl-[1,1'-biphenyl]-2-yl)phosphine (7.74 mg, 0.017 mmol), allylpalladium chloride dimer (3.02 mg, 8.26 mol), and (S)-tert-butyl (1-hydroxy-4-methylpentan-2-yl)carbamate (120 mg, 0.550 mmol) in toluene (5 mL). $N_2$ was bubbled through the solution for 10 min. The pressure tube was sealed and heated to 90° C. for 12 h. The reaction mixture was cooled to room temperature and filtered through diatomaceous earth (Celite®) washing with EtOAc. The filtrate was washed with water, dried over sodium sulphate, filtered, and concentrated under reduced pressure. The residue was purified by reverse phase HPLC (10 mmol ammonium acetate pH 4.5 adjusted with AcOH:ACN) to afford (S)-methyl (8-((2-(Boc-amino)-4-methylpentyl)oxy)-6H-isochromeno[3,4-c]pyridin-2-yl)carbamate (35 mg, 0.074 mmol, 27% yield) as a brown solid. LC/MS (ESI) m/e 472.3 [(M+H)$^+$, calcd for $C_{25}H_{34}N_3O_6$, 472.2]; LC/MS retention time (Method A2): $t_R$=1.12 min.

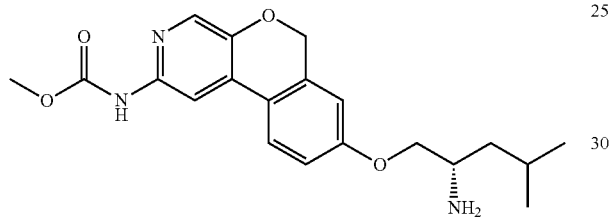

Part E: (S)-methyl (8-((2-amino-4-methylpentyl)oxy)-6H-isochromeno[3,4-c]pyridin-2-yl)carbamate To (S)-methyl (8-((2-(Boc-amino)-4-methylpentyl)oxy)-6H-isochromeno[3,4-c]pyridin-2-yl)carbamate (35 mg, 0.037 mmol) in DCM (2 mL) cooled to 0° C. was added 2N HCl in dioxane (1 mL, 4.00 mmol). The reaction mixture was stirred at 0° C. for 15 min then warmed to room temperature and stirred for 30 min. The reaction mixture was extracted with DCM (3×10 mL). The combined organic layers were washed with saturated aqueous sodium bicarbonate, water, then brine. The organic solution was dried over sodium sulphate, filtered, and concentrated under reduced pressure. The residue was purified via prep HPLC (10 mmol ammonium acetate pH 4.5 adjusted with AcOH:ACN) to afford (S)-methyl (8-((2-amino-4-methylpentyl)oxy)-6H-isochromeno[3,4-c]pyridin-2-yl)carbamate (4.0 mg, 10.45 µmol, 28% yield) as a pale yellow solid. LC/MS (ESI) m/e 372.0 [(M+H)$^+$, calcd for $C_{20}H_{26}N_3O_4$, 372.2]; LC/MS retention time (Method M): $t_R$=1.85 min; $^1$H NMR (400 MHz, METHANOL-$d_4$) δ 8.17 (s, 1H), 7.92 (s, 1H), 7.83 (d, J=8.5 Hz, 1H), 7.11 (dd, J=8.5, 3.0 Hz, 1H), 6.94 (d, J=2.5 Hz, 1H), 5.15 (s, 2H), 4.19 (dd, J=10.0, 3.5 Hz, 1H), 4.00 (dd, J=9.8, 6.8 Hz, 1H), 3.81 (s, 3H), 3.56-3.43 (m, 1H), 1.83 (dquin, J=13.6, 6.8 Hz, 1H), 1.55 (qt, J=13.8, 7.0 Hz, 2H), 1.02 (app t, J=6.5 Hz, 6H), three exchangeable protons not observed; HPLC purity (Method C1): 99% $t_R$=1.21 min.

Example 35

(S)-8-((2-amino-4-methylpentyl)oxy)-6H-isochromeno[3,4-c]pyridin-2-amine

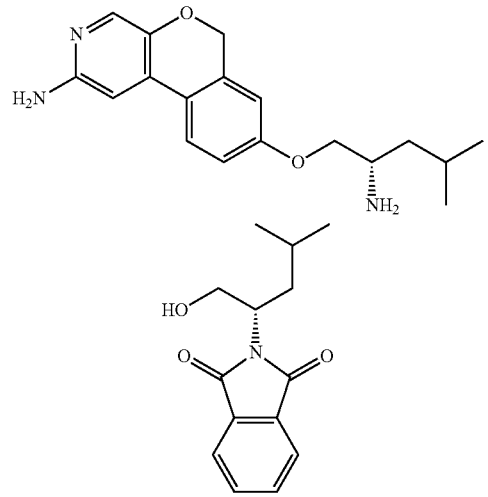

Part A: (S)-2-(1-hydroxy-4-methylpentan-2-yl)isoindoline-1,3-dione

To a 250 mL round-bottomed flask was added (S)-3-amino-5-methylhexan-1-ol (2.17 g, 16.51 mmol) and isobenzofuran-1,3-dione (2.45 g, 16.51 mmol) in toluene (60 mL) to give a colorless suspension. The mixture was heated at 110° C. for 16 h. The volatiles were removed under high vacuum to afford (S)-2-(1-hydroxy-4-methylpentan-2-yl)isoindoline-1,3-dione (4.08 g, 16.51 mmol, quantitative yield) as a light yellow dense oil. $^1$H NMR (400 MHz, CHLOROFORM-d) δ 7.94-7.81 (m, 2H), 7.78-7.69 (m, 2H), 4.56-4.41 (m, 1H), 4.06 (dd, J=11.8, 7.8 Hz, 1H), 3.88 (dd, J=11.8, 3.8 Hz, 1H), 2.07-1.95 (m, 1H), 1.61-1.47 (m, 2H), 0.96 (d, J=6.3 Hz, 3H), 0.94 (d, J=6.3 Hz, 3H), one exchangeable proton not observed; LCMS (ESI) m/e 246.2 [(M–H)$^+$, calcd $C_{14}H_{16}N_1O_3$, 246.1]; LC/MS retention time (Method K): $t_R$=1.88 min; $^1$H NMR (400 MHz, CHLOROFORM-d) δ 7.88-7.79 (m, 2H), 7.76-7.70 (m, 2H), 4.54-4.42 (m, 1H), 4.05 (dd, J=11.5, 7.8 Hz, 1H), 3.86 (dd, J=11.5, 3.8 Hz, 1H), 2.06-1.96 (m, 1H), 1.60-1.50 (m, 2H), 0.95 (d, J=6.0 Hz, 3H), 0.93 (d, J=6.3 Hz, 3H).

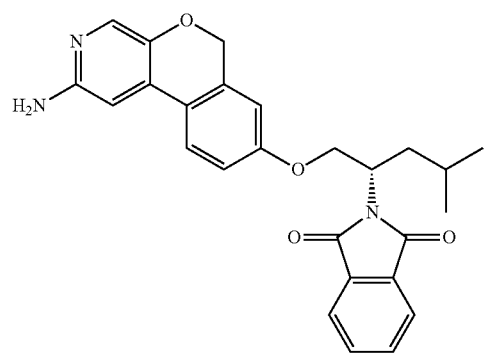 [SMILES: CC(C)C[C@@H](COc1ccc2c(c1)COc1cnc(N)cc1-2)N1C(=O)c2ccccc2C1=O]

Part B: (S)-2-(1-((2-amino-6H-isochromeno[3,4-c]pyridin-8-yl)oxy)-4-methylpentan-2-yl)isoindoline-1,3-dione In a flask was added N-(8-chloro-6H-isochromeno[3,4-c]pyridin-2-yl)acetamide (220 mg, 0.801 mmol), cesium carbonate (391 mg, 1.201 mmol), di-tert-butyl(2',4',6'-triisopropyl-3-methoxy-6-methyl-[1,1'-biphenyl]-2-yl)phosphine (15.01 mg, 0.032 mmol), allylpalladium chloride dimer (5.86 mg, 0.016 mmol), and (S)-2-(1-hydroxy-4-methylpentan-2-yl)isoindoline-1,3-dione (495 mg, 2.00 mmol) in toluene (1.5 mL). $N_2$ was bubbled through the solution for 10 min. The pressure tube was sealed and heated to 90° C. for 23 h. The reaction mixture was cooled to room temperature and filtered through diatomaceous earth (Celite®) washing with EtOAc. The filtrate was concentrated under reduced pressure. The residue was purified by prep TLC to afford (S)—N-(8-((2-(1,3-dioxoisoindolin-2-yl)-4-methylpentyl)oxy)-6H-isochromeno[3,4-c]pyridin-2-yl)acetamide (150 mg, 0.309 mmol, 39% yield) as a colorless solid. LC/MS (ESI) m/e 444.2 [(M+H)$^+$, calcd for $C_{26}H_{26}N_3O_4$, 444.2]; LC/MS retention time (Method E): $t_R$=0.91 min; $^1$H NMR (300 MHz, CHLOROFORM-d) δ 8.44 (s, 1H), 7.95 (s, 1H), 7.89-7.82 (m, 2H), 7.76-7.68 (m, 3H), 6.92-6.84 (m, 1H), 6.65 (d, J=2.3 Hz, 1H), 5.06 (s, 2H), 4.60 (t, J=9.3 Hz, 2H), 4.26-4.19 (m, 1H), 1.63-1.56 (m, 3H), 1.00 (d, J=6.0 Hz, 3H), 0.97 (d, J=6.4 Hz, 3H).

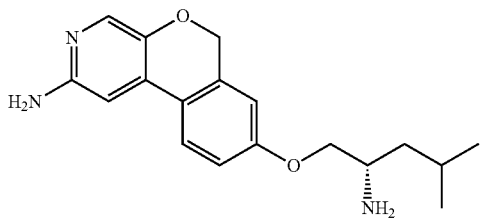 [SMILES: CC(C)C[C@H](N)COc1ccc2c(c1)COc1cnc(N)cc1-2]

Part C: (S)-8-((2-amino-4-methylpentyl)oxy)-6H-isochromeno[3,4-c]pyridin-2-amine To a solution of (S)—N-(8-((2-(1,3-dioxoisoindolin-2-yl)-4-methylpentyl)oxy)-6H-isochromeno[3,4-c]pyridin-2-yl)acetamide (30 mg, 0.062 mmol) in MeOH (0.3 mL) and water (0.3 mL) was added KOH (3.81 mg, 0.068 mmol). The mixture was heated to 70° C. for 12 h. LC/MS showed opening of the phthalate to (S)-2-((1-((2-amino-6H-isochromeno[3,4-c]pyridin-8-yl)oxy)-4-methylpentan-2-yl)carbamoyl)benzoic acid. 2N HCl in dioxane (2 mL, 65.8 mmol) was added and the mixture heated to 90° C. for 12 h. The reaction mixture was cooled to room temperature and concentrated under reduced pressure. The residue was purified via prep HPLC (0.1% TFA in ACN:water) to afford (S)-8-((2-amino-4-methylpentyl)oxy)-6H-isochromeno[3,4-c]pyridin-2-amine, 2 TFA (6 mg, 10.31 mol, 19% yield) as an off white solid. LC/MS (ESI) m/e 314.2 [(M+H)$^+$, calcd for $C_{18}H_{24}N_3O_2$, 314.2]; LC/MS retention time (Method A2): $t_R$=2.04 min; $^1$H NMR (400 MHz, METHANOL-$d_4$) δ 7.94 (d, J=9.0 Hz, 1H), 7.61 (s, 1H), 7.28 (s, 1H), 7.20 (dd, J=8.8, 2.8 Hz, 1H), 7.04 (d, J=2.5 Hz, 1H), 5.19 (s, 2H), 4.36 (dd, J=10.5, 3.5 Hz, 1H), 4.18 (dd, J=10.8, 6.3 Hz, 1H), 3.73 (qd, J=6.9, 3.0 Hz, 1H), 1.82 (dquin, J=13.7, 6.6 Hz, 1H), 1.76-1.56 (m, 2H), 1.05 (d, J=4.5 Hz, 3H), 1.04 (d, J=4.5 Hz, 3H), three exchangeable protons not observed; HPLC purity (Method A1): 97% $t_R$=7.74 min, HPLC purity (Method B1): 97% $t_R$=7.95 min.

Example 36

N-(8-((2-amino-2,4-dimethylpentyl)oxy)-6H-isochromeno[3,4-c]pyridin-2-yl)acetamide

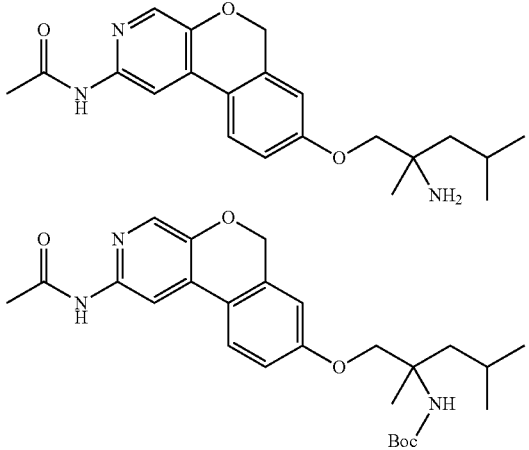

Part A: Tert-butyl (1-((2-acetamido-6H-isochromeno[3,4-c]pyridin-8-yl)oxy)-2,4-dimethylpentan-2-yl)carbamate In a pressure tube was added N-(8-chloro-6H-isochromeno[3,4-c]pyridin-2-yl)acetamide (100 mg, 0.255 mmol) (prepared in Example 33, Part C), cesium carbonate (166 mg, 0.510 mmol), di-tert-butyl(2',4',6'-triisopropyl-3-methoxy-6-methyl-[1,1'-biphenyl]-2-yl)phosphine (7.17 mg, 0.015 mmol), allylpalladium chloride dimer (2.80 mg, 7.64 µmol), and tert-butyl (1-hydroxy-2,4-dimethylpentan-2-yl)carbamate (88 mg, 0.382 mmol) (prepared in Example 7, Part B) in toluene (3.5 mL). N2 was bubbled through the solution for 10 min. The pressure tube was sealed and heated to 90° C. for 12 h. The reaction mixture was cooled to room temperature and filtered through diatomaceous earth (Celite®) washing with EtOAc. The filtrate was washed with water, dried over sodium sulphate, filtered, and concentrated under reduced pressure to afford tert-butyl (1-((2-acetamido-6H-isochromeno[3,4-c]pyridin-8-yl)oxy)-2,4-dimethylpentan-2-yl)carbamate (90 mg, 0.075 mmol, 39% yield) as a yellow solid. LC/MS (ESI) m/e 470.4 [(M+H)$^+$, calcd for $C_{26}H_{36}N_3O_5$, 470.3]; LC/MS retention time (Method B): $t_R$=1.16 min.

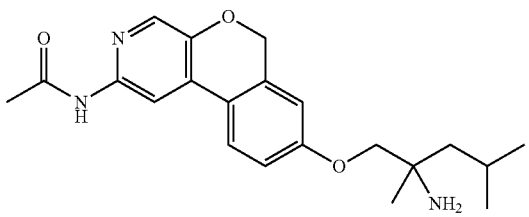 [SMILES: CC(=O)Nc1cc2c(cn1)OCc1cc(OCC(C)(N)CC(C)C)ccc1-2]

Part B: N-(8-((2-amino-2,4-dimethylpentyl)oxy)-6H-isochromeno[3,4-c]pyridin-2-yl)acetamide To tert-butyl (1-((2-acetamido-6H-isochromeno[3,4-c]pyridin-8-yl)oxy)-2,4-dimethylpentan-2-yl)carbamate (90 mg, 0.192 mmol) in DCM (3 mL) cooled to 0° C. was added 2N HCl in dioxane (2 mL, 8.00 mmol). The reaction mixture was stirred at 0° C. for 15 min then warmed to room temperature and stirred for 1 h. The reaction mixture was extracted with DCM (3×10 mL). The combined organic layers were washed with saturated aqueous sodium bicarbonate, water, then brine. The organic solution was dried over sodium sulphate, filtered, and concentrated under reduced pressure. The residue was purified via prep HPLC (10 mmol ammonium acetate pH 4.5 adjusted with AcOH: ACN) to afford N-(8-((2-amino-2,4-dimethylpentyl)oxy)-6H-isochromeno[3,4-c]pyridin-2-yl)acetamide (14 mg, 0.036 mmol, 19% yield) as an off-white solid. LC/MS (ESI) m/e 370.3 [(M+H)$^+$, calcd for $C_{21}H_{28}N_3O_3$, 370.2]; LC/MS retention time (Method B): $t_R$=0.76 min; $^1$H NMR (400 MHz, METHANOL-$d_4$) δ 8.39 (s, 1H), 7.97 (s, 1H), 7.81 (d, J=9.0 Hz, 1H), 7.09 (dd, J=8.5, 2.5 Hz, 1H), 6.93 (d, J=2.5 Hz, 1H), 5.17 (s, 2H), 3.98-3.86 (m, 2H), 2.21 (s, 3H), 1.90-1.79 (m, 1H), 1.68-1.49 (m, 2H), 1.30 (s, 3H), 1.03 (d, J=7.0 Hz, 3H), 1.00 (d, J=7.0 Hz, 3H), three exchangeable protons not observed; HPLC purity (Method A1): 96% $t_R$=9.86 min; HPLC purity (Method B1): 96% $t_R$=10.69 min.

Example 37

(S)—N-(8-((2-amino-2,4-dimethylpentyl)oxy)-6H-isochromeno[3,4-c]pyridin-2-yl)acetamide

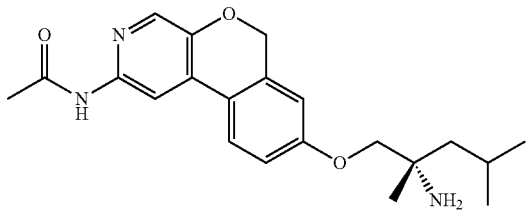 [SMILES: CC(=O)Nc1cc2c(cn1)OCc1cc(OC[C@@](C)(N)CC(C)C)ccc1-2]

Racemic N-(8-((2-amino-2,4-dimethylpentyl)oxy)-6H-isochromeno[3,4-c]pyridin-2-yl)acetamide (10 mg, 0.027 mmol) was resolved via chiral SFC (Column: Chiralpak-IA (250×4.6 mm) 5 micron; Co-solvent: 0.3% DEA in Methanol (in CO2); Total flow: 4 mL/min, CO2 flow=2.4 mL/min; co-solvent flow=1.6 mL/min; co-solvent %=40%; column temp: 22.8° C.) to afford (S)—N-(8-((2-amino-2,4-dimethylpentyl)oxy)-6H-isochromeno[3,4-c]pyridin-2-yl)acetamide (3.5 mg, 9.47 mol, 35% yield) as a pale yellow solid. LC/MS (ESI) m/e 370.2 [(M+H)$^+$, calcd for $C_{21}H_{28}N_3O_3$, 370.2]; LC/MS retention time (Method A3): $t_R$=1.88 min; $^1$H NMR (400 MHz, METHANOL-$d_4$) δ 8.38 (s, 1H), 7.96 (s, 1H), 7.79 (d, J=9.0 Hz, 1H), 7.07 (dd, J=8.5, 2.5 Hz, 1H), 6.91 (d, J=2.5 Hz, 1H), 5.16 (s, 2H), 3.96-3.77 (m, 2H), 2.20 (s, 3H), 1.83 (dquin, J=12.7, 6.2 Hz, 1H), 1.68-1.44 (m, 2H), 1.26 (s, 3H), 1.01 (d, J=7.0 Hz, 3H), 0.99 (d, J=6.5 Hz, 3H), three exchangeable protons not observed; HPLC purity (Method A1): 95% $t_R$=9.93 min; HPLC purity (Method B1): 95% $t_R$=10.79 min. Chiral HPLC (prep conditions): $t_R$=3.59 min (racemic material shows chiral HPLC: $t_R$=3.59 and 8.47 min). Absolute stereochemistry assumed based on the potency of the final compound relative to its enantiomer, with the (S)-enantiomer showing better potency then the (R)-enantiomer.

Example 38

(R)—N-(8-((2-amino-2,4-dimethylpentyl)oxy)-6H-isochromeno[3,4-c]pyridin-2-yl)acetamide

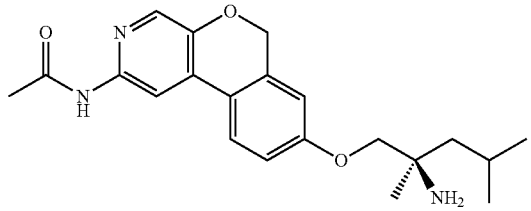 [SMILES: CC(=O)Nc1cc2c(cn1)OCc1cc(OC[C@](C)(N)CC(C)C)ccc1-2]

Racemic N-(8-((2-amino-2,4-dimethylpentyl)oxy)-6H-isochromeno[3,4-c]pyridin-2-yl)acetamide (10 mg, 0.027 mmol) was resolved via chiral SFC (Column: Chiralpak-IA (250×4.6 mm) 5 micron; Co-solvent: 0.3% DEA in Methanol (in CO$_2$); Total flow: 4 mL/min, CO$_2$ flow=2.4 mL/min; co-solvent flow=1.6 mL/min; co-solvent %=40%; column temp: 22.8° C.) to afford (R)—N-(8-((2-amino-2,4-dimethylpentyl)oxy)-6H-isochromeno[3,4-c]pyridin-2-yl)acetamide (4.5 mg, 0.012 mmol, 45% yield) as a pale yellow solid. LC/MS (ESI) m/e 370.2 [(M+H)$^+$, calcd for $C_{21}H_{28}N_3O_3$, 370.2]; LC/MS retention time (Method A3): $t_R$=1.87 min; $^1$H NMR (400 MHz, METHANOL-$d_4$) δ 8.37 (s, 1H), 7.95 (s, 1H), 7.79 (d, J=8.5 Hz, 1H), 7.07 (dd, J=8.5, 2.5 Hz, 1H), 6.90 (d, J=2.5 Hz, 1H), 5.16 (s, 2H), 3.90-3.81 (m, 2H), 2.20 (s, 3H), 1.88-1.75 (m, 1H), 1.62-1.47 (m, 2H), 1.24 (s, 3H), 1.01 (d, J=6.5 Hz, 3H), 0.99 (d, J=6.5 Hz, 3H), three exchangeable protons not observed; HPLC purity (Method A1): 94% $t_R$=9.93 min; HPLC purity (Method B1): 95% $t_R$=10.77 min. Chiral HPLC (prep conditions): $t_R$=8.47 min (racemic material shows chiral HPLC: $t_R$=3.59 and 8.47 min). Absolute stereochemistry assumed based on the potency of the final compound relative to its enantiomer, with the (S)-enantiomer showing better potency then the (R)-enantiomer.

Example 39 methyl (8-((2-amino-2,4-dimethylpentyl)oxy)-6H-isochromeno[3,4-c]pyridin-2-yl)carbamate

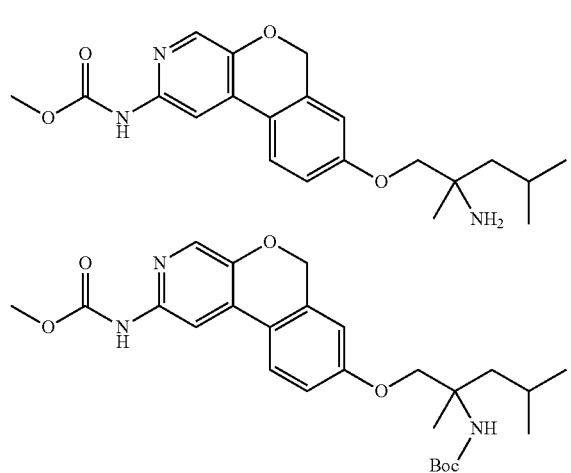

Part A: Methyl (8-((2-(Boc-amino)-2,4-dimethylpentyl)oxy)-6H-isochromeno[3,4-c]pyridin-2-yl)carbamate In a pressure tube was added methyl (8-chloro-6H-isochromeno[3,4-c]pyridin-2-yl)carbamate (200 mg, 0.482 mmol) (prepared in Example 34, Part B), $Cs_2CO_3$ (314 mg, 0.963 mmol), di-tert-butyl(2',4',6'-triisopropyl-3-methoxy-6-methyl-[1,1'-biphenyl]-2-yl)phosphine (13.54 mg, 0.029 mmol), allylpalladium chloride dimer (5.29 mg, 0.014 mmol), and tert-butyl (1-hydroxy-2,4-dimethylpentan-2-yl)carbamate (167 mg, 0.722 mmol) (prepared in Example 7, Part B) in toluene (5 mL). $N_2$ was bubbled through the solution for 10 min. The pressure tube was sealed and heated to 90° C. for 12 h. The reaction mixture was cooled to room temperature and filtered through diatomaceous earth (Celite®) washing with EtOAc. The filtrate was washed with water, dried over sodium sulphate, filtered, and concentrated under reduced pressure to afford methyl (8-((2-(Boc-amino)-2,4-dimethylpentyl)oxy)-6H-isochromeno[3,4-c]pyridin-2-yl)carbamate (30 mg, 0.062 mmol, 13% crude yield) as an off-white solid. LC/MS (ESI) m/e 486.4 [(M+H)$^+$, calcd for $C_{26}H_{36}N_3O_6$, 486.3]; LC/MS retention time (Method B): $t_R$=1.28 min.

Part B: Methyl (8-((2-amino-2,4-dimethylpentyl)oxy)-6H-isochromeno[3,4-c]pyridin-2-yl)carbamate To methyl (8-((2-(Boc-amino)-2,4-dimethylpentyl)oxy)-6H-isochromeno[3,4-c]pyridin-2-yl)carbamate (30 mg, 0.062 mmol) in DCM (5 mL) cooled to 0° C. was added 2N HCl in dioxane (1 mL, 4.00 mmol). The reaction mixture was stirred at 0° C. for 15 min then warmed to room temperature and stirred for 30 min. The reaction mixture was extracted with DCM (3×10 mL). The combined organic layers were washed with saturated aqueous sodium bicarbonate, water, then brine. The organic solution was dried over sodium sulphate, filtered, and concentrated under reduced pressure to afford methyl (8-((2-amino-2,4-dimethylpentyl)oxy)-6H-isochromeno[3,4-c]pyridin-2-yl)carbamate (20 mg, 0.047 mmol, 76% yield) as an off-white solid. LC/MS (ESI) m/e 386.2 [(M+H)$^+$, calcd for $C_{21}H_{28}N_3O_4$, 386.2]; LC/MS retention time (Method A3): $t_R$=1.97 min; $^1$H NMR (400 MHz, METHANOL-$d_4$) δ 7.95 (s, 1H), 7.94 (s, 1H), 7.91 (d, J=8.4 Hz, 1H), 7.21 (dd, J=8.4, 2.4 Hz, 1H), 7.05 (d, J=2.4 Hz, 1H), 5.23 (s, 2H), 4.22 (d, J=10.4 Hz, 1H), 4.13 (d, J=10.4 Hz, 1H), 3.87 (s, 3H), 1.89-1.68 (m, 3H), 1.50 (s, 3H), 1.06 (d, J=6.4 Hz, 3H), 1.01 (d, J=6.4 Hz, 3H), three exchangeable protons not observed; HPLC purity (Method A1): 92% $t_R$=10.95 min; HPLC purity (Method B1): 92% $t_R$=11.68 min.

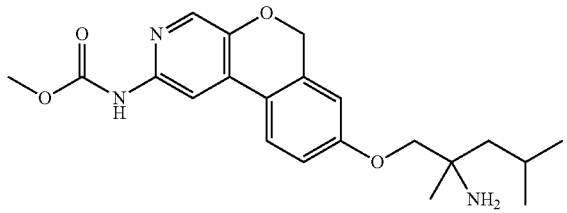 [SMILES: COC(=O)Nc1cc2c(cn1)OCc1cc(OCC(C)(N)CC(C)C)ccc1-2]

Example 40

(R)-ethyl (8-((2-amino-2,4-dimethylpentyl)oxy)-6H-isochromeno[3,4-c]pyridin-2-yl)carbamate

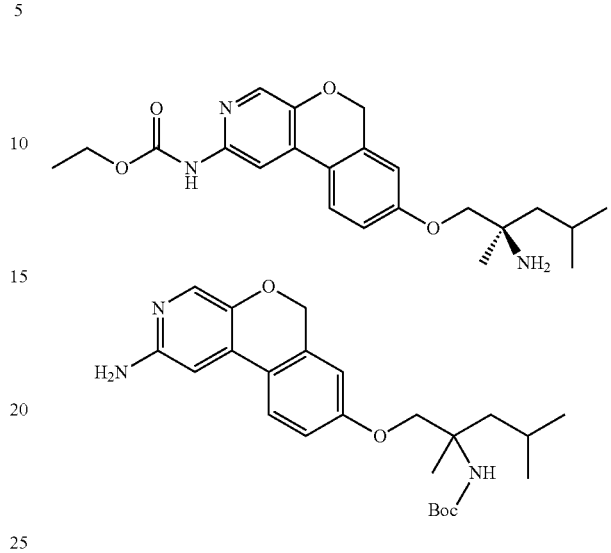

Part A: Tert-butyl (1-((2-amino-6H-isochromeno[3,4-c]pyridin-8-yl)oxy)-2,4-dimethylpentan-2-yl)carbamate To a stirred solution of tert-butyl (1-((2-acetamido-6H-isochromeno[3,4-c]pyridin-8-yl)oxy)-2,4-dimethylpentan-2-yl)carbamate (0.043 g, 0.086 mmol) (prepared in Example 36, Part A) in water (0.400 mL) and ethanol (1.2 mL) was added KOH (0.072 g, 1.291 mmol) and the solution stirred at 0° C. for 5 min, then at 65° C. for 14 h. The reaction mixture was cooled to room temperature and concentrated under reduced pressure. The residue was taken up in DCM (2 mL) and transferred to a separatory funnel containing water (5 mL). Extracted with DCM (2×10 mL). The combined the organic layers were dried over sodium sulphate, filtered, and concentrated under reduced pressure to afford tert-butyl (1-((2-amino-6H-isochromeno[3,4-c]pyridin-8-yl)oxy)-2,4-dimethylpentan-2-yl)carbamate (0.034 g, 0.072 mmol, 83% yield) as a yellow solid. The material was carried forward without further purification. LC/MS (ESI) m/e 428.4 [(M+H)$^+$, calcd for $C_{24}H_{34}N_3O_4$, 428.3]; LC/MS retention time (Method B): $t_R$=1.18 min.

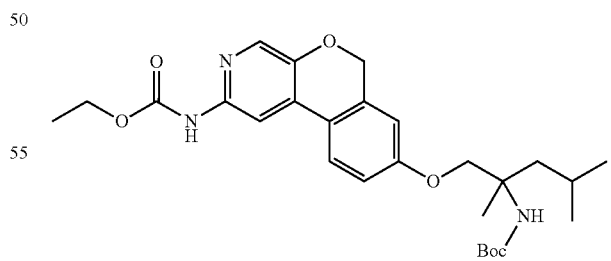

Part B: Ethyl (8-((2-(Boc-amino)-2,4-dimethylpentyl)oxy)-6H-isochromeno[3,4-c]pyridin-2-yl)carbamate To a solution of tert-butyl (1-((2-amino-6H-isochromeno[3,4-c]pyridin-8-yl)oxy)-2,4-dimethylpentan-2-yl)carbamate (0.034 g, 0.072 mmol) in CHCl₃ (1.5 mL) cooled to 0° C. was added pyridine (0.035 mL, 0.429 mmol) and ethyl carbonochloridate (0.014 mL, 0.143 mmol) dropwise followed by DMAP (0.874 mg, 7.16 μmol). The reaction mixture was stirred at room temperature for 30 min. The reaction mixture was quenched with water and extracted with DCM (2×10 mL). The combined organic layers were washed with brine (5 mL), dried, filtered, and concentrated under reduced pressure to afford ethyl (8-((2-(Boc-amino)-2,4-dimethylpentyl)oxy)-6H-isochromeno[3,4-c]pyridin-2-yl)carbamate (0.04 g, 0.054 mmol, 75% yield) as a yellow semi-solid. LC/MS (ESI) m/e 500.1 [(M+H)⁺, calcd for $C_{27}H_{38}N_3O_6$, 500.3]; LC/MS retention time (Method E): $t_R$=1.05 min.

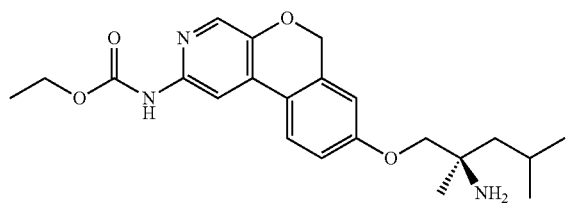 [SMILES: CCOC(=O)Nc1cc2c(cn1)OCc1cc(OC[C@](C)(N)CC(C)C)ccc1-2]

Part C: (R)-ethyl (8-((2-amino-2,4-dimethylpentyl)oxy)-6H-isochromeno[3,4-c]pyridin-2-yl)carbamate To ethyl (8-((2-(Boc-amino)-2,4-dimethylpentyl)oxy)-6H-isochromeno[3,4-c]pyridin-2-yl)carbamate (0.04 g, 0.054 mmol) in DCM (1 mL) and MeOH (0.1 mL) cooled to 0° C. was added 4N HCl in 1,4-dioxane (1 mL, 4.00 mmol). The reaction mixture was stirred at 0° C. for 5 min then warmed to room temperature and stirred for 30 min. The reaction mixture was concentrated under reduced pressure. The residue was purified via prep HPLC (Acetonitrile:water with 10 mM NH₄OAc) to afford ethyl (8-((2-amino-2,4-dimethylpentyl)oxy)-6H-isochromeno[3,4-c]pyridin-2-yl)carbamate (~40 mg) as a pale yellow solid.

Racemic ethyl (8-((2-amino-2,4-dimethylpentyl)oxy)-6H-isochromeno[3,4-c]pyridin-2-yl)carbamate (~40 mg) was resolved via chiral SFC (Column: Chiralpak-IC (250×4.6 mm) 5 micron; Co-solvent: 0.3% DEA in Methanol (in CO2); Total flow: 4 mL/min, CO2 flow=2.4 mL/min; co-solvent flow=1.6 mL/min; co-solvent %=40%; column temp: 22.8° C.). Obtained Enantiomer 1: (R)-ethyl (8-((2-amino-2,4-dimethylpentyl)oxy)-6H-isochromeno[3,4-c]pyridin-2-yl)carbamate (12 mg, 0.023 mmol, 43% yield) as a pale yellow solid; Chiral HPLC purity (SFC prep conditions): 100% $t_R$=6.08 min (racemate shows peaks at $t_R$=6.08 and 8.16 min). Absolute stereochemistry assumed based on the potency of the final compound relative to its enantiomer, with the (S)-enantiomer showing better potency then the (R)-enantiomer. LC/MS (ESI) m/e 400.0 [(M+H)⁺, calcd for $C_{22}H_{30}N_3O_4$, 400.2]; LC/MS retention time (Method J): $t_R$=1.37 min; ¹H NMR (400 MHz, METHANOL-d₄) δ 8.06 (s, 1H), 7.96 (s, 1H), 7.90 (d, J=8.5 Hz, 1H), 7.19 (dd, J=8.8, 2.8 Hz, 1H), 7.02 (d, J=2.5 Hz, 1H), 5.22 (s, 2H), 4.30 (q, J=7.4 Hz, 2H), 4.22 (d, J=10.0 Hz, 1H), 4.12 (d, J=10.5 Hz, 1H), 1.99-1.82 (m, 2H), 1.77-1.64 (m, 1H), 1.51 (s, 3H), 1.43-1.34 (m, 3H), 1.09 (d, J=6.5 Hz, 3H), 1.04 (d, J=6.0 Hz, 3H), three exchangeable protons not observed; HPLC purity (Method C1): 98% $t_R$=1.35 min.

Example 41

(S)-ethyl (8-((2-amino-2,4-dimethylpentyl)oxy)-6H-isochromeno[3,4-c]pyridin-2-yl)carbamate

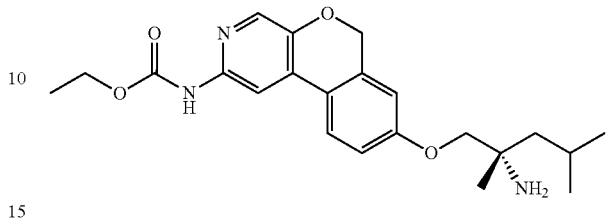

Racemic ethyl (8-((2-amino-2,4-dimethylpentyl)oxy)-6H-isochromeno[3,4-c]pyridin-2-yl)carbamate (~40 mg, prepared in Example, 40 part C) was resolved via chiral SFC (Column: Chiralpak-IC (250×4.6 mm) 5 micron; Co-solvent: 0.3% DEA in Methanol (in CO₂); Total flow: 4 mL/min, CO₂ flow=2.4 mL/min; co-solvent flow=1.6 mL/min; co-solvent %=40%; column temp: 22.8° C.). Obtained Enantiomer 2: (S)-ethyl (8-((2-amino-2,4-dimethylpentyl)oxy)-6H-isochromeno[3,4-c]pyridin-2-yl)carbamate (9 mg, 0.022 mmol, 28% yield) as a pale yellow solid; Chiral HPLC purity (SFC prep conditions): 97% $t_R$=8.16 min (racemate shows peaks at $t_R$=6.08 and 8.16 min). Absolute stereochemistry assumed based on the potency of the final compound relative to its enantiomer, with the (S)-enantiomer showing better potency then the (R)-enantiomer. LC/MS (ESI) m/e 400.0 [(M+H)⁺, calcd for $C_{22}H_{30}N_3O_4$, 400.2]; LC/MS retention time (Method J): $t_R$=1.37 min ¹H NMR (400 MHz, METHANOL-d₄) δ 8.02 (s, 1H), 7.96 (s, 1H), 7.91 (d, J=8.5 Hz, 1H), 7.20 (dd, J=8.8, 2.8 Hz, 1H), 7.03 (d, J=2.5 Hz, 1H), 5.23 (s, 2H), 4.31 (q, J=7.0 Hz, 2H), 4.25-4.19 (m, 1H), 4.12 (d, J=10.5 Hz, 1H), 1.99-1.80 (m, 2H), 1.76-1.63 (m, 1H), 1.51 (s, 3H), 1.38 (t, J=7.3 Hz, 3H), 1.09 (d, J=6.5 Hz, 3H), 1.04 (d, J=6.0 Hz, 3H), three exchangeable protons not observed; HPLC purity (Method A2): 98% $t_R$=5.58 min; HPLC purity (Method B3): 99% $t_R$=6.91 min.

Example 42

8-((2-amino-2,4-dimethylpentyl)oxy)-N-(2,2,2-trifluoroethyl)-6H-isochromeno[3,4-c]pyridin-2-amine

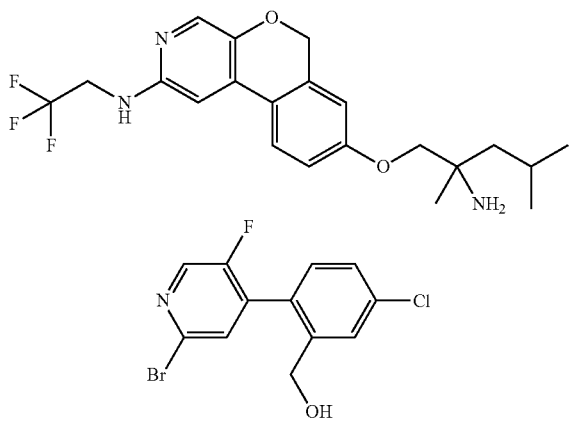

Part A: (2-(2-Bromo-5-fluoropyridin-4-yl)-5-chlorophenyl)methanol

To a solution of methyl 2-(2-bromo-5-fluoropyridin-4-yl)-5-chlorobenzoate (2.4 g, 6.97 mmol) (prepared in Example 14, part G) in tetrahydrofuran (15 mL) cooled to −30° C. was added LiAlH$_4$, 2.4M in THF (2.90 mL, 6.97 mmol) dropwise over a period of 5 min. The reaction mixture was stirred for 15 min at 0° C., then at room temperature for 1 h. The reaction mixture was quenched with saturated aqueous ammonium chloride and extracted with ethyl acetate (3×15 mL). The combined organic layers were washed with brine, dried over sodium sulphate, filtered, and concentrated under reduced pressure to afford (2-(2-bromo-5-fluoropyridin-4-yl)-5-chlorophenyl)methanol (2.2 g, 5.77 mmol, 83% yield) as a semi-solid. LC/MS (ESI) m/e 315.9 [(M+H)$^+$, calcd for C$_{12}$H$_9$BrFNO, 316.0]; LC/MS retention time (Method M): t$_R$=2.31 min; $^1$H NMR (300 MHz, CHLOROFORM-d) δ 8.34 (d, J=0.8 Hz, 1H), 7.68 (d, J=2.3 Hz, 1H), 7.46 (d, J=5.7 Hz, 1H), 7.41 (dd, J=8.3, 2.3 Hz, 1H), 7.19 (d, J=8.3 Hz, 1H), 4.56 (d, J=4.2 Hz, 2H), 1.79 (br. s., 1H).

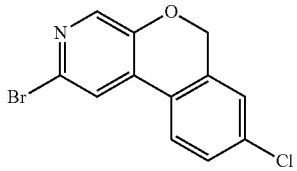 [SMILES: Clc1ccc2c(c1)COc1cnc(Br)cc1-2]

Part B: 2-Bromo-8-chloro-6H-isochromeno[3,4-c]pyridine

To a solution of (2-(2-bromo-5-fluoropyridin-4-yl)-5-chlorophenyl)methanol (2.2 g, 6.95 mmol) in tetrahydrofuran (30 mL) cooled to 0° C. was added NaH (0.556 g, 13.90 mmol). The reaction mixture was stirred at 0° C. for 15 min, then at room temperature for 1 h. The reaction mixture was quenched with ice and extracted with ethyl acetate (2×5 mL). The combined organic layers were washed with brine (5 mL), dried, filtered, and concentrated under reduced pressure. The residue was purified via silica gel chromatography (20% EtOAc in petroleum ether) to afford 2-bromo-8-chloro-6H-isochromeno[3,4-c]pyridine (2.0 g, 4.86 mmol, 70% yield) as a brown solid. LC/MS (ESI) m/e 296.3 [(M+H)$^+$, calcd for C$_{12}$H$_8$BrNO, 296.0]; LC/MS retention time (Method B): t$_R$=1.15 min; $^1$H NMR (300 MHz, CHLOROFORM-d) δ 8.13 (s, 1H), 7.70 (s, 1H), 7.66 (d, J=8.3 Hz, 1H), 7.43 (dd, J=8.3, 2.3 Hz, 1H), 7.24-7.19 (m, 1H), 5.18 (s, 2H).

Part C: Tert-butyl (2,4-dimethyl-1-((2-((2,2,2-trifluoroethyl)amino)-6H-isochromeno[3,4-c]pyridin-8-yl)oxy)pentan-2-yl)carbamate To a stirred solution of 8-chloro-N-(2,2,2-trifluoroethyl)-6H-isochromeno[3,4-c]pyridin-2-amine (0.16 g, 0.508 mmol) in toluene (10 mL) was added tert-butyl (1-hydroxy-2,4-dimethylpentan-2-yl)carbamate (0.235 g, 1.02 mmol) followed by allylpalladium chloride dimer (5.58 mg, 0.015 mmol) and Cs$_2$CO$_3$ (0.248 g, 0.763 mmol) and 2-(di-tert-butylphosphino)-3-methoxy-6-methyl-2'-4'-6'-tri-iso-propyl-1,1'-biphenyl (0.014 g, 0.031 mmol). Argon gas was bubbled through the solution over a period of 20 min, then the mixture was heated to 100° C. for 21 h. The reaction mixture was cooled to room temperature and concentrated under reduced pressure. The residue was purified via silica gel chromatography (10% Ethyl acetate in petroleum ether) to afford tert-butyl (2,4-dimethyl-1-((2-((2,2,2-trifluoroethyl)amino)-6H-isochromeno[3,4-c]pyridin-8-yl)oxy)pentan-2-yl)carbamate (0.30 g, 0.253 mmol, 50% yield) as a yellow solid. LC/MS (ESI) m/e 510.4 [(M+H)$^+$, calcd for C$_{26}$H$_{35}$F$_3$N$_3$O$_4$, 510.3]; LC/MS retention time (Method A3): t$_R$=2.54 min.

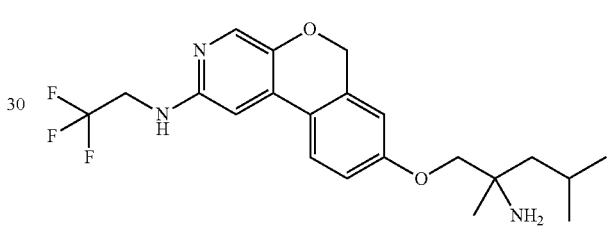

Part C: 8-((2-amino-2,4-dimethylpentyl)oxy)-N-(2,2,2-trifluoroethyl)-6H-isochromeno[3,4-c]pyridin-2-amine To tert-butyl (2,4-dimethyl-1-((2-((2,2,2-trifluoroethyl)amino)-6H-isochromeno[3,4-c]pyridin-8-yl)oxy)pentan-2-yl)carbamate (0.3 g, 0.241 mmol) in MeOH (3 mL) cooled to 0° C. was added 4N HCl in 1,4-dioxane (3 mL, 12.00 mmol). The reaction mixture was stirred at 0° C. for 5 min then warmed to room temperature and stirred for 1 h. The reaction mixture was concentrated under reduced pressure. The residue was diluted with saturated aqueous sodium bicarbonate (50 mL) and extracted with DCM (2×100 mL). The combined organic layers were dried over Na$_2$SO$_4$, filtered, and concentrated under reduced pressure. The residue was purified via prep HPLC (Acetonitrile:water with 10 mM NH$_4$OAc) to afford 8-((2-amino-2,4-dimethylpentyl)oxy)-N-(2,2,2-trifluoroethyl)-6H-isochromeno[3,4-c]pyridin-2-amine (0.03 g, 0.073 mmol, 30% yield) as a colorless solid. LC/MS (ESI) m/e 410.2 [(M+H)$^+$, calcd for C$_{21}$H$_{27}$F$_3$N$_3$O$_2$, 412.2]; LC/MS retention time (Method A3): t$_R$=1.93 min; $^1$H NMR (400 MHz, METHANOL-d$_4$) δ 7.76 (d, J=8.5 Hz, 1H), 7.73 (s, 1H), 7.04 (dd, J=8.8, 2.8 Hz, 1H), 6.94 (s, 1H), 6.89 (d, J=2.5 Hz, 1H), 5.05 (s, 2H), 4.08 (q, J=9.5 Hz, 2H), 3.87 (q, J=9.0 Hz, 2H), 1.89-1.76 (m, 1H), 1.67-1.45 (m, 2H), 1.26 (s, 3H), 1.01 (d, J=7.0 Hz, 3H), 0.99 (d, J=6.5 Hz, 3H), three exchangeable protons not observed; HPLC purity (Method A1): 98% t$_R$=10.68 min; HPLC purity (Method B3): 98% t$_R$=6.59 min.

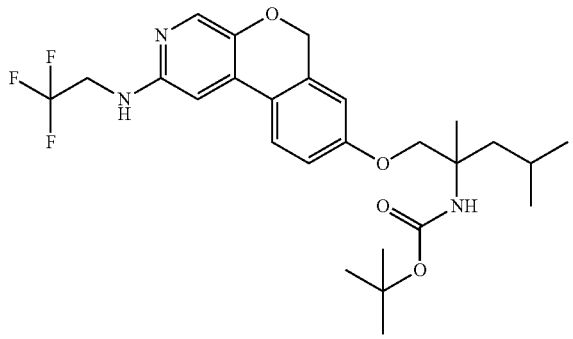 [SMILES: CC(C)CC(C)(COc1ccc2c(c1)COc1cnc(NCC(F)(F)F)cc1-2)NC(=O)OC(C)(C)C]

Example 43

(S)-8-((2-amino-2,4-dimethylpentyl)oxy)-N-(2,2,2-trifluoroethyl)-6H-isochromeno[3,4-c]pyridin-2-amine

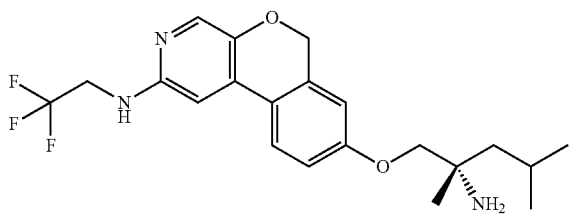 [SMILES: CC(C)C[C@](C)(N)COc1ccc2c(c1)COc1cnc(NCC(F)(F)F)cc1-2]

Racemic 8-((2-amino-2,4-dimethylpentyl)oxy)-N-(2,2,2-trifluoroethyl)-6H-isochromeno[3,4-c]pyridin-2-amine (0.03 g, 0.073 mmol) was resolved via chiral SFC (Column: Chiralpak AD-H (250×4.6 mm), 5 micron; Co-solvent: 30% (0.3% DEA in Methanol):70% CO2); Total flow: 3 g/min, column temp: 23° C.; UV: 223 nm; Run time=10 min). Obtained Enantiomer 1: (S)-8-((2-amino-2,4-dimethylpentyl)oxy)-N-(2,2,2-trifluoroethyl)-6H-isochromeno[3,4-c]pyridin-2-amine (0.01 g, 0.024 mmol, 10% yield) as a colorless solid; Chiral HPLC purity (SFC prep conditions): 100% $t_R$=2.98 min (racemate shows peaks at $t_R$=2.98 and 4.52 min). Absolute stereochemistry assumed based on the potency of the final compound relative to its enantiomer, with the (S)-enantiomer showing better potency then the (R)-enantiomer. LC/MS (ESI) m/e 410.0 [(M+H)$^+$, calcd for $C_{21}H_{27}F_3N_3O_2$, 412.2]; LC/MS retention time (Method A3): $t_R$=2.00 min; $^1$H NMR (400 MHz, METHANOL-$d_4$) δ 7.76 (d, J=8.5 Hz, 1H), 7.73 (s, 1H), 7.04 (dd, J=8.5, 2.5 Hz, 1H), 6.94 (s, 1H), 6.89 (d, J=2.5 Hz, 1H), 5.05 (s, 2H), 4.08 (q, J=9.5 Hz, 2H), 3.94-3.79 (m, 2H), 1.89-1.77 (m, 1H), 1.54 (qd, J=14.6, 5.5 Hz, 2H), 1.25 (s, 3H), 1.01 (d, J=6.5 Hz, 3H), 0.99 (d, J=7.0 Hz, 3H), three exchangeable protons not observed; HPLC purity (Method A2): 99% $t_R$=5.31 min; HPLC purity (Method B1): 99% $t_R$=12.26 min.

Example 44

(R)-8-((2-amino-2,4-dimethylpentyl)oxy)-N-(2,2,2-trifluoroethyl)-6H-isochromeno[3,4-c]pyridin-2-amine

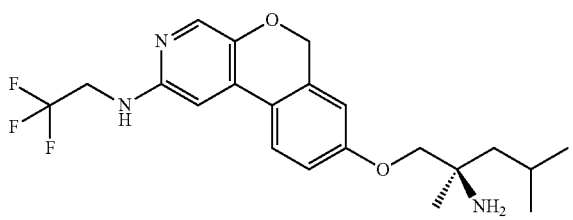 [SMILES: CC(C)C[C@@](C)(N)COc1ccc2c(c1)COc1cnc(NCC(F)(F)F)cc1-2]

Racemic 8-((2-amino-2,4-dimethylpentyl)oxy)-N-(2,2,2-trifluoroethyl)-6H-isochromeno[3,4-c]pyridin-2-amine (0.03 g, 0.073 mmol) was resolved via chiral SFC (Column: Chiralpak AD-H (250×4.6 mm), 5 micron; Co-solvent: 30% (0.3% DEA in Methanol):70% CO2); Total flow: 3 g/min, column temp: 23° C.; UV: 223 nm; Run time=10 min). Obtained Enantiomer 2: (R)-8-((2-amino-2,4-dimethylpentyl)oxy)-N-(2,2,2-trifluoroethyl)-6H-isochromeno[3,4-c]pyridin-2-amine (0.01 g, 0.024 mmol, 10% yield) as a colorless solid; Chiral HPLC purity (SFC prep conditions): 100% $t_R$=4.52 min (racemate shows peaks at $t_R$=2.98 and 4.52 min). Absolute stereochemistry assumed based on the potency of the final compound relative to its enantiomer, with the (S)-enantiomer showing better potency then the (R)-enantiomer. LC/MS (ESI) m/e 410.0 [(M+H)$^+$, calcd for $C_{21}H_{27}F_3N_3O_2$, 412.2]; LC/MS retention time (Method A3): $t_R$=2.00 min; $^1$H NMR (400 MHz, METHANOL-$d_4$) δ 7.76 (d, J=8.5 Hz, 1H), 7.73 (s, 1H), 7.04 (dd, J=8.8, 2.8 Hz, 1H), 6.94 (s, 1H), 6.89 (d, J=2.5 Hz, 1H), 5.05 (s, 2H), 4.08 (q, J=9.5 Hz, 2H), 3.94-3.80 (m, 2H), 1.89-1.76 (m, 1H), 1.64-1.45 (m, 2H), 1.25 (s, 3H), 1.01 (d, J=6.5 Hz, 3H), 0.99 (d, J=7.0 Hz, 3H), three exchangeable protons not observed; HPLC purity (Method A2): 97% $t_R$=5.33 min; HPLC purity (Method B1): 98% $t_R$=12.29 min.

Example 45

(S)-methyl (8-((2-amino-2,4-dimethylpentyl)oxy)-7-fluoro-6H-isochromeno[3,4-c]pyridin-2-yl)carbamate

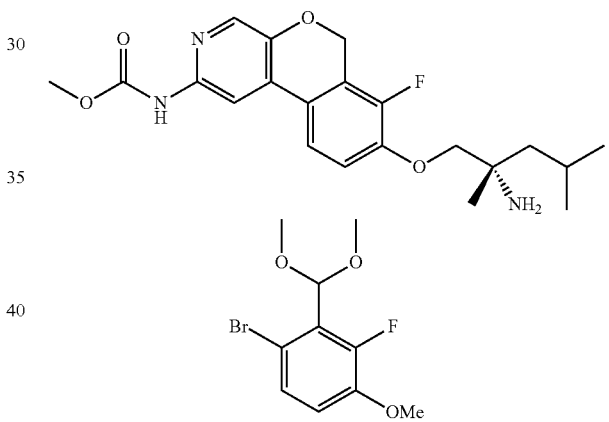

Part A: 1-Bromo-2-(dimethoxymethyl)-3-fluoro-4-methoxybenzene

To a solution of 6-bromo-2-fluoro-3-methoxybenzaldehyde (4 g, 17.16 mmol) and trimethyl orthoformate (1.90 mL, 17.16 mmol) in MeOH (40 mL) was added p-TsOH (3.27 g, 17.16 mmol) and the mixture heated to 75° C. for 5 h. The reaction mixture was concentrated under reduced pressure. The residue was taken up in ethyl acetate (250 mL). The ethyl acetate layer was washed with water (100 mL). The organic layer was separated, dried over sodium sulphate, filtered, and concentrated under reduced pressure. The residue was purified by silica gel chromatography (90:10 petroleum ether:ethyl acetate) to give 1-bromo-2-(dimethoxymethyl)-3-fluoro-4-methoxybenzene (3.0 g, 10.75 mmol, 63% yield) as a yellow oil. $^1$H NMR (400 MHz, CHLOROFORM-d) δ 7.32-7.27 (m, 1H), 6.82 (t, J=8.5 Hz, 1H), 5.73-5.63 (m, 1H), 3.87 (s, 3H), 3.48 (s, 6H).

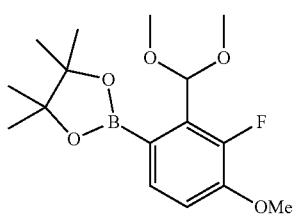 [SMILES: COc1ccc(B2OC(C)(C)C(C)(C)O2)c(C(OC)OC)c1F]

Part B: 2-(2-(Dimethoxymethyl)-3-fluoro-4-methoxyphenyl)-4,4,5,5-tetramethyl-1,3,2-dioxaborolane A solution of 1-bromo-2-(dimethoxymethyl)-3-fluoro-4-methoxybenzene (2 g, 7.17 mmol), bis(pinacolato)diboron (2.37 g, 9.32 mmol), and sodium acetate (1.76 g, 21.50 mmol) in 1,4-dioxane (20 mL) was stirred while bubbling argon gas through the solution for 20 min. $PdCl_2$(dppf) (0.262 g, 0.358 mmol) was added and the mixture was heated to 90° C. for 8 h. The reaction mixture was cooled to room temperature and filtered through diatomaceous earth (Celite®), washing with ethyl acetate. The filtrate was concentrated under reduced pressure. The residue was purified by silica gel chromatography (ethyl acetate in petroleum ether) to afford 2-(2-(dimethoxymethyl)-3-fluoro-4-methoxyphenyl)-4,4,5,5-tetramethyl-1,3,2-dioxaborolane (1.5 g, 4.14 mmol, 58% yield) as a pale yellow oil. $^1$H NMR (400 MHz, CHLOROFORM-d) δ 7.16-7.10 (m, 1H), 6.98-6.92 (m, 1H), 5.80 (s, 1H), 3.88 (s, 3H), 3.40 (s, 6H), 1.36 (s, 12H).

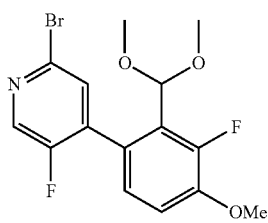 [SMILES: COc1ccc(-c2cc(Br)ncc2F)c(C(OC)OC)c1F]

Part C: 2-Bromo-4-(2-(dimethoxymethyl)-3-fluoro-4-methoxyphenyl)-5-fluoropyridine To a mixture of 2-bromo-5-fluoro-4-iodopyridine (1 g, 3.31 mmol) (prepared in Example 14, Part F), 2-(2-(dimethoxymethyl)-3-fluoro-4-methoxyphenyl)-4,4,5,5-tetramethyl-1,3,2-dioxaborolane (1.080 g, 3.31 mmol) in DME (20 mL) and water (2 mL), was added cesium carbonate (2.159 g, 6.63 mmol). Argon gas was bubbled through the stirred suspension for 5 min. Tetrakis(triphenylphosphine) palladium(0) (0.191 g, 0.166 mmol) was added and argon gas was bubbled through the stirred suspension for 5 min. The reaction mixture was stirred in a microwave at 80° C. for 8 h. The reaction mixture was cooled to room temperature filtered through diatomaceous earth (Celite®), washing with ethyl acetate. The filtrate was concentrated under reduced pressure. The residue was purified via silica gel chromatography (petroleum ether and ethyl acetate) to afford 2-bromo-4-(2-(dimethoxymethyl)-3-fluoro-4-methoxyphenyl)-5-fluoropyridine (600 mg, 1.44 mmol, 44% yield) as a pale yellow oil. LC/MS (ESI) m/e 374.2 [(M+H)$^+$, calcd for $C_{15}H_{15}BrF_2NO_3$, 374.0]; LC/MS retention time (Method B): $t_R$=1.14 min; $^1$H NMR (400 MHz, CHLOROFORM-d) δ 8.24 (s, 1H), 7.48 (d, J=7.2 Hz, 1H), 7.03-6.90 (m, 2H), 5.37 (s, 2H), 3.94 (s, 3H), 3.29 (s, 6H).

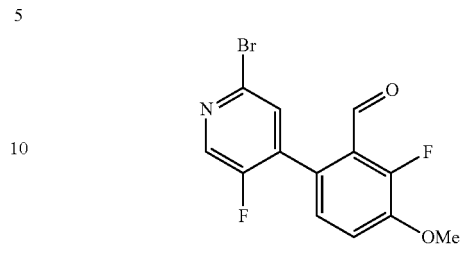

Part D: 6-(2-Bromo-5-fluoropyridin-4-yl)-2-fluoro-3-methoxybenzaldehyde

To a stirred solution of 2-bromo-4-(2-(dimethoxymethyl)-3-fluoro-4-methoxyphenyl)-5-fluoropyridine (600 mg, 1.604 mmol) in THF (6 mL) at 0° C. was added concentrated HCl (0.49 mL, 16.04 mmol). The reaction mixture was warmed to room temperature and stirred for 6 h. The reaction mixture was concentrated under reduced pressure and the residue was taken up in ethyl acetate (50 mL). The ethyl acetate layer was washed with brine (20 mL) and the layers were separated. The organic layer was dried over sodium sulphate, filtered, and concentrated under reduced pressure to afford 6-(2-bromo-5-fluoropyridin-4-yl)-2-fluoro-3-methoxybenzaldehyde (500 mg, 1.43 mmol, 89% crude yield) as a yellow semi-solid. LC/MS (ESI) m/e 328.2 [(M+H)$^+$, calcd for $C_{13}H_9BrF_2NO_2$, 328.0]; LC/MS retention time (Method B): $t_R$=0.99 min.

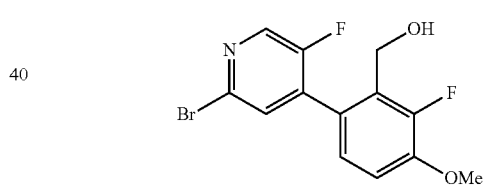

Part E: (6-(2-Bromo-5-fluoropyridin-4-yl)-2-fluoro-3-methoxyphenyl)methanol

To a solution of methyl 6-(2-bromo-5-fluoropyridin-4-yl)-2-fluoro-3-methoxybenzaldehyde (500 mg, 1.52 mmol) in tetrahydrofuran (5 mL) and MeOH (1 mL) cooled to 0° C. was added $NaBH_4$ (57.7 mg, 1.52 mmol). The reaction mixture was stirred at 0° C. for 1.5 h. The reaction mixture was quenched with saturated aqueous ammonium chloride (10 mL). The resulting suspension was concentrated under reduced pressure and the residue obtained was taken up in ethyl acetate (200 mL). The ethyl acetate layer was washed with brine (25 mL) and layers were separated. The organic layer was dried over sodium sulphate, filtered, and concentrated under reduced pressure to afford (6-(2-bromo-5-fluoropyridin-4-yl)-2-fluoro-3-methoxyphenyl)methanol (400 mg, 1.04 mmol, 68% yield) as a dark yellow solid. LC/MS (ESI) m/e 330.0 [(M+H)$^+$, calcd for $C_{13}H_{11}BrF_2NO_2$, 330.0]; LC/MS retention time (Method A3): $t_R$=2.03 min.

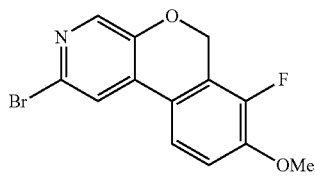 [SMILES: COc1ccc2c(c1F)COc1cnc(Br)cc1-2]

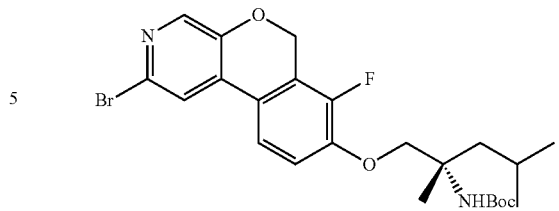

Part F: 2-Bromo-7-fluoro-8-methoxy-6H-isochromeno[3,4-c]pyridine

To a solution of (6-(2-bromo-5-fluoropyridin-4-yl)-2-fluoro-3-methoxyphenyl)methanol (300 mg, 0.909 mmol) in tetrahydrofuran (6 mL) cooled to 0° C. was added sodium hydride (43.6 mg, 1.817 mmol). The reaction mixture was stirred at 0° C. for 10 min, then at room temperature for 2 h. The reaction mixture was quenched with ice water and extracted with ethyl acetate (2×5 mL). The combined organic layers were washed with brine (5 mL), dried, filtered, and concentrated under reduced pressure to afford 2-bromo-7-fluoro-8-methoxy-6H-isochromeno[3,4-c]pyridine (200 mg, 0.580 mmol, 64% yield) as a yellow solid which was carried forward without further purification. LC/MS (ESI) m/e 310.0 [(M+H)$^+$, calcd for $C_{13}H_{10}BrFNO_2$, 310.0]; LC/MS retention time (Method A3): $t_R$=2.16 min; $^1$H NMR (400 MHz, METHANOL-$d_4$) δ 8.02 (s, 1H), 7.93 (s, 1H), 7.70 (dd, J=8.5, 1.5 Hz, 1H), 7.22 (t, J=8.8 Hz, 1H), 5.33 (d, J=1.0 Hz, 2H), 3.96 (s, 3H).

Part H: (S)-tert-butyl (1-((2-bromo-7-fluoro-6H-isochromeno[3,4-c]pyridin-8-yl)oxy)-2,4-dimethylpentan-2-yl)carbamate A solution of 2-bromo-7-fluoro-6H-isochromeno[3,4-c]pyridin-8-ol (130 mg, 0.439 mmol) and potassium carbonate (121 mg, 0.878 mmol) in DMF (2 mL) was stirred under nitrogen for 10 min. (S)-tert-butyl 4-isobutyl-4-methyl-1,2,3-oxathiazolidine-3-carboxylate 2,2-dioxide (155 mg, 0.527 mmol) was added and the mixture heated to 85° C. for 16 h. The reaction mixture was cooled to room temperature and concentrated under reduced pressure. Water (10 mL) was added to the residue and the solution was extracted with ethyl acetate (50 mL). The organic layer was separated, dried over sodium sulphate, filtered, and concentrated under reduced pressure to afford (S)-tert-butyl (1-((2-bromo-7-fluoro-6H-isochromeno[3,4-c]pyridin-8-yl)oxy)-2,4-dimethylpentan-2-yl)carbamate. (200 mg, 0.345 mmol, 79% yield) as a dark brown solid. LC/MS (ESI) m/e 509.2 [(M+H)$^+$, calcd for $C_{24}H_{31}BrFN_2O_4$, 509.2]; LC/MS retention time (Method A3): $t_R$=2.69 min.

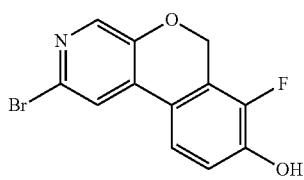 [SMILES: Oc1ccc2c(c1F)COc1cnc(Br)cc1-2]

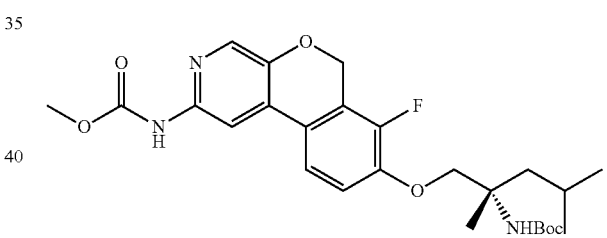

Part G: 2-Bromo-7-fluoro-6H-isochromeno[3,4-c]pyridin-8-ol

To a solution of 2-bromo-7-fluoro-8-methoxy-6H-isochromeno[3,4-c]pyridine (250 mg, 0.806 mmol) in dichloromethane (3 mL) at 0° C. was added tribromoborane, 1M in dichloromethane (4.03 mL, 4.03 mmol) and the reaction mixture was warmed to room temperature and stirred for 5 h. The reaction mixture was cooled to 0° C. and saturated aqueous sodium bicarbonate (25 mL) was added dropwise. A pale yellow solid precipitated and was collected by vacuum filtration and air dried. Obtained 2-bromo-7-fluoro-6H-isochromeno[3,4-c]pyridin-8-ol (160 mg, 0.486 mmol, 60% yield) as a pale yellow solid. LC/MS (ESI) m/e 296.0 [(M+H)$^+$, calcd for $C12H_8BrFNO_2$, 296.0]; LC/MS retention time (Method A3): $t_R$=1.95 min; $^1$H NMR (400 MHz, CHLOROFORM-d) δ 8.08 (s, 1H), 7.63 (s, 1H), 7.42 (d, J=8.5 Hz, 1H), 7.11-7.03 (m, 2H), 5.28 (s, 2H), one exchangeable proton not seen.

Part I: Methyl (S)-(8-((2-((tert-butoxycarbonyl)amino)-2,4-dimethylpentyl)oxy)-7-fluoro-6H-isochromeno[3,4-c]pyridin-2-yl)carbamate XANTPHOS (4.54 mg, 7.85 μmol) was taken up in 1,4-dioxane (4 mL) and the solution purged with argon for 10 min. PdOAc$_2$ (0.881 mg, 3.93 μmol) was added and purging was continued for 5 min. (S)-tert-butyl (1-((2-bromo-7-fluoro-6H-isochromeno[3,4-c]pyridin-8-yl)oxy)-2,4-dimethylpentan-2-yl)carbamate (200 mg, 0.393 mmol), methyl carbamate (35.4 mg, 0.471 mmol) and cesium carbonate (384 mg, 1.18 mmol) were added successively and the solution purged with argon for 5 min. The reaction mixture was heated to 70° C. in an oil bath for 8 h. The reaction mixture was diluted with ethyl acetate (25 mL) and filtered through diatomaceous earth (Celite®). The bed was washed with ethyl acetate (20 mL) and the filtrate was concentrated under reduced pressure to afford a brown residue. The residue was purified via silica gel chromatography (hexane:ethyl acetate) to afford methyl (S)-(8-((2-((tert-butoxycarbonyl)amino)-2,4-dimethylpentyl)oxy)-7-fluoro-6H-isochromeno[3,4-c]pyridin-2-yl)carbamate (100 mg, 0.195 mmol, 50% yield) as a pale yellow semi-solid. LC/MS (ESI) m/e 504.2 [(M+H)+, calcd for $C_{26}H_{35}FN_3O_6$, 504.3]; LC/MS retention time (Method $C_3$): $t_R$=3.56 min.

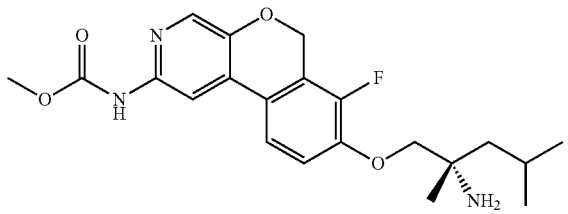 [SMILES: COC(=O)Nc1cc2c(cn1)OCc1c-2ccc(OC[C@@](C)(N)CC(C)C)c1F]

Part J: (S)-methyl (8-((2-amino-2,4-dimethylpentyl) oxy)-7-fluoro-6H-isochromeno[3,4-c]pyridin-2-yl) carbamate To a stirred solution of (S)-tert-butyl (1-((2-acetamido-5H-chromeno[3,4-c]pyridin-8-yl)oxy)-2,4-dimethylpentan-2-yl)carbamate (1.2 g, 2.56 mmol) in DCM (20 mL) cooled to 0° C., was added TFA (3.94 mL, 51.1 mmol) dropwise over 5 min. The solution was then stirred at 0° C. for 4 h. The reaction mixture was quenched with saturated aqueous sodium bicarbonate (250 mL) (added slowly over 30 min). The resulting biphasic layer was extracted with ethyl acetate (2×250 mL). The organic layer was separated, dried over sodium sulphate, filtered, and concentrated under reduced pressure to afford a pale yellow solid. The solid was washed with diethyl ether (100 mL). The solid obtained was lyophilized to afford (S)-methyl (8-((2-amino-2,4-dimethylpentyl)oxy)-7-fluoro-6H-isochromeno[3,4-c]pyridin-2-yl) carbamate (650 mg, 1.76 mmol, 69% yield) as a yellow powder. LC/MS (ESI) m/e 404.2 [(M+H)+, calcd for $C_{21}H_{27}FN_3O_4$, 404.2]; LC/MS retention time (Method A3): $t_R$=1.96 min; $^1$H NMR (400 MHz, METHANOL-$d_4$) δ 8.04 (s, 1H), 7.88 (s, 1H), 7.84 (d, J=8.5 Hz, 1H), 7.41 (t, J=8.3 Hz, 1H), 5.43 (s, 2H), 4.32 (d, J=10.5 Hz, 1H), 4.28-4.21 (m, 1H), 3.91 (s, 3H), 1.98-1.83 (m, 2H), 1.78-1.68 (m, 1H), 1.53 (s, 3H), 1.09 (d, J=6.5 Hz, 3H), 1.05 (d, J=6.0 Hz, 3H), three exchangeable protons not observed; HPLC purity (Method A2): 93% $t_R$=5.93 min; HPLC purity (Method B3): 91% $t_R$=6.95 min.

Example 46

(S)-ethyl (8-((2-amino-2,4-dimethylpentyl)oxy)-1,4-dichloro-6H-isochromeno[3,4-c]pyridin-2-yl)carbamate

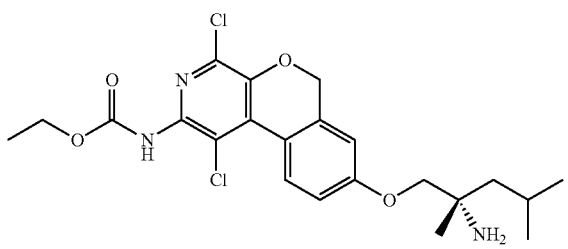 [SMILES: CCOC(=O)Nc1nc(Cl)c2c(c1Cl)-c1ccc(OC[C@@](C)(N)CC(C)C)cc1CO2]

A solution of (S)-ethyl (8-((2-amino-2,4-dimethylpentyl) oxy)-6-isochromeno[3,4-c]pyridin-2-yl)carbamate (0.03 g, 0.075 mmol) (prepared in Example 41) in acetonitrile (3 mL) was heated to reflux for 2 h. The reaction mixture was cooled to room temperature and concentrated under reduced pressure. LC/MS suggests formation of both a mono- and di-chloroproduct. The residue was purified via prep LC/MS (Acetonitrile:water with 10 mM NH$_4$OAc) to afford (S)-ethyl (8-((2-amino-2,4-dimethylpentyl)oxy)-1,4-dichloro-6H-isochromeno[3,4-c]pyridin-2-yl)carbamate (6 mg, 0.012 mmol, 16% yield) as a pale yellow powder. LC/MS (ESI) m/e 468.2 [(M+H)+, calcd for $C_{22}H_{28}Cl_2N_3O_4$, 468.2]; LC/MS retention time (Method E): $t_R$=0.85 min; $^1$H NMR (400 MHz, METHANOL-$d_4$) δ 8.53 (d, J=9.0 Hz, 1H), 7.15 (dd, J=9.0, 2.5 Hz, 1H), 7.08 (d, J=2.5 Hz, 1H), 5.18 (s, 2H), 4.24 (q, J=7.0 Hz, 2H), 4.16-4.08 (m, 1H), 4.06-3.97 (m, 1H), 1.90-1.80 (m, 1H), 1.79-1.70 (m, 1H), 1.68-1.57 (m, 1H), 1.41 (s, 3H), 1.34 (t, J=7.3 Hz, 3H), 1.06 (d, J=6.5 Hz, 3H), 1.02 (d, J=6.5 Hz, 3H), three exchangeable protons not observed; HPLC purity (Method C1): 97% $t_R$=1.95 min; HPLC purity (Method D): 85% $t_R$=1.32 min.

Example 47

(S)-ethyl (8-((2-amino-2,4-dimethylpentyl)oxy)-1-chloro-6H-isochromeno[3,4-c]pyridin-2-yl)carbamate

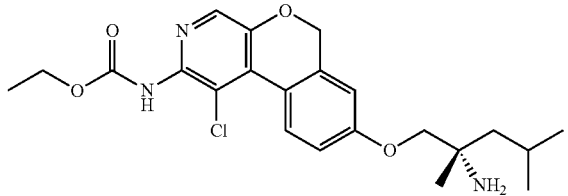 [SMILES: CCOC(=O)Nc1ncc2c(c1Cl)-c1ccc(OC[C@@](C)(N)CC(C)C)cc1CO2]

A solution of (S)-ethyl (8-((2-amino-2,4-dimethylpentyl) oxy)-6H-isochromeno[3,4-c]pyridin-2-yl)carbamate (0.03 g, 0.075 mmol) (prepared in Example 41) in acetonitrile (3 mL) was heated to reflux for 2 h. The reaction mixture was cooled to room temperature and concentrated under reduced pressure. LC/MS suggests formation of both a mono- and di-chloroproduct. The residue was purified via prep LC/MS (Acetonitrile:water with 10 mM NH$_4$OAc) to afford (S)-ethyl (8-((2-amino-2,4-dimethylpentyl)oxy)-1-chloro-6H-isochromeno[3,4-c]pyridin-2-yl)carbamate (4 mg, 8.67 μmol, 12% yield) as a pale yellow powder. LC/MS (ESI) m/e 434.2 [(M+H)+, calcd for $C_{22}H_{29}ClN_3O_4$, 434.2]; LC/MS retention time (Method E): $t_R$=0.78 min; $^1$H NMR (400 MHz, METHANOL-$d_4$) δ 8.56 (d, J=9.0 Hz, 1H), 8.09 (s, 1H), 7.16 (dd, J=9.0, 3.0 Hz, 1H), 7.06 (d, J=2.5 Hz, 1H), 5.10 (s, 2H), 4.24 (q, J=7.0 Hz, 2H), 4.17-4.10 (m, 1H), 4.09-4.02 (m, 1H), 1.86 (dq, J=12.4, 6.4 Hz, 1H), 1.81-1.73 (m, 1H), 1.70-1.61 (m, 1H), 1.44 (s, 3H), 1.39-1.31 (m, 3H), 1.06 (d, J=6.5 Hz, 3H), 1.03 (d, J=6.5 Hz, 3H), three exchangeable protons not observed; HPLC purity (Method C1): 95% $t_R$=1.36 min; HPLC purity (Method D): 94% $t_R$=1.14 min.

Example 48

(S)-1-((2-(difluoromethyl)-6H-isochromeno[3,4-c]pyridin-8-yl)oxy)-2,4-dimethylpentan-2-amine

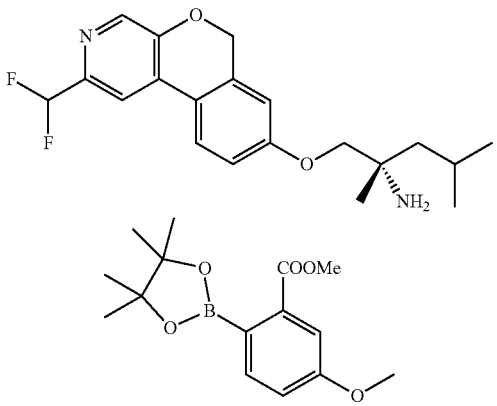

Part A: Methyl 5-methoxy-2-(4,4,5,5-tetramethyl-1,3,2-dioxaborolan-2-yl)benzoate A suspension of methyl 2-bromo-5-methoxybenzoate (2 g, 8.16 mmol), PdCl$_2$(dppf)-CH$_2$Cl$_2$ adduct (0.333 g, 0.408 mmol), bis(pinacolato)diboron (2.280 g, 8.98 mmol) and potassium acetate (2.403 g, 24.48 mmol) in 1,4-dioxane (20 mL) was degassed with nitrogen and heated to 80° C. overnight. The reaction mixture was cooled to room temperature and filtered through diatomaceous earth (Celite®), washing with EtOAc (200 mL). The collected filtrate was washed with H$_2$O (2×20 mL), and brine (1×20 mL). The organic layer was separated, dried over Na$_2$SO$_4$, filtered and concentrated under reduced pressure. The residue was purified via silica gel chromatography (15% EtOAc in petroleum ether) to afford methyl 5-methoxy-2-(4,4,5,5-tetramethyl-1,3,2-dioxaborolan-2-yl)benzoate (1.4 g, 4.79 mmol, 59% yield) as a colorless oil. LC/MS (ESI) m/e 293.2 [(M+H)$^+$, calcd for C$_{15}$H$_{22}$BO$_5$, 293.2]; LC/MS retention time (Method A3): t$_R$=2.18 min; $^1$H NMR (400 MHz, CHLOROFORM-d) δ 7.50-7.40 (m, 2H), 7.09-7.02 (m, 1H), 3.90 (s, 3H), 3.83 (s, 3H), 1.40 (s, 12H).

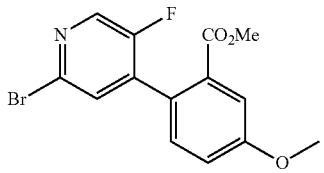 [SMILES: COC(=O)c1cc(OC)ccc1-c1cc(Br)ncc1F]

Part B: Methyl 2-(2-bromo-5-fluoropyridin-4-yl)-5-methoxybenzoate

To a mixture of 2-bromo-5-fluoro-4-iodopyridine (1.400 g, 4.64 mmol) and methyl 5-methoxy-2-(4,4,5,5-tetramethyl-1,3,2-dioxaborolan-2-yl)benzoate (1.355 g, 4.64 mmol) in DME (30 mL) and water (1 mL), was added Cs$_2$CO$_3$ (4.53 g, 13.91 mmol). Nitrogen gas was bubbled through the stirred suspension for 5 min. Tetrakis(triphenylphosphine)palladium(0) (0.268 g, 0.232 mmol) was added and nitrogen gas was bubbled through the stirred suspension for 5 min. The reaction mixture was stirred in a microwave at 80° C. for 16 h. The reaction mixture was cooled to room temperature and filtered through diatomaceous earth (Celite®), washing with EtOAc (200 mL). The collected filtrate was washed with H$_2$O (2×20 mL), and brine (1×20 mL). The organic layer was separated, dried over Na$_2$SO$_4$, filtered, and concentrated under reduced pressure. The residue was purified via silica gel chromatography (15% EtOAc in petroleum ether) to afford methyl 2-(2-bromo-5-fluoropyridin-4-yl)-5-methoxybenzoate (900 mg, 2.95 mmol, 56% yield) as an off-white solid. LC/MS (ESI) m/e 340.2 [(M+H)$^+$, calcd for C$_{14}$H$_{12}$BrFNO$_3$, 340.0]; LC/MS retention time (Method B): t$_R$=1.04 min.

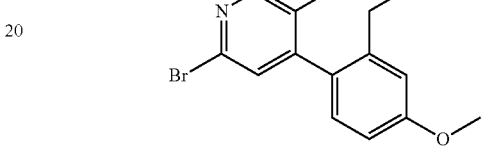

Part C: (2-(2-Bromo-5-fluoropyridin-4-yl)-5-methoxyphenyl)methanol

To a solution of methyl 2-(2-bromo-5-fluoropyridin-4-yl)-5-methoxybenzoate (800 mg, 2.35 mmol) in tetrahydrofuran (20 mL) cooled to −10° C. was added LAH, 2M in THF (1.18 mL, 2.35 mmol) dropwise over a period of 5 min. The reaction mixture was stirred at −10° C. for 1 h. The reaction mixture was quenched with saturated aqueous ammonium chloride and extracted with ethyl acetate (3×5 mL). The combined organic layers were washed with brine, dried over sodium sulphate, filtered, and concentrated under reduced pressure to afford (2-(2-bromo-5-fluoropyridin-4-yl)-5-methoxyphenyl)methanol (600 mg, 1.81 mmol, 77% yield) as a brown solid. LC/MS (ESI) m/e 312.3 [(M+H)$^+$, calcd for C$_{13}$H$_{12}$BrFNO, 312.0]; LC/MS retention time (Method B): t$_R$=0.86 min.

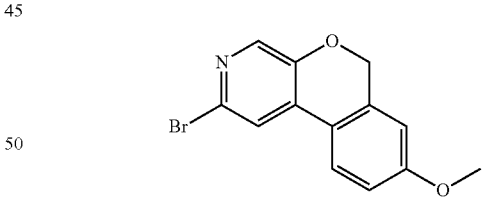

Part D: 2-bromo-8-methoxy-6H-isochromeno[3,4-c]pyridine

To a solution of (2-(2-bromo-5-fluoropyridin-4-yl)-5-methoxyphenyl)methanol (600 mg, 1.92 mmol) in tetrahydrofuran (30 mL) cooled to 0° C. was added NaH (231 mg, 5.77 mmol) in two portions over a period of 5 min. The reaction mixture was stirred at 0° C. for 5 min, then at room temperature for 1 h. The reaction mixture was quenched with ice water (10 mL) and extracted with ethyl acetate (2×50 mL). The combined organic layers were washed with brine (50 mL), dried, filtered, and concentrated under reduced pressure to afford 2-bromo-8-methoxy-6H-isochromeno[3,4-c]pyridine (500 mg, 1.660 mmol, 86% yield) as a red-orange solid. LC/MS (ESI) m/e 292.3 [(M+H)+, calcd for $C_{13}H_{11}BrNO_2$, 292.0]; LC/MS retention time (Method B): $t_R$=3.32 min; $^1$H NMR (400 MHz, METHANOL-$d_4$) δ 7.98 (s, 1H), 7.90 (s, 1H), 7.84 (d, J=8.5 Hz, 1H), 7.04 (dd, J=8.5, 2.5 Hz, 1H), 6.88 (d, J=3.0 Hz, 1H), 5.22 (s, 2H), 3.89 (s, 3H).

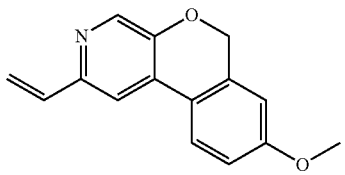 [SMILES: C=Cc1cc2c(cn1)OCc1cc(OC)ccc1-2]

Part E: 8-Methoxy-2-vinyl-6H-isochromeno[3,4-c]pyridine

A suspension of 2-bromo-8-methoxy-6H-isochromeno[3,4-c]pyridine (700 mg, 2.40 mmol), $Na_2CO_3$ (762 mg, 7.19 mmol), tetrakis(triphenylphosphine)palladium(0) (138 mg, 0.120 mmol), and 2,4,6-trivinylcyclotriboroxane pyridine complex (634 mg, 2.64 mmol) in toluene (10 mL), ethanol (3 mL) and water (0.4 mL) was degassed with nitrogen for 10 min, then heated to 90° C. overnight. The reaction mixture was cooled to room temperature and filtered through diatomaceous earth (Celite®). The pad was washed with EtOAc (100 mL). The filtrate was washed with $H_2O$ (2×20 mL), and brine (1×20 mL). The organic layer was dried over $Na_2SO_4$, filtered, and concentrated under reduced pressure. The residue was purified via silica gel chromatography (30% EtOAc in petroleum ether) to obtain 8-methoxy-2-vinyl-6H-isochromeno[3,4-c]pyridine (250 mg, 0.648 mmol, 27% yield) as an orange-red gummy solid. LC/MS (ESI) m/e 240.2 [(M+H)+, calcd for $C_{15}H_{14}NO_2$, 240.1]; LC/MS retention time (Method E): $t_R$=0.69 min.

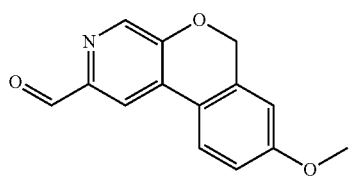 [SMILES: COc1ccc2c(c1)COc1cnc(C=O)cc1-2]

Part F: 8-Methoxy-6H-isochromeno[3,4-c]pyridine-2-carbaldehyde

To a solution of 8-methoxy-2-vinyl-6H-isochromeno[3,4-c]pyridine (260 mg, 0.674 mmol) in 1,4-dioxane (5 mL) and water (5 mL) was cooled to 0° C. was added 2,6-lutidine (0.157 mL, 1.347 mmol) and osmium tetroxide in tert-butanol (0.846 mL, 0.067 mmol). The solution was stirred at 0° C. for 10 min, then sodium periodate (576 mg, 2.69 mmol) was added. The reaction mixture was warmed to room temperature and stirred for 16 h. The reaction mixture was diluted with DCM (100 mL). The DCM layer was washed with $H_2O$ (2×20 mL), and brine (1×20 mL). The organic layer was dried over $Na_2SO_4$, filtered, and concentrated under reduced pressure. Obtained 8-methoxy-6H-isochromeno[3,4-c]pyridine-2-carbaldehyde (250 mg, 0.601 mmol, 89% yield) was as a brown gummy solid which was carried forward without further purification. LC/MS (ESI) m/e 242.3 [(M+H)+, calcd for $C_{14}H_{12}NO_3$, 242.1]; LC/MS retention time (Method E): $t_R$=0.89 min.

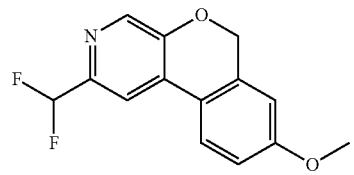 [SMILES: COc1ccc2c(c1)COc1cnc(C(F)F)cc1-2]

Part G: 2-(Difluoromethyl)-8-methoxy-6H-isochromeno[3,4-c]pyridine

A solution of 8-methoxy-6H-isochromeno[3,4-c]pyridine-2-carbaldehyde (200 mg, 0.829 mmol) in DCM (10 mL) was cooled to –70° C. Dimethylaminosulfur trifluoride (334 mg, 2.073 mmol) was added at –70° C. The reaction mixture was allowed to warm to room temperature and stirred for 1 h. The reaction mixture was cooled to 0° C. and quenched with saturated aqueous $NaHCO_3$ (10 mL). The reaction mixture was extracted with DCM (2×50 mL). The combined DCM layers were washed with water (2×15 mL), dried over $Na_2SO_4$, filtered, and concentrated under reduced pressure. Obtained 2-(difluoromethyl)-8-methoxy-6H-isochromeno[3,4-c]pyridine (170 mg, 0.646 mmol, 78% yield) as a brown solid which was carried forward without further purification. LC/MS (ESI) m/e 264.4 [(M+H)+, calcd for $C_{14}H_{12}F_2NO_2$, 264.1]; LC/MS retention time (Method B): $t_R$=0.98 min.

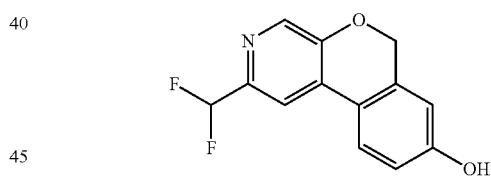

Part H: 2-(difluoromethyl)-6H-isochromeno[3,4-c]pyridin-8-ol

A solution of 2-(difluoromethyl)-8-methoxy-6H-isochromeno[3,4-c]pyridine (150 mg, 0.570 mmol) in DCM was cooled to –70° C. $BBr_3$ (0.269 mL, 2.85 mmol) was added at –70° C. The reaction mixture was allowed to warm to room temperature and stirred for 1 h. The reaction mixture was cooled to 0° C., and then quenched with saturated aqueous $NaHCO_3$ (10 mL). The reaction mixture was extracted into DCM (2×50 mL). The combined DCM layers were washed with water (2×15 mL), dried over Na2SO4, filtered, and concentrated under reduced pressure. Obtained 2-(difluoromethyl)-6H-isochromeno[3,4-c]pyridin-8-ol (150 mg, 0.289 mmol, 51% yield) as a brown gummy solid which was carried forward without further purification. LC/MS (ESI) m/e 250.3 [(M+H)+, calcd for $C_{13}H_{10}F_2NO_2$, 250.1]; LC/MS retention time (Method B): $t_R$=0.80 min.

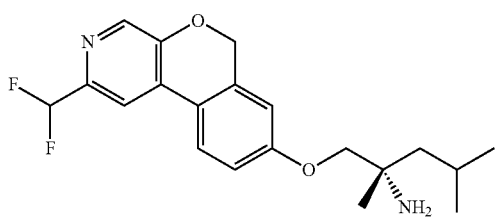 [SMILES: CC(C)C[C@](C)(N)COc1ccc2c(c1)COc1cnc(C(F)F)cc1-2]

Part I: (S)-1-((2-(difluoromethyl)-6H-isochromeno[3,4-c]pyridin-8-yl)oxy)-2,4-dimethylpentan-2-amine Prepared as described in Example 45, Parts H and J, using 2-(difluoromethyl)-6H-isochromeno[3,4-c]pyridin-8-ol (50 mg, 0.094 mmol) and (S)-tert-butyl 4-isobutyl-4-methyl-1,2,3-oxathiazolidine-3-carboxylate 2,2-dioxide (36.0 mg, 0.123 mmol) as the coupling partners. Obtained (S)-1-((2-(difluoromethyl)-6H-isochromeno[3,4-c]pyridin-8-yl)oxy)-2,4-dimethylpentan-2-amine (8.0 mg, 0.021 mmol, 23% yield for two steps) as a pale yellow solid. LC/MS (ESI) m/e 363.0 [(M+H)$^+$, calcd for $C_{20}H_{25}F_2N_2O_2$, 363.2]; LC/MS retention time (Method J): $t_R$=1.48 min; $^1$H NMR (400 MHz, METHANOL-$d_4$) δ 8.25 (s, 1H), 8.01 (s, 1H), 7.93 (d, J=8.5 Hz, 1H), 7.14 (dd, J=8.5, 2.5 Hz, 1H), 6.97 (d, J=2.5 Hz, 1H), 6.89-6.53 (m, 1H), 5.29 (s, 2H), 4.09-4.03 (m, 1H), 4.01-3.95 (m, 1H), 1.91-1.79 (m, 1H), 1.76-1.68 (m, 1H), 1.65-1.57 (m, 1H), 1.39 (s, 3H), 1.05 (d, J=6.5 Hz, 3H), 1.01 (d, J=6.5 Hz, 3H), two exchangeable protons not observed; HPLC purity (Method D): 97% $t_R$=1.48 min.

Example 49

(S)-methyl (8-((2-amino-2,4-dimethylpentyl)oxy)-9-fluoro-6H-isochromeno[3,4-c]pyridin-2-yl)carbamate

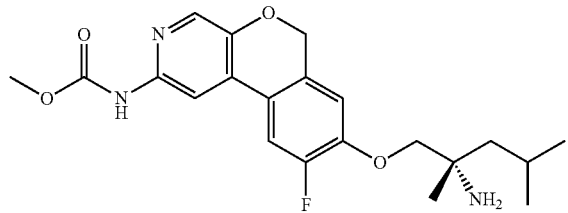 [SMILES: COC(=O)Nc1cc2c(cn1)OCc1cc(OC[C@@](C)(N)CC(C)C)c(F)cc1-2]

Prepared as described in Example 45. Obtained (S)-methyl (8-((2-amino-2,4-dimethylpentyl)oxy)-9-fluoro-6H-isochromeno[3,4-c]pyridin-2-yl)carbamate (75 mg, 0.182 mmol, 71% yield for the final step) as a pale yellow solid. LC/MS (ESI) m/e 404.2 [(M+H)$^+$, calcd for $C_{21}H_{27}FN_3O_4$, 404.2]; LC/MS retention time (Method A3): $t_R$=1.90 min; $^1$H NMR (400 MHz, METHANOL-$d_4$) δ 8.09 (s, 1H), 7.94 (s, 1H), 7.64 (d, J=12.0 Hz, 1H), 7.09 (d, J=8.0 Hz, 1H), 5.14 (s, 2H), 3.99-3.88 (m, 2H), 3.82 (s, 3H), 1.93-1.76 (m, 1H), 1.63-1.49 (m, 2H), 1.27 (s, 3H), 1.01 (app t, J=6.8 Hz, 6H), three exchangeable protons not observed; HPLC purity (Method A2): 99% $t_R$=5.97 min; HPLC purity (Method B3): 99% $t_R$=6.74 min.

Example 50

(S)-2,4-dimethyl-1-((4-methyl-6H-isochromeno[3,4-c]pyridin-8-yl)oxy)pentan-2-amine

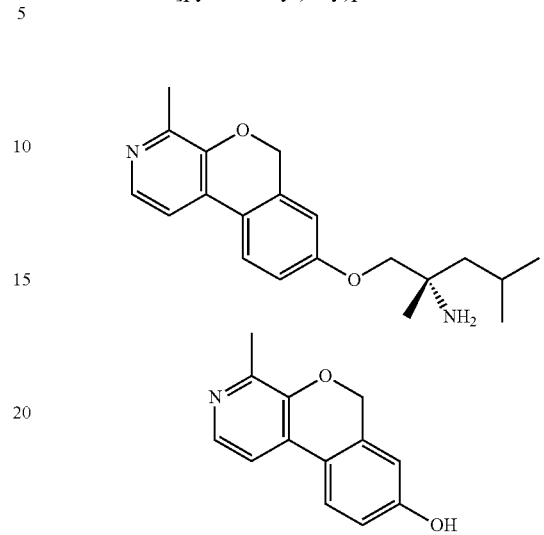

Part A: 4-Methyl-6H-isochromeno[3,4-c]pyridin-8-ol

Prepared as described in Example 29, Parts A-C. Obtained 4-methyl-6H-isochromeno[3,4-c]pyridin-8-ol (128 mg, 0.548 mmol, 83% yield for the final step) as a yellow solid. LC/MS (ESI) m/e 214.2 [(M+H)$^+$, calcd for $C_{13}H_{12}NO_2$, 214.1]; LC/MS retention time (Method E): $t_R$=0.51 min.

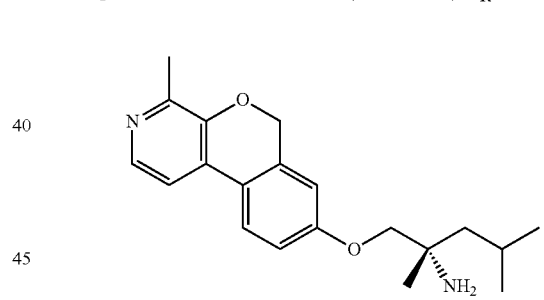

Part B: (S)-2,4-dimethyl-1-((4-methyl-6H-isochromeno[3,4-c]pyridin-8-yl)oxy)pentan-2-amine Prepared as described in Example 45, Parts H and J, using 4-methyl-6H-isochromeno[3,4-c]pyridin-8-ol (0.05 g, 0.234 mmol) and (S)-tert-butyl 4-isobutyl-4-methyl-1,2,3-oxathiazolidine-3-carboxylate 2,2-dioxide (0.083 g, 0.281 mmol) as the coupling partners. Obtained (S)-2,4-dimethyl-1-((4-methyl-6H-isochromeno[3,4-c]pyridin-8-yl)oxy)pentan-2-amine (64 mg, 0.186 mmol, 91% yield for two steps) as a pale yellow solid. LC/MS (ESI) m/e 327.3 [(M+H)$^+$, calcd for $C_{22}H_{27}N_2O_2$, 327.2]; LC/MS retention time (Method E): $t_R$=0.60 min; $^1$H NMR (400 MHz, METHANOL-$d_4$) δ 8.12 (d, J=5.5 Hz, 1H), 7.93 (d, J=9.0 Hz, 1H), 7.79 (d, J=5.5 Hz, 1H), 7.18 (dd, J=8.8, 2.8 Hz, 1H), 7.04 (d, J=2.5 Hz, 1H), 5.32 (s, 2H), 4.22 (d, J=10.0 Hz, 1H), 4.17-4.05 (m, 1H), 2.53 (s, 3H), 1.94-1.81 (m, 2H), 1.77-1.65 (m, 1H), 1.52 (s, 3H), 1.08 (d, J=6.5 Hz, 3H), 1.04 (d, J=6.5 Hz, 3H), two exchangeable protons not observed; HPLC purity (Method C1): 95% t$_R$=1.25 min; HPLC purity (Method D): 96% t$_R$=0.79 min.

Example 51

(S)-2,4-dimethyl-1-((2-methyl-6H-isochromeno[3,4-c]pyridin-8-yl)oxy)pentan-2-amine

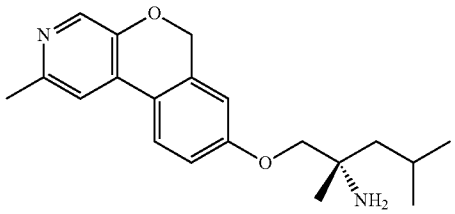

Prepared as described in Example 50. Obtained (S)-2,4-dimethyl-1-((2-methyl-6H-isochromeno[3,4-c]pyridin-8-yl)oxy)pentan-2-amine (4.4 mg, 0.013 mmol, 9% yield for the last two steps) as a pale yellow solid. LC/MS (ESI) m/e 327.2 [(M+H)$^+$, calcd for C$_{20}$H$_{27}$N$_2$O$_2$, 327.2]; LC/MS retention time (Method M): t$_R$=1.24 min; $^1$H NMR (400 MHz, METHANOL-d$_4$) δ 8.07 (s, 1H), 7.89 (d, J=8.5 Hz, 1H), 7.64 (s, 1H), 7.14 (dd, J=8.5, 2.5 Hz, 1H), 6.98 (d, J=2.5 Hz, 1H), 5.19 (s, 2H), 4.20-4.11 (m, 1H), 4.09-4.02 (m, 1H), 2.53 (s, 3H), 1.88 (dt, J=12.0, 6.0 Hz, 1H), 1.84-1.77 (m, 1H), 1.72-1.63 (m, 1H), 1.47 (s, 3H), 1.07 (d, J=6.5 Hz, 3H), 1.03 (d, J=6.5 Hz, 3H), two exchangeable protons not observed; HPLC purity (Method C1): 96% t$_R$=1.24 min.

Example 52

(S)-1-((4-chloro-6H-isochromeno[3,4-c]pyridin-8-yl)oxy)-2,4-dimethylpentan-2-amine

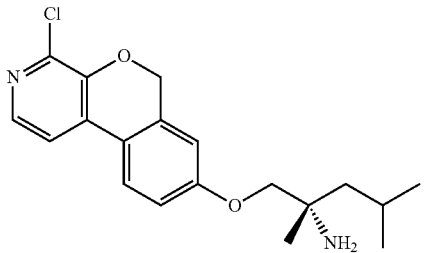 [SMILES: CC(C)C[C@](C)(N)COc1ccc2c(c1)COc1c-2ccnc1Cl]

Prepared as described in Example 50. Obtained (S)-1-((4-chloro-6H-isochromeno[3,4-c]pyridin-8-yl)oxy)-2,4-dimethylpentan-2-amine (23 mg, 0.064 mmol, 37% yield for the last two steps) as a pale yellow solid. LC/MS (ESI) m/e 347.2 [(M+H)$^+$, calcd for C$_{19}$H$_{24}$ClN$_2$O$_2$, 347.2]; LC/MS retention time (Method E): t$_R$=0.76 min; $^1$H NMR (400 MHz, METHANOL-d$_4$) δ 8.03-7.98 (m, 1H), 7.89 (d, J=9.0 Hz, 1H), 7.77-7.68 (m, 1H), 7.15 (dd, J=8.5, 2.5 Hz, 1H), 7.01 (d, J=2.5 Hz, 1H), 5.33 (s, 2H), 4.20-4.12 (m, 1H), 4.11-4.04 (m, 1H), 1.92-1.77 (m, 2H), 1.71-1.63 (m, 1H), 1.47 (s, 3H), 1.07 (d, J=6.5 Hz, 3H), 1.03 (d, J=6.5 Hz, 3H), two exchangeable protons not observed; HPLC purity (Method D): 97% t$_R$=1.24 min.

Example 53

(S)-8-((2-amino-2,4-dimethylpentyl)oxy)-6H-isochromeno[3,4-c]pyridin-2-amine

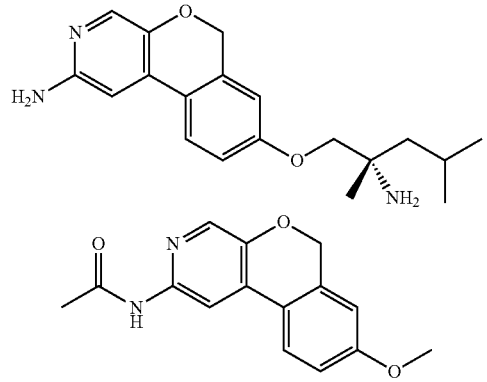

Part A: N-(8-methoxy-6H-isochromeno[3,4-c]pyridin-2-yl)acetamide

A suspension of 2-bromo-8-methoxy-6H-isochromeno[3,4-c]pyridine (2.0 g, 5.55 mmol), acetamide (0.655 g, 11.09 mmol), Cs$_2$CO$_3$ (3.61 g, 11.09 mmol), XANTPHOS (0.321 g, 0.555 mmol) and PdOAc$_2$ (0.125 g, 0.555 mmol) in 1,4-dioxane (40 mL) was degassed with nitrogen for 10 min then heated to 80° C. for 16 h. The reaction mixture was cooled to room temperature and filtered through diatomaceous earth (Celite®). The pad was washed with EtOAc (100 mL). The filtrate was washed with H$_2$O (2×30 mL) and brine (1×30 mL). The organic layer was dried over Na$_2$SO$_4$, filtered and concentrated under reduced pressure. The crude compound was triturated with diethyl ether (50 mL) and the diethyl ether layer was decanted off to afford N-(8-methoxy-6H-isochromeno[3,4-c]pyridin-2-yl)acetamide (1.2 g, 3.20 mmol, 58% yield) as a brown solid. LC/MS (ESI) m/e 271.4 [(M+H)$^+$, calcd for C$_{15}$H$_{15}$N$_2$O$_3$, 271.1]; LC/MS retention time (Method B): t$_R$=0.78 min.

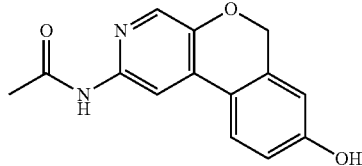 [SMILES: CC(=O)Nc1cc2c(cn1)OCc1cc(O)ccc1-2]

Part B: N-(8-hydroxy-6H-isochromeno[3,4-c]pyridin-2-yl)acetamide

A solution of N-(8-methoxy-6H-isochromeno[3,4-c]pyridin-2-yl)acetamide (1.1 g, 4.07 mmol) in DCM (20 mL) was cooled to −70° C. BBr$_3$ (1.924 mL, 20.35 mmol) was added at −70° C. The reaction mixture was allowed to warm to room temperature and stirred for 1 h. The reaction mixture was cooled to 0° C. and quenched with saturated aqueous NaHCO$_3$ (30 mL). The solid that formed was collected by vacuum filtration. The solid was washed with petroleum ether (50 mL) and air dried to obtain N-(8-hydroxy-6H- isochromeno[3,4-c]pyridin-2-yl)acetamide (1.0 g, 2.97 mmol, 73% yield) as a yellow solid. LC/MS (ESI) m/e 257.4 [(M+H)+, calcd for $C_{14}H_{13}N_2O_3$, 257.1]; LC/MS retention time (Method B): $t_R$=0.61 min.

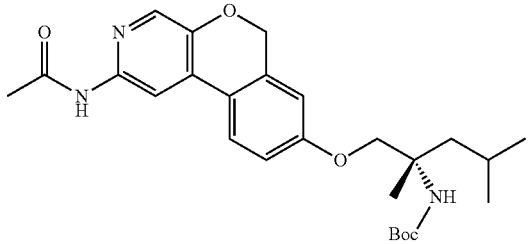 [SMILES: CC(=O)Nc1cc2c(cn1)OCc1cc(OC[C@](C)(CC(C)C)NC(=O)OC(C)(C)C)ccc1-2]

Part C: (S)-tert-butyl (1-((2-acetamido-6H-isochromeno[3,4-c]pyridin-8-yl)oxy)-2,4-dimethylpentan-2-yl)carbamate Coupled as described in Example 45, Part H using N-(8-hydroxy-6H-isochromeno[3,4-c]pyridin-2-yl)acetamide (1.10 g, 4.29 mmol) and (S)-tert-butyl 4-isobutyl-4-methyl-1,2,3-oxathiazolidine-3-carboxylate 2,2-dioxide (2.015 g, 6.87 mmol) as the coupling partners. Obtained (S)-tert-butyl (1-((2-acetamido-6H-isochromeno[3,4-c]pyridin-8-yl)oxy)-2,4-dimethylpentan-2-yl)carbamate (1.3 g, 1.66 mmol, 39% yield) as a yellow solid. LC/MS (ESI) m/e 470.4 [(M+H)+, calcd for $C_{26}H_{36}N_3O_5$, 470.3]; LC/MS retention time (Method E): $t_R$=0.95 min.

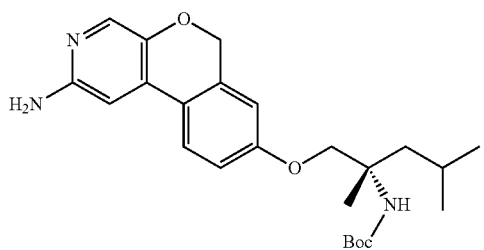 [SMILES: CC(C)C[C@@](C)(COc1ccc2c(c1)COc1cnc(N)cc1-2)NC(=O)OC(C)(C)C]

Part D: (S)-tert-butyl (1-((2-amino-6H-isochromeno[3,4-c]pyridin-8-yl)oxy)-2,4-dimethylpentan-2-yl)carbamate To a stirred solution of (S)-tert-butyl (1-((2-acetamido-6H-isochromeno[3,4-c]pyridin-8-yl)oxy)-2,4-dimethylpentan-2-yl)carbamate (1.3 g, 2.77 mmol) in EtOH (30 mL) and water (30 mL) was added KOH (6.21 g, 111 mmol) and the mixture heated to 80° C. for 5 h. The reaction mixture was cooled to room temperature and concentrated under reduced pressure. The residue was taken up in ethyl acetate (100 mL) and washed with water (1×20 mL) and brine (1×25 mL). The organic layer was dried over Na2SO4, filtered, and concentrated under reduced pressure. Obtained (S)-tert-butyl (1-((2-amino-6H-isochromeno[3,4-c]pyridin-8-yl)oxy)-2,4-dimethylpentan-2-yl)carbamate (1 g, 2.04 mmol, 74% yield) as a yellow solid. LC/MS (ESI) m/e 428.2 [(M+H)+, calcd for $C_{24}H_{34}N_3O_4$, 428.3]; LC/MS retention time (Method A3): $t_R$=1.89 min.

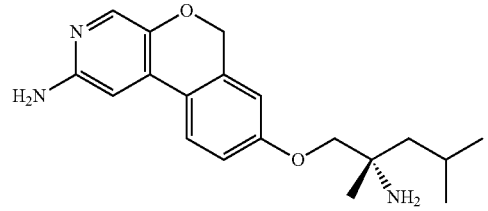 [SMILES: CC(C)C[C@](C)(N)COc1ccc2c(c1)COc1cnc(N)cc1-2]

Part E: (S)-8-((2-amino-2,4-dimethylpentyl)oxy)-6H-isochromeno[3,4-c]pyridin-2-amine To a stirred solution of (S)-tert-butyl (1-((2-amino-6H-isochromeno[3,4-c]pyridin-8-yl)oxy)-2,4-dimethylpentan-2-yl)carbamate (80 mg, 0.131 mmol) in DCM (2 mL) cooled to 0° C., was added HCl, 4M in 1,4-dioxane (5 mL, 165 mmol). The solution was warmed to room temperature and stirred for 30 min. The reaction mixture was diluted with DCM (50 mL) and washed with saturated aqueous sodium bicarbonate (1×20 mL) then water (1×20 mL). The organic layer was separated, dried over sodium sulphate, filtered, and concentrated under reduced pressure to afford a pale yellow solid. The residue was purified via prep LC/MS (acetonitrile:water with 10 mM NH4OAc) to afford (S)-8-((2-amino-2,4-dimethylpentyl)oxy)-6H-isochromeno[3,4-c]pyridin-2-amine (8.6 mg, 0.026 mmol, 20% yield) as a pale yellow solid. LC/MS (ESI) m/e 328.0 [(M+H)+, calcd for $C_{19}H_{26}N_3O_2$, 328.2]; LC/MS retention time (Method M): $t_R$=0.99 min; 1H NMR (400 MHz, DMSO-$d_6$) δ 7.65 (t, J=4.3 Hz, 2H), 7.02 (dd, J=8.5, 2.5 Hz, 1H), 6.92 (d, J=2.5 Hz, 1H), 6.78 (s, 1H), 5.49 (s, 2H), 4.99 (s, 2H), 1.80 (dquin, J=12.9, 6.2 Hz, 1H), 1.47-1.30 (m, 2H), 1.12 (s, 3H), 0.93 (app t, J=7.0 Hz, 6H), four exchangeable protons not observed; HPLC purity (Method C1): 99% $t_R$=0.99 min.

Example 54

(S)-isopropyl (8-((2-amino-2,4-dimethylpentyl)oxy)-6H-isochromeno[3,4-c]pyridin-2-yl)carbamate

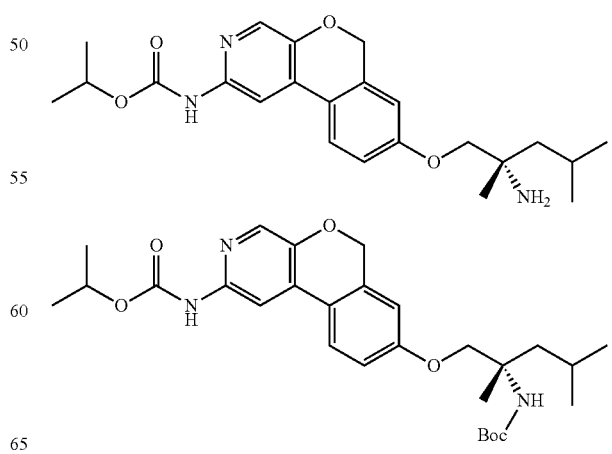

Part A: (S)-isopropyl (8-((2-(Boc-amino)-2,4-dimethylpentyl)oxy)-6H-isochromeno[3,4-c]pyridin-2-yl)carbamate To a stirred solution of (S)-tert-butyl (1-((2-amino-6H-isochromeno[3,4-c]pyridin-8-yl)oxy)-2,4-dimethylpentan-2-yl)carbamate (100 mg, 0.234 mmol) (Prepared in Example 43, Part D) in pyridine (4 mL) at 0° C. was added DMAP (2.86 mg, 0.023 mmol). The mixture was stirred for 5 min. Isopropyl chloroformate, 1M in toluene (0.234 mL, 0.234 mmol) was added at 0° C. The reaction mixture was allowed to warm to room temperature and stirred for 16 h. The reaction mixture was concentrated under reduced pressure. The residue was taken up in DCM (50 mL). The DCM layer was washed with water (1×20 mL) and brine (1×25 mL). The organic layer was dried over Na2SO4, filtered, and concentrated under reduced pressure. Obtained (S)-isopropyl (8-((2-(Boc-amino)-2,4-dimethylpentyl)oxy)-6H-isochromeno[3,4-c]pyridin-2-yl)carbamate (100 mg, 0.152 mmol, 65% yield) as a yellow gummy solid. LC/MS (ESI) m/e 514.2 [(M+H)$^+$, calcd for $C_{28}H_{40}N_3O_6$, 514.3]; LC/MS retention time (Method $C_3$): $t_R$=2.53 min.

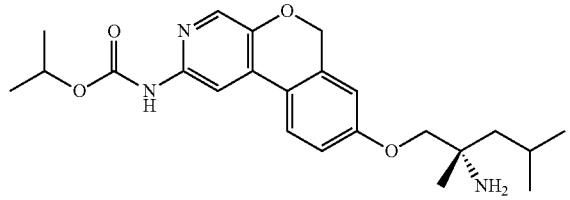 [SMILES: CC(C)C[C@](C)(N)COc1ccc2c(c1)COc1cnc(NC(=O)OC(C)C)cc1-2]

Part B: (S)-8-((2-amino-2,4-dimethylpentyl)oxy)-6H-isochromeno[3,4-c]pyridin-2-amine To a stirred solution of (S)-isopropyl (8-((2-(Boc-amino)-2,4-dimethylpentyl)oxy)-6H-isochromeno[3,4-c]pyridin-2-yl)carbamate (100 mg, 0.195 mmol) in DCM (2 mL) cooled to 0° C., was added 4 M HCl in 1,4-dioxane (5 mL, 165 mmol). The solution was warmed to room temperature and stirred for 30 min. The reaction mixture was diluted with DCM (50 mL) and washed with saturated aqueous sodium bicarbonate (1×20 mL) then water (1×20 mL). The organic layer was separated, dried over sodium sulphate, filtered, and concentrated under reduced pressure to afford a pale yellow solid. The residue was purified via prep LC/MS (acetonitrile:water with 10 mM NH$_4$OAc) to afford (S)-8-((2-amino-2,4-dimethylpentyl)oxy)-6H-isochromeno[3,4-c]pyridin-2-amine (27.6 mg, 0.066 mmol, 34% yield) as a pale yellow solid. LC/MS (ESI) m/e 414.2 [(M+H)$^+$, calcd for $C_{23}H_{32}N_3O_4$, 414.2]; LC/MS retention time (Method M): $t_R$=1.56 min; $^1$H NMR (400 MHz, METHANOL-d$_4$) δ 8.19 (s, 1H), 7.93 (s, 1H), 7.85 (d, J=8.5 Hz, 1H), 7.14 (dd, J=8.5, 2.5 Hz, 1H), 6.97 (d, J=2.5 Hz, 1H), 5.16 (s, 2H), 5.04 (dt, J=12.5, 6.3 Hz, 1H), 4.22-4.09 (m, 1H), 4.07-3.99 (m, 1H), 1.87 (dq, J=12.5, 6.2 Hz, 1H), 1.82-1.73 (m, 1H), 1.70-1.60 (m, 1H), 1.44 (s, 3H), 1.36 (d, J=6.0 Hz, 6H), 1.07 (d, J=6.5 Hz, 3H), 1.03 (d, J=6.5 Hz, 3H), three exchangeable protons not observed; HPLC purity (Method C1): 99% $t_R$=1.56 min.

Example 55

(S)—N-(8-((2-amino-2,4-dimethylpentyl)oxy)-6H-isochromeno[3,4-c]pyridin-2-yl)methanesulfonamide

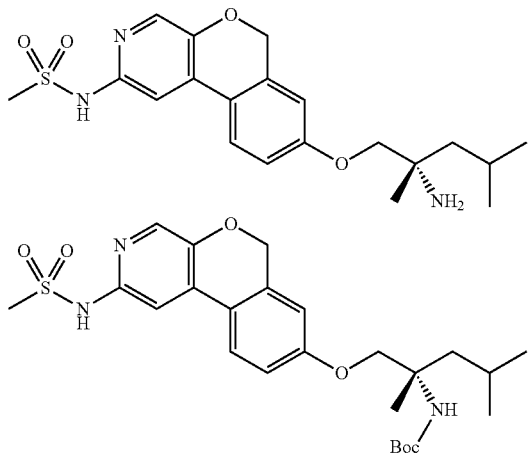

Part A: (S)-tert-butyl (2,4-dimethyl-1-((2-(methylsulfonamido)-6H-isochromeno[3,4-c]pyridin-8-yl)oxy)pentan-2-yl)carbamate To a stirred solution of (S)-tert-butyl (1-((2-amino-6H-isochromeno[3,4-c]pyridin-8-yl)oxy)-2,4-dimethylpentan-2-yl)carbamate (100 mg, 0.234 mmol) (Prepared in Example 43, Part D) in pyridine (4 mL) at 0° C. was added DMAP (2.86 mg, 0.023 mmol). The mixture was stirred for 5 min then methanesulfonyl chloride (0.018 mL, 0.234 mmol) was added at 0° C. The reaction mixture was allowed to warm to room temperature and stirred for 16 h. The reaction mixture was concentrated under reduced pressure. The residue was taken up in DCM (50 mL). The DCM layer was washed with water (1×20 mL) and brine (1×25 mL). The organic layer was dried over Na2SO4, filtered and concentrated under reduced pressure. Obtained (S)-tert-butyl (2,4-dimethyl-1-((2-(methylsulfonamido)-6H-isochromeno[3,4-c]pyridin-8-yl)oxy)pentan-2-yl)carbamate (100 mg, 0.138 mmol, 52% yield) as a brown gummy solid. LC/MS (ESI) m/e 506.2 [(M+H)$^+$, calcd for $C_{25}H_{36}N_3O_6S$, 506.2]; LC/MS retention time (Method A3): $t_R$=2.28 min.

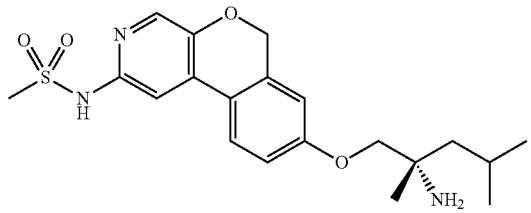 [SMILES: CC(C)C[C@](C)(N)COc1ccc2c(c1)COc1cnc(NS(C)(=O)=O)cc1-2]

Part B: (S)—N-(8-((2-amino-2,4-dimethylpentyl)oxy)-6H-isochromeno[3,4-c]pyridin-2-yl)methanesulfonamide To a stirred solution of (S)-tert-butyl (2,4-dimethyl-1-((2-(methylsulfonamido)-6H-isochromeno[3,4-c]pyridin-8-yl)

oxy)pentan-2-yl)carbamate (80 mg, 0.158 mmol) in DCM (2 mL) cooled to 0° C., was added 4 M HCl in 1,4-dioxane (5 ml, 165 mmol). The solution was warmed to room temperature and stirred for 30 min. The reaction mixture was diluted with DCM (50 mL) and washed with saturated aqueous sodium bicarbonate (1×20 mL) then water (1×20 mL). The organic layer was separated, dried over sodium sulphate, filtered, and concentrated under reduced pressure to afford a pale yellow solid. The residue was purified via prep LC/MS (acetonitrile:water with 10 mM NH$_4$OAc) to afford (S)—N-(8-((2-amino-2,4-dimethylpentyl)oxy)-6H-isochromeno[3,4-c]pyridin-2-yl)methanesulfonamide (29.9 mg, 0.072 mmol, 46% yield) as a pale yellow solid. LC/MS (ESI) m/e 406.0 [(M+H)$^+$, calcd for $C_{20}H_{28}N_3O_4S$, 406.2]; LC/MS retention time (Method M): $t_R$=1.07 min; $^1$H NMR (400 MHz, METHANOL-d$_4$) δ 7.98 (s, 1H), 7.82 (d, J=8.5 Hz, 1H), 7.40 (s, 1H), 7.14 (dd, J=8.8, 2.8 Hz, 1H), 6.98 (d, J=2.5 Hz, 1H), 5.17 (s, 2H), 4.17-4.09 (m, 1H), 4.08-3.97 (m, 1H), 3.33 (s, 3H), 1.87 (dt, J=12.2, 6.2 Hz, 1H), 1.82-1.74 (m, 1H), 1.66 (dd, J=14.3, 5.3 Hz, 1H), 1.45 (s, 3H), 1.07 (d, J=6.5 Hz, 3H), 1.03 (d, J=6.5 Hz, 3H), three exchangeable protons not observed; HPLC purity (Method C1): 98% $t_R$=1.07 min.

Example 56

(S)—N-(8-((2-amino-2,4-dimethylpentyl)oxy)-6H-isochromeno[3,4-c]pyridin-2-yl)cyclopropanesulfonamide

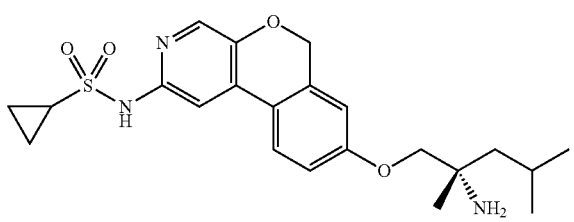 [SMILES: CC(C)C[C@](C)(N)COc1ccc2c(c1)COc1cnc(NS(=O)(=O)C3CC3)cc1-2]

Prepared as in Example 55 using cyclopropanesulfonyl chloride (99 mg, 0.702 mmol) as the coupling agent. Obtained (S)—N-(8-((2-amino-2,4-dimethylpentyl)oxy)-6H-isochromeno[3,4-c]pyridin-2-yl)cyclopropanesulfonamide (70 mg, 0.156 mmol, 33% yield) as an orange-red solid. LC/MS (ESI) m/e 432.2 [(M+H)$^+$, calcd for $C_{22}H_{30}N_3O_4S$, 432.2]; LC/MS retention time (Method A1): $t_R$=1.99 min; $^1$H NMR (400 MHz, METHANOL-d$_4$) δ 7.96 (s, 1H), 7.81 (d, J=8.5 Hz, 1H), 7.50 (s, 1H), 7.13 (dd, J=8.8, 2.8 Hz, 1H), 6.97 (d, J=2.5 Hz, 1H), 5.17 (s, 2H), 4.18-4.06 (m, 1H), 4.05-3.94 (m, 1H), 2.95-2.81 (m, 1H), 1.91-1.80 (m, 1H), 1.80-1.71 (m, 1H), 1.68-1.58 (m, 1H), 1.42 (s, 3H), 1.20-1.11 (m, 2H), 1.06 (d, J=6.5 Hz, 3H), 1.02 (d, J=6.5 Hz, 3H), 1.04-0.99 (m, 2H), three exchangeable protons not observed; HPLC purity (Method A2): 98% $t_R$=6.09 min, HPLC purity (Method B3): 97% $t_R$=7.34 min.

Example 57

(S)-1-((2-fluoro-6H-isochromeno[3,4-c]pyridin-8-yl)oxy)-2,4-dimethylpentan-2-amine

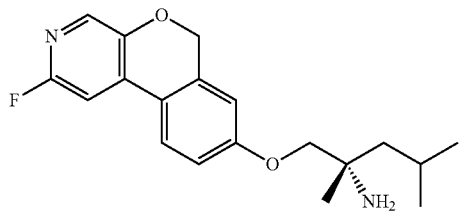 [SMILES: CC(C)C[C@](C)(N)COc1ccc2c(c1)COc1cnc(F)cc1-2]

Prepared as in Example 50. Obtained (S)-1-((2-fluoro-6H-isochromeno[3,4-c]pyridin-8-yl)oxy)-2,4-dimethylpentan-2-amine (35 mg, 0.102 mmol, 44% yield) as an orange gummy solid. LC/MS (ESI) m/e 331.2 [(M+H)$^+$, calcd for $C_{19}H_{24}FN_2O_2$, 331.2]; LC/MS retention time (Method A1): $t_R$=1.92 min; $^1$H NMR (400 MHz, METHANOL-d$_4$) δ 7.91 (d, J=8.5 Hz, 1H), 7.83 (d, J=1.5 Hz, 1H), 7.42 (d, J=2.0 Hz, 1H), 7.14 (dd, J=8.5, 2.5 Hz, 1H), 7.00 (d, J=2.5 Hz, 1H), 5.21 (s, 2H), 4.18-4.10 (m, 1H), 4.09-3.99 (m, 1H), 1.92-1.82 (m, 1H), 1.82-1.73 (m, 1H), 1.69-1.61 (m, 1H), 1.45 (s, 3H), 1.07 (d, J=6.5 Hz, 3H), 1.03 (d, J=6.5 Hz, 3H), two exchangeable protons not observed; HPLC purity (Method A2): 96% $t_R$=6.97 min, HPLC purity (Method B3): 97% $t_R$=8.01 min.

Example 58

(S)-methyl (8-((2-amino-2,4-dimethylpentyl)oxy)-1-chloro-9-fluoro-6H-isochromeno[3,4-c]pyridin-2-yl)carbamate Prepared as described in Examples 45 and 47. Obtained (S)-methyl (8-((2-amino-2,4-dimethylpentyl)oxy)-1-chloro-9-fluoro-6H-isochromeno[3,4-c]pyridin-2-yl)carbamate, HCl (12 mg, 0.025 mmol, 67% yield) as an off-white solid. LC/MS (ESI) m/e 438.0 [(M+H)$^+$, calcd for $C_{21}H_{26}ClFN_3O_4$, 438.2]; LC/MS retention time (Method B): $t_R$=1.27 min; $^1$H NMR (400 MHz, METHANOL-d$_4$) δ 8.13 (s, 1H), 7.70 (d, J=12.0 Hz, 1H), 7.20 (d, J=8.0 Hz, 1H), 5.23 (s, 2H), 4.32-4.23 (m, 1H), 4.21-4.14 (m, 1H), 3.81 (s, 3H), 1.95-1.81 (m, 2H), 1.77-1.65 (m, 1H), 1.52 (s, 3H), 1.08 (d, J=6.5 Hz, 3H), 1.05 (d, J=6.5 Hz, 3H), three exchangeable protons not observed; HPLC purity (Method A2): 95% $t_R$=7.35 min, HPLC purity (Method B3): 98% $t_R$=8.46 min.

Example 59

(S)-2,4-dimethyl-1-((2-(methylsulfonyl)-6H-isochromeno[3,4-c]pyridin-8-yl)oxy)pentan-2-amine

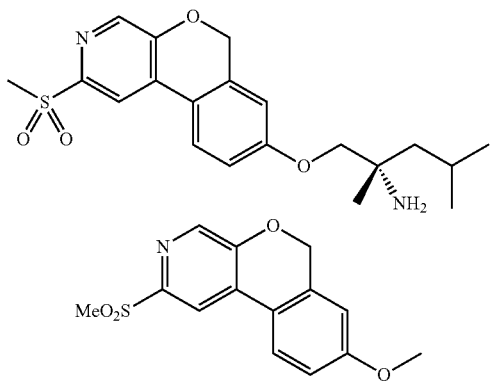

Part A: 8-Methoxy-2-(methylsulfonyl)-6H-isochromeno[3,4-c]pyridine

A suspension of 2-bromo-8-methoxy-6H-isochromeno[3,4-c]pyridine (380 mg, 1.30 mmol), sodium methanesulfinate (1328 mg, 13.0 mmol), copper(I) iodide (248 mg, 1.30 mmol), NaOH (83 mg, 2.081 mmol), and L-proline (150 mg, 1.30 mmol) in DMSO (4 mL) was degassed with nitrogen and heated to 120° C. for 16 h. The reaction mixture was filtered through diatomaceous earth (Celite®) and the bed was washed with EtOAc (50 mL). The filtrate was washed with water (3×20 mL). The organic layer was dried over Na2SO4, filtered, and concentrated under reduced pressure to afford 8-methoxy-2-(methylsulfonyl)-6H-isochromeno[3,4-c]pyridine (250 mg, 0.601 mmol, 46% yield) as a brown gummy solid which was carried forward without further purification. LC/MS (ESI) m/e 292.2 [(M+H)$^+$, calcd for $C_{14}H_{14}NO_4S$, 292.1]; LC/MS retention time (Method A3): $t_R$=1.93 min.

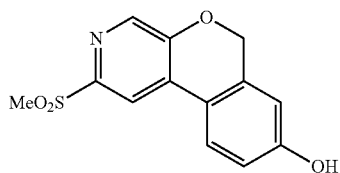 [SMILES: CS(=O)(=O)c1cc2c(cn1)OCc1cc(O)ccc1-2]

Part B: 2-(Methylsulfonyl)-6H-isochromeno[3,4-c]pyridin-8-ol

To a solution of 8-methoxy-2-(methylsulfonyl)-6H-isochromeno[3,4-c]pyridine (150 mg, 0.360 mmol) in DCM cooled to −30° C. was added BBr$_3$ (0.27 mL, 2.85 mmol). The reaction mixture was allowed to warm to room temperature and stirred for 30 min. The reaction mixture was cooled to 0° C., and then quenched with saturated aqueous NaHCO$_3$ (10 mL). The reaction mixture was extracted into DCM (2×50 mL). The combined DCM layers were washed with water (1×10 mL), brine (1×10 mL), dried over Na$_2$SO$_4$, filtered, and concentrated under reduced pressure. Obtained 2-(methylsulfonyl)-6H-isochromeno[3,4-c]pyridin-8-ol (120 mg, 0.325 mmol, 90% yield) as a brown gummy solid which was carried forward without further purification. LC/MS (ESI) m/e 278.0 [(M+H)$^+$, calcd for $C_{13}H_{12}NO_4S$, 278.1]; LC/MS retention time (Method B): $t_R$=0.63 min.

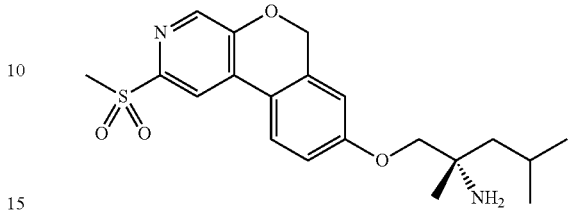

Part C: (S)-2,4-dimethyl-1-((2-(methylsulfonyl)-6H-isochromeno[3,4-c]pyridin-8-yl)oxy)pentan-2-amine Prepared as described in Example 45, Parts H and J, using 2-(methylsulfonyl)-6H-isochromeno[3,4-c]pyridin-8-ol (100 mg, 0.270 mmol) and (S)-tert-butyl 4-isobutyl-4-methyl-1,2,3-oxathiazolidine-3-carboxylate 2,2-dioxide (127 mg, 0.433 mmol) as the coupling partners. Obtained (S)-2,4-dimethyl-1-((2-(methylsulfonyl)-6H-isochromeno[3,4-c]pyridin-8-yl)oxy)pentan-2-amine (10 mg, 0.024 mmol, 16% yield for two steps) as an off-white solid. LC/MS (ESI) m/e 391.2 [(M+H)$^+$, calcd for $C_{20}H_{27}N_2O_4S$, 391.2]; LC/MS retention time (Method A3): $t_R$=1.64 min; $^1$H NMR (400 MHz, METHANOL-d$_4$) δ 8.40 (s, 1H), 8.35 (s, 1H), 7.97 (d, J=8.5 Hz, 1H), 7.19 (d, J=11.5 Hz, 1H), 7.01 (s, 1H), 5.37 (s, 2H), 4.15 (d, J=9.5 Hz, 1H), 4.10-4.00 (m, 1H), 3.25 (s, 3H), 1.91-1.61 (m, 3H), 1.46 (s, 3H), 1.07 (d, J=7.0 Hz, 3H), 1.03 (d, J=6.5 Hz, 3H), two exchangeable protons not observed; HPLC purity (Method A2): 96% $t_R$=6.06 min, HPLC purity (Method B3): 96% $t_R$=7.31 min.

Example 60

(S)-8-((2-amino-2,4-dimethylpentyl)oxy)-6H-isochromeno[3,4-c]pyridin-4-amine

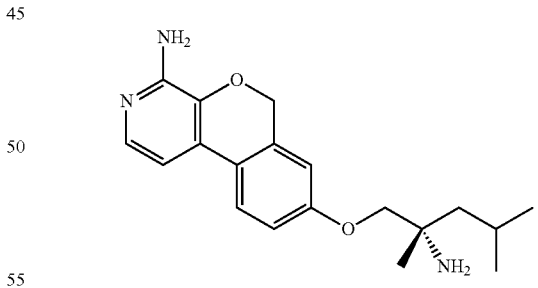

Prepared as described in Example 53. Obtained (S)-8-((2-amino-2,4-dimethylpentyl)oxy)-6H-isochromeno[3,4-c]pyridin-4-amine (11 mg, 0.031 mmol, 42% yield for the final two steps) as a pale yellow solid. LC/MS (ESI) m/e 328.0 [(M+H)$^+$, calcd for $C_{19}H_{26}N_3O_2$, 328.2]; LC/MS retention time (Method J): $t_R$=0.78 min; $^1$H NMR (400 MHz, METHANOL-d$_4$) δ 7.73 (d, J=8.5 Hz, 1H), 7.60 (d, J=5.5 Hz, 1H), 7.08 (dd, J=8.5, 2.5 Hz, 1H), 7.02 (d, J=5.5 Hz, 1H), 6.94 (d, J=2.5 Hz, 1H), 5.21 (s, 2H), 4.10-4.02 (m, 1H), 4.02-3.94 (m, 1H), 1.91-1.80 (m, 1H), 1.76-1.68 (m, 1H), 1.66-1.56 (m, 1H), 1.40 (s, 3H), 1.05 (d, J=6.5 Hz, 3H), 1.02

(d, J=6.5 Hz, 3H), four exchangeable protons not observed; HPLC purity (Method D): 93% $t_R$=0.78 min.

Example 61

(S)-8-((2-amino-2,4-dimethylpentyl)oxy)-7-chloro-6H-isochromeno[3,4-c]pyridin-2-amine

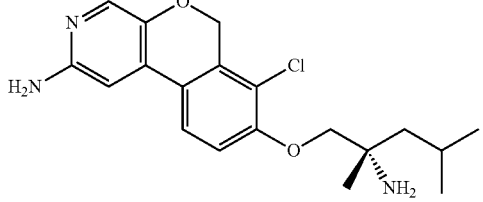

Prepared as described in Example 53. Obtained (S)-8-((2-amino-2,4-dimethylpentyl)oxy)-7-chloro-6H-isochromeno[3,4-c]pyridin-2-amine (1.01 mg, 2.76 mol, 16% yield for the final two steps) as a pale yellow solid. LC/MS (ESI) m/e 362.0 [(M+H)+, calcd for $C_{19}H_{25}ClN_3O_2$, 362.2]; LC/MS retention time (Method J): $t_R$=0.87 min; 1H NMR (400 MHz, METHANOL-$d_4$) δ 7.81 (d, J=8.5 Hz, 1H), 7.70 (s, 1H), 7.24 (d, J=9.0 Hz, 1H), 6.97 (s, 1H), 5.23 (s, 2H), 4.15 (q, J=10.0 Hz, 2H), 1.93-1.81 (m, 2H), 1.74-1.62 (m, 1H), 1.48 (s, 3H), 1.07 (d, J=6.5 Hz, 3H), 1.03 (d, J=6.0 Hz, 3H), four exchangeable protons not observed; HPLC purity (Method D): 99% $t_R$=0.87 min.

Example 62

(S)-methyl (8-((2-amino-2,4-dimethylpentyl)oxy)-7-chloro-6H-isochromeno[3,4-c]pyridin-2-yl)carbamate

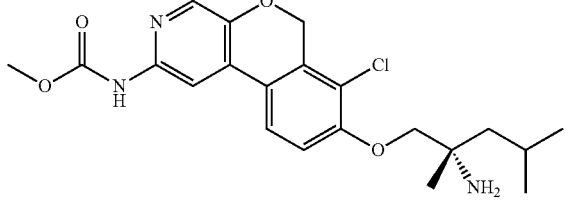

Prepared as described in Example 45. Obtained (S)-methyl (8-((2-amino-2,4-dimethylpentyl)oxy)-7-chloro-6H-isochromeno[3,4-c]pyridin-2-yl)carbamate, HCl (7 mg, 0.014 mmol, 92% yield for the final step) as an off-white solid. LC/MS (ESI) m/e 420.2 [(M+H)+, calcd for $C_{21}H_{27}ClN_3O_4$, 420.2]; LC/MS retention time (Method A3): $t_R$=1.94 min; 1H NMR (400 MHz, METHANOL-$d_4$) δ 8.08-8.01 (m, 2H), 7.94 (d, J=9.0 Hz, 1H), 7.35 (d, J=8.5 Hz, 1H), 5.40 (s, 2H), 4.32-4.23 (m, 2H), 3.86 (s, 3H), 2.01-1.84 (m, 2H), 1.74 (dd, J=14.1, 5.0 Hz, 1H), 1.56 (s, 3H), 1.09 (d, J=6.5 Hz, 3H), 1.04 (d, J=6.5 Hz, 3H), three exchangeable protons not observed; HPLC purity (Method A2): 93% $t_R$=6.27 min; HPLC purity (Method B3): 94% $t_R$=7.34 min.

Example 63

(S)-methyl (8-((2-amino-2,4-dimethylpentyl)oxy)-1,4,7-trichloro-6H-isochromeno[3,4-c]pyridin-2-yl) carbamate

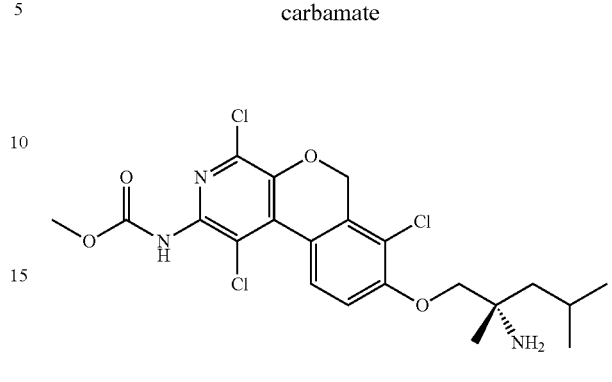

Prepared as described in Examples 46 and 53. Obtained (S)-methyl (8-((2-amino-2,4-dimethylpentyl)oxy)-1,4,7-trichloro-6H-isochromeno[3,4-c]pyridin-2-yl)carbamate (3.0 mg, 5.83 μmol, 22% yield for the final two steps) as an off-white solid. LC/MS (ESI) m/e 488.2 [(M+H)+, calcd for $C_{21}H_{25}Cl_3N_3O_4$, 488.1]; LC/MS retention time (Method M): $t_R$=1.72 min; 1H NMR (400 MHz, METHANOL-$d_4$) δ 8.52 (d, J=8.5 Hz, 1H), 7.28 (d, J=9.0 Hz, 1H), 5.37 (s, 2H), 4.23-4.04 (m, 2H), 3.80 (s, 3H), 1.86 (dq, J=12.4, 6.3 Hz, 1H), 1.82-1.74 (m, 1H), 1.69-1.59 (m, 1H), 1.42 (s, 3H), 1.05 (d, J=6.5 Hz, 3H), 1.02 (d, J=6.5 Hz, 3H), three exchangeable protons not observed; HPLC purity (Method C1): 95% $t_R$=1.72 min.

Example 64

(S)-methyl (8-((2-amino-2,4-dimethylpentyl)oxy)-6H-isochromeno[3,4-c]pyridin-4-yl)carbamate

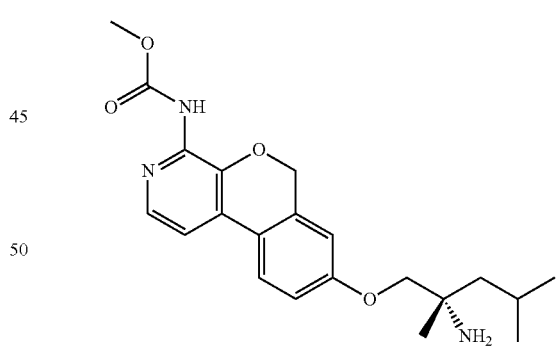

Prepared as described in Example 45. Obtained (S)-methyl (8-((2-amino-2,4-dimethylpentyl)oxy)-6H-isochromeno[3,4-c]pyridin-4-yl)carbamate (10.0 mg, 0.026 mmol, 5% yield for the final two steps) as a pale yellow solid. LC/MS (ESI) m/e 386.2 [(M+H)+, calcd for $C_{21}H_{28}N_3O_4$, 386.2]; LC/MS retention time (Method B): $t_R$=0.73 min; 1H NMR (400 MHz, METHANOL-$d_4$) δ 7.99 (d, J=5.5 Hz, 1H), 7.86 (d, J=8.5 Hz, 1H), 7.54 (d, J=5.0 Hz, 1H), 7.15 (dd, J=8.5, 2.5 Hz, 1H), 7.00 (d, J=2.5 Hz, 1H), 5.25 (s, 2H), 4.20 (d, J=10.0 Hz, 1H), 4.10 (d, J=10.5 Hz, 1H), 3.80 (s, 3H), 1.95-1.79 (m, 2H), 1.78-1.62 (m, 1H), 1.51 (s, 3H), 1.08 (d, J=6.5 Hz, 3H), 1.04 (d, J=6.5 Hz, 3H), three exchangeable protons not observed; HPLC purity (Method C1): 99% $t_R$=1.00 min, HPLC purity (Method D): 90% $t_R$=0.76 min.

Methods

AAK1 Kinase Assay

The assays were performed in U-bottom 384-well plates. The final assay volume was 30 μl prepared from 15 μl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM $MgCl_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 μl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 μM; (5-FAM)-Aha-KEEQSQITSQVTGQIGWR-NH2, 1.5 μM; GST-Xa-hAAK1, 3.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

HEK281 Cell-Based Assay

HEK293F cells were cultured in media containing DMEM (Gibco, cat. #11965), 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP_055726.2), 45 μg Flag/AP2MI/pcDNA (full length human), and 1.5 ml OPTI-MEM. The Lipofectamine 2000 is made up of a mixture (per 10 cm dish) containing 144 μl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% $CO_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 μl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 μl of cell suspension transferred into each well of 96-well TC plate. Finally, 100 μl of 2× compound diluted in DMEM+0.5% FBS was then added into wells containing cell suspension for a 1× final concentration. Plates were then incubated at 37° C. and 5% $CO_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat.# NP0008)+2×Halt phosphatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 μl per sample was loaded into each lane of a 4-20% Tris-Glycine Criterion 26-well gel (Biorad, cat.#345-0034) for the phospho-mu2 blot and 10 μl per lane in a 4-12% Bis-Tris (+MES buffer) NuPAGE 26-well gel (Invitrogen, cat.# WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat.# F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; BioRad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.#RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 μl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay.* J Appl Physiol., 2001; 90:2386-402.

AAK1 functional potency for select compounds are listed as $IC_{50}$s in Table 3.

TABLE 3

| Example | AAK1 $IC_{50}$ (nM) |
|---|---|
| 1 | 9.5 |
| 2 | 37 |
| 3 | 3.2 |
| 4 | 14 |

TABLE 3-continued

| Example | AAK1 $IC_{50}$ (nM) |
|---|---|
| 5 | 87 |
| 6 | 3.7 |
| 7 | 31 |
| 8 | 2.6 |
| 9 | 49 |
| 10 | 35 |
| 11 | 92 |
| 12 | 30 |
| 13 | 117 |
| 14 | 8.1 |
| 15 | 59 |
| 16 | 24 |
| 17 | |
| 18 | 3.0 |
| 19 | 1335 |
| 20 | 4.1 |
| 21 | 1129 |
| 22 | 3.2 |
| 23 | 46 |
| 24 | 69 |
| 25 | 227 |
| 26 | 5.4 |
| 27 | 1.7 |
| 28 | 611 |
| 29 | 13 |
| 30 | 17 |
| 31 | 235 |
| 32 | 3.2 |
| 33 | 2.1 |
| 34 | 3.8 |
| 35 | 11 |
| 36 | 2.6 |
| 37 | 2.4 |
| 38 | 7.7 |
| 39 | 8.1 |
| 40 | 1.3 |
| 41 | 0.62 |
| 42 | 88 |
| 43 | 56 |
| 44 | 181 |
| 45 | 0.91 |
| 46 | 45 |
| 47 | 26 |
| 48 | 13 |
| 49 | 5.4 |
| 50 | 11 |
| 51 | 121 |
| 52 | 2.2 |
| 53 | 4.4 |
| 54 | 2.1 |
| 55 | 123 |
| 56 | 37 |
| 57 | 34 |
| 58 | 18 |
| 59 | 184 |
| 60 | 0.74 |
| 61 | 0.41 |
| 62 | 0.81 |
| 63 | 15 |
| 64 | 7.8 |

What is claimed is:

1. A compound of formula (I)

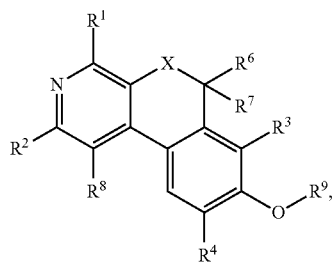

or a pharmaceutically acceptable salt thereof, wherein:

X is selected from O and $NR^5$;

$R^1$ and $R^2$ are independently selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, $C_1$-$C_3$alkylsulfonyl, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, halo$C_1$-$C_3$alkyl, $C_2$-$C_3$haloalkylamino, $C_2$-$C_3$haloalkylcarbonylamino, hydroxy, $C_1$-$C_3$alkylsulfonylamino, and $C_3$-$C_6$cycloalkylsulfonylamino;

$R^3$ and $R^4$ are independently selected from hydrogen, $C_1$-$C_3$alkoxy, $C_1$-$C_3$alkyl, cyano, —$CH_2OH$, —$CH_2OCH_3$, $CH(CH_3)OH$, $C(CH_3)_2OH$, $C_3$cycloalkyl, halo, and $C_1$-$C_3$haloalkyl;

$R^5$ is selected from hydrogen, —$CD_3$, $C_1$-$C_4$alkyl, $C_3$-$C_6$cycloalkyl, $C_1$-$C_4$hydroxyalkyl;

$R^6$ and $R^7$ are independently selected from hydrogen and $C_1$-$C_3$alkyl, or, $R^6$ and $R^7$, together with the carbon atom to which they are attached, from a carbonyl group;

$R^8$ is selected from hydrogen, $C_1$-$C_3$alkoxy, $C_1$-$C_3$alkyl, cyano, and halo;

$R^9$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxy$C_2$-$C_3$alkylamino, amino, aryl, deuterium, halo, $C_1$-$C_3$haloalkyl, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;

$R^x$ and $R^y$, together with the nitrogen atom to which they are attached, form a three- to six-membered ring; and Y is selected from

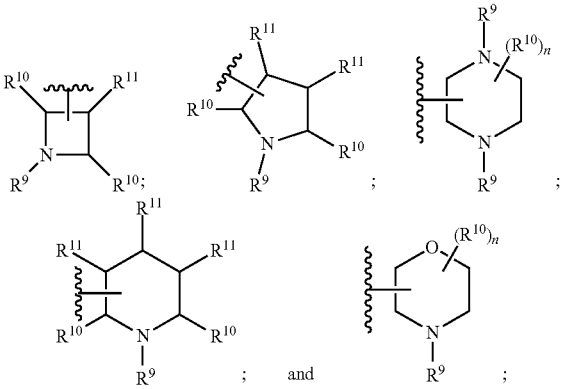

wherein $R^9$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^{10}$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and each $R^{11}$ is independently selected from hydrogen, $C_1$-$C_3$alkoxy and hydroxy.

2. A compound of claim 1, or a pharmaceutically acceptable salt thereof, wherein $R^9$ is $C_5$-$C_7$alkyl optionally substituted with one, two or three groups independently selected from amino, deuterium, and halo.

3. A compound of claim 2, or a pharmaceutically acceptable salt thereof, wherein X is $NR^5$ and $R^6$ and $R^7$, together with the carbon atom to which they are attached, from a carbonyl group.

4. A compound of claim 3, or a pharmaceutically acceptable salt thereof, wherein $R^1$, $R^2$, $R^3$, and $R^4$ are each independently selected from hydrogen, cyano, halo, and $C_1$alkyl.

5. A compound of claim 2, or a pharmaceutically acceptable salt thereof, wherein X is O and $R^6$ and $R^7$ are independently selected from hydrogen and $C_1$alkyl.

6. A compound of claim 5, or a pharmaceutically acceptable salt thereof, wherein:
$R^1$ is selected from hydrogen, $C_1$alkoxycarbonylamino, $C_1$alkyl, amino and halo;
$R^2$ is selected from hydrogen, $C_1$-$C_3$alkoxycarbonylamino, $C_1$alkyl, $C_1$alkylcarbonylamino, $C_1$-$C_3$alkylsulfonyl, amino, halo, halo$C_1$alkyl, $C_2$haloalkylamino, $C_1$-alkylsulfonylamino, and $C_3$cycloalkylsulfonylamino;
$R^3$ and $R^4$ are independently selected from hydrogen, $C_1$alkyl, and halo.

7. A compound selected from:
(S)-8-((2-amino-4-methylpentyl)oxy)benzo[c][1,7]naphthyridin-6(5H)-one;
(S)-8-((2-amino-4-methylpentyl)oxy)-5-methylbenzo[c][1,7]naphthyridin-6(5H)-one;
(S)-8-((2-amino-4-methylpentyl)oxy)-5,9-dimethylbenzo[c][1,7]naphthyridin-6(5H)-one;
(S)-8-((2-amino-4-methylpentyl)oxy)-4,5,9-trimethylbenzo[c][1,7]naphthyridin-6(5H)-one;
(S)-8-((2-amino-4-methylpentyl)oxy)-9-chloro-4,5-dimethylbenzo[c][1,7]naphthyridin-6(5H)-one;
8-((2-amino-5,5,5-trifluoropentyl)oxy)-5,9-dimethylbenzo[c][1,7]naphthyridin-6(5H)-one;
8-((2-amino-2,4-dimethylpentyl)oxy)-5-methylbenzo[c][1,7]naphthyridin-6(5H)-one;
8-((2-amino-2,4-dimethylpentyl)oxy)benzo[c][1,7]naphthyridin-6(5H)-one;
8-((2-amino-2,4-dimethylpentyl)oxy)-4,5-dimethylbenzo[c][1,7]naphthyridin-6(5H)-one;
(S)-8-((2-amino-2,4-dimethylpentyl)oxy)-4,5-dimethylbenzo[c][1,7]naphthyridin-6(5H)-one;
(R)-8-((2-amino-2,4-dimethylpentyl)oxy)-4,5-dimethylbenzo[c][1,7]naphthyridin-6(5H)-one;
8-((2-amino-1,1-dideutero-2,4-dimethylpentyl)oxy)-9-chloro-5-ethyl-4-methylbenzo[c][1,7]naphthyridin-6(5H)-one;
8-((2-amino-1,1-dideutero-2,4-dimethylpentyl)oxy)-4,5-dimethylbenzo[c][1,7]naphthyridin-6(5H)-one;
(S)-8-((2-amino-2,4-dimethylpentyl)oxy)-2,5-dimethylbenzo[c][1,7]naphthyridin-6(5H)-one;
(S)-8-((2-amino-2,4-dimethylpentyl)oxy)-7-chloro-4,5-dimethylbenzo[c][1,7]naphthyridin-6(5H)-one;
(S)-8-((2-amino-2,4-dimethylpentyl)oxy)-9-chloro-5-ethyl-4-methylbenzo[c][1,7]naphthyridin-6(5H)-one;
(S)-8-((2-amino-2,4-dimethylpentyl)oxy)-9-chloro-2,5-dimethylbenzo[c][1,7]naphthyridin-6(5H)-one;
(S)-8-((2-amino-2,4-dimethylpentyl)oxy)-7-chloro-2,5-dimethylbenzo[c][1,7]naphthyridin-6(5H)-one;
(S)-8-((2-amino-2,4-dimethylpentyl)oxy)-5-ethyl-4-methylbenzo[c][1,7]naphthyridin-6(5H)-one;
(S)-8-((2-amino-2,4-dimethylpentyl)oxy)-2,5,7-trimethylbenzo[c][1,7]naphthyridin-6(5H)-one;
(S)-8-((2-amino-2,4-dimethylpentyl)oxy)-5-(2-hydroxyethyl)-4-methylbenzo[c][1,7]naphthyridin-6(5H)-one;
(S)-8-((2-amino-2,4-dimethylpentyl)oxy)-9-chloro-4-methyl-5-(trideuteromethyl)benzo[c][1,7]naphthyridin-6(5H)-one;
(S)-8-((2-amino-2,4-dimethylpentyl)oxy)-4-methyl-5-(trideuteromethyl)benzo[c][1,7]naphthyridin-6(5H)-one;
(S)-8-((2-amino-2,4-dimethylpentyl)oxy)-5-cyclopropyl-4-methyl-6-oxo-5,6-dihydrobenzo[c][1,7]naphthyridine-9-carbonitrile;
(S)-8-((2-amino-2,4-dimethylpentyl)oxy)-9-chloro-5-isopropyl-4-methylbenzo[c][1,7]naphthyridin-6(5H)-one;
(S)-8-((2-amino-2,4-dimethylpentyl)oxy)-4,5,9-trimethylbenzo[c][1,7]naphthyridin-6(5H)-one;
(S)-8-((2-amino-2,4-dimethylpentyl)oxy)-9-chloro-4,5-dimethylbenzo[c][1,7]naphthyridin-6(5H)-one;
(S)-8-((2-amino-2,4-dimethylpentyl)oxy)-9-chloro-4-methylbenzo[c][1,7]naphthyridin-6(5H)-one;
(S)-1-((6H-isochromeno[3,4-c]pyridin-8-yl)oxy)-4-methylpentan-2-amine;
(2S)-4-methyl-1-((6-methyl-6H-isochromeno[3,4-c]pyridin-8-yl)oxy)pentan-2-amine;
(S)-1-((6,6-dimethyl-6H-isochromeno[3,4-c]pyridin-8-yl)oxy)-4-methylpentan-2-amine;
(S)-4-methyl-1-((9-methyl-6H-isochromeno[3,4-c]pyridin-8-yl)oxy)pentan-2-amine;
(S)—N-(8-((2-amino-4-methylpentyl)oxy)-6H-isochromeno[3,4-c]pyridin-2-yl)acetamide;
(S)-methyl (8-((2-amino-4-methylpentyl)oxy)-6H-isochromeno[3,4-c]pyridin-2-yl)carbamate;
(S)-8-((2-amino-4-methylpentyl)oxy)-6H-isochromeno[3,4-c]pyridin-2-amine;
N-(8-((2-amino-2,4-dimethylpentyl)oxy)-6H-isochromeno[3,4-c]pyridin-2-yl)acetamide;
(S)—N-(8-((2-amino-2,4-dimethylpentyl)oxy)-6H-isochromeno[3,4-c]pyridin-2-yl)acetamide;
(R)—N-(8-((2-amino-2,4-dimethylpentyl)oxy)-6H-isochromeno[3,4-c]pyridin-2-yl)acetamide;
methyl (8-((2-amino-2,4-dimethylpentyl)oxy)-6H-isochromeno[3,4-c]pyridin-2-yl)carbamate;
(R)-ethyl (8-((2-amino-2,4-dimethylpentyl)oxy)-6H-isochromeno[3,4-c]pyridin-2-yl)carbamate;
(S)-ethyl (8-((2-amino-2,4-dimethylpentyl)oxy)-6H-isochromeno[3,4-c]pyridin-2-yl)carbamate;
8-((2-amino-2,4-dimethylpentyl)oxy)-N-(2,2,2-trifluoroethyl)-6H-isochromeno[3,4-c]pyridin-2-amine;
(S)-8-((2-amino-2,4-dimethylpentyl)oxy)-N-(2,2,2-trifluoroethyl)-6H-isochromeno[3,4-c]pyridin-2-amine;
(R)-8-((2-amino-2,4-dimethylpentyl)oxy)-N-(2,2,2-trifluoroethyl)-6H-isochromeno[3,4-c]pyridin-2-amine;
(S)-methyl (8-((2-amino-2,4-dimethylpentyl)oxy)-7-fluoro-6H-isochromeno[3,4-c]pyridin-2-yl)carbamate;
(S)-ethyl (8-((2-amino-2,4-dimethylpentyl)oxy)-1,4-dichloro-6H-isochromeno[3,4-c]pyridin-2-yl)carbamate;
(S)-ethyl (8-((2-amino-2,4-dimethylpentyl)oxy)-1-chloro-6H-isochromeno[3,4-c]pyridin-2-yl)carbamate;
(S)-1-((2-(difluoromethyl)-6H-isochromeno[3,4-c]pyridin-8-yl)oxy)-2,4-dimethylpentan-2-amine;
(S)-methyl (8-((2-amino-2,4-dimethylpentyl)oxy)-9-fluoro-6H-isochromeno[3,4-c]pyridin-2-yl)carbamate;
(S)-2,4-dimethyl-1-((4-methyl-6H-isochromeno[3,4-c]pyridin-8-yl)oxy)pentan-2-amine;
(S)-2,4-dimethyl-1-((2-methyl-6H-isochromeno[3,4-c]pyridin-8-yl)oxy)pentan-2-amine;
(S)-1-((4-chloro-6H-isochromeno[3,4-c]pyridin-8-yl)oxy)-2,4-dimethylpentan-2-amine;
(S)-8-((2-amino-2,4-dimethylpentyl)oxy)-6H-isochromeno[3,4-c]pyridin-2-amine;
(S)-isopropyl (8-((2-amino-2,4-dimethylpentyl)oxy)-6H-isochromeno[3,4-c]pyridin-2-yl)carbamate;
(S)—N-(8-((2-amino-2,4-dimethylpentyl)oxy)-6H-isochromeno[3,4-c]pyridin-2-yl)methanesulfonamide;
S)—N-(8-((2-amino-2,4-dimethylpentyl)oxy)-6H-isochromeno[3,4-c]pyridin-2-yl)cyclopropanesulfonamide;
(S)-1-((2-fluoro-6H-isochromeno[3,4-c]pyridin-8-yl)oxy)-2,4-dimethylpentan-2-amine;

(S)-methyl (8-((2-amino-2,4-dimethylpentyl)oxy)-1-chloro-9-fluoro-6H-isochromeno[3,4-c]pyridin-2-yl)carbamate;

(S)-2,4-dimethyl-1-((2-(methylsulfonyl)-6H-isochromeno[3,4-c]pyridin-8-yl)oxy)pentan-2-amine;

(S)-8-((2-amino-2,4-dimethylpentyl)oxy)-6H-isochromeno[3,4-c]pyridin-4-amine;

(S)-8-((2-amino-2,4-dimethylpentyl)oxy)-7-chloro-6H-isochromeno[3,4-c]pyridin-2-amine;

(S)-methyl (8-((2-amino-2,4-dimethylpentyl)oxy)-7-chloro-6H-isochromeno[3,4-c]pyridin-2-yl)carbamate;

(S)-methyl (8-((2-amino-2,4-dimethylpentyl)oxy)-1,4,7-trichloro-6H-isochromeno[3,4-c]pyridin-2-yl)carbamate; and (S)-methyl (8-((2-amino-2,4-dimethylpentyl)oxy)-6H-isochromeno[3,4-c]pyridin-4-yl)carbamate;

or a pharmaceutically acceptable salt thereof.

8. A composition comprising a pharmaceutically acceptable amount of a compound of claim 1, or a pharmaceutically acceptable salt thereof, and a pharmaceutically acceptable carrier.

9. A method of inhibiting adaptor associated kinase 1 (AAK1) activity, comprising contacting AAK1 with a compound of claim 1, or a pharmaceutically acceptable salt thereof.

10. A method for treating or managing a disease or a disorder mediated by AAK1 activity, wherein the disease or disorder is selected from the group consisting of Alzheimer's disease, bipolar disorder, pain, Parkinson's disease, and schizophrenia.

11. The method of claim 10 wherein the pain is neuropathic pain.

12. The method of claim 11 wherein the neuropathic pain is peripheral neuropathy or the pain is caused by fibromyalgia.

* * * * *

UNITED STATES PATENT AND TRADEMARK OFFICE
CERTIFICATE OF CORRECTION

PATENT NO. : 10,174,044 B2
APPLICATION NO. : 15/563697
DATED : January 8, 2019
INVENTOR(S) : Susheel Nara et al.

Page 1 of 1

It is certified that error appears in the above-identified patent and that said Letters Patent is hereby corrected as shown below:

On the Title Page

Item (72), Column 1, Line 6-7:
Delete "Rajamani Ramkumar, Woodbridge, CT (US);" and insert -- Ramkumar Rajamani, Acton, MA (US); --

Under Other Publications, Column 2, Line 4:
Delete "2" and insert -- µ2 --

In the Claims

In Claim 7, Column 145, Line 66-67:
Delete "naphthyridine-" and insert -- naphthyridin- --

In Claim 7, Column 146, Line 63:
Delete "S)" and insert -- (S) --

Signed and Sealed this
Fifteenth Day of December, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1

Phe Ala Met Ala His Ala Lys Glu Glu Gln Ser Gln Ile Thr Ser Gln
1               5                   10                  15

Val Thr Gly Gln Ile Gly Trp Arg Asn His
            20                  25
```